US012735707B2

(12) United States Patent
Kim et al.

(10) Patent No.: US 12,735,707 B2
(45) **Date of Patent: *Sep. 15, 2026**

(54) RUNX1 INHIBITION FOR TREATMENT OF PROLIFERATIVE VITREORETINOPATHY AND CONDITIONS ASSOCIATED WITH EPITHELIAL TO MESENCHYMAL TRANSITION

(71) Applicants: The Schepens Eye Research Institute, Inc., Boston, MA (US); Massachusetts Eye and Ear Infirmary, Boston, MA (US)

(72) Inventors: Leo A. Kim, Boston, MA (US); Joseph F. Arboleda-Velasquez, Newton, MA (US); Dhanesh Amarnani, Allston, MA (US); Dean Eliott, Carlsbad, CA (US)

(73) Assignee: Massachusetts Eye and Ear Infirmary, Boston, MA (US)

(*) Notice: Subject to any disclaimer, the term of this patent is extended or adjusted under 35 U.S.C. 154(b) by 141 days.

This patent is subject to a terminal disclaimer.

(21) Appl. No.: 18/351,320

(22) Filed: Jul. 12, 2023

(65) Prior Publication Data

US 2024/0175022 A1 May 30, 2024

Related U.S. Application Data

(63) Continuation of application No. 16/763,880, filed as application No. PCT/US2018/061110 on Nov. 14, 2018, now Pat. No. 11,739,326.

(60) Provisional application No. 62/586,067, filed on Nov. 14, 2017.

(51) Int. Cl.

| | |
|---|---|
| ***C12N 15/113*** | (2010.01) |
| ***A61K 9/00*** | (2006.01) |
| ***A61K 31/4025*** | (2006.01) |
| ***A61K 31/5513*** | (2006.01) |
| ***A61K 31/7105*** | (2006.01) |
| ***A61K 45/06*** | (2006.01) |
| ***A61P 27/02*** | (2006.01) |
| ***G01N 33/68*** | (2006.01) |

(52) U.S. Cl.

CPC .......... *C12N 15/113* (2013.01); *A61K 9/0048* (2013.01); *A61K 31/4025* (2013.01); *A61K 31/5513* (2013.01); *A61K 31/7105* (2013.01); *A61K 45/06* (2013.01); *A61P 27/02* (2018.01); *G01N 33/6893* (2013.01); *C12N 2310/14* (2013.01); *G01N 2333/4706* (2013.01); *G01N 2800/164* (2013.01)

(58) Field of Classification Search

None

See application file for complete search history.

(56) References Cited

U.S. PATENT DOCUMENTS

| | | | |
|---|---|---|---|
| 3,405,122 | A | 10/1968 | Berger et al. |
| 4,309,404 | A | 1/1982 | Deneale et al. |
| 4,309,406 | A | 1/1982 | Guley et al. |
| 4,521,210 | A | 6/1985 | Wong |
| 4,556,552 | A | 12/1985 | Porter et al. |
| 4,704,295 | A | 11/1987 | Porter et al. |
| 4,816,567 | A | 3/1989 | Cabilly et al. |
| 4,853,224 | A | 8/1989 | Wong |
| 4,997,652 | A | 3/1991 | Wong |
| 5,036,101 | A | 7/1991 | Hsu et al. |
| 5,041,438 | A | 8/1991 | Hsu |
| 5,141,735 | A | 8/1992 | Bellemin et al. |
| 5,164,188 | A | 11/1992 | Wong |
| 5,164,376 | A | 11/1992 | Hsu et al. |
| 5,443,505 | A | 8/1995 | Wong et al. |
| 5,501,856 | A | 3/1996 | Ohtori et al. |
| 5,545,806 | A | 8/1996 | Lonbera et al. |
| 5,545,807 | A | 8/1996 | Surani et al. |
| 5,569,825 | A | 10/1996 | Lonbera et al. |
| 5,582,981 | A | 12/1996 | Toole et al. |
| 5,625,126 | A | 4/1997 | Lonberg et al. |
| 5,633,425 | A | 5/1997 | Lonbera et al. |
| 5,641,673 | A | 6/1997 | Haseloff et al. |
| 5,641,750 | A | 6/1997 | Louis |
| 5,641,773 | A | 6/1997 | Pardee et al. |
| 5,661,016 | A | 8/1997 | Lonbera et al. |
| 5,731,005 | A | 3/1998 | Ottoboni et al. |
| 5,766,242 | A | 6/1998 | Wong et al. |
| 5,824,072 | A | 10/1998 | Wong |
| 5,837,226 | A | 11/1998 | Junaherr et al. |

(Continued)

FOREIGN PATENT DOCUMENTS

| | | |
|---|---|---|
| EP | 1163910 | 12/2001 |
| EP | 1256574 | 11/2002 |

(Continued)

OTHER PUBLICATIONS

[No Author Listed], "Retinopathy of Prematurity," American Association for Pediatric Ophthalmology and Strabismus, retrieved from URL<https://aapos.org/glossary/retinopathy-of-prematurity>, available on or before Apr. 2020, 4 pages.

Ackermann et al., "Pulmonary Vascular Endothelialitis, Thrombosis, and Angiogenesis in Covid-19," New England Journal of Medicine, Jul. 2020, 383(2):120-8.

Alder et al., "Diagnostic utility of telomere length testing in a hospital-based setting," Proceedings of the National Academy of Sciences of the United States of America, Mar. 2018, 115(10):E2358-E2365.

Amarnani et al., "Effect of Methotrexate on an In Vitro Patient-Derived Model of Proliferative Vitreoretinopathy," Invest Ophthalmol Vis Sci., Aug. 2017, 58(10):3940-3949.

(Continued)

*Primary Examiner* — Brian Whiteman

(74) *Attorney, Agent, or Firm* — Fish & Richardson P.C.

(57) ABSTRACT

The present subject matter provides compositions. formulations and methods for preventing or reducing proliferation or migration of retinal cells or epithelial to mesenchymal transition in ocular cells or cells from other tissues.

6 Claims, 35 Drawing Sheets

Specification includes a Sequence Listing.

(56) References Cited

U.S. PATENT DOCUMENTS

| | | | |
|---|---|---|---|
| 5,869,079 A | 2/1999 | Wong et al. | |
| 6,074,661 A | 6/2000 | Oleinik et al. | |
| 6,331,313 B1 | 12/2001 | Wong et al. | |
| 6,369,116 B1 | 4/2002 | Wong et al. | |
| 6,699,493 B2 | 3/2004 | Wong | |
| 6,719,971 B1 | 4/2004 | Carter et al. | |
| 7,354,574 B2 | 4/2008 | Peyman | |
| 7,563,906 B2 | 7/2009 | Hagihara et al. | |
| 8,053,454 B2 | 11/2011 | Kearney et al. | |
| 8,293,210 B2 | 10/2012 | Huana et al. | |
| 8,394,826 B2 | 3/2013 | deLong et al. | |
| 8,414,912 B2 | 4/2013 | Ciolino et al. | |
| 8,450,344 B2 | 5/2013 | deLong et al. | |
| 8,484,010 B2 | 7/2013 | Tuszynski et al. | |
| 8,697,359 B1 | 4/2014 | Zhang | |
| 9,023,649 B2 | 5/2015 | Mali et al. | |
| 9,074,199 B1 | 7/2015 | Chavez et al. | |
| 9,133,269 B2 | 9/2015 | McConnell et al. | |
| 9,446,048 B2 | 9/2016 | Liu et al. | |
| 10,562,890 B2 | 2/2020 | Bushweller | |
| 10,828,306 B2 | 11/2020 | Eliott et al. | |
| 11,229,662 B2 | 1/2022 | Arboleda-Velasquez et al. | |
| 11,739,326 B2 * | 8/2023 | Kim ...................... | A61K 45/06 514/44 A |
| 2004/0229816 A1 | 11/2004 | Paris et al. | |
| 2006/0034834 A1 | 2/2006 | Marasco et al. | |
| 2006/0142193 A1 | 6/2006 | Wei et al. | |
| 2006/0257452 A1 | 11/2006 | Hughes et al. | |
| 2006/0264380 A1 | 11/2006 | Hellstrom et al. | |
| 2007/0141066 A1 | 6/2007 | Phillips et al. | |
| 2008/0014180 A1 | 1/2008 | Lanza et al. | |
| 2008/0131484 A1 | 6/2008 | Robinson et al. | |
| 2009/0203011 A1 | 8/2009 | Liebenberg et al. | |
| 2009/0220488 A1 | 9/2009 | Gardner | |
| 2009/0285786 A1 | 11/2009 | Zon et al. | |
| 2010/0143380 A1 | 6/2010 | Crabb et al. | |
| 2010/0233194 A1 | 9/2010 | Combal et al. | |
| 2010/0330114 A1 | 12/2010 | Verdin et al. | |
| 2011/0305641 A1 | 12/2011 | Kazlauskas et al. | |
| 2012/0202793 A1 | 8/2012 | Sweetnam et al. | |
| 2013/0156795 A1 | 6/2013 | Iavarone et al. | |
| 2014/0004082 A1 | 1/2014 | Liu et al. | |
| 2014/0249135 A1 | 9/2014 | Buraer et al. | |
| 2015/0174138 A1 | 6/2015 | Bernstein et al. | |
| 2017/0049760 A1 | 2/2017 | Schonbrunn et al. | |
| 2017/0296617 A1 | 10/2017 | Schwartz et al. | |
| 2018/0170939 A1 | 6/2018 | Accetta et al. | |
| 2019/0350961 A1 | 11/2019 | Arboleda-Velasquez et al. | |
| 2020/0102384 A1 | 4/2020 | Arboleda-Velasquez et al. | |
| 2020/0103419 A1 | 4/2020 | Arboleda-Velasquez et al. | |
| 2020/0375899 A1 | 12/2020 | Kim et al. | |
| 2022/0341915 A1 | 10/2022 | Tata | |
| 2023/0190959 A1 | 6/2023 | Arboleda-Velasquez | |
| 2023/0310446 A1 | 10/2023 | Kim et al. | |

FOREIGN PATENT DOCUMENTS

| | | | |
|---|---|---|---|
| EP | 1270570 | 1/2003 | |
| WO | WO 1993011161 | 6/1993 | |
| WO | WO 1997023222 | 7/1997 | |
| WO | WO 1999020620 | 4/1999 | |
| WO | WO 1999064011 | 12/1999 | |
| WO | WO 2001056988 | 8/2001 | |
| WO | WO 2002053143 | 7/2002 | |
| WO | WO 2002076976 | 10/2002 | |
| WO | WO 2002076977 | 10/2002 | |
| WO | WO 2002100833 | 12/2002 | |
| WO | WO 2003078662 | 9/2003 | |
| WO | WO 2003082808 | 10/2003 | |
| WO | WO 2005074643 | 8/2005 | |
| WO | WO 2007017065 | 2/2007 | |
| WO | WO 2008015001 | 2/2008 | |
| WO | WO 2008130315 | 10/2008 | |
| WO | WO 2009146456 | 12/2009 | |
| WO | WO 2009152901 | 12/2009 | |
| WO | WO 2010104851 | 9/2010 | |
| WO | WO 2011143484 | 11/2011 | |
| WO | WO 2011163669 | 12/2011 | |
| WO | WO 2012174419 | 12/2012 | |
| WO | WO 2015049356 | 4/2015 | |
| WO | WO 2016019165 | 2/2016 | |
| WO | WO 2016025744 | 2/2016 | |
| WO | WO 2016182904 | 11/2016 | |
| WO | WO 2017112823 | 6/2017 | |
| WO | WO-2017117538 A1 * | 7/2017 | ................ A61P 9/10 |
| WO | WO 2018183216 | 10/2018 | |
| WO | WO 2019040448 A1 | 2/2019 | |
| WO | WO 2019221959 | 11/2019 | |
| WO | WO 2021062412 | 4/2021 | |
| WO | WO 2021216378 | 10/2021 | |

OTHER PUBLICATIONS

Antonetti et al., "Vascular Endothelial Growth Factor Induces Rapid Phosphorylation of Tight Junction Proteins Occludin and Zonula Occluden 1," J Biol Chem., Aug. 1999, 274(33):23463-23467.

Arevalo et al., "Tractional Retinal Detachment Following Intravitreal Bevacizumab (Avastin) in Patients With Severe Proliferative Diabetic Retinopathy," Br. J. Ophthalmol., Feb. 2008, 92(2):213-216.

Asato et al., "Comparison of gene expression profile of epiretinal membranes obtained from eyes with proliferative vitreoretinopathy to that of secondary epiretinal membranes," PLoS One, 2013, 8(1):e54191, 8 pages.

Barberis et al., "Discovery of N-Substituted 7-Azaindoles as Pan-PIM Kinase Inhibitors—Lead Series Identification—Part II," Bioorganic & Medicinal Chemistry Letters, Sep. 2017, 27(20):4735-4740.

Bataille et al., "Thiazolidine Derivatives as Potent and Selective Inhibitors of the PIM Kinase Family," Bioorganic & Medicinal Chemistry, May 2017, 25(9):2657-2665.

Bataller and Brenner, "Liver fibrosis," J Clin Invest., Feb. 2005, 15(2):209-18.

Beigel et al., "Remdesivir for the Treatment of Covid-19—Final Report," New England Journal of Medicine, Nov. 2020, 383(19):1813-26, 14 pages.

Bellissimo et al., "Runx1 negatively regulates inflammatory cytokine production by neutrophils in response to Toll-like receptor signaling," Blood Advances, Mar. 2020, 4(6):1145-58.

Belser et al., "Ocular tropism of respiratory viruses," Microbiol Mol Biol Rev., Mar. 2013, 77(1):144-56.

Berge et al., "Pharmaceutical Salts", Journal of Pharmaceutical Sciences, Jan. 1977, 66(1):1-19.

Bergers et al., "Tumorigenesis and the Angiogenic Switch," Nature Reviews Cancer, Jun. 2003, 3(6):401-410.

Blackwell et al., "Sequence-specific DNA Binding by the c-Myc Protein," Science, Nov. 1990, 250(4984):1149-1151.

Boerner et al., "Production of Antigen-Specific Human Monoclonal Antibodies from in Vitro-Primed Human Splenocytes," J. Immunol., Jul. 1991, 147(1):86-95.

Bonniaud et al., "Smad3 Null Mice Develop Airspace Enlargement and Are Resistant to TGF-β-Mediated Pulmonary Fibrosis," The Journal of Immunology, Aug. 2004, 173(3):2099, 11 pages.

Boyd, "Diabetic Retinopathy Diagnosis," American Academy of Ophthamology, 2013, retrieved on Sep. 8, 2020, retrieved from URL <https://www.aao.org/eye-health/diseases/diabetic-retinopathy-diagnosis>, 6 pages.

Bravo et al., "The leukemia-associated AML1 (Runx1)-CBFbeta complex functions as a DNA-induced molecular clamp," Nature Structural Biology, Apr. 2001, 8(4):371-8.

Burns et al., "Hematopoietic Stem Cell Fate Is Established by the Notch-Runx Pathway," Genes & Development, Oct. 2005, 19(19):2331-2342.

Butko et al., "Complex regulation of HSC emergence by the Notch signaling pathway," Dev. Biol., Jan. 2016, 409(1):129-138.

Castilla et al., "Failure of Embryonic Hematopoiesis and Lethal Hemorrhages in Mouse Embryos Heterozygous for a Knocked-In Leukemia Gene CBFB-MYH11," Cell, Nov. 1996, 87(4):687-696.

(56) References Cited

OTHER PUBLICATIONS

Castoreno et al., "Small molecules discovered in a pathway screen target the Rho pathway in cytokinesis," Nat Chem Biol., Jun. 2010, 6(6):457-463, 21 pages (Author Manuscript).
Chang et al., "PIM Kinase Inhibitors Downregulate STAT3Tyr705 Phosphorylation," Mol Cancer Ther., Sep. 2010, 9(9):2478-2487.
Cheema et al., "Keratoconjunctivitis as the initial medical presentation of the novel coronavirus disease 2019 (COVID-19)," Can J Ophthalmol., Aug. 2020, 55(4):e125-e129.
Cheloufi et al., "A Dicer-independent miRNA biogenesis pathway that requires Ago catalysis," Nature, Jun. 2010, 465(7298):584-589.
Chen et al., "Intracellular Antibodies as a New Class of Therapeutic Molecules for Gene Therapy," Human Gene Therapy, 1994, 5(5):595-601.
Chen et al., "Ocular manifestations of a hospitalised patient with confirmed 2019 novel coronavirus disease," Br J Ophthalmol., Jun. 2020, 104(6):748-751.
Chen et al., "Runx1 is required for the endothelial to haematopoietic cell transition but not thereafter," Nature, Feb. 2009, 457(7231):887-891.
Chothia et al., "Canonical Structures for the Hypervariable Regions of Immunoglobulins," J. Mol. Biol., Aug. 1987, 196(4):901-917.
Chothia et al., "Conformations of immunoglobulin hypervariable regions," Nature, Dec. 1989, 342:877-883.
Chung et al., "Developmental and Pathological Angiogenesis," Annu. Rev. Cell Dev. Biol., Nov. 2011, 27:563-584.
Ciolino et al., "A drug-eluting contact lens," Invest Ophthalmol Vis Sci., Jul. 2009, 50(7):3346-3352.
Cole, "Monoclonal Antibodies," Can. Fam. Physician, 1987, 33:369-372.
Colyer et al., "Perforating globe injuries during operation Iraqi Freedom," Ophthalmology, 2008, 115:2087-2093.
Connor et al., "Quantification of oxygen-induced retinopathy in the mouse: a model of vessel loss, vessel regrowth and pathological angiogenesis," Nat Protoc., Oct. 2009, 4(11):1565-1573.
Cunningham et al., "Identification of benzodiazepine Ro5-3335 as an inhibitor of CBF leukemia through quantitative high throughput screen against RUNX1-CBFβ interaction," PNAS, Sep. 2012, 109(36):14592-14597.
Daxer, "The Fractal Geometry of Proliferative Diabetic Retinopathy: Implications for the Diagnosis and the Process of Retinal Vasculogenesis," Current Eye Research, Dec. 1993, 12(12):1103-1109.
Delgado-Tirado et al., "Topical delivery of a small molecule RUNX1 transcription factor inhibitor for the treatment of proliferative vitreoretinopathy," Scientific Reports, Nov. 2020, 10(1):20554, 15 pages.
Diabetes Control and Complications Trial Research Group, "The Relationship of Glycemic Exposure (HbA1c) to the Risk of Development and Progression of Retinopathy in the Diabetes Control and Complications Trial," Diabetes, Aug. 1995, 44(8):968-983.
Dua et al., "The ocular surface as part of the mucosal immune system: conjunctival mucosa-specific lymphocytes in ocular surface pathology," Eye (Lond.), 1995, 9(Pt 3):261-7.
Dubois et al., "Evidence that furin is an authentic transforming growth factor-beta1-converting enzyme," Am J Pathol., Jan. 2001, 158(1):305-16.
Eapen et al., "Endothelial to mesenchymal transition: a precursor to post-COVID-19 interstitial pulmonary fibrosis and vascular obliteration?," European Respiratory Journal, Oct. 2020, 56(4):2003167, 3 pages.
Edgar et al., "Gene Expression Omnibus: NCBI gene expression and hybridization array data repository," Nucleic Acids Research, Jan. 2002, 30(1):207-210.
Elbashir et al., "Functional anatomy of siRNAs for mediating efficient RNAi in *Drosophila melanogaster* embryo lysate," The EMBO Journal, Dec. 2001, 20(23):6877-6888.
Eliott et al., "Smoking is a risk factor for proliferative vitreoretinopathy after traumatic retinal detachment," Retina, 2017, 37(7):1229-1235.
Espinoza et al., "Notch Inhibitors for Cancer Treatment," Pharmacol Ther., Aug. 2013, 139(2):95-110.
Extended European Search Report in European Application No. 17871449.9, dated May 25, 2020, 13 pages.
Extended European Search Report in European Appln. No. 18878909.3, dated Jul. 22, 2021, 7 pages.
Eye.Hms.Harvard.edu [online], "Harvard Medical School Dept. of Ophthalmology Home/News," Apr. 2017, retrieved on Dec. 10, 2021, retrieved from URL<https://eye.hms.harvard.edu/news/researchers-identify-new-target-abnormal-blood-vessel-growth-eyes>, 3 pages.
Fehniger et al., "Single-agent lenalidomide induces complete remission of acute myeloid leukemia in patients with isolated trisomy 13," Blood, 2009, 113(5):1002-1005.
Fire et al., "Potent and Specific Genetic Interference by Double-Stranded RNA in Caenorhabditis Elegans," Nature, 1998, 391:806-810.
Fishwild et al., "High-Avidity Human IgG Kappa Monoclonal Antibodies from a Novel Strain of Minilocus Transgenic Mice," Nature Biotechnology, Aug. 1996, 14(7):845-851.
Frangogiannis, "Fibroblast-Extracellular Matrix Interactions in Tissue Fibrosis," HHS Public Access Author Manuscript, doi:10.1007/s40139-016-0099-1, published online Feb. 5, 2016, 14 pages; Published in final edited form as: Curr Pathobiol Rep., Mar. 2016, 4(1):11-18.
Fràter-Schröder et al., "Tumor necrosis factor type alpha, a potent inhibitor of endothelial cell growth in vitro, is angiogenic in vivo," Proc Natl Acad Sci USA, Aug. 1987, 84(15):5277-81.
Friedlander, "Fibrosis and diseases of the eye," J Clin Invest., 2007, 117(3):576-586.
Fu et al., "The effects of the Rho-kinase inhibitor Y-27632 on arachidonic acid-, GTPγS-, and phorbol ester-induced $Ca^{2+}$-sensitization of smooth muscle," FEBS Lett, Nov. 1998, 440(1-2):183-187.
Geback et al., "TScratch: A novel and simple software tool for automated analysis of monolayer wound healing assays," Biotechniques, Apr. 2009, 46(4):265-274.
GenBank Accession No. AAI41856.1, "Pim-3 oncogene [*Homo sapiens*]," May 8, 2007, 2 pages.
GenBank Accession No. AB114795.1, "*Homo sapiens* pim-3 mRNA for serine/threonine kinase Pim-3, Complete cds," Nov. 9, 2017, 2 pages.
GenBank Accession No. AK292005.1, "*Homo sapiens* cDNA FLJ75766 complete cds, highly similar to *Homo sapiens* pim-3 oncogene (PIM3), mRNA," Jan. 9, 2008, 2 pages.
GenBank Accession No. BAD42438.1, "serine/threonine kinase Pim-3 [*Homo sapiens*]," Nov. 9, 2017, 1 page.
GenBank Accession No. BAF84694.1, "Unnamed protein product [*Homo sapiens*]," Jan. 9, 2008, 2 pages.
GenBank Accession No. BC141855.1, "*Homo sapiens* pim-3 oncogene, mRNA (cDNA clone MGC: 167042 IMAGE:8860375), complete cds," May 8, 2007, 2 pages.
GenBank Accession No. NM_000598.4, "*Homo sapiens* insulin like growth factor binding protein 3 (IGFBP3), transcript variant 2, mRNA," May 28, 2019, 4 pages.
GenBank Accession No. NM_001001852.4, "*Homo sapiens* Pim-3 proto-oncogene, serine/threonine kinase (PIM3), mRNA," May 8, 2020, 4 pages.
GenBank Accession No. NM_001001890.2, "*Homo sapiens* RUNX Family Transcription Factor 1 (RUNX1), Transcript Variant 2, mRNA," May 28, 2019, 8 pages.
GenBank Accession No. NM_001013398.1, "*Homo sapiens* insulin like growth factor binding protein 3 (IGFBP3), transcript variant 1, mRNA," Oct. 13, 2018, 4 pages.
GenBank Accession No. NM_001122607.2, "*Homo sapiens* RUNX Family Transcription Factor 1 (RUNX1), Transcript Variant 3, mRNA", Jun. 7, 2020, 4 pages.
GenBank Accession No. NM_001754.4, "*Homo sapiens* RUNX Family Transcription Factor 1 (RUNX1), Transcript Variant 1, mRNA," Feb. 9, 2020, 6 pages.
GenBank Accession No. NP_000589.2, "Insulin-like growth factor-binding protein 3 isoform b precursor [*Homo sapiens*], " Jun. 14, 2020, 3 pages.

(56) References Cited

OTHER PUBLICATIONS

GenBank Accession No. NP_001013416.1, "Insulin-like growth factor-binding protein 3 isoform a precursor [*Homo sapiens*]," Jun. 14, 2020, 3 pages.
GenBank Accession No. XM_005261068.3, "Predicted: *Homo sapiens* RUNX Family Transcription Factor 1 (RUNX1), Transcript Variant X2, mRNA," May 28, 2020, 3 pages.
GenBank Accession No. XM_005261069.4, "Predicted: *Homo sapiens* RUNX family transcription factor 1 (RUNX1 ), transcript variant X5, mRNA," May 28, 2020, 3 pages.
GenBank Accession No. XM_011529766.2, "Predicted: *Homo sapiens* RUNX family transcription factor 1 (RUNX1 ), transcript variant X1, mRNA," May 28, 2020, 3 pages.
GenBank Accession No. XM_011529768.2, "Predicted: *Homo sapiens* RUNX family transcription factor 1 (RUNX1 ), transcript variant X6, mRNA," May 28, 2020, 3 pages.
GenBank Accession No. XM_011529770.2, "Predicted: *Homo sapiens* RUNX Family Transcription Factor 1 (RUNX1), Transcript Variant X8, mRNA", May 28, 2020, 2 pages.
GenBank Accession No. XM_017028487.1, "Predicted: *Homo sapiens* RUNX family transcription factor 1 (RUNX1 ), transcript variant X4, mRNA," May 28, 2020, 3 pages.
GenBank Accession No. XR_937576.2, "Predicted: *Homo sapiens* RUNX family transcription factor 1 (RUNX1), transcript variant X7, misc_RNA", May 28, 2020, 3 pages.
George et al., "Pulmonary fibrosis and COVID-19: the potential role for antifibrotic therapy," The Lancet Respiratory Medicine, Aug. 2020, 8(8):807-15.
ghr.nlm.nih.gov [online], "Age-related macular degeneration," Aug. 2016, retrieved from URL <https://ghr.nlm.nih.gov/condition/age-related-macular-degeneration>, 8 pages.
Giani et al., "In Vivo Evaluation of Laser-Induced Choroidal Neovascularization Using Spectral-Domain Optical Coherence Tomography," Investigative Ophthalmology & Visual Science, 2011, 52(6):3880-3887.
Glinsky, "Tripartite Combination of Candidate Pandemic Mitigation Agents: Vitamin D, Quercetin, and Estradiol Manifest Properties of Medicinal Agents for Targeted Mitigation of the COVID-19 Pandemic Defined by Genomics-Guided Tracing of SARS-CoV-2 Targets in Human Cells," Biomedicines, May 2020, 8(5):129, 26 pages.
Graney and Lee, "Impact of novel antifibrotic therapy on patient outcomes in idiopathic pulmonary fibrosis: patient selection and perspectives," Patient Relat Outcome Meas., 2018, 9:321-8.
Haghjou et al., "Sustained release intraocular drug delivery devices for treatment of uveitis," J Ophthalmic Vis Res., Oct. 2011, 6(4):317-329.
Hakeem et al., "Retinopathy of Prematurity: A Study of Prevalence and Risk Factors," Middle East African Journal of Ophthalmology, 2012, 19(3):289-294.
Harris et al., "Glucose Metabolism Impacts the Spatiotemporal Onset and Magnitude of HSC Induction in Vivo," Blood, Mar. 2013, 121(13):2483-2493.
Haubrich et al., "A Randomized Trial of the Activity and Safety of Ro 24-7429 (Tat Antagonist) Versus Nucleoside for Human Immunodeficiency Virus Infection," The Journal of Infectious Diseases, Nov. 1995, 172(5): 1246-1252.
Heckl et al., "Generation of mouse models of myeloid malignancy with combinatorial genetic lesions using CRISPR-Cas9 genome editing," Nat. Biotechnol., 2014, 32(9):941-946, 14 pages.
Hendren et al., "Description and Proposed Management of the Acute COVID-19 Cardiovascular Syndrome," Circulation, Apr. 2020, 141(23):1903-1914, 19 pages.
Hiscott et al., "Pathobiology of epiretinal and subretinal membranes: possible roles for the matricellular proteins thrombospondin 1 and osteonectin (SPARC)," Eye (Lond)., Jul. 2002, 16(4):393-403.
Hiscott et al., "Retinal pigment epithelial cells in epiretinal membranes: an immunohistochemical study," Br J Ophthalmol., Oct. 1984, 68(10):708-15.
Holliger et al., "'Diabodies': Small Bivalent and Bispecific Antibody Fragments," Proceedings of the National Academy of Sciences of the United States of America, Jul. 1993, 90(14):6444-6448.
Hong et al., "Runx1 stabilizes the mammary epithelial cell phenotype and prevents epithelial to mesenchymal transition," Oncotarget, Mar. 2017, 8(11):17610-17627.
Hoogenboom et al., "By-Passing immunisation: Human Antibodies from Synthetic Repertoires of Germline VH Gene Segments Rearranged in Vitro," Journal of Molecular Biology, Sep. 1992, 227(2):381-388.
Hoyt et al., "Alterations in pulmonary mRNA encoding procollagens, fibronectin and transforming growth factor-beta precede bleomycin-induced pulmonary fibrosis in mice," J Pharmacol Exp Ther., Aug. 1988, 246(2):765-71.
Hsu et al., "Combined Tractional and Rhegmatogenous Retinal Detachment in Proliferative Diabetic Retinopathy in the Anti-VEGF Era", Journal of Ophthalmology, Jun. 2014, Article ID 917375, 2014(7):11 pages.
Hsu et al., "Inhibition of type 1 human immunodeficiency virus replication by a tat antagonist to which the virus remains sensitive after prolonged exposure in vitro," Proc Natl Acad Sci USA, Jun. 1993, 90(14):6395-9.
Huang et al., "Bioinformatics Enrichment Tools: Paths Toward the Comprehensive Functional Analysis of Large Gene Lists," Nucleic Acids Research, Jan. 2009, 37(1):1-13.
Huertas et al., "Endothelial cell dysfunction: a major player in SARS-CoV-2 infection (COVID-19)?," European Respiratory Journal, Jul. 2020, 56(1):2001634, 5 pages.
Hutchinson et al., "Global incidence and mortality of idiopathic pulmonary fibrosis: a systematic review," European Respiratory Journal, Sep. 2015, 46(3):795-806.
Ikenoya et al., "Inhibition of rho-kinase-induced myristoylated alanine-rich C kinase substrate (MARCKS) phosphorylation in human neuronal cells by H-1152, a novel and specific Rho-kinase inhibitor," J. Neurochem., Apr. 2002, 81(1):9-16.
Illendula et al., "Small Molecule Inhibitor of CBFβ-RUNX Binding for RUNX Transcription Factor Driven Cancers," EBioMedicine, Nov. 2017, 8:117-131.
Imanirad et al., "HIF1α is a Regulator of Hematopoietic Progenitor and Stem Cell Development in Hypoxic Sites of the Mouse Embryo," Stem Cell Res., Jan. 2014, 12(1):24-35.
International Preliminary Report on Patentability in International Appln. No. PCT/US2017/061620, dated May 21, 2019, 17 pages.
International Preliminary Report on Patentability in International Appln. No. PCT/US2018/061110, dated May 28, 2020, 12 pages.
International Search Report and the Written Opinion in International Appln. No. PCT/US2018/061110, dated Mar. 25, 2019, 17 pages.
International Search Report and Written Opinion in International Appln. No. PCT/US2021/027798, dated Sep. 28, 2021, 13 pages.
International Search Report and Written Opinion in International Appln. No. PCT/US2021/049322, dated Feb. 8, 2022, 12 pages.
International Search Report in International Appln. No. PCT/US2017/061620, dated Mar. 19, 2018, 24 pages.
Ishikawa et al., "Microarray Analysis of Gene Expression in Fibrovascular Membranes Excised From Patients With Proliferative Diabetic Retinopathy," Investigative Ophthalmology & Visual Science, Feb. 2015, 56(2):932-946.
Ishizaki et al., "Pharmacological properties of Y-27632, a specific inhibitor of rho-associated kinases," Mol Pharmacol., May 2000, 57(5):976-83.
Ito et al., "RUNX Transcription Factors as Key Targets of TGF-beta Superfamily Signaling," Current Opinion in Genetics and Development, Feb. 2003, 13(1):43-47.
Iwatsuki et al., "Runx1 Promotes Angiogenesis by Downregulation of Insulin-Like Growth Factor-Binding Protein-3", Oncogene, Feb. 2005, 24(7):1129-1137.
Ji et al., "Inflammatory regulatory network mediated by the joint action of NF-kB, STAT3, and AP-1 factors is involved in many human cancers," Proceedings of the National Academy of Sciences, May 2019, 116(19):9453-9462.
Jo et al., "Animal Models of Diabetic Retinopathy: Doors to Investigate Pathogenesis and Potential Therapeutics," Journal of Biomedical Science, 2013, 20:38, 13 pages.

(56) References Cited

OTHER PUBLICATIONS

Jones et al., "Replacing the Complementarity-Determining Regions in a Human Antibody with those from a Mouse," Nature, May 1986, 321(6069):522-525.
Joyce, "Amplification, Mutation and Selection of Catalytic RNA," Gene, Oct. 1989, 82(1):83-87.
Kalev-Zylinska et al., "Runx1 is Required for Zebrafish Blood and Vessel Development and Expression of a Human RUNX1-CBF2T1 Transgene Advances a Model for Studies of Leukemogenesis," Development, 2002, 129(8):2015-2030.
Kategaya et al., "USP7 Small-Molecule Inhibitors Interfere With Ubiquitin Binding," Nature, Oct. 2017, 550(7677):534-538, 33 pages.
Kim et al., "A Brief History of Anti-VEGF for the Treatment of Ocular Angiogenesis," The American Journal of Pathology, 2012, 181(2):376-379.
Kim et al., "Characterization of Cells from Patient-Derived Fibrovascular Membranes in Proliferative Diabetic Retinopathy," Molecular Vision, Jun. 2015, 21:673-687.
Kim et al., "Controlled drug release from an ocular implant: an evaluation using dynamic three-dimensional magnetic resonance imaging," Invest. Ophthalmol. Vis. Sci., Aug. 2004, 45(8):2722-2731.
Kim et al., "Inhibition of Runx1 by the Ro5-3335 benzodiazepine derivative reduces aberrant retinal angiogenesis," Abstract, Presented at Annual Meeting of the Association for Research in Vision and Ophthalmology (ARVO), Baltimore, MD, USA; May 7-11, 2017; IOVS, Jun. 2017, 58(8):4029, 3 pages.
Kim et al., "Pim-1 Kinase Phosphorylates and Stabilizes RUNX3 and Alters Its Subcellular Localization," Journal of Cellular Biochemistry, Nov. 2008, 105(4):1048-1055.
Kim et al., "RUNX1 is essential for mesenchymal stem cell proliferation and myofibroblast differentiation," Proc Natl Acad Sci USA, Nov. 2014, 111(46):16389-94.
Kita et al., "Role of TGF-beta in proliferative vitreoretinal diseases and ROCK as a therapeutic target," Proceedings of the National Academy of Science, Nov. 2008, 105(45):17504-17509.
Knipe et al., "The Rho Kinases: Critical Mediators of Multiple Profibrotic Processes and Rational Targets for New Therapies for Pulmonary Fibrosis," Pharmacol Rev., Jan. 2015, 67(1):103-117.
Köhler et al., "Continuous Cultures of Fused Cells Secreting Antibody of Predefined Specificity," Nature, Aug. 1975, 256(5517):495-497.
Korol et al., "RhoA/ROCK signaling regulates TGFβ-induced epithelial-mesenchymal transition of lens epithelial cells through MRTF-A," Mol Med., Dec. 2016, 22:713-723.
Kozlowski et al., "A Human Melanoma Line Heterogeneous With Respect to Metastatic Capacity in Athymic Nude Mice," Journal of the National Cancer Institute, Apr. 1984, 72(4):913-917.
Kuiper et al., "The Angio-Fibrotic Switch of VEGF and CTGF in Proliferative Diabetic Retinopathy," PLoS ONE, Jul. 2008, 3(7):e2675, 7 pages.
Lam et al., "Identification of RUNX1 as a Mediator of Aberrant Retinal Angiogenesis," Diabetes, 2017, 66:1950-1956.
Lederer et al., "Idiopathic Pulmonary Fibrosis," New England Journal of Medicine, May 2018, 378(19):1811-23.
Lee et al., "TGF-β regulates cell fate during epithelial-mesenchymal transition by upregulating survivin," Cell Death & Disease, Jul. 2013, 4(7):e714, 10 pages.
Li et al., "RUNX1 promotes tumour metastasis by activating the WNT/beta-catenin signalling pathway and EMT in colorectal cancer," J Exp Clin Cancer Res, Aug. 2019, 38(1):334, 13 pages.
Liang et al., "In Vitro Scratch Assay: A Convenient and Inexpensive Method for Analysis of Cell Migration in Vitro," Nature Protocols, Mar. 2007, 2(2):329-333.
Liao et al., "Rho kinase (ROCK) inhibitors," J Cardiovasc Pharmacol, Jul. 2007, 50(1):17-24.
Liberati et al., "Smads bind directly to the Jun family of AP-1 transcription factors," Proc Natl Acad Sci USA, Apr. 1999, 96(9):4844-9.
Lichtinger et al., "Chromatin Regulation by RUNX1," Blood Cells, Molecules and Diseases, Apr. 2010, 44(4):287-290.
Lie-A-Ling et al., "RUNX1 Positively Regulates a Cell Adhesion and Migration Program in Murine Hemogenic Endothelium Prior to Blood Emergence," Blood, Sep. 2014, 124(11):e11-e20.
Lin et al., "Discovery and Preclinical Development of Netarsudil, a Novel Ocular Hypotensive Agent for the Treatment of Glaucoma," J Ocul Pharmacol Ther., 2018, 34(1-2):40-51.
Lin et al., "LncRNA Hoxaas3 promotes lung fibroblast activation and fibrosis by targeting miR-450b-5p to regulate Runx1," Cell Death & Disease, Aug. 2020, 11(8):706, 14 pages.
Liu et al., "Conjunctiva is not a preferred gateway of entry for SARS-CoV-2 to infect respiratory tract," Med Virol., Sep. 2020, 92(9):1410-1412.
Lofqvist et al., "IGFBP3 suppresses retinopathy through suppression of oxygen-induced vessel loss and promotion of vascular regrowth," PNAS, 2007, 104(25):10589-10594.
Lonberg et al., "Antigen-Specific Human Antibodies from Mice Comprising Four Distinct Genetic Modifications," Nature, Apr. 1994, 368:856-859.
Lonberg et al., "Human Antibodies from Transgenic Mice," Intern. Rev. Immunol., 1995, 13(1):65-93.
Lucas et al., "Abstract: Formation of abdominal adhesions is inhibited by antibodies to transforming growth factor-beta 1," J Surg Res., Oct. 1996, 65(2):135-8, 4 pages.
Ludwig, "The Use of Mucoadhesive Polymers in Ocular Drug Delivery," Advanced Drug Delivery Reviews, 2005, 57(11):1595-1639.
Maher, "PROFILEing idiopathic pulmonary fibrosis: rethinking biomarker discovery," European Respiratory Review, Jun. 2013, 22(128):148-52.
Malaviya et al., "Anti-TNFα therapy in inflammatory lung diseases," HHS Public Access Author Manuscript, doi:10.1016/j.pharmthera.2017.06.008, published online Nov. 4, 2017, 23 pages; Published in final edited form as: Pharmacol Ther., Dec. 2017, 180:90-8.
Malaviya et al., "Attenuation of Nitrogen Mustard-Induced Pulmonary Injury and Fibrosis by Anti-Tumor Necrosis Factor-α Antibody," Toxicological Sciences, Nov. 2015, 148(1):71-88.
Marks et al., "By-Passing Immunization: Human Antibodies from V-Gene Libraries Displayed on Phage," J. Mol. Biol., Dec. 1991, 222(3):581-597.
Martin et al., "TGF-β1 and radiation fibrosis: a master switch and a specific therapeutic target?," Int J Radiat Oncol Biol Phys., May 2000, 47(2):277-90.
Martines et al., "Pathology and Pathogenesis of SARS-CoV-2 Associated with Fatal Corona virus Disease, United States," Emerg Infect Dis., Sep. 2020, 26(9):2005-15.
Martinez-Hoyer et al., "RUNX1 Loss of Function Drives Resistance to Lenalidomide in Del(5Q) Myelodysplastic Syndrome Patients," Leukemia Research, 2017, 1(55):S43-S44.
Masoumpour et al., "Current and Future Techniques in Wound Healing Modulation after Glaucoma Filtering Surgeries," Open Ophthalmol J., 2016, 10:68-85.
mayoclinic.org [online], "Diabetic Retinopathy," Mar. 2015, via Internet archive: Wayback Machine URL <http://web.archive.org/web/20180308085607/https://www.mayoclinic.org/diseases-conditions/diabetic-retinopathy/diagnosis-treatment/drc-20371617>, retrieved on Sep. 30, 2021, URL <https://www.mayoclinic.org/diseases-conditions/diabetic-retinopathy/diagnosis-treatment/drc-20371617>, 7 pages.
mayoclinic.org [online], "Dry Macular Degeneration," 2015, retrieved from URL <https://www.mayoclinic.org/diseasesconditions/drymaculardegeneration/diagnosis-treatment/drc-20350381>, 5 pages.
mayoclinic.org [online], "Wet Macular Degeneration," 2015, retrieved from URL <https://www.mayoclinic.org/diseasesconditions/wet-macular-degeneration/diagnosis-treatment/drc-20351113>, 6 pages.
McAuley et al., "Vitreous Biomarkers in Diabetic Retinopathy: A Systematic Review and Meta-Analysis," Journal of Diabetic Complications, 2014, 28(3):419-425.
McLeod et al., "From Blood Islands to Blood Vessels: Morphologic Observations and Expression of Key Molecules during Hyaloid

(56) References Cited

OTHER PUBLICATIONS

Vascular System Development," Investigative Ophthalmology & Visual Science, Dec. 2012, 53(13):7912-7927.
Medlineplus.gov [online], "Retinal vein occlusion," Available on or before Mar. 6, 2018, retrieved Feb. 22, 2019, retrieved from URL <https://medlineplus.gov/ency/article/007330.htm>, 4 pages.
Michaud et al., "Integrative Analysis of RUNX1 Downstream Pathways and Target Genes," BMC Genomics, Jul. 2008, 9:363, 17 pages.
Morrison, "Success in Specification," Nature, Apr. 1994, 368:812-813.
Moshfeghi et al., "Retinal Capillary Angioma," American Academy of Ophthalmology, Oct. 2013, 7 pages.
Moshirfar et al., "Use of Rho kinase Inhibitors in Ophthalmology: A Review of the Literature," Med Hypothesis Discov Innov Ophthalmol., Fall 2018, 7(3):101-111.
Mukhopadhyay et al., "Role of TNFα in pulmonary pathophysiology," Respiratory Research, 2006, 7(1):125, 9 pages.
my.clevelandclinic.org [online], "Retinal Vein Occlusion (RVO)," 2015, retrieved from URL <https://my.clevelandclinic.org/health/diseases/14206-retinal-vein-occlusion-rvo>, 4 pages.
Nakano et al., "Design and Synthesis of an in Vivo-Efficacious PIM3 Kinase Inhibitor as a Candidate Anti-Pancreatic Cancer Agent," Bioorganic & Medicinal Chemistry Letters, Dec. 2015, 25(24):5687-5693.
Namba et al., "Indispensable Role of the Transcription Factor PEBP2/CBF in Angiogenic Activity of a Murine Endothelial Cell MSS31," Oncogene, Jan. 2000, 19(1):106-114.
nei.nih.gov [online], "Facts About Retinopathy of Prematurity (ROP)," National Eye Institute, available on or before Jun. 2014, retrieved on Feb. 22, 2019, retrieved from URL <https://nei.nih.gov/health/rop/rop>, 3 pages.
Neuberger, "Generating High-Avidity Human Mabs in Mice," Nature Biotechnology, Jul. 1996, 14(7):826, 1 page.
Nicholls et al., "An Improved Method for Generating Single-Chain Antibodies From Hybridomas," Journal of Immunological Methods, Sep. 1993, 165(1):81-91.
Office Action in Australian Appln. No. 2018369784, dated Nov. 8, 2022, 4 pages.
Office Action in European Appln. No. 17871449.9, dated Jul. 5, 2022, 15 pages.
Office Action in Japanese Appln. No. 2020-544393, dated Nov. 14, 2022, 8 pages (with English translation).
O'Hare et al., "Targeting Runt-Related Transcription Factor 1 Prevents Pulmonary Fibrosis and Reduces Expression of Severe Acute Respiratory Syndrome Coronavirus 2 Host Mediators," The American Journal of Pathology, Jul. 2021, 191(7):1193-1208.
Ojo et al., "Pulmonary Fibrosis in COVID-19 Survivors: Predictive Factors and Risk Reduction Strategies," Pulmonary Medicine, Aug. 2020, 2020:6175964, 10 pages.
Palakurthi et al., "Investigation of kinetics of methotrexate for therapeutic treatment of intraocular lymphoma," Current Eye Research, Oct. 2010, 35(12):1105-1115.
Pandya et al., "Neovascular Glaucoma," Medscape, available on or before Oct. 2016, retrieved from URL <https://emedicine.medscape.com/article/1205736-overview#a6>, 15 pages.
Pashaei et al., "Immunotherapy for SARS-CoV-2: potential opportunities," Expert Opin Biol Ther., Oct. 2020, 20(10):1111-5.
Pettus et al., "Discovery and Optimization of Quinazolinone-pyrrolopyrrolones as Potent and Orally Bioavailable Pan-Pim Kinase Inhibitors," J. Med. Chem., Jun. 2016, 59(13):6407-6430.
Pluckthun, "Antibodies from *Escherichia coli*," The Pharmacology of Monoclonal Antibodies, 1994, 113:269-315.
Polak et al., "A systematic review of pathological findings in COVID-19: a pathophysiological timeline and possible mechanisms of disease progression," Mod Pathol., Nov. 2020, 33(11):2128-38.
Pratt et al., "Abstract 1010: Identification of evolutionarily conserved transcription response elements associated with regulation of cadherin expression in retinal pigment epithelial cells," Molecular Biology of the Cell, 2004, 15(Suppl. S):182A, 1 page.
Presta, "Antibody Engineering," Current Opinion in Structural Biology, 1992, 2(4):593-596.
Rakoczy et al., "Characterization of a Mouse Model of Hyperglycemia and Retinal Neovascularization," The American Journal of Pathology, Nov. 2010, 177(5):2659-2670.
Ran et al., "γ-Secretase Inhibitors in Cancer Clinical Trials are Pharmacologically and Functionally Distinct," EMBO Molecular Medicine, Jul. 2017, 9(7):950-966.
Riddell et al., "RUNX1: an emerging therapeutic target for cardiovascular disease," Cardiovasc Res., Mar. 2020, 116(8):1410-1423.
Riechmann et al., "Reshaping Human Antibodies for Therapy," Nature, Mar. 1988, 332:323-327.
Robert et al., "A Drug Delivery System for Administration of Anti-TNF-α Antibody," Transl Vis Sci Technol., Mar. 2016, 5(2):11, 11 pages.
Sainson et al., "TNF primes endothelial cells for angiogenic sprouting by inducing a tip cell phenotype," Blood, May 2008, 111(10):4997-5007.
Saint-Geniez et al., "Endogenous VEGF Is Required for Visual Function: Evidence for a Survival Role on Muller Cells and Photoreceptors," PLoS ONE, Nov. 2008, 3(11):e3554, 13 pages.
Sang et al., "Is Blockade of Vascular Endothelial Growth Factor Beneficial for all Types of Diabetic Retinopathy?" Diabetologia, Jul. 2008, 51(9): 1570-1573.
Schaefer et al., "In situ detection of SARS-CoV-2 in lungs and airways of patients with COVID-19," Modern Pathology, Jun. 2020, 33(11):2104-14.
Scholle, "Ocular Ischemic Syndrome," Medscape, 2019, retrieved Sep. 8, 2020, retrieved from URL <https://emedicine.medscape.com/article/1201678-overview>, 3 pages.
Selman et al., "Idiopathic pulmonary fibrosis: an epithelial fibroblastic cross-talk disorder," Respir Res., 2002, 3(1):3, 8 pages.
Shah et al., "Alk5/Runx1 signaling mediated by extracellular vesicles promotes vascular repair in acute respiratory distress syndrome," Clin Transl Med, Jun. 2018, 7(1):19, 18 pages.
Shaki-Loewenstein et al., "A universal strategy for stable intracellular antibodies", Journal of Immunological Methods, Aug. 2005, 303(1-2):19-39.
Shao et al., "Choroid Sprouting Assay: An Ex Vivo Model of Microvascular Angiogenesis," PLoS ONE, Jul. 2013, 8(7):e69552, 11 pages.
Shaw et al., "Topical administration of a Rock/Net inhibitor promotes retinal ganglion cell survival and axon regeneration after optic nerve injury," Exp Eye Res., May 2017, 158:33-42, 19 pages.
Shazly et al., "Neovascular Glaucoma: Etiology, Diagnosis and Prognosis," Seminars in Ophthalmology, Mar. 2009, 24(2):113-121.
Shen et al., "Discovery of Novel ROCK1 Inhibitors via Integrated Virtual Screening Strategy and Bioassays," Scientific Reports, Nov. 2015, 5:16749, 14 pages.
Shen et al., "Isolation and Culture of Primary Mouse Retinal Pigment Epithelial (RPE) Cells with Rho-Kinase and TGFβR-1/ALK5 Inhibitor," Med Sci Monit., Dec. 2017, 23:6132-6136.
Sinha and Ware, "Selective tumour necrosis factor receptor-1 inhibition in acute lung injury: a new hope or a false dawn?," Thorax, Aug. 2018, 73(8):699-701.
Smith et al., "Oxygen-Induced Retinopathy in the Mouse," Invest Ophthalmol Vis Sci, Jan. 1994, 35(1):101-111.
Sohn et al., "Angiofibrotic Response to Vascular Endothelial Growth Factor Inhibition in Diabetic Retinal Detachment," Arch Ophthalmol, Sep. 2012, 130(9):1127-1134.
Strongman et al., "Incidence, Prevalence, and Survival of Patients with Idiopathic Pulmonary Fibrosis in the UK," Adv Ther., May 2018, 35(5):724-36.
Sui et al., "oPOSSUM: Identification of Over-represented Transcription Factor Binding Sites in Co-Expressed Genes," Nucleic Acids Research, 2005, 33(10):3154-3164.
Taheri et al., "Nanoparticles of conjugated methotrexate-human serum albumin: preparation and cytotoxicity evaluations" J Nanomaterials, Jan. 2011, 2011:768201, 7 pages.
Tang et al., "Runt-Related Transcription Factor 1 Regulates LPS-Induced Acute Lung Injury via NF-κB Signaling," Am J Respir Cell Mol Biol., 2017, 57(2):174-83.

(56) References Cited

OTHER PUBLICATIONS

Tashiro et al., "Exploring Animal Models That Resemble Idiopathic Pulmonary Fibrosis," Frontiers in Medicine, Jul. 2017, 4:118, 11 pages.
Terelak-Borys et al., "Ocular Ischemic Syndrome—A Systematic Review," Med Sci Monit, Aug. 2012, 18(8):RA138-RA144.
The RECOVERY Collaborative Group, "Dexamethasone in Hospitalized Patients with Covid-19—Preliminary Report," New England Journal of Medicine, Feb. 2021, 384(8):693-704, 11 pages.
Thomas, "Furin at the cutting edge: from protein traffic to embryogenesis and disease," HHS Public Access Author Manuscript, doi: 10.1038/nrm934, published online 2002, 32 pages; Published in final edited form as Nat Rev Mol Cell Biol., Oct. 2002, 3(10):753-66.
Tober et al., "Taking the leap: Runx1 in the formation of blood from endothelium," Current Topics in Developmental Biology, Feb. 2016, 118:113-162.
Trapnell et al., "TopHat: Discovering Splice Junctions with RNA-Seq," Bioinformatics, Apr. 2009, 25(9):1105-1111.
Tuerk et al., "Systematic Evolution of Ligands by Exponential Enrichment: RNA Ligands to Bacteriophage T4 DNA Polymerase," Science, Aug. 1990, 249(4968):505-510.
Turell et al., "Vascular Tumors of the Retina and Choroid: Diagnosis and Treatment," Middle East Afr J Ophthalmol., 2010, 17(3):191-200.
Ulrich et al. "CD147 as a Target for COVID-19 Treatment: Suggested Effects 2, 4-6, 19, 21-23 of Azithromycin and Stem Cell Engagement," Stem Cell Reviews and Reports, Apr. 2020, 16:434-440, 7 pages.
UniProt Accession No. P17936, "Insulin-like growth factor-binding protein 3," Nov. 1, 1990, 8 pages.
UniProt Accession No. Q01196-10, "Runt-related transcription factor 1," Apr. 1, 1993, 1 page.
UniProt Accession No. Q01196-11, "RUNX1_HUMAN Isoform AML-1L of Runt-related transcription factor 1," Apr. 1, 1993, 1 page.
UniProt Accession No. Q01196-2, "RUNX1_Human Isoform AML-1A of Runt-related transcription factor 1," Apr. 1, 1993, 1 page.
UniProt Accession No. Q01196-3, "RUNX1_Human Isoform AML-1C of Runt-related transcription factor 1," Apr. 1, 1993, 1 page.
UniProt Accession No. Q01196-4, "RUNX1_Human Isoform AML-1E of Runt-related transcription factor 1," Apr. 1, 1993, 1 page.
UniProt Accession No. Q01196-5, "RUNX1_HUMAN Isoform AML-1FA of Runt-related transcription factor 1," Apr. 1, 1993, 1 page.
UniProt Accession No. Q01196-6, "RUNX1_HUMAN Isoform AML-1FB of Runt-related transcription factor 1," Apr. 1, 1993, 1 page.
UniProt Accession No. Q01196-7, "RUNX1_HUMAN Isoform AML-1FC of Runt-related transcription factor 1," Apr. 1, 1993, 1 page.
UniProt Accession No. Q01196-8, "RUNX1_Human Isoform AML-1G of Runt-related transcription factor 1," Apr. 1, 1993, 1 page.
UniProt Accession No. Q01196-9, "RUNX1_HUMAN Isoform AML-1H of Runt-related transcription factor 1," Apr. 1, 1993, 1 page.
UniProt Accession No. Q86V86, "Serine/threonine-protein kinase pim-3," Nov. 21, 2003, 6 pages.
Van Geest et al., "A Shift in the Balance of Vascular Endothelial Growth Factor and Connective Tissue Growth Factor by Bevacizumab Causes the Angiofibrotic Switch in Proliferative Diabetic Retinopathy," Br J Ophthalmol, Jan. 2012, 96(4):587-590.
Vancheri et al., "Nintedanib with Add-on Pirfenidone in Idiopathic Pulmonary Fibrosis. Results of the INJOURNEY Trial," Am J Respir Crit Care Med., Feb. 2018, 197(3):356-63.
Velez and Whitcup, "New developments in sustained release drug delivery for the treatment of intraocular disease," Br J Ophthalmol, 1999, 83:1225-1229.
Verhoeyen et al., "Reshaping Human Antibodies: Grafting an Antilysozyme Activity," Science, Mar. 1988, 239(4847):1534-1536.
Vijayaragavan et al., "Controlled Release of Methotrexate Using Alpha-Lactalbumin Microparticles," Int J Pharm Res, 2011, 3(1):39-44.
Wang et al. "Discovery of 5-Azaindazole (GNE-955) as a Potent Pan-Pim Inhibitor With Optimized Bioavailability," J. Med. Chem., Apr. 2017, 60(10):4458-4473.
Whitmore et al., "TNF-α signaling regulates RUNX1 function in endothelial cells," The FASEB Joumal, Feb. 2021, 35(2):e21155, 17 pages.
Wikipedia.org [online], "Rho kinase inhibitor," last updated Feb. 20, 2023, retrieved on Mar. 14, 2023, retrieved from URL<https://en.wikipedia.org/wiki/Rho_kinase_inhibitor>, 5 pages.
Wu et al., "Characteristics of Ocular Findings of Patients With Coronavirus Disease 2019 (COVID-19) in Hubei Province, China," JAMA Ophthalmol., May 2020, 138(5):575-578.
Wu et al., "The ROCK inhibitor, thiazovivin, inhibits human corneal endothelial-to-mesenchymal transition/epithelial-to-mesenchymal transition and increases ionic transporter expression," Int J Mol Med., Oct. 2017, 40(4):1009-1018.
Xie et al., "Single-Cell Deconvolution of Fibroblast Heterogeneity in Mouse Pulmonary Fibrosis," Cell Rep., Mar. 2018, 22(13):3625-40.
Yadav et al., "Tumour Angiogenesis and Angiogenic Inhibitors: A Review," J Clin Diagn Res., Jun. 2015, 9(6):XE01-XE05.
Yamaguchi et al., "Rho-Kinase/ROCK as a Potential Drug Target for Vitreoretinal Diseases," J Ophthalmol., 2017, 2017:8543592, 8 pages.
Yan et al., "Feedback regulation of TGF-β signaling," Acta Biochimica et Biophysica Sinica, Jan. 2018, 50(1):37-50.
Yang et al., "Mechanisms of epithelial—mesenchymal transition in proliferative vitreoretinopathy," Discov Med., Oct. 2015, 20(110):207-217, 21 pages.
Yarrow et al., "Screening for cell migration inhibitors via automated microscopy reveals a Rho-kinase inhibitor," Chem. Biol., Mar. 2005, 12(3):385-395.
Yoshida et al., "Gene expression profile of fibrovascular membranes from patients with proliferative diabetic retinopathy," Br J Ophthalmol., 2010, 94(6):795-801.
Yuan et al., "Notch Signaling: An Emerging Therapeutic Target for Cancer Treatment," Cancer Letters, Dec. 2015, 369(1):20-27.
Yue et al., "TGF-β: Titan of Lung Fibrogenesis," HHS Public Access Author Manuscript, doi: 10.2174/10067, Oct. 2013, 20 pages; Published in final edited form as: Curr Enzym Inhib., Jul. 2010, 6(2):10.2174/10067.
Yzaguirre et al., "The Role of Runx1 in Embryonic Blood Cell Formation," RUNX Proteins in Development and Cancer, Singapore: Springer Singapore, Groner et al. (eds.), 2017, pp. 47-64.
Zapata et al., "Engineering Linear F(ab')2 Fragments for Efficient Production in *Escherichia coli* and Enhanced Anti-Proliferative Activity," Protein Engineering, Oct. 1995, 8(10): 1057-1062.
Zhou et al., "Runt-Related Transcription Factor 1 (RUNX1) Promotes TGF-f3-Induced Renal Tubular Epithelial-to-Mesenchymal Transition (EMT) and Renal Fibrosis through the PI3K Subunit p110δ," EBioMedicine, May 2018, 31:217-25.
Zhou et al., "RUNX proteins desensitize multiple myeloma to lenalidomide via protecting IKZFs from degradation," Leukemia, 2019, 33:2006-2021.
Zhou et al., "Sustained subconjunctival delivery of infliximab protects the cornea and retina following alkali burn to the eye," Invest Ophthalmol Vis Sci., Jan. 2017, 58(1):96-105.
Notice of Allowance in Japanese Appln. No. 2020-544393, dated Dec. 14, 2023, 6 pages (with English translation).
Office Action in European Appln. No. 18878909.3, mailed on Apr. 4, 2025, 4 pages.
Office Action in Canadian Appln. No. 3,082,643, mailed on Dec. 2, 2024, 5 pages.
Huang et al., "Kidney fibrosis: from mechanisms to therapeutic medicines," Signal Transduction and Targeted Therapy, Mar. 2023, 8(1):129, 20 pages.
Illendula et al., "A small-molecule inhibitor of the aberrant transcription factor CBFβ-SMMHC delays leukemia in mice," Science, Feb. 2015, 347(6223):779-84.

(56) References Cited

OTHER PUBLICATIONS

MedicalNewsToday.com [online], "What is pulmonary fibrosis?," Jan. 2023, retrieved on Jul. 23, 2025, retrieved from URL <https://www.medicalnewstoday.com/articles/pulmonary-fibrosis>, 15 pages.
My.ClevelandClinic.org [online], "Pulmonary Fibrosis," May 2025, retrieved on Jul. 23, 2025, retrieved from URL, <https://my.clevelandclinic.org/health/diseases/10959-pulmonary-fibrosis>, 13 pages.
News. Vumc.org [online], "VUMC team finds potential treatment for kidney fibrosis," Mar. 2024, retrieved on Jul. 23, 2025, retrieved from URL <https://news.vumc.org/2024/03/25/vumc-team-finds-potential-treatment-for-kidney-fibrosis/>, 2 pages.
Trujillo et al., "Angiogenesis in acute myeloid leukemia and opportunities for novel therapies," Journal of Oncology, 2012; 2012(1):128608, 9 pages.
Zhang et al., "Treatment of liver fibrosis: Past, current, and future," World journal of Hepatology, Jun. 2023, 15(6):755, 21 pages.
Kaelin "Use and abuse of RNAi to study mammalian gene function," Science, Jul. 2012, 337(6093):421-422, 4 pages (Author Manuscript).
Weiss et al., "Recognizing and exploiting differences between RNAi and small-molecule inhibitors," Nature Chemical Biology, Dec. 2007, 3(12):739-744, 12 pages (Author Manuscript).

* cited by examiner

DAPI
RUNX1
Merge
A
B
C
D
E
F
Negative control (No primary antibody)
RUNX1 primary antibody

RUNX1

Control

CONTROL
RUNX1 Inhibitor (150uM)
A
B
C
D
4x
10x

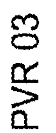
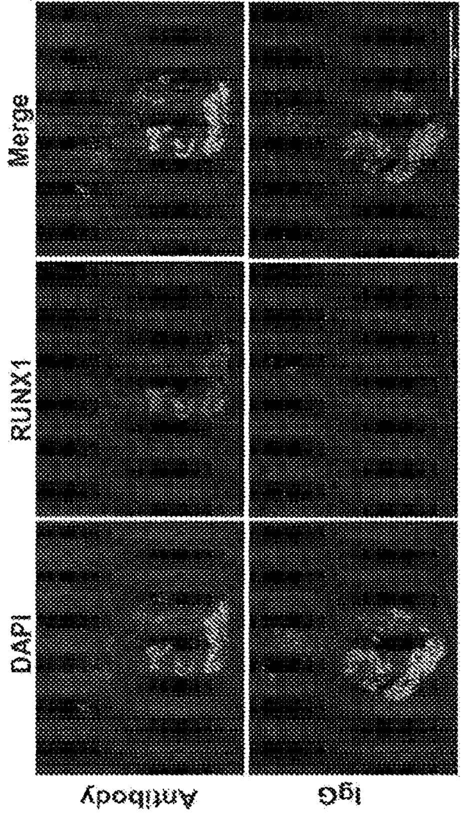
FIG. 19A
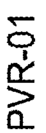
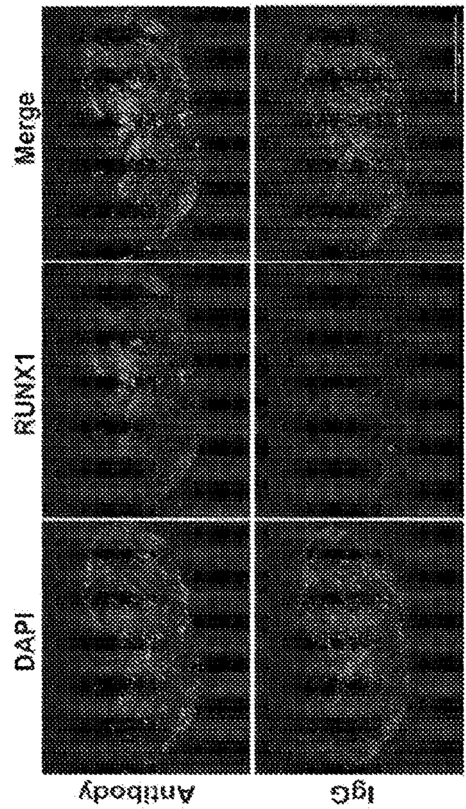
FIG. 19B

Day 3
Day 7
Con
TGFβ2
TNFα
Combo
Ladder
Con
TGFβ2
TNFα
Combo
Runx1
Actin
Repeat
Actin

N=3

With Ro5-3335
Smooth muscle actin
Fibronectin
Cytokeratin
CONTROL
TGFβ2
TNFα
Combo Without Ro5-3335
Smooth muscle actin
Fibronectin
Cytokeratin
CONTROL
TGFβ2
TNFα
Combo

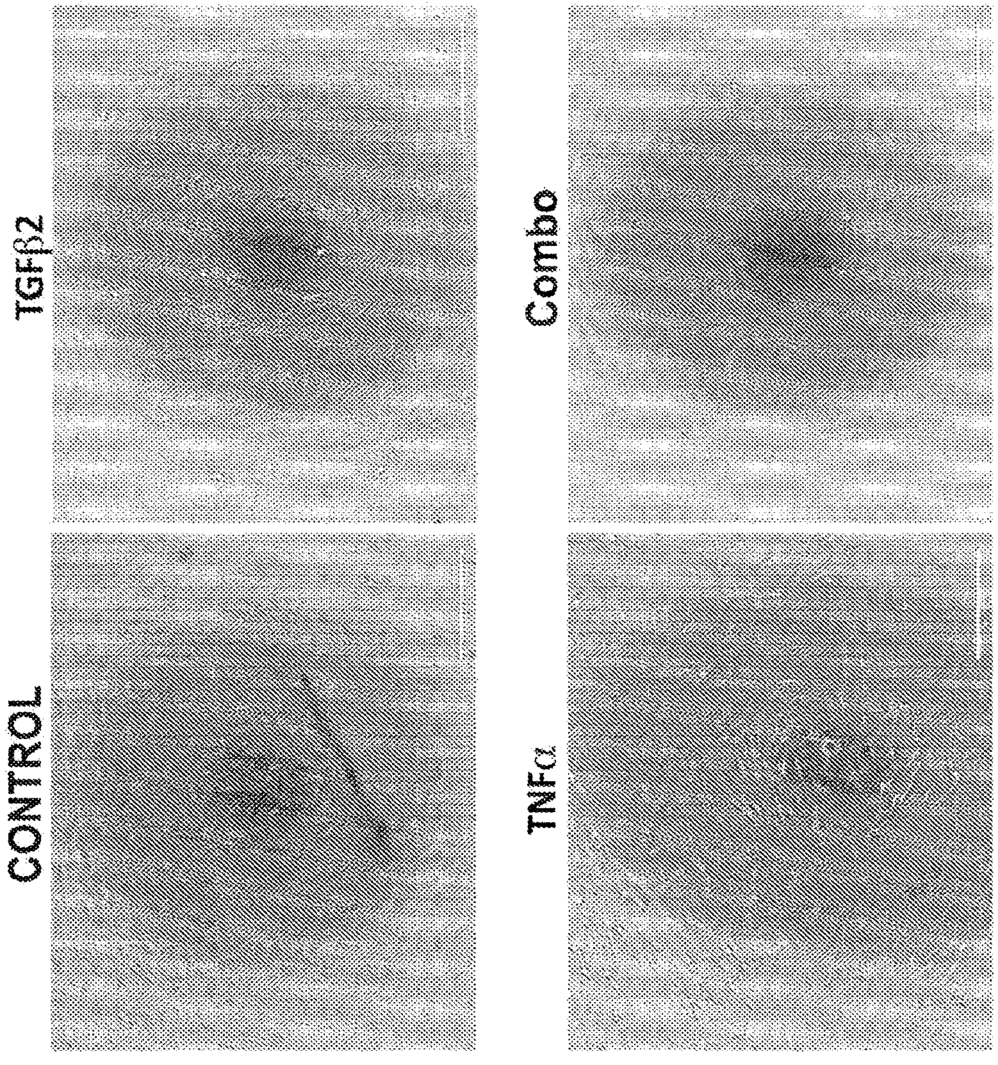
FIG: 24

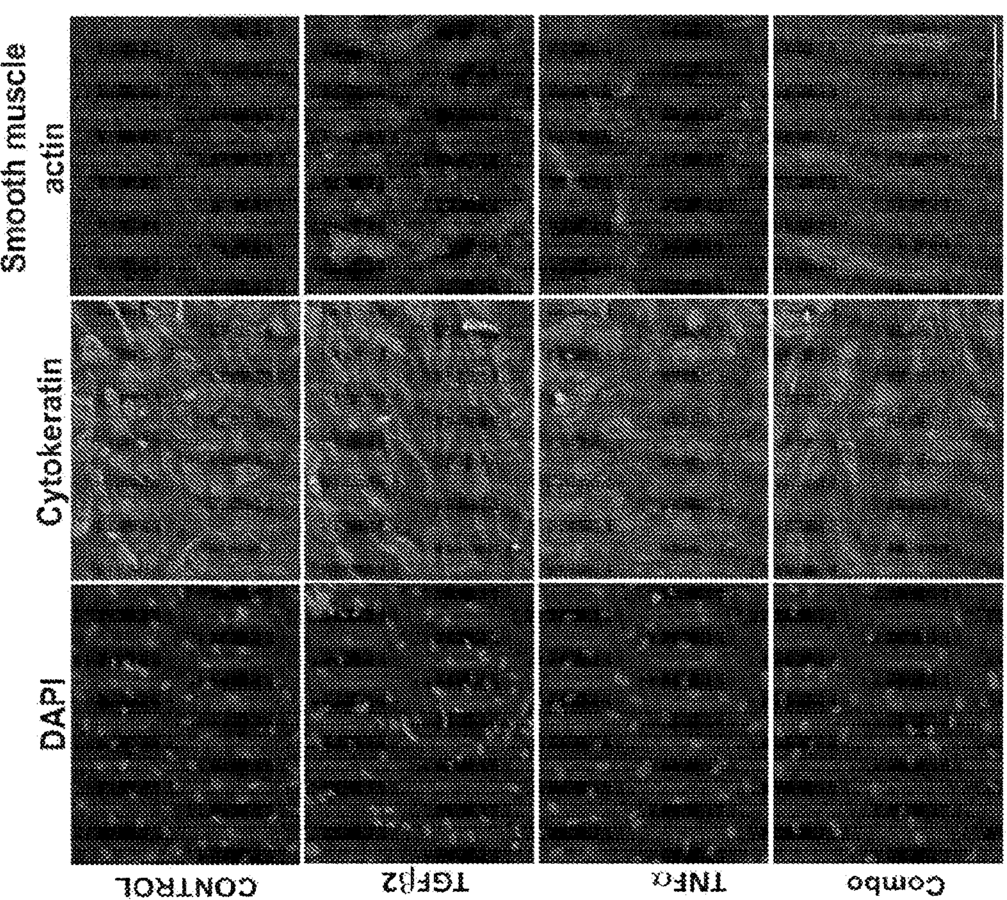
FIG: 25

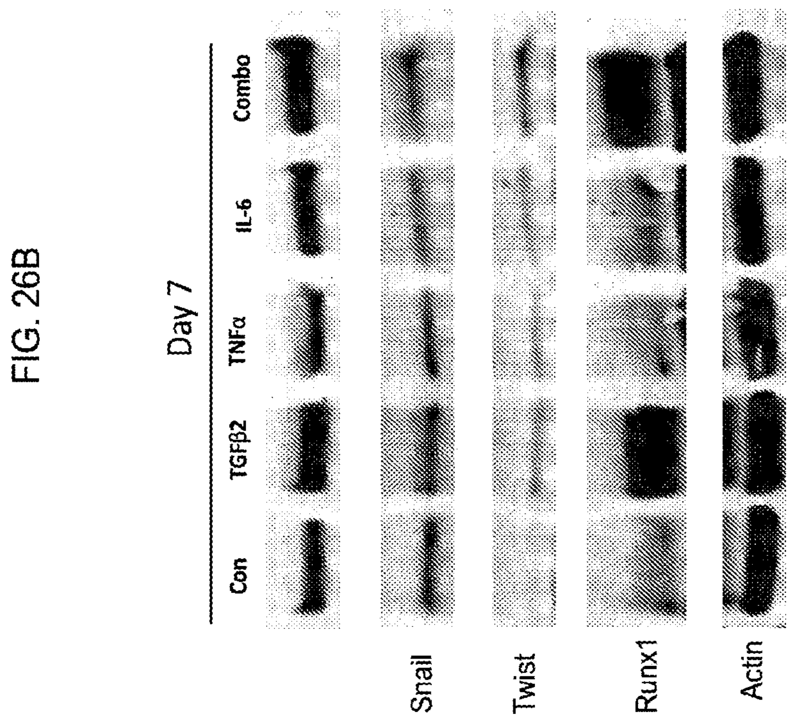
FIG. 26B
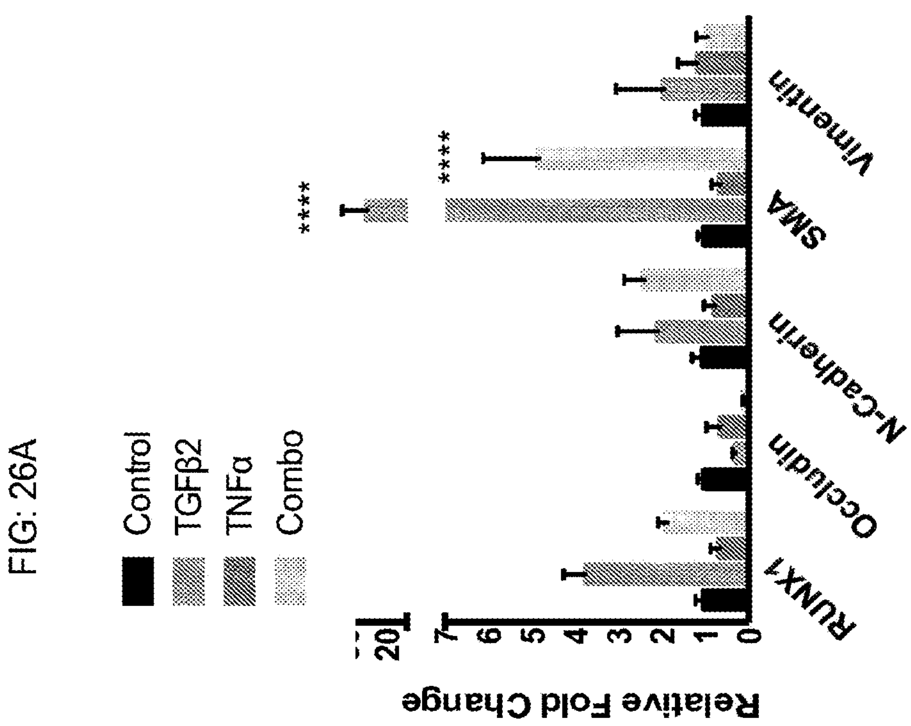
FIG: 26A

ARPE-19 cells

ARPE-19 cells 48 hours
Percent live cells/ normalized to control
125
100
75
50
25
0
Control
MTX 400
MTX 100
MTX 10
Ro5 100
Ro5 50
Ro5 25
MTX 400+ Ro5 100
MTX 400+ Ro5 50
Treatments
C-PVR cells

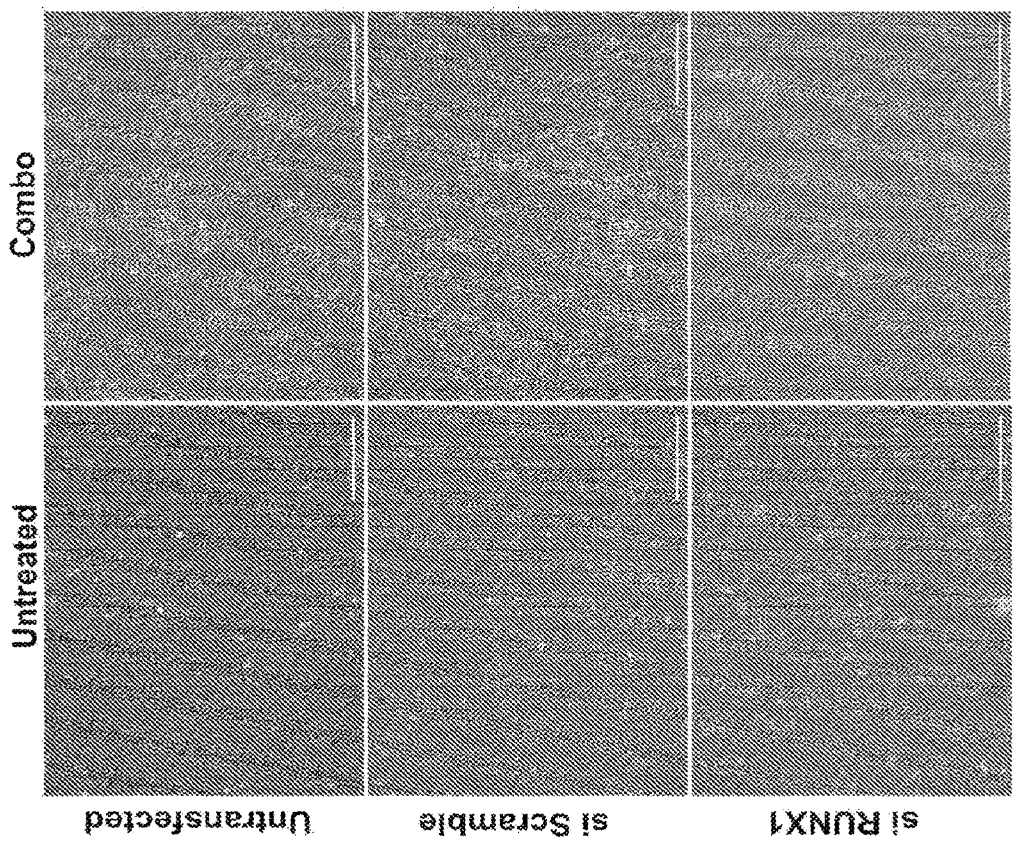
FIG: 29

FIG: 30A
Blot A
Untransfected Untreated
Scramble Untreated
RUNX1- Untreated
Untransfected TGFβ2
Scramble TGFβ2
RUNX1- TGFβ2
Untransfected TNFα
Scramble TNFα
RUNX1- TNFα
Runx1
GAPDH Blot B
Untransfected Untreated
Scramble Untreated
RUNX1- Untreated
Untransfected IL-6
Scramble IL-6
RUNX1- IL-6
Untransfected Combo
Scramble Combo
RUNX1- Combo
Runx1
GAPDH

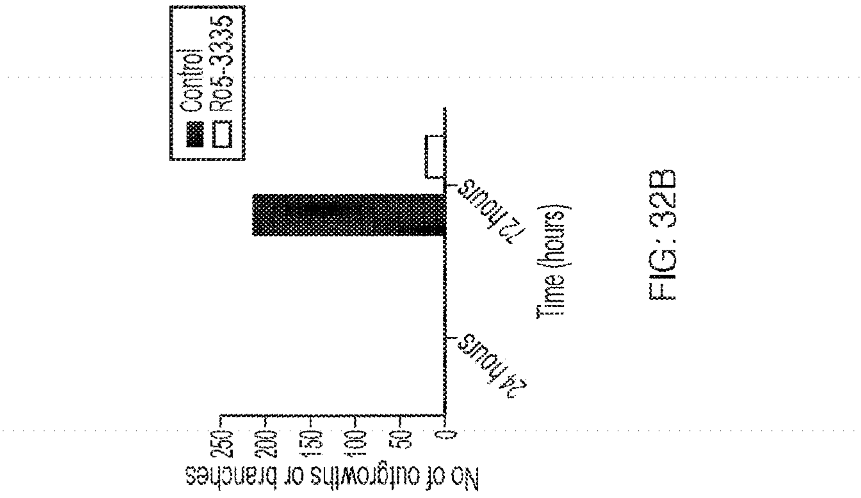
FIG: 32B
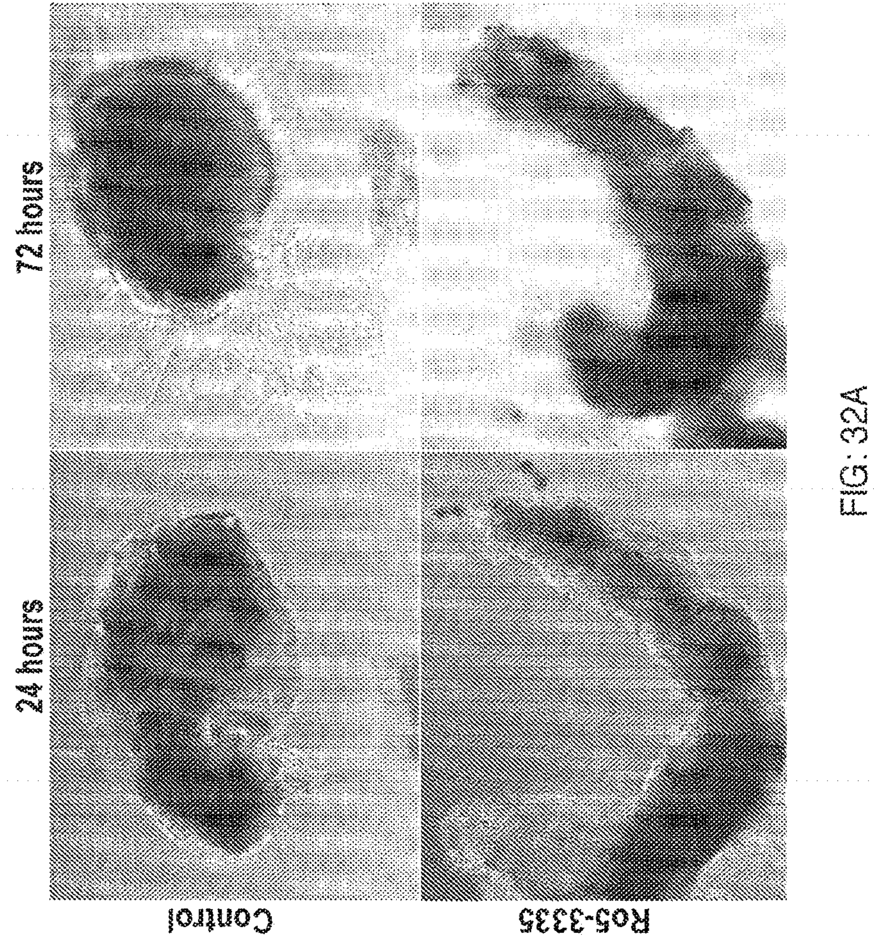
FIG: 32A

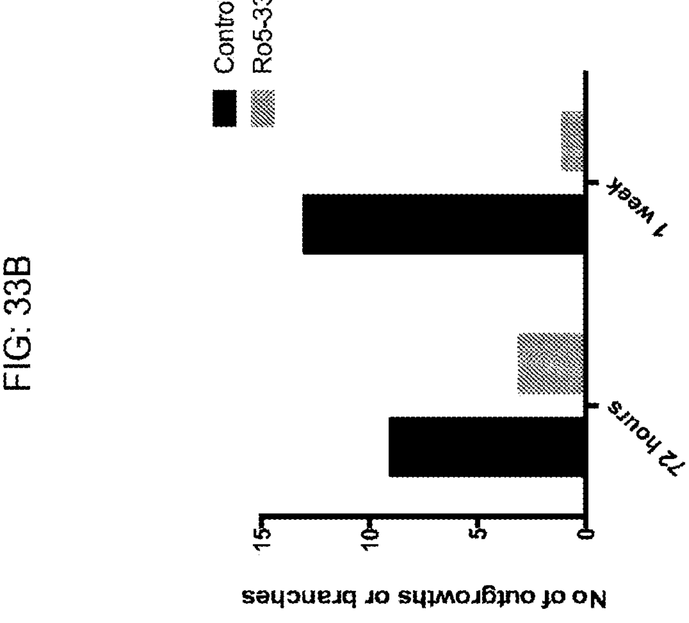
FIG: 33A
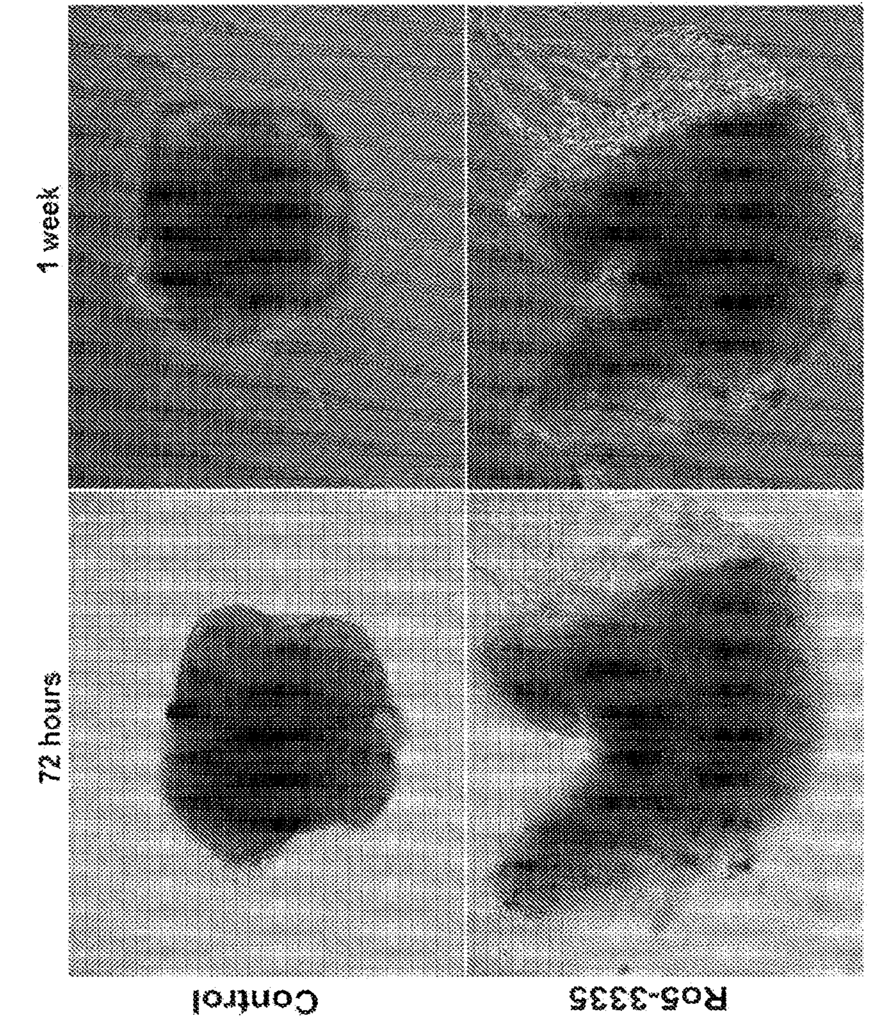

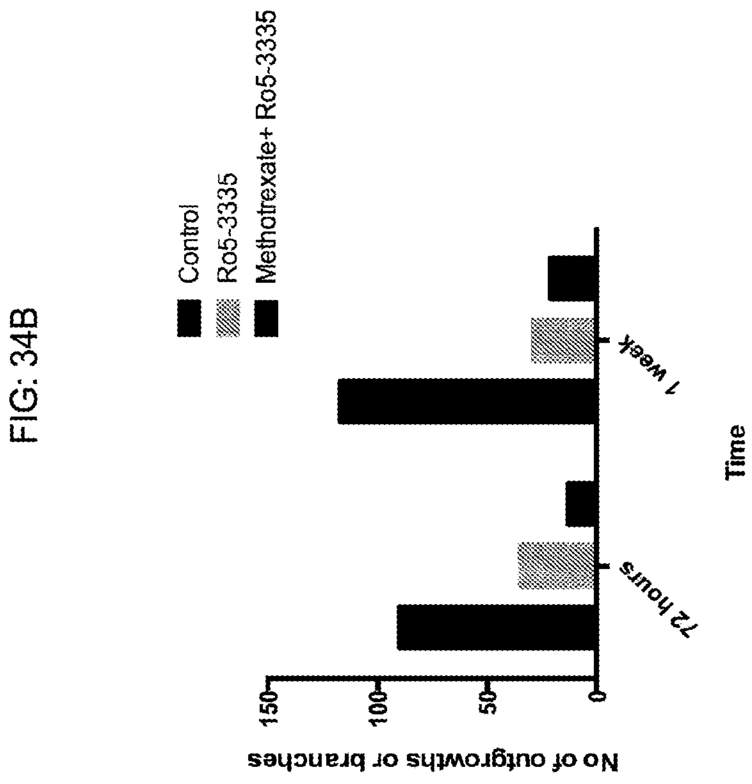
FIG: 34B
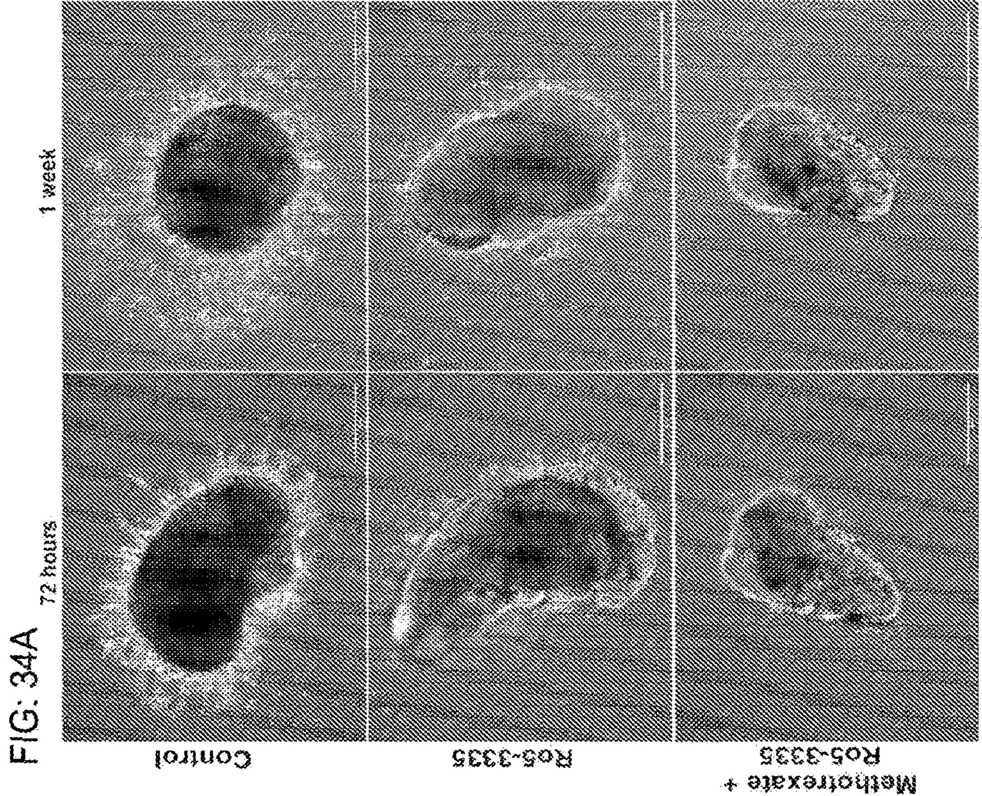
FIG: 34A

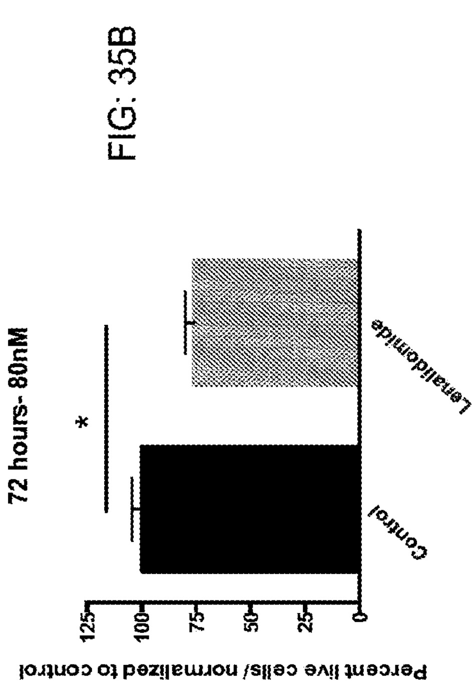
FIG: 35B
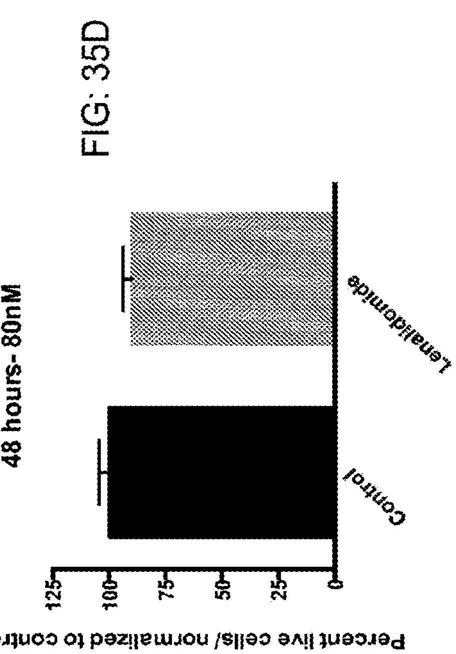
FIG: 35D
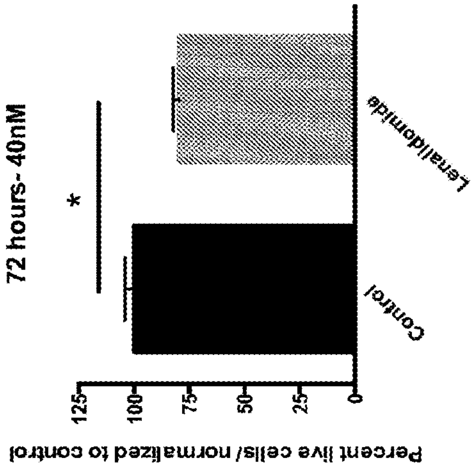
FIG: 35A
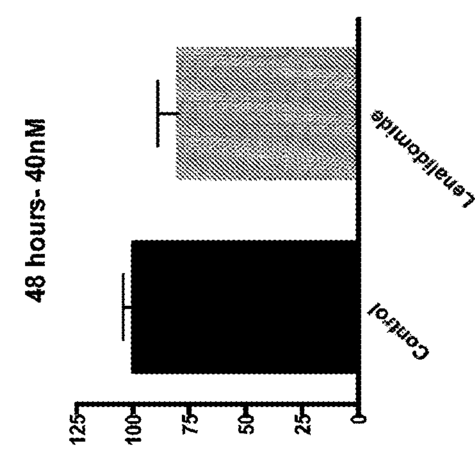
FIG: 35C

RUNX1 INHIBITION FOR TREATMENT OF PROLIFERATIVE VITREORETINOPATHY AND CONDITIONS ASSOCIATED WITH EPITHELIAL TO MESENCHYMAL TRANSITION

RELATED APPLICATIONS

This application is a continuation application of U.S. patent application Ser. No. 16/763,880, filed May 13, 2020, which is a national stage application filed under 35 U.S.C. § 371, of International Patent Application No PCT/US2018/061110, filed on Nov. 14, 2018, which claims the benefit of priority to U.S. Provisional Application No. 62/586,067, filed Nov. 14, 2017, the entire contents of which is incorporated herein by reference.

STATEMENT AS TO FEDERALLY SPONSORED RESEARCH

This invention was made with government support under EY021624 awarded by the National Institutes of Health and under W81XWH-17-2-0006 award by the Department of Defense. The Government has certain rights in the invention.

SEQUENCE LISTING

This application contains a Sequence Listing that has been submitted electronically as an XML file named "00633-0305002_SL_ST26.XML." The XML file, created on Jul. 12, 2023, is 146,433 bytes in size. The material in the XML file is hereby incorporated by reference in its entirety.

FIELD OF THE INVENTION

The present invention relates to preventing or reducing proliferation, migration, or mesenchymal transition of retinal pigment epithelial cells.

BACKGROUND

Retinal detachment (RD) is an important cause of sudden visual loss in the United States, with approximately 40,000 cases occurring annually. Permanent visual loss will result if treatment is delayed. A retinal detachment is the separation of the neurosensory retina from the retinal pigment epithelium (RPE). In the nonpathologic state, the retinal pigment epithelium is a continuous epithelial monolayer occluded by tight junctions, which maintain a strict separation of the underlying choroidal capillary beds from the photoreceptors of the sensory retina, thus forming the outer blood-retina barrier. Its functions include the nourishment of photoreceptors, elimination of waste products, and reabsorption of subretinal fluid.

The definitive treatment of retinal detachment is surgical repair. Multiple operative techniques are available to the treating retinologist, but the principles underlying treatment of retinal detachment remain the same: removal of fluid from the subretinal space, relief of any existing traction, and treatment and prophylaxis against the underlying cause for the ingression of fluid, whether it be due to a retinal break or an exudative process.

Proliferative vitreoretinopathy (PVR) is the most common cause for failure of retinal detachment surgery, a complication which occurs in 5-10% of all retinal detachment surgeries. PVR can also occur spontaneously in the absence of surgery. PVR is most likely to develop following repeated surgical procedures of the eye, following significant physiologic insult to the eye such as in trauma, as well as in retinal detachments complicated by multiple tears, giant tears, vitreous hemorrhage, or in eyes with uveitis. PVR is especially prevalent after retinal detachment associated with open globe injury, where it occurs in approximately 50% of cases (Colyer M., et al. Perforating globe injuries during operation Iraqi Freedom. *Ophthalmology.* 2008;115:2087-2093, and Eliott D. et al., Smoking is a risk factor for proliferative vitreoretinopathy after traumatic retinal detachment. *Retina.* 2017;37:1229-1235).

PVR is also a common complication of post-traumatic eye surgery. In this case, cells also grow uncontrollably beneath or on top of the retina triggering pre/sub-retinal membrane formation, tractional retinal detachment, and permanent vision loss. PVR occurs in 40-60% of patients with open globe injury. Hence PVR is highly relevant for the military and military-related eye trauma. Colyer, M. H., et al., Perforating globe injuries during operation Iraqi Freedom. Ophthalmology, 2008.115(11): p. 2087-93.

Currently, there are no medical treatments for PVR. Current standard of care for PVR includes invasive and complex surgery that often yields disappointing results.

SUMMARY OF THE INVENTION

Provided herein are solutions to the clinical problems described above. The present subject matter provides methods for preventing or reducing proliferation or migration or mesenchymal transition of retinal pigment epithelial (RPE) cells or other cells including retinal glial cells, macrophages, and fibroblasts in a subject who comprises a retinal hole or a retinal tear, the method comprising administering to the subject a Runt-Related Transcription Factor 1 (RUNX1) inhibitor. For example, the methods are useful for preventing or reducing proliferation, migration, or mesenchymal transition of retinal pigment epithelial cells, corneal epithelial cells, conjunctival epithelial cells, and other cells within the eye. PVR is diagnosed by the observation of cell outgrowths, membranes and bands in the vitreous during an ophthalmological exam, fundus or optical coherence tomography (OCT). The methods and compositions described herein are also useful for RUNX1 inhibition for treatment of proliferative vitreoretinopathy and other conditions associated with epithelial to mesenchymal transition (EMT). Thus, the invention encompasses a composition for preventing or reducing proliferation or migration of retinal pigment epithelial (RPE) cells in a subject who comprises a retinal hole or retinal tear, the composition comprising a RUNX1, inhibitor, e.g., a pharmaceutical composition comprising the inhibitor and a pharmaceutically-acceptable carrier or excipient. An excipient is an inactive substance that serves as the vehicle or medium for a drug or other active substance.

In embodiments, the subject comprises proliferative vitreoretinopathy (PVR). In other aspects, the subject comprises retinal detachment, wherein the retinal detachment comprises rhegmatogenous retinal detachment, exudative detachment, or tractional retinal detachment.

In embodiments. the RUNX1 inhibitor decreases the expression and/or activity of RUNX1. The RUNX1 inhibitor, may comprise a small molecule or an inhibitory nucleic acid. In aspects, the inhibitory nucleic acid comprises an RNA interfering agent (RNAi) or an RNA expressing/encoding an inhibitory protein. In particular aspects, the RNAi comprises siRNA. In other aspects, the RUNX1 inhibitor is a small molecule. In embodiments, the small molecule comprises the structure of Formula 1:

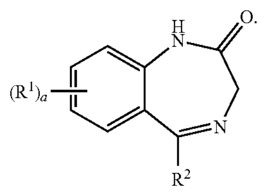

In other embodiments, the RUNX1 small molecule of Formula I comprises Ro5-3335. In embodiments, the small molecule inhibitor comprises the structure of Formula III:

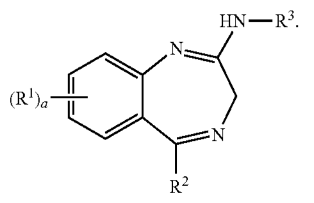

In other embodiments, the RUNX1 small molecule of Formula III comprises Ro 24-7429. In other embodiments, the RUNX1 small molecule inhibitor comprises the structure of Formula V:

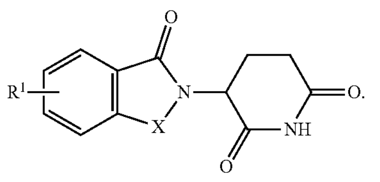

In embodiments, the small molecule of Formula V comprises lenalidomide. In other examples, the method further comprises administering methotrexate.

In embodiments, the RUNX1 inhibitor may be formulated into a composition. In other embodiments, the composition may be formulated as a solution, suspension, semi-liquid, emulsion, ointment, cream, foam gel, powder or a controlled-release/sustain-release formulation.

In aspects, the composition is administered topically or by intravitreal injection. In other aspects, the composition may be administered to the eye in a concentration of about 0.001 mg to about 10 mg of the inhibitor per eye.

In embodiments, the composition may be administered to the eye of a subject in an amount from about 50 μL to about 100 μL per eye.

In further embodiments, the composition may further comprise an anti-inflammatory agent, e.g., a combination therapy treatment approach such as one in which a RUNX1 inhibitor is administered and an anti-inflammatory agent is administered before, after, or concurrently with the anti-inflammatory agent. In embodiments, the anti-inflammatory agent comprises a steroid or a nonsteroidal anti-inflammatory drug (NSAID). For example, the anti-inflammatory agent comprises prednisolone acetate, diclofenac sodium, or a combination thereof.

In further aspects, the inhibitor may be at a concentration of about 0.001% w/v to about 100% w/v.

The subject to be treated is preferably a manual in need of such treatment, e.g., has been diagnosed with, is suffering from/has, or is at risk of developing one or more disorders or diseases described herein. The mammal can be, e.g., any mammal, e.g., a human, a primate, a mouse, a rat, a dog, a cat, a cow, a horse, or a pig. In a preferred embodiment, the mammal is a human.

In other aspects, the subject has not been diagnosed with aberrant angiogenesis. In other aspects, the subject has not been diagnosed with small vessel disease.

In aspects, the subject has not undergone surgery. In additional aspects, the inhibitor may be administered prior to a surgery, during a surgery or after a surgery. The surgery may comprise of retinal detachment surgery, glaucoma surgery, corneal surgery, cataract surgery, or any penetrating surgery of the eye. In other aspects, the subject has suffered a trauma to the eye.

Also provided herein are methods for diagnosing aberrant epithelial to mesenchymal transition (EMT) of retinal and ocular cells in a subject, the methods comprising: providing a test sample from said subject (e.g., via ocular surgery), assaying the level of runt-related transcription factor 1 (RUNX1) protein or mRNA in the test sample; and, and thereby diagnosing the subject as having aberrant EMT of retinal cells if the level of RUNX1 protein or mRNA is elevated in the test sample compared to a normal control. In embodiments, diagnosis of aberrant epithelial to mesenchymal transition of retinal cells may be performed by clinical exam or imaging. Such methods may also be used to measure RUNX1 levels, e.g., level of expression, as a biomarker for PVR and/or an indication of the severity of the disorder. The methods are also useful to monitor the effect/efficacy of treatment.

In embodiments, levels of RUNX1 may be measured using ELISA, Q-RT-PCR, Western blot analysis, immunohistochemistry, or immunofluorescence. In other embodiments, the test sample from the subject may be obtained during ocular surgery.

Also provided herein are methods for treating or reducing the severity of proliferative vitreoretinopathy (PVR) in a subject, the method comprising: identifying a subject comprising PVR, and administering to said subject a runt-related transcription factor 1 (RUNX1) inhibitor.

Each embodiment disclosed herein is contemplated as being applicable to each of the other disclosed embodiments. Thus, all combinations of the various elements described herein are within the scope of the invention.

Also described herein are methods for monitoring whether a disease (e.g., that comprises proliferative vitreoretinopathy (PVR) as well as a number of other disorders described herein, e.g., pathologic ocular fibrosis, or pathologic ocular proliferation, is progressing in a subject who has been diagnosed with the disease. The method comprises periodically determining the level of RUNX1 protein or mRNA in said subject, and identifying the disease as worsening if the level of RUNX1 protein or mRNA increases over time: identifying the disease as improving if the level of RUNX1 protein or mRNA decreases over time; identifying the disease as neither worsening or improving if the level of RUNX1 protein or mRNA remains the same or about the same over time, wherein determining the level of RUNX1 protein or mRNA comprises providing a test sample from said subject; and assaying the level of RUNX1 protein or mRNA in the test sample.

Described herein is a method for diagnosing a proliferative vitreoretinopathy (PVR) in a subject, the method comprising providing a test sample from said subject, assaying the level of runt-related transcription factor 1 (RUNX1) protein or mRNA in the test sample; and diagnosing the subject as having aberrant PVR if the level of RUNX1 protein or mRNA is elevated in the test sample compared to a normal control.

Also provided herein are methods for identifying whether a therapy has reduced or ameliorated a disease that comprises proliferative vitreoretinopathy (PVR) in a subject, the method comprising providing a pre-therapy test sample from said subject, assaying the pre-therapy level of RUNX1 protein or mRNA in the pre-therapy test sample; administering the therapy to the subject; providing a post-therapy test sample from said subject; assaying the post-therapy level of RUNX1 protein or mRNA in the post-therapy test sample; and identifying the therapy as having reduced or ameliorated said disease if the level of RUNX1 protein or mRNA in the post-therapy test sample is lower than the level of RUNX1 protein or mRNA in the pre-therapy sample.

In other examples, described herein are methods of reducing proliferation and migration of cells undergoing epithelial to mesenchymal transition (EMT) within an eye of a subject, the method comprising administering a runt-related transcription factor 1 (RUNX1) inhibitor to the subject. In embodiments, the EMT related disease comprises pathologic ocular fibrosis, proliferation, conjunctival fibrosis, ocular cicatricial pemphigoid, corneal scarring, corneal epithelial down growth, or aberrant post-surgical fibrosis. In some examples, the inhibitor is administered during or after glaucoma surgery, cataract surgery, or Laser-Assisted in situ keratomileusis (LASIK). In other examples, the inhibitor is administered during or after intraocular surgery.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 2A is an image depicting the immunofluorescence staining of patient sample 5 (membranes obtained from patient with PVR), counterstained with DAPI. FIG. 2B is an image depicting the immunofluorescence staining of RUNX1 in patient sample 5. FIG. 2C is a merged image of FIG. 2A and 2B. FIG. 2D is an image depicting the immunofluorescence staining of patient sample 3, counterstained with DAPI. FIG. 2E is an image depicting the immunofluorescence staining of RUNX1 in patient sample 3. FIG. 2F is a merged image of FIG. 2D and 2E. FIG. 20 is an image depicting the immunofluorescence staining of patient sample 11 (membranes obtained from patient with PVR) counterstained with DAPI. FIG. 2H is an image depicting he immunofluorescence staining of RUNX1 in patient sample 11. FIG. 2I is a merged image of FIG. 2G and 2H. FIG. 2A-2I indicated that RUNX1 was present in Cells from human PVR (C-PVR) from several patient donors.

FIG. 4A is an image depicting the immunofluorescence staining of membranes from patients with PVR counterstained with DAPI. FIB. 4B is an image depicting the immunofluorescence staining of membranes from patients with PVR stained with RUNX1. FIG. 4C is a merged image of FIG. 4A and 4B. FIG. 4D is an image depicting the immunofluorescence staining of membranes from patients with PVR counterstained with DAPI. FIG. 4E is an image depicting the immunofluorescence staining of membranes from patients with PVR stained with RUNX1. FIG. 4F is a merged image of FIG. 4D and 4E. FIG. 4A-4F showed additional images of staining of RUNX1 in PVR.

FIG. 9A is an image depicting a control (vehicle treated) Ki67 staining 48 hours post treatment. FIG. 9B is an image depicting Ki67 staining 48 hours post treatment with RUNX1 inhibitor, Ro5-3335 at 150 μM. A significant reduction in cell number and proliferative capacity of C-PVR cells was observed.

FIG. 10A-10E are a higher magnification than FIG. 9A and 9B; and depict a significant reduction in the cell number and proliferative capacity of C-PVR cells.

FIG. 11A and 11B showed epithelial-mesenchymal transition (FIG. 11B) compared to control (FIG. 11A).

FIG. 16 is magnified data from FIG. 13.

FIG. 19A are immunofluorescence staining images of RUNX1 and counterstained with DAPI in membranes obtained from patients with PVR (Case 1 "PVR 01" and Case 3 "PVR 03"). These images showed that RUNX1 expression was a common feature in membranes from different donors with PVR. Scale bars-400 microns.

FIG. 19B are immunofluorescence staining images of RUNX1 and counterstained with DAPI in membranes obtained from patients with PVR (Case 1 and Case 3). These images showed that RUNX1 expression was a common feature in membranes from different donors with PVR. Scale bars- 400 microns.

FIG. 20A are immunofluorescence staining images of Ki67 (also known ask antigen Ki-67 or Ki-67 or MKI67) (bottom, middle, FIG. 20B), RUNX1 (top, middle, FIG. 20A) and counterstained with DAPI in contiguous sections of membranes obtained from patients with PVR. These images showed that the population of cells expressing RUNX1 within PVR membranes actively proliferated, as demonstrated by their expression of Ki67. Scale bars-400 microns.

FIG. 21A are images depicting immunoblots indicating that RUNX1 protein expression levels were increased in growth factor induced Epithelial to Mesenchymal Transition (EMT). The increase in RUNX1 protein was observed upon treatment with growth factors: transforming growth factor beta 2 (TGFβ2), tumor necrosis factor alpha (TNFα) and combination treatment, including TGFβ2, TNFα, and interleukin-6 (IL-6), at 3 and 7 days post treatment.

FIG. 24 are bright field images of C-PVR cells 7 days post treatment with TGFβ2, TNFα, and a combination of TGFβ2, TNFα and IL-6, which showed EMT compared to control (top, left picture). EMT was assessed as morphological changes including cell shape with more elongated, fibroblast-like shaped cells in the combination treatment. This experiment showed that TNFα, TGFβ2 and IL-6 induced EMT in C-PVR cells derived from human proliferative vitreoretinopathy membranes. Scale bars—400 microns.

FIG. 25 are immunofluorescence staining images of C-PVR cells 7 days post treatment with TGFβ2, TNFα and a combination of TGFβ2, TNFα and IL-6 (10 ng/ml each), which showed a reduction in the epithelial marker (cytokeratin—middle panel) and increase in the mesenchymal marker (smooth muscle actin—right panel) in the treatments compared to controls (top row). This experiment demonstrated that these growth factors induced EMT in C-PVR cells from human proliferative vitreoretinopathy. Scale bar—200 microns.

FIG. 26A is a bar graph depicting that RUNX1 expression levels were increased in growth factor-induced EMT. An increase in RUNX1 RNA was observed along with an increase in mesenchymal markers, N-Cadherin, Smooth muscle actin and vimentin and a decrease in Epithelial marker, occludin was on treatment with growth factors TGFβ2, TNFα and combination treatment of TGFβ2, TNFα and IL-6 at 7 days post treatment.

FIG. 26B are images of immunoblots showing that an increase in the protein for RUNX1, N-Cadherin (Mesenchymal marker), Snail, and Twist (Snail and Twist are EMT transition markers) was observed compared to β-actin, which was used as a loading control on treatment with growth factors at 7 days post treatment. ****P<0.0001.

FIG. 29 are bright field images of ARPE-19 cells. RUNX1 knockdown using siRNA was effective at inhibiting EMT in cells treated with a growth factor cocktail including TGF822, TNFα and IL-6, compared to untransfected (right top) and si-scramble (right middle). EMT was determined by morphological changes including cell shape. This data demonstrated that RUNX1 inhibition using siRNA resulted in inhibition of EMT. Scale bars-400 microns.

FIG. 30A is an image of an immunoblot showing RUNX1 protein levels in ARPE-19 cells treated with TGFβ2 and TNFα. These data showed that each of these growth factors induced protein expression of RUNX1. The data also showed that siRNA treatment efficiently reduced the induction of RUNX1 triggered by each of these growth factors alone. These data demonstrated that RUNX1 inhibition can be used to limit the effect of these growth factors as it relates to PVR.

FIG. 32A is a series of images indicating that apoptosis, less branching and a faster regression of the branches was observed in human PVR explants treated with RUNX1 inhibitor, Ro5-3335 at 150 μm. Detachment of the branches from the primary tissue was also observed. Top panels showed explant treated with DMSO (vehicle) and bottom panels showed explant after treatment with Ro5-3335.

FIG. 32B is a bar graph indicating the number of outgrowths (or branches) after 24 hours and 72 hours with the control (DMSO) and with Ro5-3335.

FIG. 33A is a series of images indicating that apoptosis, less branching and a faster regression of the branches was observed in another human PVR explant treated with RUNX1 inhibitor, Ro5-3335 at 150 μm. Detachment of the branches from the primary tissue was also observed. Top panels showed explant treated with DMSO (vehicle) and bottom panels showed explant after treatment with Ro5-3335.

FIG. 33B is a bar graph indicating the number of outgrowths (or branches) after 24 hours and 72 hours with the control (DMSO) and with Ro5-3335.

FIG. 34A is a series of images indicating that the RUNX1 inhibitor. Ro5-3335 reduced growth of human PVR membranes in an explant model. A synergistic effect was observed with methotrexate+Ro5-3335. Less branching, a faster regression of the branches and apoptosis was observed in human PVR explants treated with RUNX1 inhibitor (Ro5-3335 at 150 μM), or a combination of Ro5-3335 (150 μM) and methotrexate (400 μM). Detachment of the branches from the primary tissue was also observed in Ro-3335 alone, but the combination (synergistic) effect of the drugs was surprising and even more significant. Top panels showed explant treated with DMSO (vehicle), middle panels showed explant after treatment with Ro5-3335 and bottom panels showed the effect of combination treatment (Ro5-3335 and methotrexate).

FIG. 34B is a bar graph indicating the number of outgrowths (or branches) after 24 hours and 72 hours with the control (DMSO), Ro5-3335, and combination of methotrexate and Ro5-3335.

FIG. 35A is a bar graph indicating that at 40 nM and 72 hours lenalidomide inhibited proliferation in C-PVR cells. The data were compared to vehicle treated, and showed a significant reduction in percent live cells at 72 hours. $^*P<0.05$.

FIG. 35B is a bar graph indicating that at 80 nM and 72 hours, lenalidomide inhibited proliferation in C-PVR cells. The data were compared to vehicle treated, and showed a significant reduction in percent live cells at 72 hours. $^*P<0.05$.

FIG. 35C is a bar graph indicating that at 40 nM and 48 hours, lenalidomide inhibited proliferation in C-PVR cells. $^*P<0.05$.

FIG. 35D is a bar graph indicating that at 80 nM and 48 hours, lenalidomide inhibited proliferation in C-PVR cells. $^*p<0.05$.

DETAILED DESCRIPTION

Figures 1A, 1B, 1C, 1D, 1E, 1F:
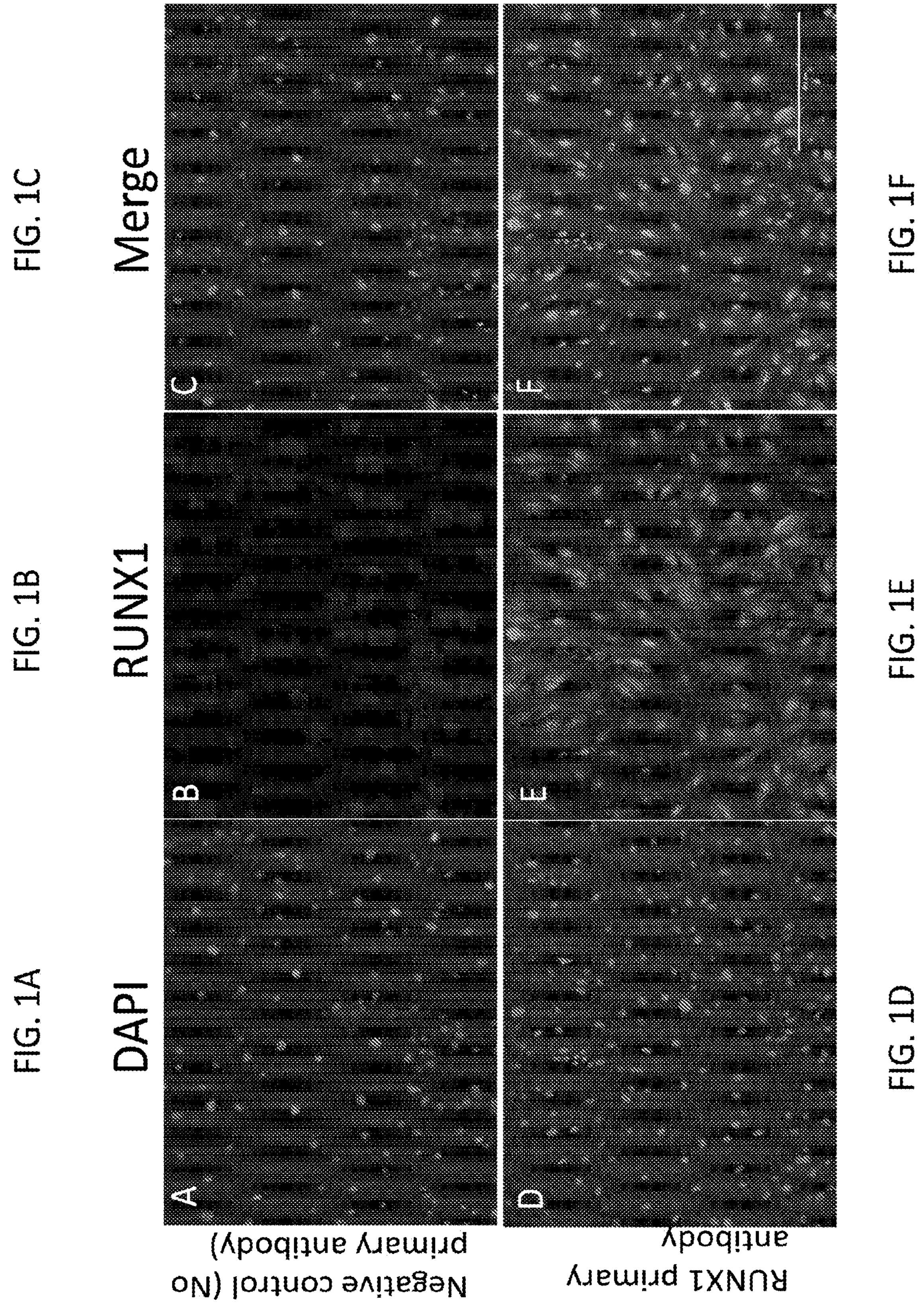
FIG. 1A is an image depicting the immunofluorescence staining of a negative control counterstained with DAPI.
FIG. 1B is an image depicting the immunofluorescence staining of a negative control of staining of RUNX1.
FIG. 1C is a merged image depicting the immunofluorescence staining of FIG. 1A and FIG. 1B.
FIG. 1D is an image depicting the immunofluorescence staining of the RUNX1 primary antibody counterstained with DAPI.
FIG. 1E is an image depicting the immunofluorescence staining of the RUNX1.
FIG. 1F is a merged image depicting the immunofluorescence staining of FIG. 1D and 1E.
Figures 2A, 2B, 2C, 2D, 2E, 2F, 2G, 2H, 2I:
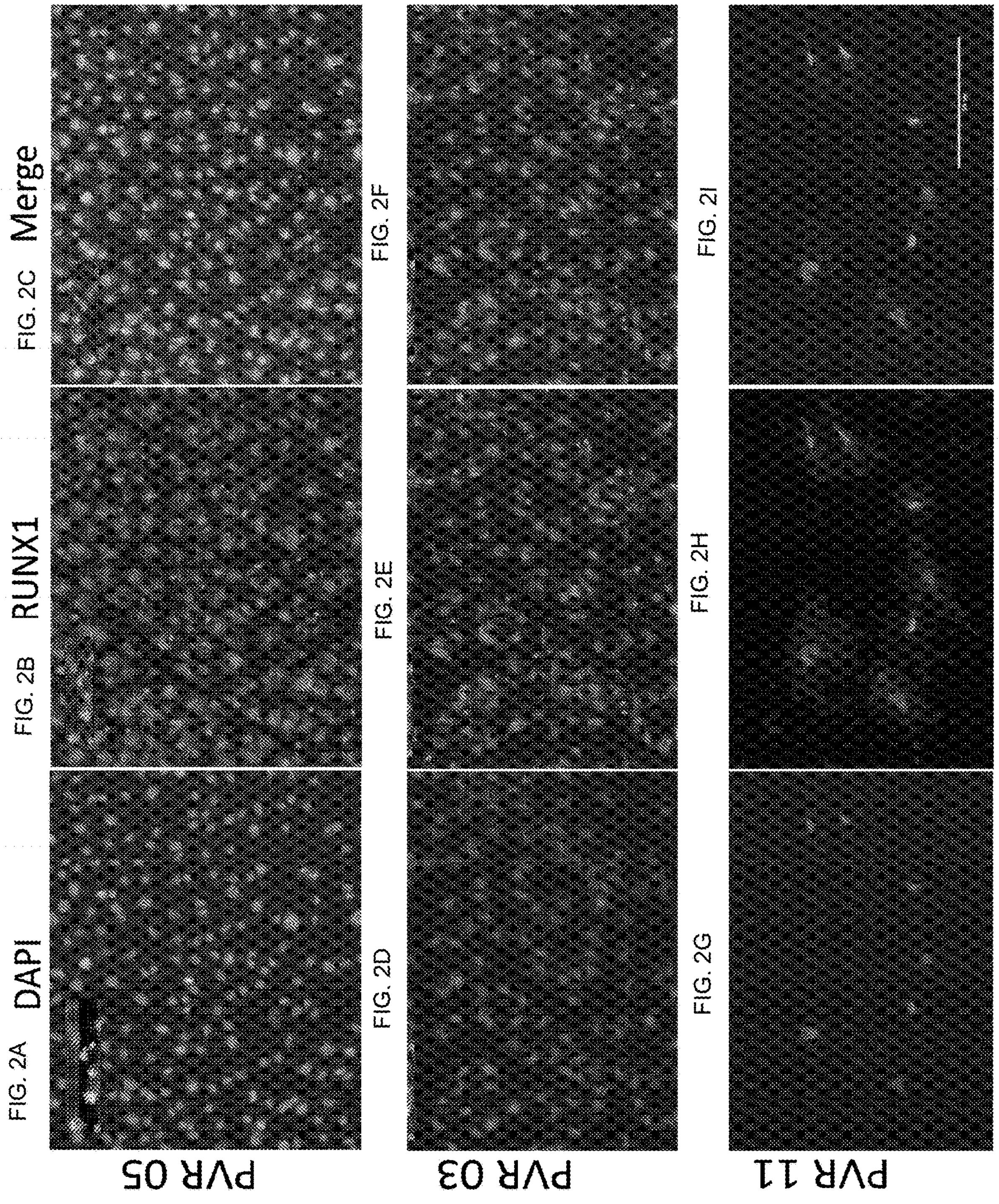
Figures 3A, 3B, 3C, 3D:
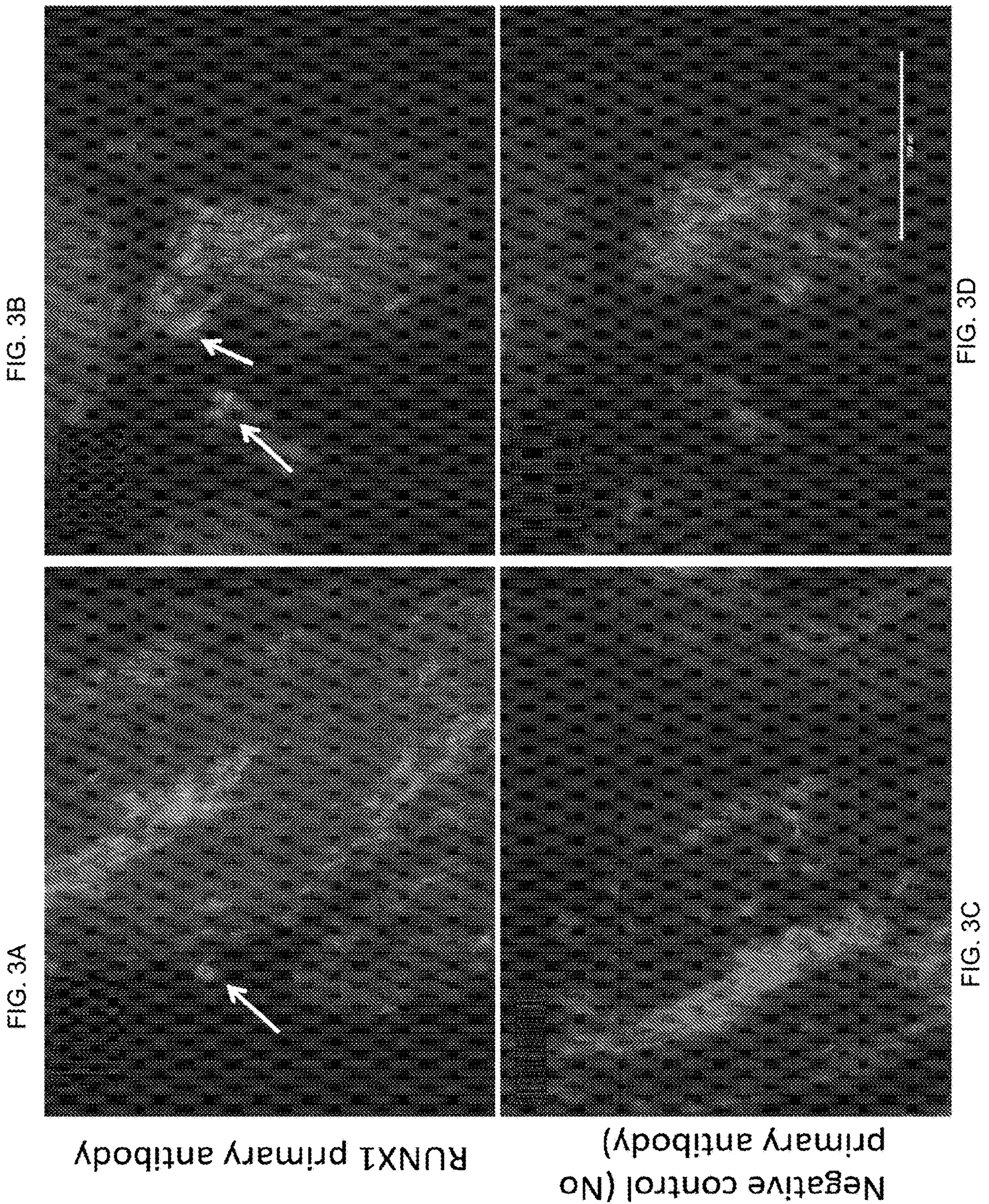
FIG. 3A is an image depicting the immunofluorescence staining of RUNX1 in human PVR membranes (e.g., patients with PVR).
FIG. 3B is an image depicting the immunofluorescence staining of RUNX1 in human PVR membranes counterstained with DAPI.
FIG. 3C is an image depicting the immunofluorescence staining of a negative control counterstained with DAPI.
FIG. 3D is an image depicting the immunofluorescence staining of a negative control counterstained with DAPI.
Figures 4A, 4B, 4C, 4D, 4E, 4F:
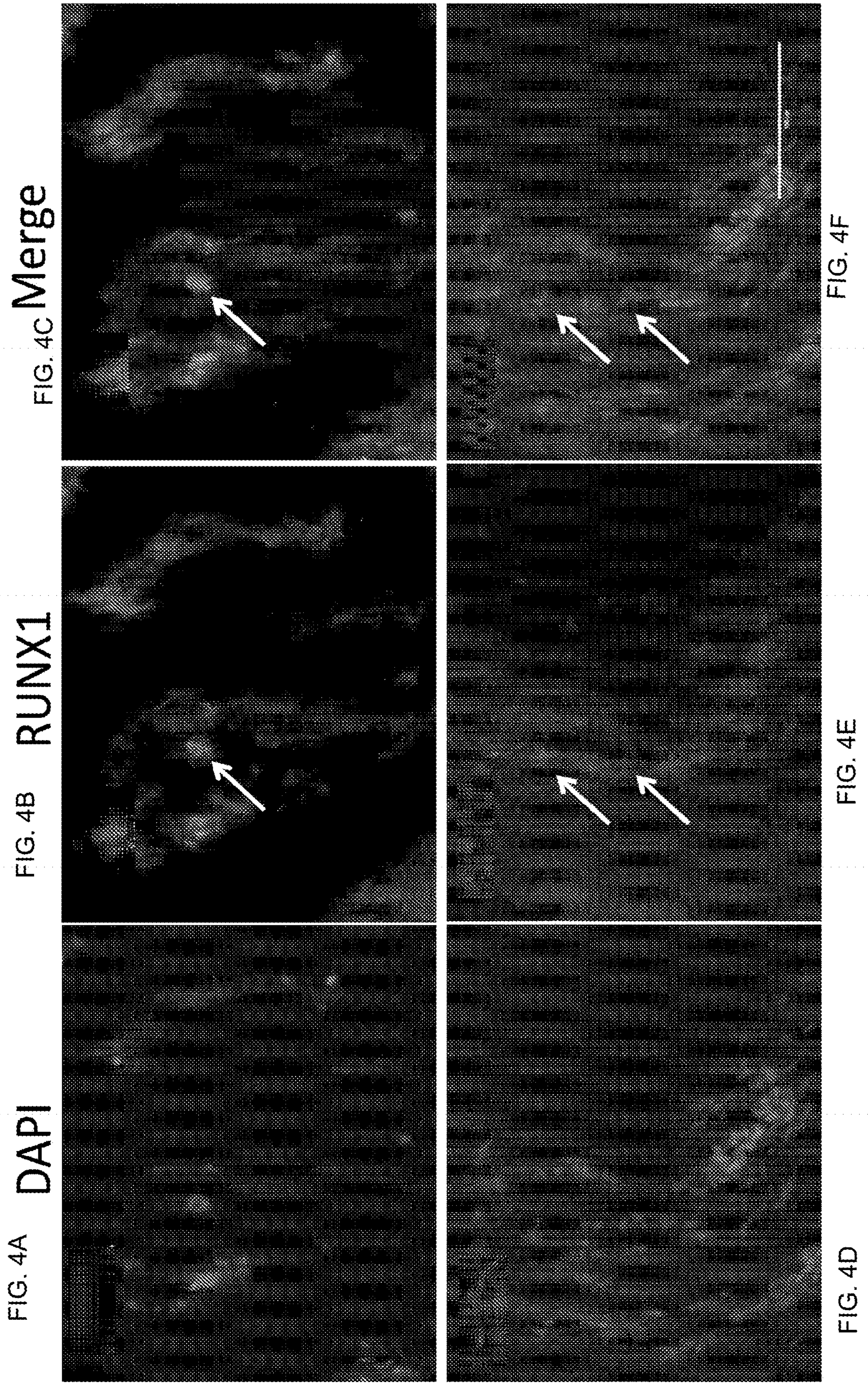

The present disclosure relates to methods for treating retinal detachment disorders, (e.g., proliferative vitreoretinopathy, PVR). Currently there are no medical (e.g., no non-surgical) treatments or management for PVR, which is a severe complication of retinal detachment, and commonly associated with eye trauma. Current management of PVR includes a potentially risky and invasive surgical method to remove the membrane directly from the eye. The compositions and methods are useful for the treatment of diseases afflicted with proliferation or migration of retinal pigment epithelial cells, glial, inflammatory cells, and mesenchymal cells as found in PVR.

The disclosure described herein is based on the surprising discovery that the Runt-Related Transcription Factor 1 (RUNX1) is highly expressed in surgically removed human PVR membranes, and cells derived from them (C-PVR). RUNX1 has been implicated in other biological processes including endothelial-cell derived blood vessel formation during embryonic development and normal angiogenesis. However, a role for RUNX1 in PVR (or EMT in retinal cells) has not previously been described. The disclosure herein describes actual patient-derived PVR membranes as a resource to highlight the specific expression of RUNX1 and to study its effect on RUNX1 inhibition. Current methods rely on surrogate cell types thought to be involved in the pathogenesis of PVR.

Additionally, RUNX1 expression is enhanced in an in vitro model of retinal pigment epithelial (RPE) cells undergoing epithelial to mesenchymal transition (EMT). The inhibition or RUNX1 via siRNA or a small molecule inhibitor significantly reduced the growth and migration of C-PVR culture. RUNX1 inhibition also significantly reduced the growth of human PVR membrane explants in culture.

Additionally, RUNX1 inhibition significantly reduced EMT in two in vitro models using ARPE-19 and C-PVR cultures. Reduction of EMT was characterized by morphological changes, increased expression in epithelial markers, and decreased expression of mesenchymal markers.

Accordingly, provided herein, are methods for preventing and treating PVR and other conditions associated with EMT by targeting RUNX1. This will allow for specific medical management of membranes, and caused their regression and impeded their growth and thus potentially avoiding the need for surgery.

Retinal Detachment Disorder

Retinal detachment is a disorder of the eye in which the neurosensory retina separates from the retinal pigment epithelial layer underneath. The mechanism most commonly involves a break in the retina that then allows the fluid in the eye to get behind the retina. A break in the retina can occur from a posterior vitreous detachment, injury to the eye, or inflammation of the eye. Other risk factors include being short sighted and previous cataract surgery. Typically, diagnosis is accomplished by either looking at the back of the eye with an ophthalmoscope or by ultrasound.

Symptoms include an increase in the number of floaters, flashes of light, and worsening of the outer part of the visual field, which may be described as a curtain over part of the field of vision. In about 7% of cases both eyes are affected. Without treatment permanent loss of vision may occur. In patients with a retinal tear, efforts to prevent it becoming a detachment include cryotherapy using a cold probe or photocoagulation using a laser. Treatment of retinal detachment should be carried out in a timely manner.

Retinal detachment can be examined by fundus photography or ophthalmoscopy. Ultrasound has diagnostic accuracy similar to that of examination by an ophthalmologist. Recent meta-analysis shows the diagnostic accuracy of emergency department (ED) ocular ultrasonography is high. The sensitivity and specificity ranged from 97% to 100% and 83% to 100%. The typical feature of retinal detachment when viewed on ultrasound is "flying angel sign," it shows the detached retina moving with a fixed point under the B mode, linear probe 10 MHZ. In embodiments, retinal detachment may be visualized by a fundus exam. Alternatively, a B-scan or wide-field fundus photography may be used to visualize retinal detachment.

Retinal detachments affect between 0.6 and 1.8 people per 10,000 per year. About 0.3% of people are affected at some point in their life. It is most common in people who are in their 60s or 70s, and males are more often affected than females. The long term outcomes depend on the duration of the detachment and whether the macula was detached. If treated before the macula detaches outcomes are generally good. Optionally, the subject has not been diagnosed or characterized with some other ocular disorder comprising age-related macular degeneration or an ocular angiogenesis disease or disorder.

When the retina is pulled away from the back of the eye, it is a retinal detachment. Typically, the vitreous moves away from the retina without causing problems. But sometimes the vitreous pulls hard enough to tear the retina in one or more places, and thus causing a retinal tear. Fluid may pass through a retinal tear, lifting the retina off the back of the eye. The symptoms of vitreous separation, retinal tear, and retinal detachment are similar and sometimes can overlap. On occasion, the patient may notice the floaters and flashing lights (photopsia) more commonly associated with isolated vitreous separation. An ophthalmologist, optometrist, or primary care physician may be suspicious about a more serious problem if symptoms are of very recent or sudden onset and are accompanied by a shower of spots or "cobwebs." Of even greater concern is the loss of peripheral vision, which may present as a shadow moving toward the center of one's field of vision.

Additionally, in retinal detachment, a retinal hole may develop. Because the vitreous is attached to the retina with tiny strands of collagen, it can pull on the retina as it shrinks. Sometimes, this shrinkage can tear off a small piece of the retina in the periphery, causing a hole or tear of the periphery retina. If this missing piece of retina is in the macula, it's called a macular hole. Additionally, another direct cause of macular holes due to vitreous shrinkage is when the collagen strands stay attached to the retina forming an epiretinal membrane. These membranes can contract around the macula, causing the macula to develop a hole from the traction. Retinal detachments commonly occur secondary to peripheral retinal tears/holes, and rarely form macular holes.

In other aspects, a minority of retinal detachments result from trauma, including blunt blows to the orbit, penetrating trauma, and concussions to the head.

There are three types of retinal detachment:

(1) Rhegmatogenous retinal detachment—A rhegmatogenous retinal detachment occurs due to a break in the retina (e.g., a retinal tear) that allows fluid to pass from the vitreous space into the subretinal space between the sensory retina and the retinal pigment epithelium. Retinal breaks are divided into three types—holes, tears and dialyses. Holes form due to retinal atrophy especially within an area of lattice degeneration. Tears are due to vitreoretinal traction. Dialyses are very peripheral and circumferential, and may be either tractional or atrophic. The atrophic form most often occurs as idiopathic dialysis of the young.

(2) Exudative serous, or secondary retinal detachment—An exudative retinal detachment occurs due to inflammation, injury or vascular abnormalities that results in fluid accumulating underneath the retina without the presence of a hole, tear, or break. In evaluation of retinal detachment it is critical to exclude exudative detachment as surgery will make the situation worse, not better. Although rare, exudative detachment can be caused by the growth of a tumor on the layers of tissue beneath the retina, namely the choroid. This cancer is called a choroidal melanoma.

(3) Tractional retinal detachment—A tractional retinal detachment occurs when fibrous (from PVR membrane) or fibrovascular (from neovascular disorders such as proliferative diabetic retinopathy) tissue, caused by an injury, inflammation or neovascularization, pulls the sensory retina from the retinal pigment epithelium Proliferative Vitreoretinopathy Proliferative vitreoretinopathy (PVR) is a clinical syndrome that develops as a complication of rhegmatogenous retinal detachment and is also commonly associated with eye trauma. PVR is the most common cause of failure in retinal detachment surgery, however, it can also occur with untreated eyes with retinal detachment. In particular, PVR can occur with vitreous hemorrhage, after cryotherapy, after laser retinopexy, pneumatic retinopexy, scleral buckling, or vitrectomy, and after a variety of surgical complications. PVR is also common after eye traumas (e.g., penetrating injuries) and other conditions associated with prolonged inflammation.

PVR occurs in about 8-10% of patients undergoing primary retinal detachment surgery and prevents the successful surgical repair of rhegmatogenous retinal detachment. PVR can be treated with surgery to reattach the retina, however, the visual outcome of the surgery is very poor. If PVR is progressive, then despite complex surgery, low vision in the eye results.

Pathophysiology

PVR is characterized by proliferation or migration of cells derived from retinal pigment epithelium (RPE), glia, or inflammatory recruitment on the retinal surface and within the vitreous gel. These cells transdifferentiate and take on contractile properties. The process of PVR can start when there is an interruption to the surface lining (e.g., through posterior vitreous detachment and local preretinal membrane formation or retinal tears in the periphery). The PVR process is self-propagating and is often considered an inappropriate excess wound-healing response. The cellular proliferation can increase the influx of inflammatory cytokines and inflammatory cells.

In embodiments, as described herein proliferation or migration of RPE cells describes their transdifferentiation to assume contractile properties through internal cellular contractile proteins and by laying down extracellular collagen. The cells can multiply and grow along any available scaffolding (e.g., the retinal surfaces or elements of the residual vitreous gel). The mass contraction can lead to retinal wrinkles, folds, tears, and traction retinal detachment.

During rhegmatogenous retinal detachment, fluid from the vitreous humor enters a retinal hole. The accumulation of fluid in the subretinal space and the tractional force of the vitreous on the retina result in rhegmatogenous retinal detachment. During this process the retinal cell layers come in contact with vitreous cytokines. These cytokines trigger the ability of the retinal pigmented epithelium (RPE) to proliferate and migrate. The process involved resembles fibrotic wound healing by the RPE cells. The RPE cells undergo epithelial-mesenchymal transition (EMT) and develop the ability to migrate out into the vitreous. During this process the RPE cell layer-neural retinal adhesion and RPE-ECM (extracellular matrix) adhesions are lost. The RPE cells lay down fibrotic membranes while they migrate and these membranes contract and pull at the retina. Thus, this leads to secondary retinal detachment after primary retinal detachment surgery.

During RPE disruption, inflammation may play an important role in the development of PVR. Cytokines IL-6, IL-1, TNF-α and IFN-γ have been identified in high concentrations in the vitreous in the early, proliferative stages of PVR, but they decrease to normal levels in the scarring phase. Other molecules involved in PVR include TGFβ and IL-6.

Risk Factors and Clinical Signs

As described above, the most common development of PVR is after a retinal detachment surgery and/or repair, although patients can develop PVR spontaneously with retinal detachment prior to surgery or with longstanding primary detachments. Multiple factors have been associated with the formation of PVR. In general, processes that increase vascular permeability are more likely to increase the probability of PVR formation. Specific risk factors that have been identified include: uveitis; large, giant, or multiple tears; vitreous hemorrhage, preoperative or postoperative choroidal detachments; aphakia; multiple previous surgeries; and large detachments involving greater than 2 quadrants of the eye.

Early signs of PVR are often subtle and can include cellular dispersion in the vitreous and on the retinal surface, which can appear as a white opacification of the retinal surface and small wrinkles or folds. More developed PVR is characteristic with fixed folds and retinal detachment. Diagnosis is typically done by indirect ophthalmoscopy and slit-lamp biomicroscopy. Additionally, an ultrasound can help visualize immobile retinal folds of detachment and prominent vitreous membranes. Also, wide-field fundus photography can be used to visualize retinal detachments. However, the clinical history and exam is often enough to make the diagnosis of a retinal detachment.

Development Stages

Ocular wound healing typically occurs in 3 stages: (1) an inflammatory stage, (2) a proliferative stage, and (3) a modulatory stage. PVR can be viewed in a similar fashion, with the wound being the retinal detachment. This healing response often takes place over many weeks. Early on, preretinal PVR adopts an immature appearance and consistency. During this phase, the retina may still remain compliant, and the PVR membrane may be difficult to remove due to its amorphous form. By 6 to 8 weeks, however, the PVR membrane becomes more mature, taking on a white, fibrotic appearance. In this stage, the PVR is more easily identifiable, causes rigidity of the retina, and can be more identifiably removed.

Classification

The extent of PVR in patients is often classified (or graded) depending on the severity. The most commonly used classification system was published by the Retina Society Terminology Committee. It classifies the appearance of PVR based on clinical signs and its geographic location (Grade A, B, C, or D). Grade A is characterized by the appearance of vitreous haze and RPE cells in the vitreous, or by pigment clumping. Grade B is characterized by wrinkling of the edges of the retinal tear or the inner retinal surface. Grade C is characterized by posterior or anterior full thickness retinal folds with the presence of epi/subretinal membranes/bands. Grade D is characterized by fixed retinal folds in all four quadrants. Diagnosis via clinical examination and imaging for PVR is known in the art, e.g., as described in the classification of retinal detachment with proliferative vitreoretinopathy. Ophthalmology, 1983; 90(2): p. 121-5. Clinical examination and classification schemes are further described in Di Lauro et al., J Ophthalmol. 2016; Volume 2016, Article ID 7807596, 6 pages 2016: 7807596. (PMCID: PMC4939352); hereby incorporated by reference.

PVR is Distinct from Proliferative Diabetic Retinopathy

PVR is a condition distinct from proliferative diabetic retinopathy (PDR). PVR is a condition distinct from a small blood vessel disease. The fundamental process involved in PDR is aberrant angiogenesis, and therefore impacting vascular endothelial cells. To the contrary, in PVR, the fundamental processes is the aberrant epithelial to mesenchymal transition (EMT) of retinal pigment epithelial derived cells, and other cells within the eye. Accordingly, the disclosure herein provides the surprising discovery that targeting RUNX1 may be used as a therapeutic target for the management of PVR.

Retinal Pigment Eepithelium

The retinal pigment epithelium (RPE) is the pigmented cell layer just outside the neurosensory retina that nourishes retinal visual cells, and is firmly attached to the underlying choroid and overlying retinal visual cells. The RPE forms a monolayer of cells beneath the sensory retina that is normally mitotically inactive except when it is participating in retinal wound repair, where it plays a central role. When wound repair is complete, the RPE usually stops proliferating; failure to do so can result in blinding disorders such as proliferative vitreoretinopathy (PVR) and disciform scarring. For instance, after detachment of the sensory retina, the RPE changes in morphology and begins to proliferate. Multilayered colonies of dedifferentiated RPE cells are formed. Cells then begin to migrate into the subretinal space where they engulf rod outer segments. In some instances, cells migrate onto the surface of the retina and form epiretinal membranes. These events have been implicated in the pathogenesis of proliferative vitreoretinopathy, severe scarring occurring in association with macular degeneration, and poor or delayed recovery of vision after retinal reattachment. Despite these important consequences, little is known about the stimuli involved in RPE dedifferentiation and loss of density-dependent growth control.

Other conditions associated with EMT including cancer, e.g., mesothelioma, Ocular Chronic Graft-Versus-Host Disease, corneal scarring, corneal epithelial downgrowth, conjunctival scarring, eye tumors like melanoma, ocular fibrosis, fibrosis, and complication of glaucoma surgery such as fibrosis (post surgical fibrosis as described in, e.g., Current and Future Techniques in Wound Healing Modulation after Glaucoma Filtering Surgeries. Masoumpour M B, et al. Open Ophthalmol J. 2016. Open Ophthalmol J. 2016 Feb 29;10:68-85. doi: 10.2174/1874364101610010068. eCollection 2016) as well as fibrosis and glaucoma (Friedlander et al., J Clin Invest. 2007, Mar. 1; 117(3): 576-586. Published online 2007 Mar. 1. doi: [10.1172/JC131030] PMCID: MC1804382 PMID). RUNX1 inhibition is useful for reduction, treatment, or prevention of aberrant or pathological EMT occurring in the eye. For example, the methods described herein are used for reducing proliferation and migration of cells within the eye undergoing epithelial to mesenchymal transition, e.g., inhibitors are administered to subjects diagnosed with, suffering from, or having EMT-associated diseases of pathologic ocular fibrosis and proliferation. Diseases include but are not limited to: conjunctival fibrosis (e.g. ocular cicatricial pemphigoid), corneal scarring, corneal epithelial down growth, and/or aberrant post-surgical fibrosis (e.g. after glaucoma surgery, cataract surgery, LASIK, or any intraocular surgery).

Runt-Related Transcription Factor 1

Runt-related transcription factor 1 (RUNX1), also known as acute myeloid leukemia 1 protein (AML1) or core-binding factor subunit alpha-2 (CBFA2), is a protein that in humans is encoded by the RUNX1 gene.

RUNX1 is a transcription factor that regulates the differentiation of hematopoietic stem cells into mature blood cells. RUNX1 also plays a role in the development of the neurons that transmit pain. It belongs to the Runt-related transcription factor (RUNX) family of genes which are also called core binding factor-α (CBFα). RUNX proteins form a heterodimeric complex with core binding factor β (CBFβ) which confers increased deoxyribonucleic acid (DNA) binding and stability to the complex.

In humans, the RUNX1 gene is 260 kilobases (kb) in length, and is located on chromosome 21 (21q22.12). The gene can be transcribed from 2 alternative promoters, promoter 1 (distal) or promoter 2 (proximal). As a result, various isoforms of RUNX1 can be synthesized, facilitated by alternative splicing. The full-length RUNX1 protein is encoded by 12 exons. Among the exons are two defined domains, namely the runt homology domain (RHD) or the runt domain (exons 2, 3 and 4), and the transactivation domain (TAD) (exon 6). These domains are necessary for RUNX1 to mediate DNA binding and protein-protein interactions respectively. The transcription of RUNX1 is regulated by 2 enhancers (regulatory element 1 and regulatory element 2), and these tissue specific enhancers enable the binding of lymphoid or erythroid regulatory proteins, therefore the gene activity of RUNX1 is highly active in the hematopoietic system.

An exemplary isoform of RUNX1 (Q01196-1; SEQ ID NO: 1) has 453 amino acids. As a transcription factor (TF), its DNA binding ability is encoded by the runt domain (residues 50-177 of SEQ ID NO: 1), which is homologous to the p53 family. Without wishing to be bound by any scientific theory, the runt domain of RUNX1 is believed to bind to the core consensus sequence TGTGGNNN of SEQ ID NO: 1 (where NNN can represent either TTT or TCA). DNA recognition is achieved by loops of the 12-stranded β-barrel and the C-terminus "tail" (residues 170-177 of SEQ ID NO: 1), which clamp around the sugar phosphate backbone and fits into the major and minor grooves of DNA. Specificity is achieved by making direct or water-mediated contacts with the bases. RUNX1 can bind DNA as a monomer, but its DNA binding affinity is enhanced by 10 fold if it heterodimerizes with the CBFβ, also via the runt domain. The RUNX family is often referred to as α-subunits, together with binding of a common β-subunit CBFβ, RUNX can behave as heterodimeric transcription factors collectively called the core binding factors (CBFs).

An amino acid sequence for human RUNX1 is publically available in the UniProt database under accession number Q01196-1 (SEQ ID NO: 1) and is as follows:

```
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQSYQYLGSIASPSVHPATPISPGRASGMTTLSAELSSRLSTAPDL
```

-continued

```
TAFSDPRQFPALPSISDPRMHYPGAFTYSPTPVTSGIGIGMSAMGSATRY

HTYLPPPYPGSSQAQGGPFQASSPSYHLYYGASAGSYQFSMVGGERSPPR

ILPPCTNASTGSALLNPSLPNQSDVVEAEGSHSNSPTNMAPSARLEEAVW

RPY
```

Amino acid sequences of additional isoforms are publically available in the UniProt database under accession numbers Q01196-2 (SEQ ID NO: 2); Q01196-3 (SEQ ID NO: 3); Q01196-4 (SEQ ID NO: 4); Q01196-5 (SEQ ID NO: 5); Q01196-6 (SEQ ID NO: 6); Q01196-7 (SEQ ID NO: 7); Q01196-8 (SEQ ID NO: 8); Q01196-9 (SEQ ID NO: 9); Q01196-10 (SEQ ID NO: 10); and Q01196-11 (SEQ ID NO: 11).

Exemplary landmark sequences and domains include, residues 80-84 (DNA binding domain), residues 135-143 (DNA binding domain), residues 168-177 (DNA binding domain), residues 291-371 (interaction with K(lysine) acetyltransferase 6A (KATAGA)), residues 307-400 (interaction with K(lysine) acetyltransferase 6B (KATA6B)), and residues 362-402 (interaction with forkhead box P3 (FOXP3)).

A nucleotide sequence that encodes human RUNX1 is publically available in the GenBank database under accession number NM_001001890.2 (SEQ ID NO: 12) and is as follows (start and stop codon are bolded and underlined):

```
CATAGAGCCAGCGGGCGCGGGCGGGACGGGCGCCCCGCGGCCGGACCCAG

CCAGGGCACCACGCTGCCCGGCCCTGCGCCGCCAGGCACTTCTTTCCGGG

GCTCCTAGGGACGCCAGAAGGAAGTCAACCTCTGCTGCTTCTCCTTGGCC

TGCGTTGGACCTTCCTTTTTTTGTTGTTTTTTTTTGTTTTTCCCCTTTCT

TCCTTTTGAATTAACTGGCTTCTTGGCTGGATGTTTTCAACTTCTTTCCT

GGCTGCGAACTTTTCCCCAATTGTTTTCCTTTTACAACAGGGGGAGAAAG

TGCTCTGTGGTCCGAGGCGAGCCGTGAAGTTGCGTGTGCGTGGCAGTGTG

CGTGGCAGGATGTGCGTGCGTGTGTAACCCGAGCCGCCCGATCTGTTTCG

ATCTGCGCCGCGGAGCCCTCCCTCAAGGCCCGCTCCACCTGCTGCGGTTA

CGCGGCGCTCGTGGGTGTTCGTGCCTCGGAGCAGCTAACCGGCGGGTGCT

GGGCGACGGTGGAGGAGTATCGTCTCGCTGCTGCCCGAGTCAGGGCTGAG

TCACCCAGCTGATGTAGACAGTGGCTGCCTTCCGAAGAGTGCGTGTTTGC

ATGTGTGTGACTCTGCGGCTGCTCAACTCCCAACAAACCAGAGGACCAGC

CACAAACTTAACCAACATCCCCAAACCCGAGTTCACAGATGTGGGAGAGC

TGTAGAACCCTGAGTGTCATCGACTGGGCCTTCTTATGATTGTTGTTTTA

AGATTAGCTGAAGATCTCTGAAACGCTGAATTTTCTGCACTGAGCGTTTT

GACAGAATTCATTGAGAGAACAGAGAACATGACAAGTACTTCTAGCTCAG

CACTGCTCCAACTACTGAAGCTGATTTTCAAGGCTACTTAAAAAAATCTG

CAGCGTACATTAATGGATTTCTGTTGTGTTTAAATTCTCCACAGATTGTA

TTGTAAATATTTTATGAAGTAGAGCATATGTATATATTTATATATACGTG

CACATACATTAGTAGCACTACCTTTGGAAGTCTCAGCTCTTGCTTTTCGG

GACTGAAGCCAGTTTTGCATGATAAAAGTGGCCTTGTTACGGGAGATAAT

TGTGTTCTGTTGGGACTTTAGACAAAACTCACCTGCAAAAAACTGACAGG
```

-continued

CATTAACTACTGGAACTTCCAAATAATGTGTTTGCTGATCGTTTTACTCT
TCGCATAAATATTTTAGGAAGTGTATGAGAATTTTGCCTTCAGGAACTTT
TCTAACAGCCAAAGACAGAACTTAACCTCTGCAAGCAAGATTCGTGGAAG
ATAGTCTCCACTTTTTAATGCACTAAGCAATCGGTTGCTAGGAGCCCATC
CTGGGTCAGAGGCCGATCCGCAGAACCAGAACGTTTTCCCCTCCTGGACT
GTTAGTAACTTAGTCTCCCTCCTCCCCTAACCACCCCCGCCCCCCCCCAC
CCCCCGCAGTAATAAAGGCCCCTGAACGTGTATGTTGGTCTCCCGGGAGC
TGCTTGCTGAAGATCCGCGCCCCTGTCGCCGTCTGGTAGGAGCTGTTTGC
AGGGTCCTAACTCAATCGGCTTGTTGTGATGCGTATCCCCGTAGATGCCA
GCACGAGCCGCCGCTTCACGCCGCCTTCCACCGCGCTGAGCCCAGGCAAG
ATGAGCGAGGCGTTGCCGCTGGGCGCCCCGGACGCCGGCGCTGCCCTGGC
CGGCAAGCTGAGGAGCGGCGACCGCAGCATGGTGGAGGTGCTGGCCGACC
ACCCGGGCGAGCTGGTGCGCACCGACAGCCCCAACTTCCTCTGCTCCGTG
CTGCCTACGCACTGGCGCTGCAACAAGACCCTGCCCATCGCTTTCAAGGT
GGTGGCCCTAGGGGATGTTCCAGATGGCACTCTGGTCACTGTGATGGCTG
GCAATGATGAAAACTACTCGGCTGAGCTGAGAAATGCTACCGCAGCCATG
AAGAACCAGGTTGCAAGATTTAATGACCTCAGGTTTGTCGGTCGAAGTGG
AAGAGGGAAAAGCTTCACTCTGACCATCACTGTCTTCACAAACCCACCGC
AAGTCGCCACCTACCACAGAGCCATCAAAATCACAGTGGATGGGCCCCGA
GAACCTCGAAGACATCGGCAGAAACTAGATGATCAGACCAAGCCCGGGAG
CTTGTCCTTTTCCGAGCGGCTCAGTGAACTGGAGCAGCTGCGGCGCACAG
CCATGAGGGTCAGCCCACACCACCCAGCCCCCACGCCCAACCCTCGTGCC
TCCCTGAACCACTCCACTGCCTTTAACCCTCAGCCTCAGAGTCAGATGCA
GGATACAAGGCAGATCCAACCATCCCCACCGTGGTCCTACGATCAGTCCT
ACCAATACCTGGGATCCATTGCCTCTCCTTCTGTGCACCCAGCAACGCCC
ATTTCACCTGGACGTGCCAGCGGCATGACAACCCTCTCTGCAGAACTTTC
CAGTCGACTCTCAACGGCACCCGACCTGACAGCGTTCAGCGACCCGCGCC
AGTTCCCCGCGCTGCCCTCCATCTCCGACCCCCGCATGCACTATCCAGGC
GCCTTCACCTACTCCCCGACGCCGGTCACCTCGGGCATCGGCATCGGCAT
GTCGGCCATGGGCTCGGCCACGCGCTACCACACCTACCTGCCGCCGCCCT
ACCCCGGCTCGTCGCAAGCGCAGGGAGGCCCGTTCCAAGCCAGCTCGCCC
TCCTACCACCTGTACTACGGCGCCTCGGCCGGCTCCTACCAGTTCTCCAT
GGTGGGCGGCGAGCGCTCGCCGCCGCGCATCCTGCCGCCCTGCACCAACG
CCTCCACCGGCTCCGCGCTGCTCAACCCCAGCCTCCCGAACCAGAGCGAC
GTGGTGGAGGCCGAGGGCAGCCACAGCAACTCCCCCACCAACATGGCGCC
CTCCGCGCGCCTGGAGGAGGCCGTGTGGAGGCCCTACTGAGGCGCCAGGC
CTGGCCCGGCTGGGCCCCGCGGGCCGCCGCCTTCGCCTCCGGGCGCGCGG
GCCTCCTGTTCGCGACAAGCCCGCCGGGATCCCGGGCCCTGGGCCCGGCC
ACCGTCCTGGGGCCGAGGGCGCCCGACGGCCAGGATCTCGCTGTAGGTCA
GGCCCGCGCAGCCTCCTGCGCCCAGAAGCCCACGCCGCCGCCGTCTGCTG

-continued

GCGCCCCGGCCCTCGCGGAGGTGTCCGAGGCGACGCACCTCGAGGGTGTC
CGCCGGCCCCAGCACCCAGGGGACGCGCTGGAAAGCAAACAGGAAGATTC
CCGGAGGGAAACTGTGAATGCTTCTGATTTAGCAATGCTGTGAATAAAAA
GAAAGATTTTATACCCTTGACTTAACTTTTTAACCAAGTTGTTTATTCCA
AAGAGTGTGGAATTTTGGTTGGGGTGGGGGGAGAGGAGGGATGCAACTCG
CCCTGTTTGGCATCTAATTCTTATTTTTAATTTTTCCGCACCTTATCAAT
TGCAAAATGCGTATTTGCATTTGGGTGGTTTTTATTTTTATATACGTTTA
TATAAATATATATAAATTGAGCTTGCTTCTTTCTTGCTTTGACCATGGAA
AGAAATATGATTCCCTTTTCTTTAAGTTTTATTTAACTTTTCTTTTGGAC
TTTTGGGTAGTTGTTTTTTTTTGTTTTGTTTTGTTTTTTTGAGAAACAGC
TACAGCTTTGGGTCATTTTTAACTACTGTATTCCCACAAGGAATCCCCAG
ATATTTATGTATCTTGATGTTCAGACATTTATGTGTTGATAATTTTTTAA
TTATTTAAATGTACTTATATTAAGAAAAATATCAAGTACTACATTTTCTT
TTGTTCTTGATAGTAGCCAAAGTTAAATGTATCACATTGAAGAAGGCTAG
AAAAAAAGAATGAGTAATGTGATCGCTTGGTTATCCAGAAGTATTGTTTA
CATTAAACTCCCTTTCATGTTAATCAAACAAGTGAGTAGCTCACGCAGCA
ACGTTTTTAATAGGATTTTTAGACACTGAGGGTCACTCCAAGGATCAGAA
GTATGGAATTTTCTGCCAGGCTCAACAAGGGTCTCATATCTAACTTCCTC
CTTAAAACAGAGAAGGTCAATCTAGTTCCAGAGGGTTGAGGCAGGTGCCA
ATAATTACATCTTTGGAGAGGATTTGATTTCTGCCCAGGGATTTGCTCAC
CCCAAGGTCATCTGATAATTTCACAGATGCTGTGTAACAGAACACAGCCA
AAGTAAACTGTGTAGGGGAGCCACATTTACATAGGAACCAAATCAATGAA
TTTAGGGGTTACGATTATAGCAATTTAAGGGCCCACCAGAAGCAGGCCTC
GAGGAGTCAATTTGCCTCTGTGTGCCTCAGTGGAGACAAGTGGGAAAACA
TGGTCCCACCTGTGCGAGACCCCCTGTCCTGTGCTGCTCACTCAACAACA
TCTTTGTGTTGCTTTCACCAGGCTGAGACCCTACCCTATGGGGTATATGG
GCTTTTACCTGTGCACCAGTGTGACAGGAAAGATTCATGTCACTACTGTC
CGTGGCTACAATTCAAAGGTATCCAATGTCGCTGTAAATTTTATGGCACT
ATTTTTATTGGAGGATTTGGTCAGAATGCAGTTGTTGTACAACTCATAAA
TACTAACTGCTGATTTTGACACATGTGTGCTCCAAATGATCTGGTGGTTA
TTTAACGTACCTCTTAAAATTCGTTGAAACGATTTCAGGTCAACTCTGAA
GAGTATTTGAAAGCAGGACTTCAGAACAGTGTTTGATTTTTATTTTATAA
ATTTAAGCATTCAAATTAGGCAAATCTTTGGCTGCAGGCAGCAAAAACAG
CTGGACTTATTTAAAACAACTTGTTTTTGAGTTTTCTTATATATATATTG
ATTATTTGTTTTACACACATGCAGTAGCACTTTGGTAAGAGTTAAAGAGT
AAAGCAGCTTATGTTGTCAGGTCGTTCTTATCTAGAGAAGAGCTATAGCA
GATCTCGGACAAACTCAGAATATATTCACTTTCATTTTTGACAGGATTCC
CTCCACAACTCAGTTTCATATATTATTCCGTATTACATTTTTGCAGCTAA
ATTACCATAAAATGTCAGCAAATGTAAAAATTTAATTTCTGAAAAGCACC
ATTAGCCCATTTCCCCCAAATTAAACGTAAATGTTTTTTTTCAGCACATG
TTACCATGTCTGACCTGCAAAAATGCTGGAGAAAAATGAAGGAAAAAATT

-continued

```
ATGTTTTTCAGTTTAATTCTGTTAACTGAAGATATTCCAACTCAAAACCA

GCCTCATGCTCTGATTAGATAATCTTTTACATTGAACCTTTACTCTCAAA

GCCATGTGTGGAGGGGGCTTGTCACTATTGTAGGCTCACTGGATTGGTCA

TTTAGAGTTTCACAGACTCTTACCAGCATATATAGTATTTAATTGTTTCA

AAAAAAATCAAACTGTAGTTGTTTTGGCGATAGGTCTCACGCAACACATT

TTTGTATGTGTGTGTGTGTGCGTGTGTGTGTGTGTGTGAAAAATTGCA

TTCATTGACTTCAGGTAGATTAAGGTATCTTTTTATTCATTGCCCTCAGG

AAAGTTAAGGTATCAATGAGACCCTTAAGCCAATCATGTAATAACTGCAT

GTGTCTGGTCCAGGAGAAGTATTGAATAAGCCATTTCTACTGCTTACTCA

TGTCCCTATTTATGATTTCAACATGGATACATATTTCAGTTCTTTCTTTT

TCTCACTATCTGAAAATACATTTCCCTCCCTCTCTTCCCCCCAATATCTC

CCTTTTTTTCTCTCTTCCTCTATCTTCCAAACCCCACTTTCTCCCTCCTC

CTTTTCCTGTGTTCTCTTAAGCAGATAGCACATACCCCCACCCAGTACCA

AATTTCAGAACACAAGAAGGTCCAGTTCTTCCCCCTTCACATAAAGGAAC

ATGGTTTGTCAGCCTTTCTCCTGTTTATGGGTTTCTTCCAGCAGAACAGA

GACATTGCCAACCATATTGGATCTGCTTGCTGTCCAAACCAGCAAACTTT

CCTGGGCAAATCACAATCAGTGAGTAAATAGACAGCCTTTCTGCTGCCTT

GGGTTTCTGTGCAGATAAACAGAAATGCTCTGATTAGAAAGGAAATGAAT

GGTTCCACTCAAATGTCCTGCAATTTAGGATTGCAGATTTCTGCCTTGAA

ATACCTGTTTCTTTGGGACATTCCGTCCTGATGATTTTTATTTTTGTTGG

TTTTTATTTTTGGGGGGAATGACATGTTTGGGTCTTTTATACATGAAAAT

TTGTTTGACAATAATCTCACAAAACATATTTTACATCTGAACAAAATGCC

TTTTTGTTTACCGTAGCGTATACATTTGTTTTGGGATTTTTGTGTGTTTG

TTGGGAATTTTGTTTTTAGCCAGGTCAGTATTGATGAGGCTGATCATTTG

GCTCTTTTTTTCCTTCCAGAAGAGTTGCATCAACAAAGTTAATTGTATTT

ATGTATGTAAATAGATTTTAAGCTTCATTATAAAATATTGTTAATGCCTA

TAACTTTTTTTCAATTTTTTTGTGTGTGTTTCTAAGGACTTTTTCTTAGG

TTTGCTAAATACTGTAGGGAAAAAAATGCTTCTTTCTACTTTGTTTATTT

TAGACTTTAAAATGAGCTACTTCTTATTCACTTTTGTAAACAGCTAATAG

CATGGTTCCAATTTTTTTTAAGTTCACTTTTTTTGTTCTAGGGGAAATGA

ATGTGCAAAAAAAGAAAAAGAACTGTTGGTTATTTGTGTTATTCTGGATG

TATAAAAATCAATGGAAAAAAATAAACTTTCAAATTGAAATGACGGTATA

ACACATCTACTGAAAAAGCAACGGGAAATGTGGTCCTATTTAAGCCAGCC

CCCACCTAGGGTCTATTTGTGTGGCAGTTATTGGGTTTGGTCACAAAACA

TCCTGAAAATTCGTGCGTGGGCTTCTTTCTCCCTGGTACAAACGTATGGA

ATGCTTCTTAAAGGGGAACTGTCAAGCTGGTGTCTTCAGCCAGATGACAT

GAGAGAATATCCCAGAACCCTCTCTCCAAGGTGTTTCTAGATAGCACAGG

AGAGCAGGCACTGCACTGTCCACAGTCCACGGTACACAGTCGGGTGGGCC

GCCTCCCCTCTCCTGGGAGCATTCGTCGTGCCCAGCCTGAGCAGGGCAGC

TGGACTGCTGCTGTTCAGGAGCCACCAGAGCCTTCCTCTCTTTGTACCAC
```

-continued

```
AGTTTCTTCTGTAAATCCAGTGTTACAATCAGTGTGAATGGCAAATAAAC

AGTTTGACAAGTACATACACCATA
```

Additional RUNX1-encoding nucleotide sequences are publically available in the GenBank database under accession numbers NM_001754.4 (homo sapiens, SEQ ID NO: 13); NM_001122607.1 (homo sapiens, SEQ ID NO: 14); XM_005261068.3 (homo sapiens, SEQ ID NO: 15); XM_011529770.2 (homo sapiens, SEQ ID NO: 16); XR_937576.2 (homo sapiens, SEQ ID NO: 17); XM_011529768.2 (homo sapiens, SEQ ID NO: 18); XM_005261069.4 (homo sapiens, SEQ ID NO: 19); XM_017028487.1 (homo sapiens, SEQ ID NO: 20); XM_011529767.2 (homo sapiens, SEQ ID NO: 21); and XM_011529766.2 (homo sapiens, SEQ ID NO: 22).

Runt-Related Transcription Factor 2

Runt-related transcription factor 2 (RUNX2), also known as core-binding factor subunit alpha-1, is a protein that in humans is encoded by the RUNX2 gene. RUNX2 has been is a transcription factor that has been associated with osteoblast differentiation.

An amino acid sequence for human RUNX2 is publically available in the GenBank Database under accession number NP_001019801.3 (SEQ ID NO: 23), and is as follows:

```
  1 masnslfstv tpcqqnffwd pstsrrfspp ssslqpgkms
    dvspvvaaqq qqqqqqqqqq
 61 qqqqqqqqqq qeaaaaaaaa aaaaaaaaav prlrpphdnr
    tmveiiadhp aelvrtdspn
121 flcsvlpshw rcnktlpvaf kvvalgevpd gtvvtvmagn
    denysaelrn asavmknqva
181 rfndlrfvgr sgrgksftlt itvftnppqv atyhraikvt
    vdgpreprrh rqklddskps
241 lfsdrlsdlg riphpsmrvg vppqnprpsl nsapspfnpq
    gqsqitdprq aqssppwsyd
301 qsypsylsqm tspsihsttp lsstrgtglp aitdvprris
    dddtatsdfc lwpstlskks
361 qagaselgpf sdprqfpsis sltesrfsnp rmhypatfty
    tppvtsgmsl gmsatthyht
421 ylpppypgss qsqsgpfqts stpylyygts sgsyqfpmvp
    ggdrspsrml ppctttsngs
481 tllnpnlpnq ndgvdadgsh sssptvlnss grmdesvwrp
    y
```

Exemplary landmark sequences and domains include, residues 49-71 (polyglutamine repeat), residues 73-89 (polyalanine repeat), residues 109-230 (runt domain), residues 242-258 (domain for interaction with forkhead Box O1 (FOXO1)), residues 336-439 (domain for interaction with K(lysine) acetyltransferase 6A (KATA6A)), residues 374-488 (domain for interaction with K(lysine) acetyltransferase 6B (KATA6B)), and residues 430-521 (RUNX1 inhibition domain).

Additional amino acid sequences of human RUNX2 isoforms are publically available in the GenBank database under accession numbers: NP_001015051.3 (homo sapiens, SEQ ID NO: 24), Q13950.2 (homo sapiens, SEQ ID NO: 25), and NP_001265407.1 (homo sapiens SEQ ID NO: 26). Amino acid sequences of additional RUNX2 isoforms are publically available in the GenBank database under accession numbers NP_001139392.1 (mus musculus, SEQ ID NO: 27) NP_001139510.1 (mus musculus, SEQ ID NO: 28), NP 001258556.1 (mus musculus, SEQ ID NO: 29), NP_001258559.1 (mus musculus, SEQ ID NO: 30), and NP_001258560.1 (mus musculus, SEQ ID NO: 31).

Nucleic acids of additional RUNX2 human isoforms are publically available in the GenBank database under accession numbers: NM_001015051.3 (homo sapiens, SEQ ID NO: 32), NM 001024630.3 (homo sapiens, SEQ ID NO: 33), and NM_001278478.1 (homo sapiens, SEQ ID NO: 34). Nucleic acid sequences of additional RUNX2 isoforms are publically available in the GenBank database under accession numbers NM_001145920.2 (mus musculus, SEQ ID NO: 35), NM_001146038.2 (mus musculus, SEQ ID NO: 36), NM_001271627.1 (mus musculus, SEQ ID NO: 37), NM_001271630.1 (mus musculus, SEQ ID NO: 38), and NM_001271631.1 (mus musculus, SEQ ID NO: 39).

Exemplary Inhibitors

Aspects of the present subject matter relate to the administration of an RUNX1 inhibitor. In various embodiments, an inhibitor may be, e.g., an aptamer, an oligonucleotide (e.g., an antisense oligonucleotide, a ribozyme, or an RNA interfering molecule), a peptide, an antibody or a fragment thereof, or a small molecule, that specifically binds to RUNX1 or a polynucleotide that encodes RUNX1.

Small Molecule CBFβ-RUNX1 Inhibitors

In various embodiments, the RUNX1 inhibitor is a small molecule inhibitor. Non-limiting examples include:

(Formula I)

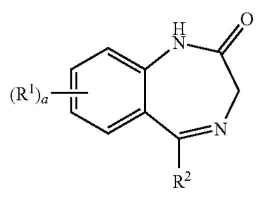

or pharmaceutically acceptable salts or esters thereof, wherein each $R^1$ is individually selected from halogen, alkyl, aryl, heteroaryl, or alkoxy; $R^2$ is selected from aryl or heteroaryl; and a is 0 to 4;

(Formula II)

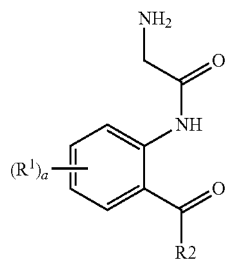

or a pharmaceutically acceptable salt or ester thereof, wherein each $R^1$ is individually selected from halogen, alkyl, aryl, heteroaryl, or alkoxy; $R^2$ is selected from aryl or heteroaryl; and a is 0 to 4; or (Formula III)

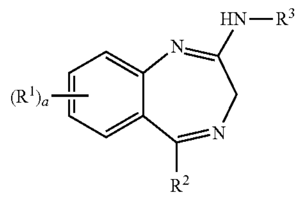

or a pharmaceutically acceptable salt or ester thereof, wherein each $R^1$ is individually selected from halogen, alkyl, aryl, heteroaryl, or alkoxy; R2 is selected from aryl or heteroaryl; $R^3$ is alkyl or aryl; and a is 0 to 4.

In certain embodiments of formulae I-III, $R^2$ is a heteroaryl, particularly pyrrolyl, and especially pyrrol-2-yl. In certain embodiments of formulae I-III, $R^1$ is a halogen, particularly Cl or F. In certain embodiments of formula III, $R^3$ is a lower alkyl. In certain embodiments of formulae I-III, $R^2$ is a heteroaryl, particularly pyrrolyl, and especially pyrrol-2-yl; and $R^1$ is a halogen, particularly Cl or F. In certain embodiments of formula III, R2 is a heteroaryl, particularly pyrrolyl, and especially pyrrol-2-yl; $R^1$ is a halogen, particularly Cl or F; and $R^3$ is a lower alkyl.

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure —ROR, wherein R is an alkyl group.

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "derivative" refers to a compound or portion of a compound that is derived from or is theoretically derivable from a parent compound.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

In some embodiments relating to a small molecule inhibitor that binds RUNX1, the small molecule inhibitor comprises Ro5-3335, Ro24-7429, NSC140873, MLS000548294, MLS001048862, or NSC156594. See, e.g., Cunningham et al. (2012) Proc Natl Acad Sci USA, 109(36): 14592-14597,Haubrich, R. et al., J Infect Dis 172(5): 1246-52, and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141,735; 5,041,438; 5,036,101; and 3,405,122, as well as U.S. Patent Application Publication No. 2014/0004082, the entire contents of each of which are hereby incorporated herein by reference.

Ro5-3335 has the following structure:

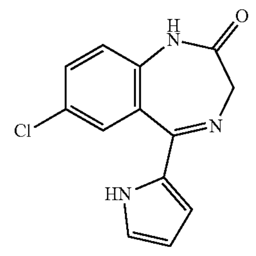 [SMILES: O=C1CN=C(c2ccc[nH]2)c2cc(Cl)ccc2N1]

The CAS Registry Number for Ro5-3335 is 30195-30-3.

Ro24-7429 has the following structure:

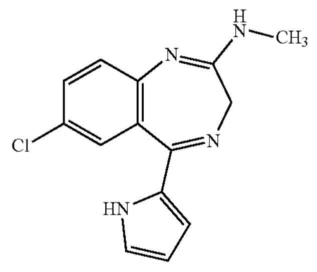 [SMILES: CNC1=Nc2ccc(Cl)cc2C(c2ccc[nH]2)=NC1]

The CAS Registry Number for Ro24-7429 is 13939-45-0.

NSC140873 has the following structure:

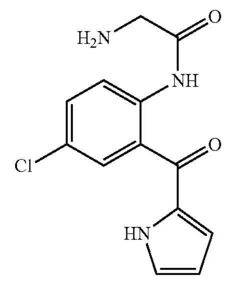 [SMILES: NCC(=O)Nc1ccc(Cl)cc1C(=O)c1ccc[nH]1]

The CAS Registry Number for NSC140873 is 106410-13-3.

MLS000548294 has the following structure:

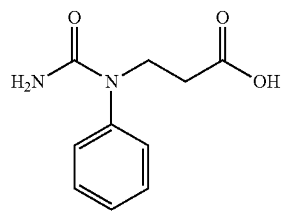 [SMILES: NC(=O)N(CCC(=O)O)c1ccccc1]

The PubChem ID for MLS000548294 is 768985.

MLS001048862 has the following structure:

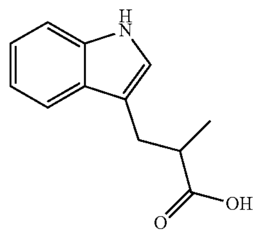

The PubChem ID for MLS001048862 is 2772042.

NSC156594 has the following structure:

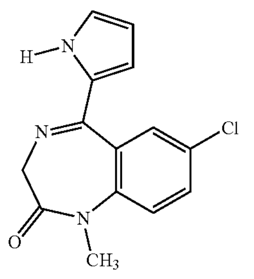 [SMILES: CN1C(=O)CN=C(c2ccc[nH]2)c2cc(Cl)ccc21]

The PubChem ID for NSC156594 is 457993.

The synthesis of several of the compounds disclosed above and analogs thereof have been previously described, for example, in U.S. Pat. Nos. 5,641,773; 5,164,376; 5,141,735: 5,041,438; 5,036,101; and 3,405,122, the entire contents of each of which are incorporated herein by reference.

In some embodiments, the RUNX1 inhibitor inhibits RUNX1 via inhibition of CBFβ, which is the transcriptional partner of RUNX1.

Non-limiting examples of CBFβ inhibitors include:

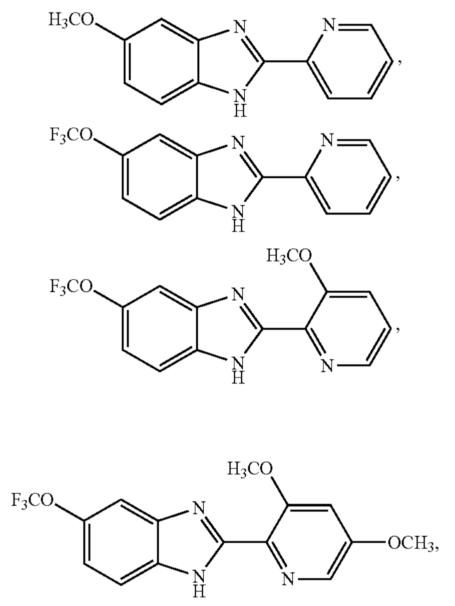

-continued

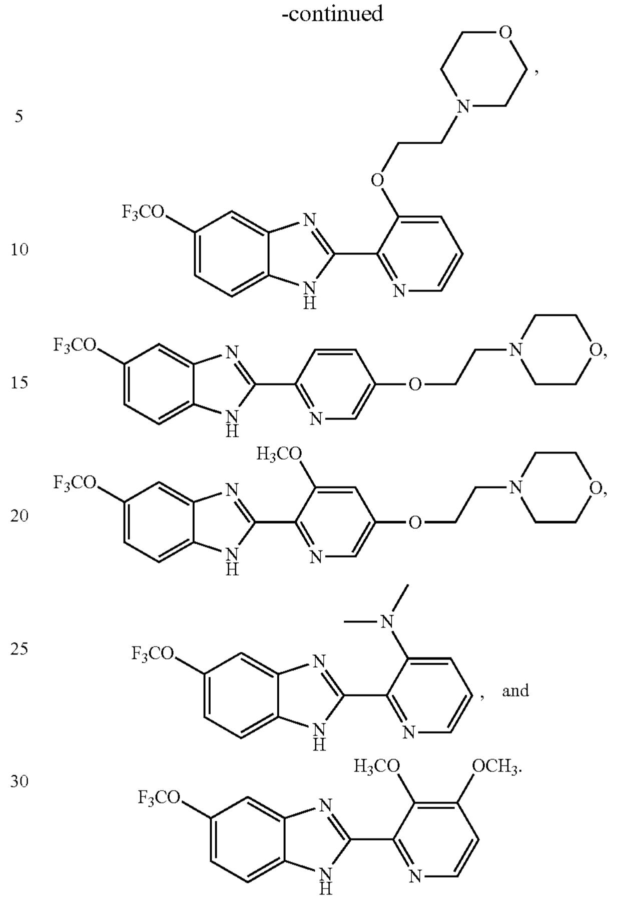

and

Non-limiting descriptions of CBFβ inhibitors and aspects thereof are described in Illendula et al. (2016) *EBioMedicine* 8: 117-131, the entire content of which is incorporated herein by reference. In some examples, the inhibitor comprises a pyridyl benzimidazole.

Proteins and Peptides

In some embodiments, a protein, peptide, or a fragment thereof is used to inhibit RUNX1. A non-limiting example of such an inhibitor for RUNX1 is a dominant negative CBF-Beta protein (CBFB-MYH11). See, e.g., Castilla et al. (1996) *Cell.* 1996;87:687-696, the entire content of which is hereby incorporated herein by reference.

RNA

In some embodiments, a RNA is used to encode a protein that inhibits RUNX1 or the RNA itself has inhibitory properties.

Aptamers

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are have a relatively low molecular weight. Peptide-based aptamers are generally less than thirty residues long while nucleotide-based aptamers are typically less than one hundred residues long.

Non-limiting examples of methods that are useful for designing aptamers that target a particular protein, such as RUNX1, are described in U.S. Pat. Nos. 8,484,010; 5,582,981: PCT International Patent Application No. WO 2015/049356; Blackwell et al., (1993) Science 250:1104-1110;

Blackwell, et al., (1990) Science 250:1149-1152; Tuerk and Gold (1990) Science 249:505-510; and Joyce (1989) Gene 82:83-87, the entire contents of each of which are incorporated herein by reference.

Antisense Oligonucleotides

As used herein, an "antisense oligonucleotide" is an oligonucleotide that inhibits gene expression by a mechanism other than RNAi. Non-limiting examples of antisense oligonucleotides which decrease the amount of RUNX1 produced by cells that can be employed in the methods described herein include antisense oligonucleotides that are complementary (e.g., at least about 90, 95, 96, 97, 98, 99, or 100% complementary) to a stretch of at least about 10, 11, 12, 13, 14, 15, 16, 17, 18, 19, 20, 21, 22, 23, 24, 25. 26, 27, 28, 29 or 30 consecutive nucleotides having a sequence found within a nucleotide sequence that encodes RUNX1, such as any of the RUNX1-encoding nucleotide sequences disclosed herein.

Antisense oligonucleotides comprise nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of RUNX1 gene products in the cell.

Antisense oligonucleotides can comprise deoxyribonucleotides, ribonucleotides, or a combination of both. Antisense oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Antisense oligonucleotides that target the transcription initiation site, e.g., between positions −10 and +10 from the start site, are used in some embodiments. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). Antisense oligonucleotides that are complementary to a sequence that includes the translational start site, and/or that are complementary to a portion of a target mRNA within 10 nucleotides of the translational start site, are used in various embodiments. An antisense oligonucleotide also can be designed to block translation of mRNA by preventing the transcript from binding to ribosomes.

Precise complementarity is not required for successful complex formation between an antisense oligonucleotide and the complementary sequence of a RUNX1 polynucleotide. Antisense oligonucleotides which comprise, for example, 2, 3, 4, or 5 or more stretches of contiguous nucleotides which are precisely complementary to a RUNX1, each separated by a stretch of contiguous nucleotides which are not complementary to adjacent RUNX1 nucleotides, can provide sufficient targeting specificity for RUNX1 mRNA. In some embodiments, each stretch of complementary contiguous nucleotides is at least 4, 5, 6, 7, or 8 or more nucleotides in length. Noncomplementary intervening sequences may be, e.g., 1, 2, 3, or 4 nucleotides in length. One skilled in the art can easily use the calculated melting point of an antisense-sense pair to determine the degree of mismatching which will be tolerated between a particular antisense oligonucleotide and a particular RUNX1 polynucleotide sequence. Antisense oligonucleotides can be modified without affecting their ability to hybridize to a RUNX1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3' or 5'-substituted oligonucleotide in which the 3' hydroxyl group and/or the 5' phosphate group is substituted, also can be employed in a modified antisense oligonucleotide. These modified antisense oligonucleotides can be prepared by methods well known in the art.

Ribozymes

Ribozymes are RNA molecules with catalytic activity (Uhlmann et al., 1987, Tetrahedron. Lett. 215, 3539-3542). Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a polynucleotide can be used to generate ribozymes which will specifically bind to mRNA transcribed from the polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an RNA target can be identified by scanning the target molecule for ribozyme cleavage sites which include the following sequences: QUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate RNA targets also can be evaluated by testing accessibility to hybridization with complementary oligonucleotides using ribonuclease protection assays. The nucleotide sequences shown in SEQ ID NOs: 1-26 and their complements provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease RUNX1 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

RNA Interference

As used herein, an "RNA interference" inducing compound refers to a compound capable of inducing RNA interference or "RNAi" of target gene (e.g., RUNX1) expression, depending on the context. RNAi involves mRNA degradation. The use of RNAi has been described in Fire et al. (1998) Nature 19;391(6669):806-11. Elbashir et al. (2001) EMBO J. 20(23): 6877-6888, and Cheloufi et al. (2010) Nature 465, 584-589, the entire contents of each of which are incorporated herein by reference.

Isolated RNA molecules can mediate RNAi. That is, the isolated RNA molecules of the present subject matter mediate degradation or block expression of mRNA that is the transcriptional product of the gene, which is also referred to as a target gene. For convenience, such mRNA may also be referred to herein as mRNA to be degraded. RNAi molecules may be, e.g., double-stranded RNA, small interfering RNA (siRNA), hairpin RNA. microRNA molecules which may be altered compared to naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules may be referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In some embodiments, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA. In some embodiments, an RNAi molecule comprises a stretch of about 16 to 29, 18 to 23, 21-23, or at least 12, 13, 14, 15, 16, 17, 18, 19, 20, 21, 22, 23, 24, or 25 nucleotides having a sequence that is at least about 90. 95, 96, 97, 98, 99, or 100% complementary to a target sequence. As noted above, the RNA molecules of the present invention may comprise an RNA portion and some additional portion, for example a deoxyribonucleotide portion.

Antibodies

In some embodiments, the RUNX1 inhibitor is an antibody or a fragment thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimerie, single chain, $F_{ab}$, $F_{ab'}$ and $F_{(ab')2}$ fragments, an Fab expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d>10^{-6}$) with other polypeptides.

An "antibody fragment" refers to a molecule other than an intact antibody that comprises a portion of an intact antibody that binds the antigen to which the intact antibody binds. The terms "full length antibody." "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al ., Proc . Natl. Acad. Sci. USA, 90:6444-6448 (1993).

The expression "linear antibodies" refers to the antibodies described in Zapata et al., Protein Eng. 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci. such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 μM; preferably ≤100 nM and most preferably ≤10 nM.

Antibodies can be produced according to any method known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally. either peripheral blood lymphocytes ("PBLs") are used if cells of human origin are desired. or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, Fab, Fats, Fiabe or other antigen-binding subsequences of antibodies) which contain minimal sequence derived from non-human immunoglobulin.

Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeven et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art. including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement. assembly, and antibody repertoire. This approach is described, e.g., in U.S. Pat. Nos. 5,545,807: 5.545,806; 5,569,825; 5,625,126: 5,633,425; 5,661,016, and in the following scientific publications: Marks et al. 1992. Bio/Technology 10:779-783; Lonberg et al. 1994. Nature 368:856-859; Morrison. 1994. Nature 368:812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

In some embodiments, an intrabody is used to inhibit RUNX1. An "intrabody" (from intracellular and antibody) is an antibody that works within the cell to bind to an intracellular antigen. Intrabodies typically lack disulfide bonds and are capable of modulating the expression or activity of target genes through their specific binding activity. Intrabodies include single domain fragments such as isolated VH and VL domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions. In various embodiments, the intrabody is expressed within a target cell, e.g., by a viral or plasmid expression vector that has been introduced into the target cell. An intrabody may remain in the cytoplasm, or it may have a nuclear localization signal, or it may undergo cotranslational translocation across the membrane into the lumen of the endoplasmic reticulum, provided that it is retained in that compartment through a KDEL sequence. Because antibodies ordinarily are designed to be secreted from the cell, intrabodies require special alterations, including the use of single-chain antibodies (scFvs), modification of immunoglobulin VL domains for hyperstability, selection of antibodies resistant to the more reducing intracellular environment, or expression as a fusion protein with maltose binding protein or other stable intracellular proteins. Non-limiting aspects of intrabodies are described, e.g., in U.S. Pat. No. 9.133,269; U.S. Patent Application Publication No. 2006/0034834; Chen et al. (1994) Human gene therapy 5 (5): 595-601; and Shaki-Loewenstein et al. (2005) Journal of immunological methods 303 (1-2): 19-39, the entire contents of each of which are incorporated herein by reference.

Exemplary antibodies against RUNX1 include, but are not limited to, antibodies obtained from Abcam (Cambridge, MA, USA) (e.g., Cat. Nos. ab23980, ab35962, ab 189172, ab 189153, and ab91002), antibodies obtained from Novus Biologicals (Littleton, CO, USA) (e.g., Cat. Nos. NBP1-89105, H00000861-M05, H00000861-M06, MAB2399, and H00000861-M02), and antibodies obtained from ThermoFisher Scientific (Cambridge, MA, USA) (e.g., 710233, MAS-15814, PA 1-41078, OSR00271W, PAS-17434, PAS-19638, PAS-12409, PA5-40076, and PAS-17351).

Gene Therapy

In some embodiments, a gene editing method is used to modulate (e.g., reduce) RUNX1 expression and/or activity. Non-limiting examples of gene editing systems useful in such embodiments include the clustered regularly interspaced short palindromic repeat (CRISPR)-Cas system; zinc finger nuclease (ZFN) systems, and transcription activator-like effector-based nuclease (TALEN) systems.

Exemplary aspects of the CRISPR-Cas system are described in, e.g., U.S. Pat. No. 9,023,649, issued May 5, 2015; U.S. Pat. No. 9,074,199, issued Jul. 7, 2015; and U.S. Pat. No. 8,697,359, issued Apr. 15, 2014 the entire contents of each of which are incorporated herein by reference.

With their highly flexible but specific targeting, CRISPR-Cas systems can be manipulated and redirected to become powerful tools for genome editing. CRISPR-Cas technology permits targeted gene cleavage and gene editing in a variety of eukaryotic cells, and editing can be directed to virtually any genomic locus. Exemplary CRISPR Cas genes include Cas1, Cas2, Cas3', Cas3", Cas4, Cas5, Cas6, Cas6e (formerly referred to as CasE, Cse3), Cas6f (i.e., Csy4), Cas7, Cas8a1, Cas8a2, Cas8b, Cas8c, Cas9, Cas10, Cas10d, Csy1, Csy2, CPf1, Csy3, Cse1, Cse2, Cse1, Cse2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf11, Csf2, Csf3, and Csf4. These enzymes are known; for example, the amino acid sequence of *Streptococcus pyogenes* Cas9 protein may be found in the SwissProt database under accession number Q99ZW2.

Other non-limiting examples of approaches for gene editing include the use of zinc finger nucleases, which are artificial restriction enzymes generated by fusing a zinc finger DNA-binding domain to a DNA-cleavage domain. A zinc finger nuclease is a site-specific endonuclease designed to bind and cleave DNA at specific positions. There are two protein domains. The first domain is the DNA binding domain, which consists of eukaryotic transcription factors and contain the zinc finger. The second domain is the nuclease domain, which consists of the Fokl restriction enzyme and is responsible for the catalytic cleavage of DNA. The DNA-binding domains of individual ZFNs typically contain between three and six individual zinc finger repeats and can each recognize between 9 and 18 basepairs. If the zinc finger domains are perfectly specific for their intended target site then even a pair of 3-finger ZFNs that recognize a total of 18 basepairs can, in theory, target a single locus in a mammalian genome. Various strategies have been developed to engineer Cys2His2 zinc fingers to bind desired sequences. These include both "modular assembly" and selection strategies that employ either phage display or cellular selection systems. The most straightforward method to generate new zinc-finger arrays is to combine smaller zinc-finger "modules" of known specificity. The most common modular assembly process involves combining three separate zinc fingers that can each recognize a 3 basepair DNA sequence to generate a 3-finger array that can recognize a 9 basepair target site. Other procedures can utilize either 1-finger or 2-finger modules to generate zinc-finger arrays with six or more individual zinc fingers. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells. The non-specific cleavage domain from the type IIs restriction endonuclease FoKI is typically used as the cleavage domain in ZENs. This cleavage domain must dimerize in order to cleave DNA and thus a pair of ZENs are required to target non-palindromic DNA sites. Standard ZENs fuse the cleavage domain to the C-terminus of each zinc finger domain. In order to allow the two cleavage domains to dimerize and cleave DNA, the two individual ZENs must bind opposite strands of DNA with their C-termini a certain distance apart. The most commonly used linker sequences between the zinc finger domain and the cleavage domain requires the 5' edge of each binding site to be separated by 5 to 7 bp.

TALENs are restriction enzymes that can be engineered to cut specific sequences of DNA. They are made by fusing a TAL effector DNA-binding domain to a DNA cleavage domain. Transcription activator-like effectors (TALEs) can be engineered to bind practically any desired DNA sequence. so when combined with a nuclease, DNA can be cut at specific locations. The restriction enzymes can be introduced into cells, for use in gene editing or for genome editing in situ. Alongside zinc finger nucleases and CRISPR/Cas9, TALEN is a prominent tool in the field of genome editing.

NOTCH Signaling Inhibition

Notch signaling is an upstream regulator of the expression of Runx genes (Burns CE, et al., Genes and Development, 2005, 19:2331-2342). Modalities for preventing or reducing proliferation or migration of RPE cells is based on inhibition of the Notch receptors (Notch 1, Notch 2, Notch 3, Notch 4) and its ligands (Delta like 1, Delta like 2, Delta like 5, Jagged 1 and Jagged 2) or other modulators of the Notch pathway operate via regulation of RUNX1. These modalities of treatment include inhibition of gamma-secretase, modulating antibodies against the receptors and the ligands, and other small molecules, biologicals and genetic approaches that inhibit RUNX1 expression via modulation of Notch signaling activity.

In some embodiments, NOTCH signaling is modulated to reduce RUNX1 function. For example, a NOTCH inhibitor is used to reduce RUNX1 expression or activity. Non-limiting examples of NOTCH inhibitors include aptamers, oligonucleotides (e.g., antisense oligonucleotides, ribozymes, and RNAi molecules), peptides (e.g., a portion of or the entire extracellular domain of a NOTCH protein), antibodies, antibody fragments, and small molecules that specifically bind to a NOTCH protein or a polynucleotide that encodes a NOTCH protein. Non-limiting examples of small molecule inhibitors for NOTCH proteins include compounds having the following structures:

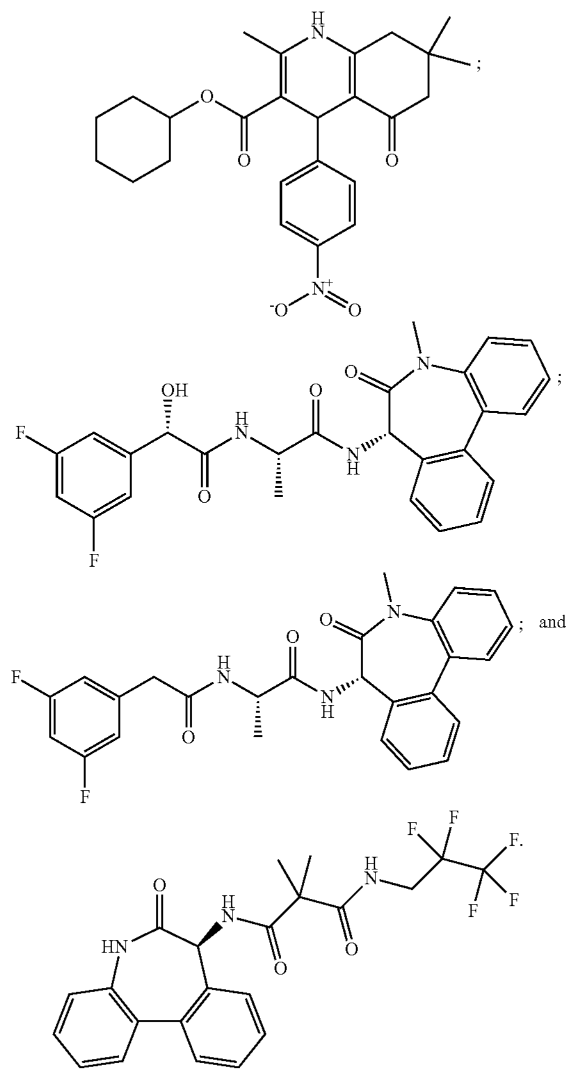

Additional non-limiting examples of NOTCH inhibitors (as well as aspects of NOTCH signaling) are described in Espinoza and Miele, *Pharmacol Ther.* 2013,139(2): 95-110;

and Yuan et al., *Cancer Letters* 2015, 369(1) 20-27, the entire contents of each of which are incorporated herein in their entireties.

Immunomodulatory Imide Drug (IMID) Inhibitors

In some examples, the RUNX1 inhibitor comprises an immunomodulatory imide drug (IMiD). IMiDs are a class of immunomodulatory drugs containing an imide group. In non-limiting examples, the IMID includes thalidomide and its analogs, e.g., lenalidomide, pomalidomide, and apremilast.

In various embodiments, the IMiD comprises:

(Formula IV)

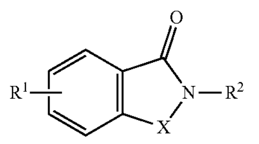

or pharmaceutically acceptable salts or esters thereof, wherein:

$R^1$=H, $NH_2$, $NHC(O)CH_3$

X=$CH_2$, C(O)

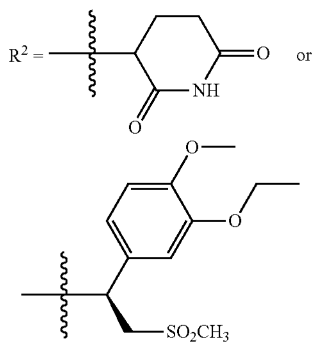

or

For example, Formula IV encompasses lenalidomide, pomalidomide, thalidomide, and/or apremilast.

(Formula V)

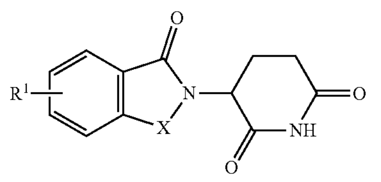

or pharmaceutically acceptable salts or esters thereof, wherein:

$R^1$=H, $NH_2$, $NHC(O)CH_3$

X=$CH_2$, C(O)

For example, Formula V encompasses lenalidomide, pomalidomide, and/or anthalidomide.

In some examples, the IMID is lenalidomide. The IUPAC name for lenalidomide is 3-(7-amino-3-oxo-1H-isoindol-2-yl)piperidine-2,6-dione. The CAS Registry Number for lenalidomide is 191732-72-6.

Lenalidomide has the following structure:

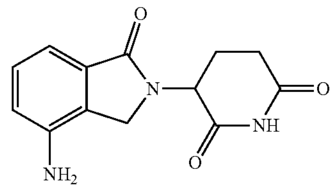 [SMILES: Nc1cccc2c1CN(C1CCC(=O)NC1=O)C2=O]

In some examples, the IMiD is thalidomide. The IUPAC name for thalidomide is 2-(2,6-dioxopiperidin-3-yl)isoindole-1,3-dione. The CAS Registry Number for thalidomide is 50-35-1.

Thalidomide has the following structure:

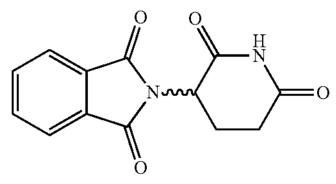 [SMILES: O=C1CCC(N2C(=O)c3ccccc3C2=O)C(=O)N1]

In some examples, the IMID is pomalidomide. The IUPAC name for pomalidomide is 4-amino-2-(2,6-dioxopiperidin-3-yl)isoindole-1,3-dione. The CAS Registry Number for pomalidomide is 19171-19-8.

Pomalidomide has the following structure:

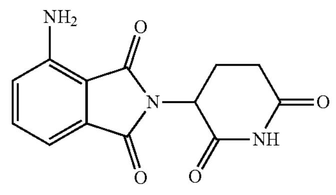 [SMILES: Nc1cccc2c1C(=O)N(C1CCC(=O)NC1=O)C2=O]

In some examples, the IMID is apremilast. The IUPAC name for apremilast is N-[2-[(1S)-1-(3-ethoxy-4-methoxyphenyl)-2-methylsulfonylethyl]-1,3-dioxoisoindol-4-yl]acetamide. The CAS Registry Number for apremilast is 608141-41-9.

Apremilast has the following structure:

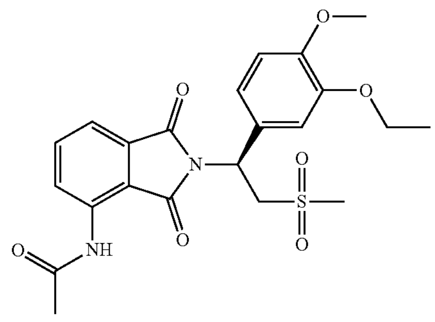 [SMILES: CCOc1cc([C@@H](CS(C)(=O)=O)N2C(=O)c3cccc(NC(C)=O)c3C2=O)ccc1OC]

In other examples, the IMiD comprises phosphodiesterase type 4 (PDE4) inhibitor, e.g., rolipram The IUPAC name for rolipram is 4-(3-cyclopentyloxy-4-methoxyphenyl)pyrrolidin-2-one. The CAS Registry Number for rolipram is 61413-54-5.

Rolipram has the following structure:

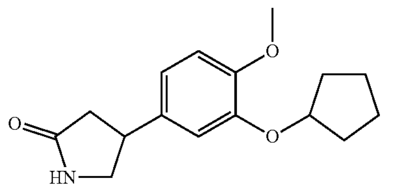 [SMILES: COc1ccc(C2CNC(=O)C2)cc1OC1CCCC1]

The RUNX1 inhibitors may have one or more chiral centers, and thus can exist as one or more stereoisomers. Such stereoisomers can exist as a single enantiomer, a mixture of enantiomers, a mixture of diastereomers, or a racemic mixture.

As used herein, the term “stereoisomers” refers to compounds made up of the same atoms having the same bond order but having different three-dimensional arrangements of atoms that are not interchangeable. The three-dimensional structures are called configurations. As used herein, the term “enantiomers” refers to two stereoisomers that are non-superimposable mirror images of one another. As used herein, the term “optical isomer” is equivalent to the term “enantiomer”. As used herein the term “diastereomer” refers to two stereoisomers which are not mirror images but also not superimposable. The terms “racemate”, “racemic mixture” or “racemic modification” refer to a mixture of equal parts of enantiomers. The term “chiral center” refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., “Enantiomers, Racemates, and Resolutions”, John Wiley and Sons, Inc. 1981).

Pharmaceutical Formulations and Delivery

Dosages, formulations, dosage volumes, regimens, and methods for administering a RUNX1 inhibitor may vary. Thus, minimum and maximum effective dosages vary depending on the method of administration.

“Administering” an inhibitor described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. Topical administration also includes administration of the inhibitor(s) by eye drop, e.g., contacting the surface of the eye with a liquid (aqueous, lipid, or combination thereof) or gel formulation. In other embodiments, administration is carried by injection. e.g., using a needle, or via a catheter.

As used herein, “effective” when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, “pharmaceutically acceptable” carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

As used herein, a “monotherapy” is therapy that is administered to inhibit, treat, or prevent a disorder, such as proliferation or migration of retinal pigment epithelial (RPE) in a subject who comprise a retinal hole or a retinal tear, such as found in PVR), without any other therapy that is used to treat the disorder. A monotherapy for treating a disorder may optionally be combined with another treatment that is used to ameliorate a symptom of the disorder while not being directed against the disorder, for example an analgesic compound. an antipyretic compound, and/or an anti-inflammatory compound (e.g., aspirin, ibuprofen, naproxen, or acetaminophen) may be administered concurrently with the monotherapy. In various embodiments of the invention, a composition comprising a RUNX1 inhibitor may be administered only once or multiple times. For example, a RUNX1 inhibitor may be administered using a method disclosed herein at least about once, twice, three times, four times, five times, six times, or seven times per day, week, month, or year. In some embodiments, a composition comprising a RUNX1 inhibitor is administered once per month. In certain embodiments, the composition is administered once per week, once every two weeks, once a month via intravitreal injection. In various embodiments, such as embodiments involving eye drops, a composition is self-administered.

For the treatment of an ocular disorder, a RUNX1 inhibitor (e.g., a pharmaceutical composition comprising a RUNX1 inhibitor) may be administered locally, e.g., as a topical eye drop, peri-ocular injection (e.g., sub-tenon), intraocular injection, intravitreal injection, retrobulbar injection, intraretinal injection, subretinal injection, suprachoroidal. subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils. For treatments of the eye or other external tissues, such as the mouth or skin, the formulations (e.g., a pharmaceutical composition comprising a RUNX1 inhibitor) may be applied as a topical ointment or cream. When formulated in an ointment, a RUNX1 inhibitor may be employed with either a paraffinic or a water-miscible ointment base. Alternatively, a RUNX1 inhibitor may be formulated in a cream with an oil-in-water cream base or a water-in-oil base.

The present subject matter provides compositions comprising a RUNX1 inhibitor and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio. 20) Pharmaceutical formulations adapted for topical administrations to the eye include eye drops wherein a RUNX1 inhibitor is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations of the present invention may be in the form of liquid, solid or semisolid dosage form. The ophthalmic formulations of the present invention may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition of the invention, including acids such as acetic, boric, citric, lactic, phosphoric, and hydrochloric acids: bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC). methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a RUNX1 inhibitor (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D),L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3: 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164, 188; 5,443,505; 5,501,856: 5.766,242; 5,824,072; 5,869,079: 6,074.661; 6,331,313: 6.369,116; 6,699,493; and 8,293,210, the entire contents of each of which are incorporated herein by reference.

The implants may be monolithic, i.e. having the active agent (e.g., a RUNX1 inhibitor) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a RUNX1 inhibitor, may be distributed in a non-homogenous pattern in the matrix. For example, the implant may include a portion that has a greater concentration of a RUNX1 inhibitor relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 g. For example, an implant may be about 500 ug. or about 1000 ug. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 nim and the fiber length will generally be in the range of about 0.5-10 mm. Spheres may be in the range of 0.5 um to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4, 556,552; 4,309,404; and 4,309,406, the entire contents of each of which are incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C:" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg. 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds, e.g., nucleic acid molecules, polynucleotides, polypeptides, proteins, or small molecules are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally- occurring state. Similarly, a purified peptide or protein (e.g., identified by a specific amino acid sequence) is free of the amino acids that flank it in its naturally-occurring state. Purified also defines a degree of sterility that is safe for administration to a human subject, e.g ., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising." which is synonymous with "including." "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a buman.

As used herein, the singular forms "a," "an." and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression of a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g ., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W. T. and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989) alignments (B) of 50, expectation (E) of 10, M=5, N=−4, and a comparison of both strands.

A "control" sample or value refers to a sample that serves as a reference, usually a known reference, for comparison to a test sample. For example, a test sample can be taken from a test subject, e.g., a subject in need of diagnosis for a disease, and compared to samples from known conditions, e.g., a subject (or subjects) that does not have the disease (a negative or normal control), or a subject (or subjects) who does have the disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein) refers to a normal amount of the protein in an individual known not to be diagnosed with a disease that comprises increased proliferation or migration of RPE cells in a subject who comprises a retinal hole or retinal tear. The amount of a protein can be measured in a test sample and compared to the "normal control" level, utilizing techniques such as reference limits, discrimination limits, or risk defining thresholds to define cutoff points and abnormal values (e.g., for a particular retinal detachment complication or a symptom thereof). The normal control level means the level of one or more proteins or combined protein indices typically found in a subject known not suffering from a disease that comprises increased proliferation or migration of RPE cells in a subject who comprises a retinal hole or retinal tear. Such normal control levels and cutoff points may vary based on whether a protein is used alone or in a formula combining with other proteins into an index. Alternatively, the normal control level can be a database of protein patterns from previously tested subjects who did not develop increased proliferation or migration of RPE cells (in a subject also comprising a retinal hole or retinal tear) or a particular symptom thereof (e.g., in the event the disease develops or a subject already having the disease is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein level) refers to any % increase above a control level. In various embodiments, the increased level may be at least or about a 5% increase, at least or about a 10% increase, at least or about a 15% increase, at least or about a 20% increase, at least or about a 2.5% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level Relative to a control level, the level that is determined may a decreased level. As used herein, the term "decreased" with respect to level (e.g., protein level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

"Risk" in the context of the present disclosure, relates to the probability that an event will occur over a specific time period, as in the development of a neovascularization disorder or a symptom thereof, and can mean a subject's "absolute" risk or "relative" risk. In various embodiments, a "high risk" subject is a subject who is likely to develop a disease that comprises increased proliferation or migration of RPE cells in a subject who comprises a retinal hole or retinal tear or a symptom thereof within, e.g., about 1, 2, 3, 4, or 5 years. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used [odds are according to the formula p/(1-p) where p is the probability of event and (1-p) is the probability of no event] to no-conversion.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EMT

Epithelial-mesenchymal transition (EMT) is characterized by a loss of cell adhesion, which leads to constriction and extrusion of new mesenchymal cells. EMT is a process by which epithelial cells lose their cell polarity and cell-cell adhesion, and gain migratory and invasive properties to become mesenchymal stem cells (which are multipotent stromal cells that can differentiate into a variety of cell types. EMT is essential for numerous developmental processes including mesoderm formation and neural tube formation. EMT has also been shown to occur in wound healing, in organ fibrosis and in the initiation of metastasis in cancer progression. EMT, and its reverse process, MET (mesenchymal-epithelial transition) are critical for development of many tissues and organs in the developing embryo, and numerous embryonic events such as gastrulation, neural crest formation, heart valve formation, palatogenesis and myogenesis. Epithelial cells are closely connected to each other by tight junctions, gap junctions and adherens junctions, have an apico-basal polarity, polarization of the actin cytoskeleton and are bound by a basal lamina at their basal surface. Mesenchymal cells, on the other hand, lack this polarization, have a spindle-shaped morphology and interact with each other only through focal points. Epithelial cells express high levels of E-cadherin, whereas mesenchymal cells express those of N-cadherin, fibronectin and vimentin. Thus, EMT entails profound morphological and phenotypic changes to a cell. Based on the biological context, EMT has been categorized into 3 types: developmental (Type I), fibrosis and wound healing (Type II), and cancer (Type III).

Loss of E-cadherin is a fundamental event in EMT. Many transcription factors (TFs) that can repress E-cadherin directly or indirectly are considered as EMT-TF (EMT inducing TFs). SNAI1/Snail 1, SNAI2/Snail 2 (also known as Slug or Zinc finger protein), Zinc finger E-box binding homeobox 1 and 2 (ZEB1 and ZEB2), transcription factor 3 (TCF3) and krueppel-like factor 8 (KLF8) can bind to the E-cadherin promoter and repress its transcription, whereas factors such as Twist (also referred to as class A basic helix-loop-helix protein 38: bHLHa38), Goosecoid, transcription factor 4 (TCF4), homeobox protein Sineoculis homeobox homolog 1 (SIX1) and fork-head box protein C2 (FOXC2) repress E-cadherin indirectly.

Several signaling pathways (transforming growth factor beta (TGF-β), fibroblast growth factor (FGF), epidermal growth factor (EGF), hepatocyte growth factor (HGF), Wnt/beta-catenin and Notch) and hypoxia may induce EMT. In particular, Ras-MAPK (mitogen-activated protein kinases) activates Snail and Slug. Slug triggers the steps of desmosomal disruption, cell spreading, and partial separation at cell-cell borders, which comprise the first and necessary phase of the EMT process.

Wnt signaling pathway regulates EMT in gastrulation, cardiac valve formation and cancer. Activation of Wnt pathway in breast cancer cells induces the EMT regulator SNAIL and upregulates the mesenchymal marker, vimentin. Also, active Wnt/beta-catenin pathway correlates with poor prognosis in breast cancer patients in the clinic. Similarly, TGF-β activates the expression of SNAIL and ZEB to regulate EMT in heart development, palatogenesis, and cancer. The breast cancer bone metastasis has activated TGF-β signaling, which contributes to the formation of these lesions. However, on the other hand, tumor protein 53 (p53), a well-known tumor suppressor, represses EMT by activating the expression of various microRNAs—miR-200 and miR-34 that inhibit the production of protein ZEB and SNAIL, and thus maintain the epithelial phenotype.

After the initial stage of embryogenesis, the implantation of the embryo and the initiation of placenta formation are associated with EMT. The trophoectoderm cells undergo EMT to facilitate the invasion of endometrium and appropriate placenta placement, thus enabling nutrient and gas exchange to the embryo. Later in embryogenesis, during gastrulation. EMT allows the cells to ingress in a specific area of the embryo—the primitive streak in amniotes, and the ventral furrow in Drosophila. The cells in this tissue express E-cadherin and apical-basal polarity.

During wound healing, keratinocytes at the border of the wound undergo EMT and undergo re-epithelialization or MET when the wound is closed. Snail2 expression at the migratory front influences this state, as its overexpression accelerates wound healing. Similarly, in each menstrual cycle, the ovarian surface epithelium undergoes EMT during post-ovulatory wound healing.

Initiation of metastasis requires invasion, which is enabled by EMT. Carcinoma cells in a primary tumor lose cell-cell adhesion mediated by E-cadherin repression and break through the basement membrane with increased invasive properties, and enter the bloodstream through intravasation. Later, when these circulating tumor cells (CTCs) exit the bloodstream to form micro-metastases, they undergo MET for clonal outgrowth at these metastatic sites. Thus, EMT and MET form the initiation and completion of the invasion-metastasis c ascade. At this new metastatic site, the tumor may undergo other processes to optimize growth. For example, EMT has been associated with programmed death ligand 1 (PD-L1) expression, particularly in lung cancer. Increased levels of PD-L1 suppresses the immune system which allows the cancer to spread more easily.

EMT has been shown to be induced by androgen deprivation therapy in metastatic prostate cancer. Activation of EMT programs via inhibition of the androgen axis provides a mechanism by which tumor cells can adapt to promote disease recurrence and progression. Brachyury, Axl (tyrosine protein kinase receptor UFO), MEK, and Aurora kinase A are molecular drivers of these programs, and inhibitors are currently in clinical trials to determine therapeutic applications. Oncogenic protein kinase C iota type (PKC-jota) can promote melanoma cell invasion by activating Vimentin during EMT. PKC-iota inhibition or knockdown resulted an increase E-cadherin and ras homolog gene family. member A (RhoA) levels while decreasing total Vimentin, phophorylated Vimentin (S39) and partitioning defective 6 homolog alpha (Par6) in metastatic melanoma cells. Cells that undergo EMT gain stem cell-like properties, thus giving rise to Cancer Stem Cells (CSCs).

In addition to the treatment of PVR, the compositions and methods described herein can be used for the treatment and prevention of Epithelial-mesenchymal transition (EMT)-associated diseases. For example, EMT-associated diseases comprise pathological ocular fibrosis and pathological ocular proliferation. Additional diseases and conditions are described by Masoumpour, M. et al., in a journal article entitled, "Current and Future Techniques in Wound Healing Modulation after Glaucoma Filtering Surgeries" *The Open Ophthalmology Journal,* 2016 (10); 68-85, incorporated herein by reference in its entirety. Other exemplary EMT-associated diseases are described in an article by Friedlander. M., entitled, "Fibrosis and diseases of the eye" *The Journal of Clinical Investigation* 117(3): 576-586 (2007), incorporated herein by reference in its entirety. For example, the article describes diseases in the anterior segment of the eye (e.g., corneal opacification and glaucoma), dystrophies, herpetic keratitis, inflammation (e.g., pterygiun), macula edema, retinal and vitreous hemorrhage, fibrovascular scarring, neovascular glaucoma, age-related macular degeneration (ARMD), diabetic retinopathy (DR), retinopathy of prematurity (ROP), subretinal fibrosis, epiretinal fibrosis, and gliosis.

Example 1: Expression of RUNX1 in Cells Derived from Human PVR Membranes (C-PVR)

Figure 5B:
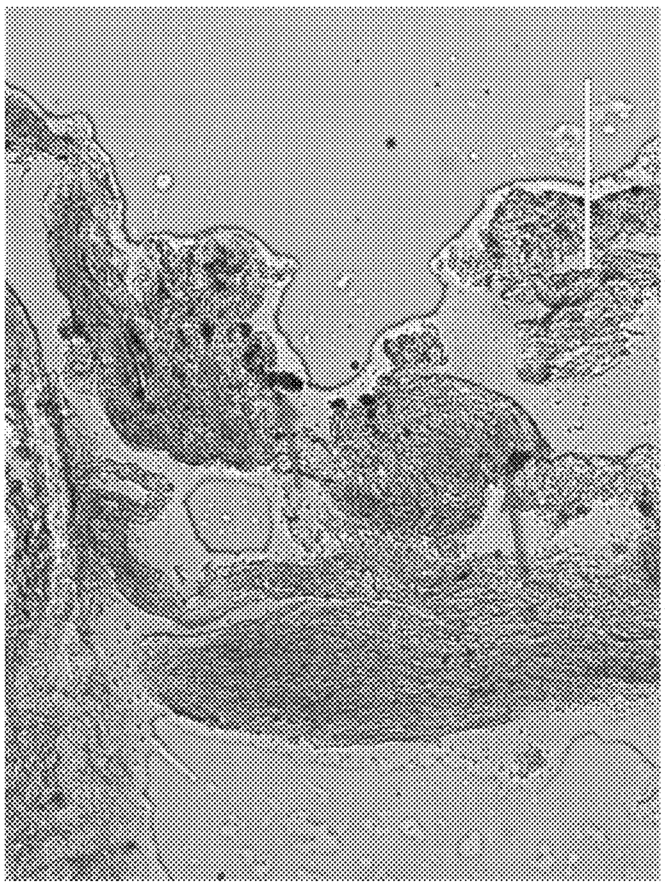
FIG. 5B is an image depicting the immunohistochemical staining of human PVR membranes of RUNX1, counterstained with hematoxylin in membranes obtained from patients with PVR.
Figure 5A:
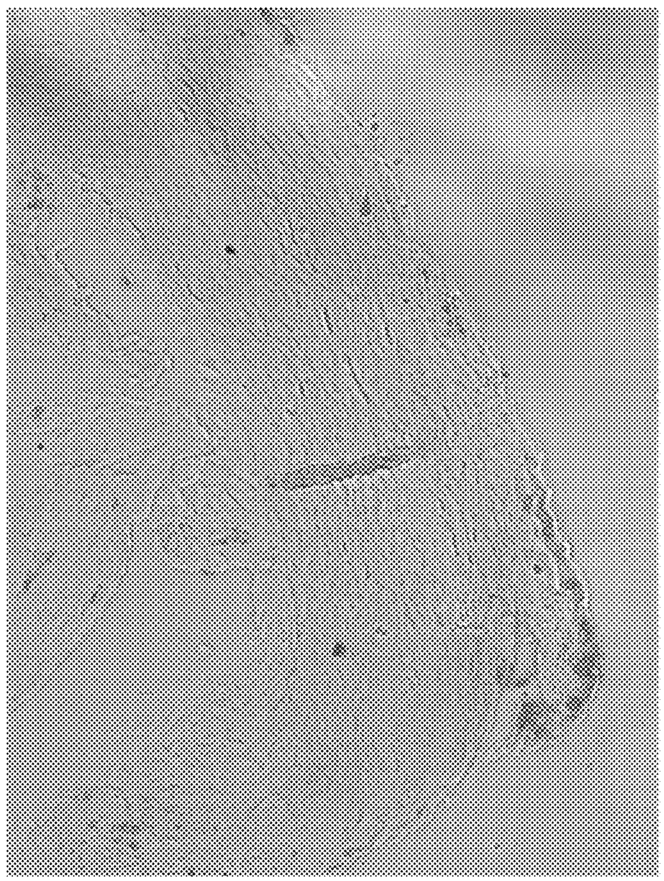
FIG. 5A is an image depicting the immunohistochemical staining of human PVR membranes of a control, counterstained with hematoxylin in membranes obtained from patients with PVR.

Immunofluorescence staining of RUNX1 in C-PVR cells showed expression of RUNX1 in C-PVR cells (FIG. 1). Immunofluorescence staining of RUNX1 in human PVR membranes (from patients with PVR) showed expression of RUNX1 (FIG. 3A-3D). Additionally, human PVR membrane from a patient (e.g., case 5) showed expression of RUNX1 (FIG. 3A-3D and FIG. 4A-4F). Additionally, immunohistochemistry of human PVR membranes showed RUNX1 expression (FIG. 5A and 5B).

Methods

C-PVR cells were grown in a 48 well plate for 24-72 hours, fixed in 4% paraformaldehyde overnight at 4° C. and stained with rabbit anti-RUNX1 primary antibody (1:100; LifeSpan Biosciences). Cells were incubated with goat anti-rabbit 594 secondary antibody (1:300; Life Technologies) and DAPI for 2 hours, then washed and imaged. Human PVR membrane tissue (e.g., case 5) was freshly obtained and was fixed in 10% formalin overnight and sectioned (6 μm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody rabbit anti-RUNX1 (1:100; LifeSpan Biosciences) overnight at 4° C. followed by incubation with secondary goat anti-rabbit Alexa Fluor 594 (1:300 Life Technologies) and DAPI for two hours at room temperature. Slides were then washed and imaged (FIG. 3A-3D and 4A-4F).

Immunohistochemistry

Human PVR membrane (e.g., case 5) freshly obtained was fixed in 10% formalin overnight and sectioned (6 μm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody mouse anti-RUNX1 (1:100); Santa Cruz Biotechnologies) overnight at 4° C. The following day, sections were incubated in a biotinylated secondary antibody (1:300; Life Technologies) followed by tyramide amplification system and 3,3' Diaminobenzidine chromagen staining. Slides were then washed and imaged (FIG. 5A and 5B).

Example 2: Inhibition of RUNX1 in Cells Derived from Human PVR Membrane

Figure 9C:
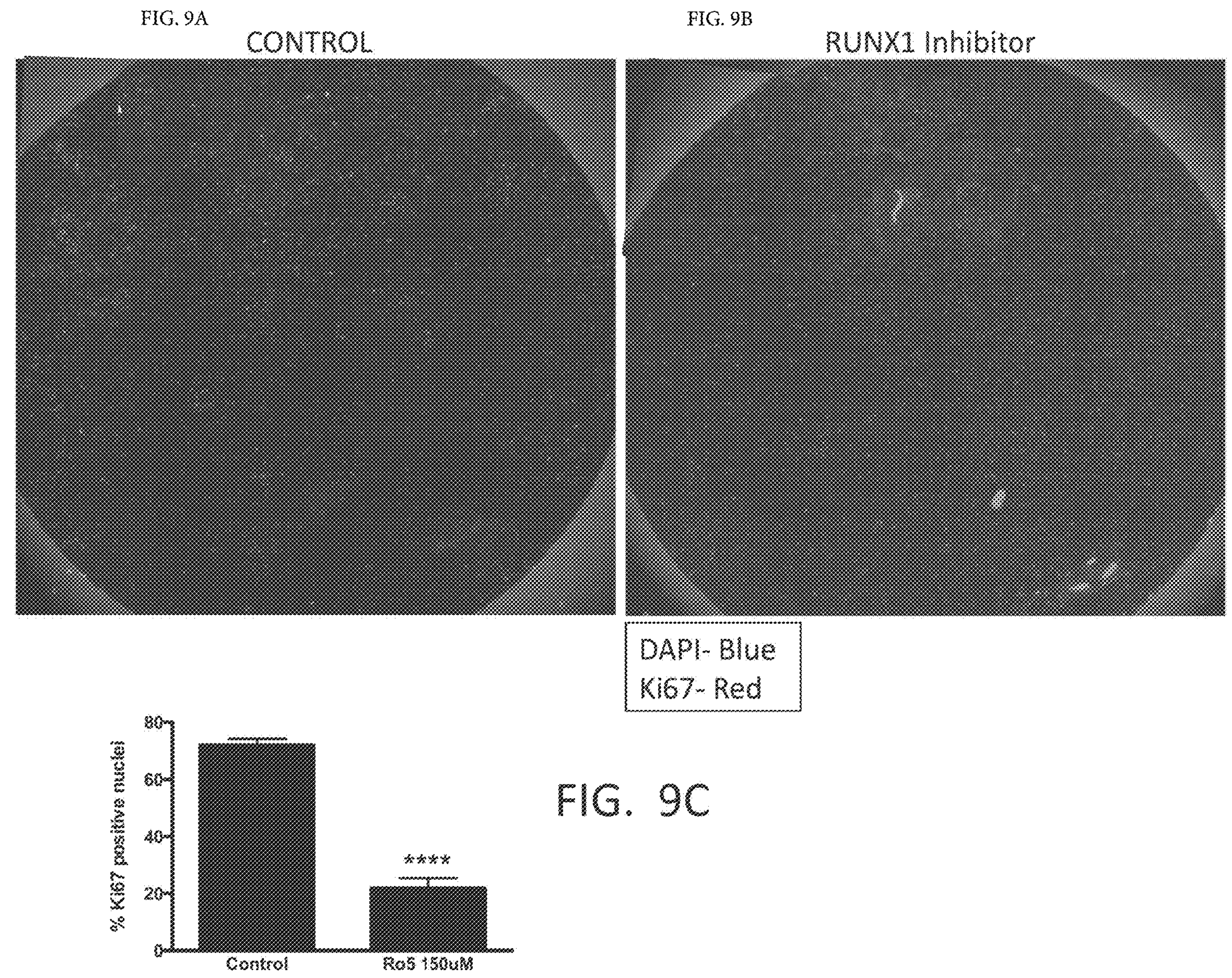
FIG. 9C is a bar graph depicting the quantitation of images from FIG. 9A and 9B.
Figures 10A, 10B, 10C, 10D, 10E, 10F:
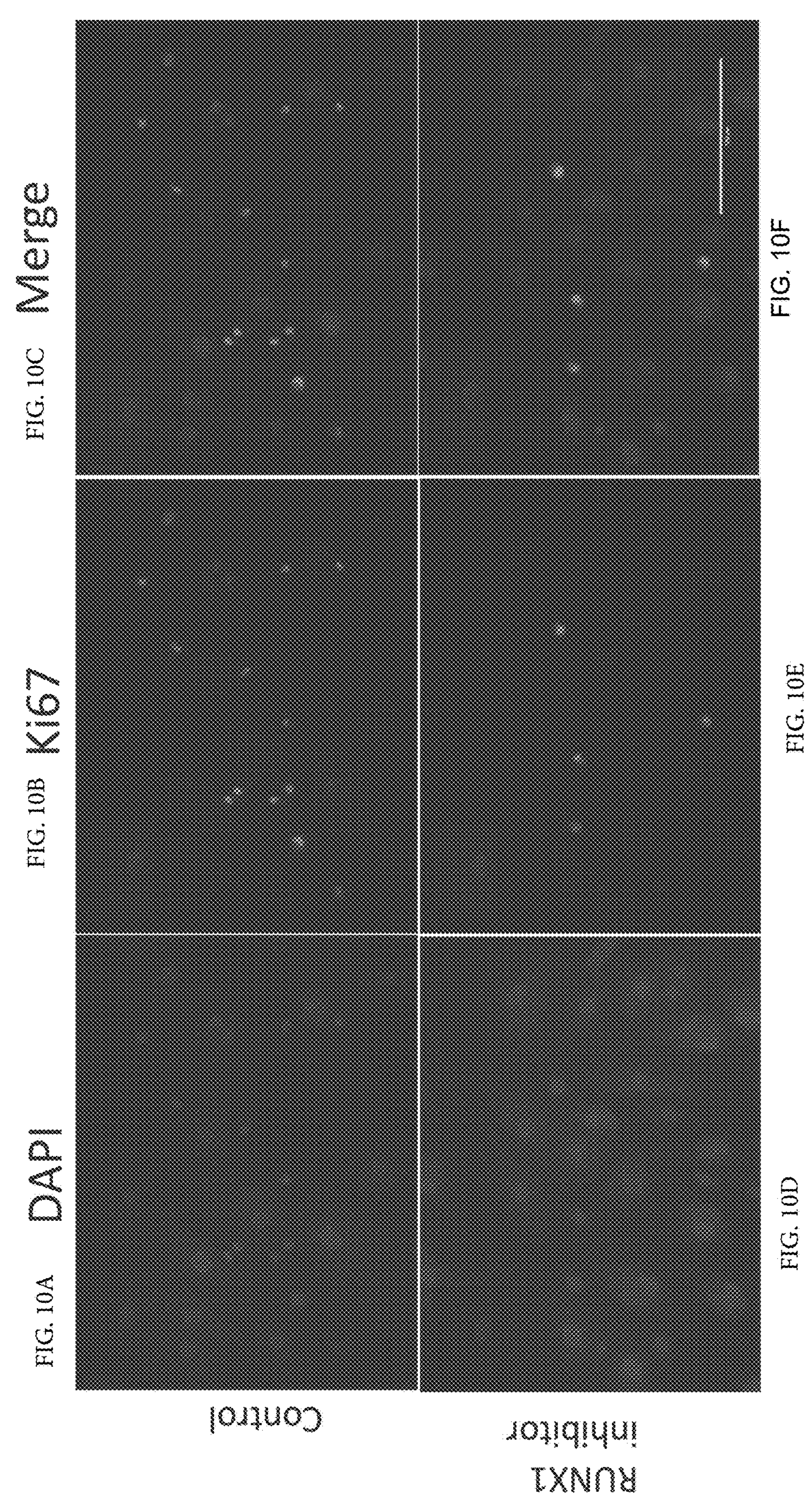
FIG. 10A is an image depicting DAPI staining of untreated controls.
FIG. 10B is an image depicting Ki67 staining of untreated controls.
FIG. 10C is a merged image of FIG. 10A and 10B.
FIG. 10D is an image depicting DAPI staining of cells treated with RUNX1 inhibitor, Ro5-3335.
FIG. 10E is an image depicting Ki67 staining of cells treated with RUNX1 inhibitor, Ro5-3335.
FIG. 10F is a merged image of FIG. 10D and 10E.

Proliferation of cells derived from human PVR membrane (C-PVR) was inhibited by the RUNX1 inhibitor, Ro5-335 (FIG. 9A-9C). A significant reduction in the cell number and proliferative capacity of C-PVR cells was observed (FIG. 9A-9C). The RUNX1 inhibitor, Ro5-335 reduced the growth of human PVR membranes in an explant model (FIG. 18A-18D). Growth was observed from control explants (FIG. 18A and 18C) as compared to the explants treated with RUNX1 inhibitor, Ro5-335 (FIG. 18B and 18D), which showed now growth after four days.

Figure 6:
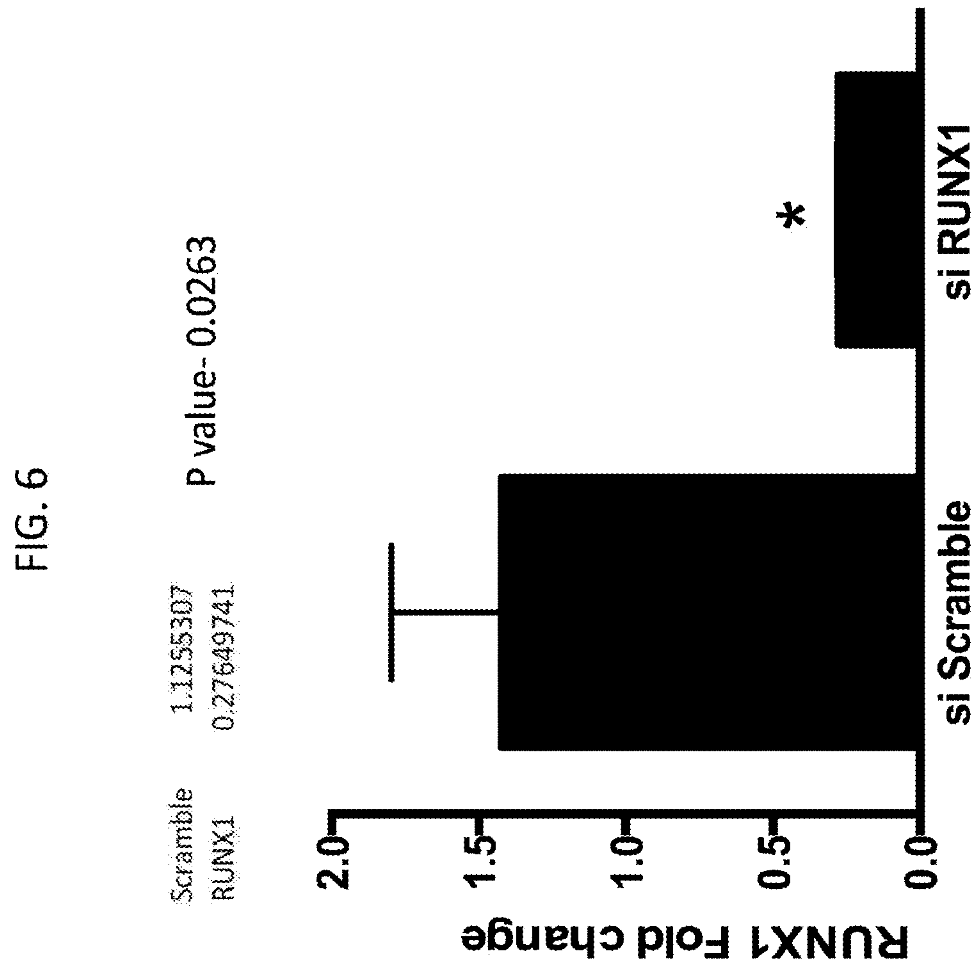
FIG. 6 is a bar graph depicting that siRNA effectively knocked down expression of RUNX1 in C-PVR cells. A significant reduction was observed in the gene expression of RUNX1 in C-PVR cells 48 hours after transfection with siRUNX1compared to siScramble.
Figures 7A, 7B, 7C, 7D, 7E, 7F, 7G, 7H, 7I:
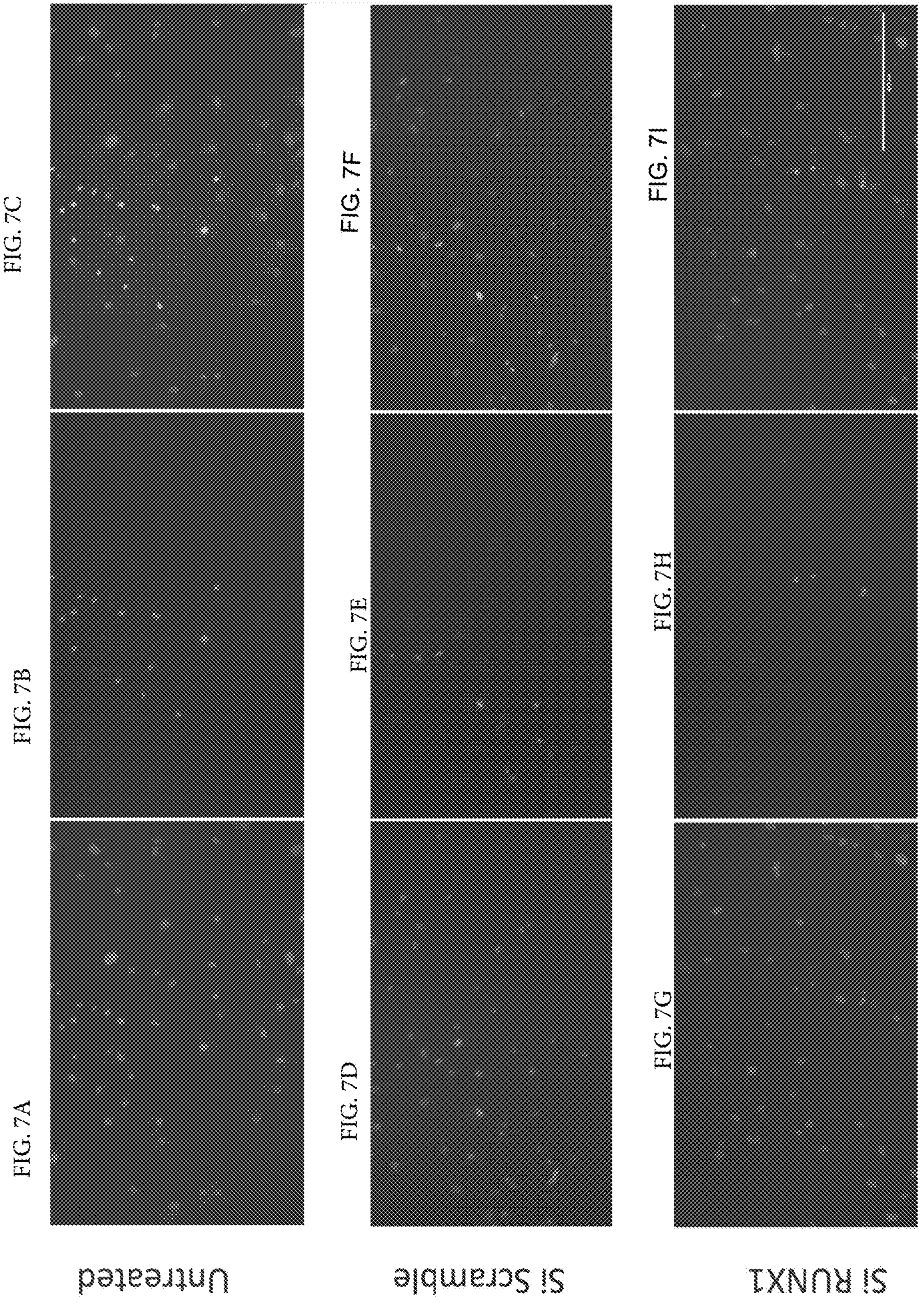
FIG. 7A is an image depicting DAPI staining of untreated controls.
FIG. 7B is an image depicting RUNX1 staining of untreated controls.
FIG. 7C is a merged image of FIG. 7A and 7B.
FIG. 7D is an image depicting DAPI staining of siScramble.
FIG. 7E is an image depicting RUNX1 staining of siScramble.
FIG. 7F is a merged image of FIG. 7E and 7F.
FIG. 7G is an image depicting DAPI staining of siRUNX1.
FIG. 7H is an image depicting RUNX1 staining of siRUNX1.
FIG. 7I is a merged image of FIG. 7G and 7H. Ki67 staining 48 hours post siRNA knockdown of RUNX1 (FIG. 7G-7I) compared to scramble (FIG. 7D-7F) and untreated controls (FIG. 7A-7C) showed a significant reduction in cell number and proliferative capacity of C-PVR cells.
Figure 8:
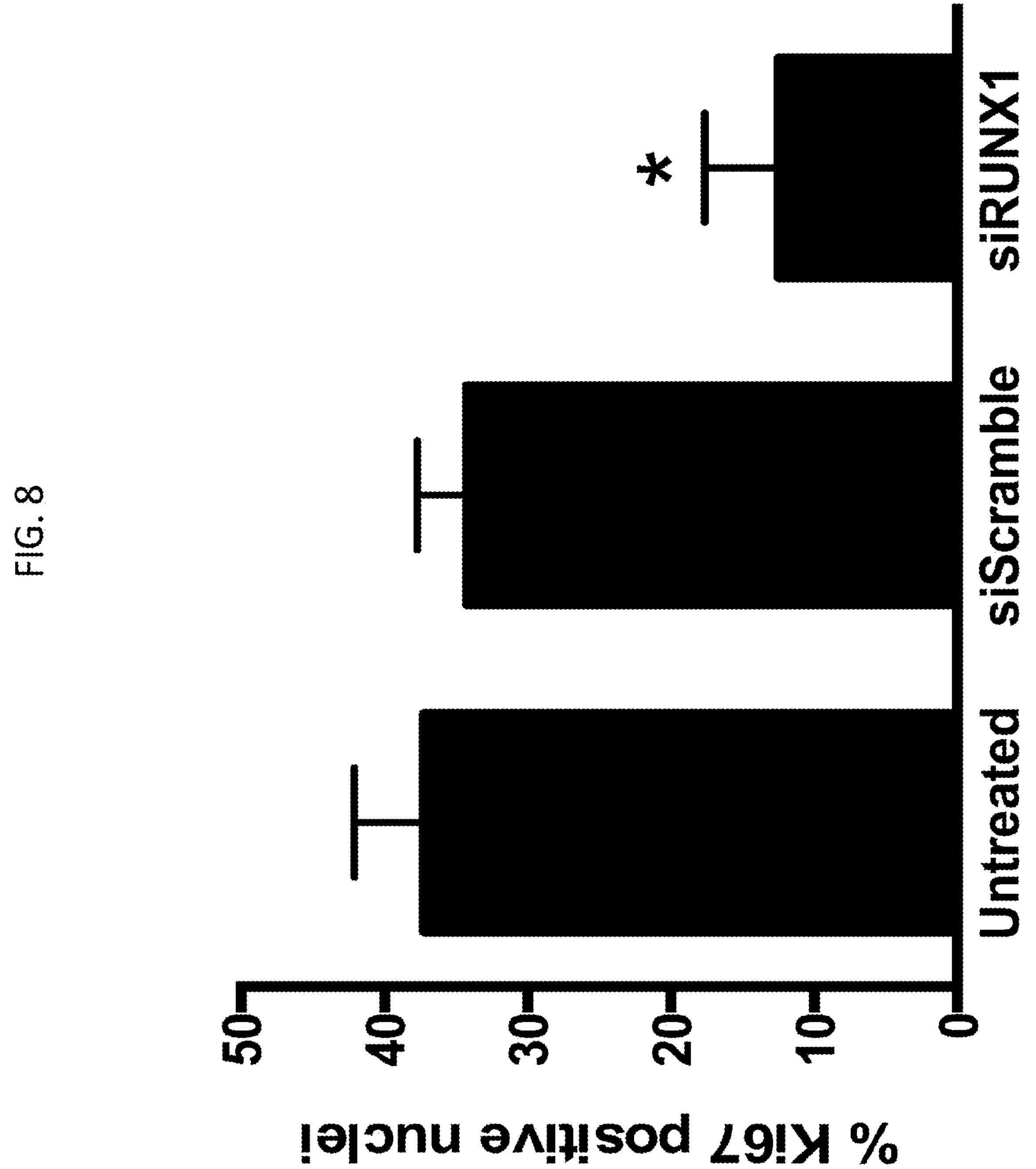
FIG. 8 is a bar graph depicting the quantification of proliferation from siRUNX1, siScramble and untreated cells. A significant reduction was observed in the number of Ki67 positive proliferating cells 48 hours after transfection with siRUNX1 compared to siScramble and untreated cells. The graph depicts quantification of images from FIG. 7A-7F.

SiRNA knocked down RUNX1 expression in C-PVR cells (FIG. 6). A significant reduction in gene expression of RUNX1 in C-PVR was observed 48 hours after transfection with siRNUNXI compared to siScramble. Ki67 staining 48 hours post siRNA knockdown of RUNX1 (FIG. 7G) compared to scramble (FIG. 7D and 7F) and untreated controls (FIG. 7A-7C) showed a significant reduction in cell number and proliferative capacity of C-PVR. cells.

SIRNA

C-PVR cells (e.g., case S) were grown in a 48 well plate for 24 hours and transfected with siRNUNX1 or siScramble using Darmafect (Dharmacon). 48 hours post-transfection, cells were washed and RNA was collected and PCR was performed (FIG. 6).

Ki67 Staining of siRNA

C-PVR (e.g., case 5) cells were transfected with the siRUNX1 or siScramble for 48 hours and washed and fixed with 4% paraformaldehyde for 10 minutes at room temperature. The cells were washed with PBS and blocked for an hour in (10% goat serum in PBS) incubated with rabbit anti-Ki67 antibody (1:50; Novus Biologicals) overnight at 4 degrees. Cells were incubated with secondary antibody goat anti-rabbit 594 (1:300; Life Technologies) for 2 hours along with DAPI, then were washed and imaged (FIG. 7A-7I; quantitation depicted in FIG. 8).

Treatment with RUNX1 Inhibitor

C-PVR cells (e.g., case 5) were cultured in 48 well plates for 24, followed by treatment with 150 μM RUNX1 inhibitor (Ro5-3335, Calbiochem), or vehicle only for a period of 48 hours. The cells were washed and fixed with 4% paraformaldehyde for 10 minutes at room temperature. The cells were washed with PBS and blocked for an hour in (10% goat serum in PBS) incubated with rabbit anti-Ki67 antibody (1:50; Novus Biologicals) overnight at 4 degrees. Cells were incubated with secondary antibody goat anti-rabbit 594

(1:300; Life Technologies) for 2 hours along with DAPI, washed, imaged and quantified using Image J (FIG. 9A and 9B).

Ki67 Staining of Treatment with RUNX1 Inhibitor

C-PVR cells (e.g., case 5) were cultured in 48 well plates for 24. followed by treatment with 150pM RUNX1 inhibitor (Ro5-3335, Calbiochem), or vehicle only for a period of 48 hours. The cells were washed and fixed with 4% paraformaldehyde for 10 minutes at room temperature. The cells were washed with PBS and blocked for an hour in (10% goat serum in PBS) incubated with rabbit anti-Ki67 antibody (1:50; Novas Biologicals) overnight at 4 degrees. Cells were incubated with secondary antibody goat anti-rabbit 594 (1:300); Life Technologies) for 2 hours along with DAPI, washed and imaged.

Example 3: Effect of TGEβ, TNFα and IL-6 on ARPE-19 Cells

Figures 11A, 11B:
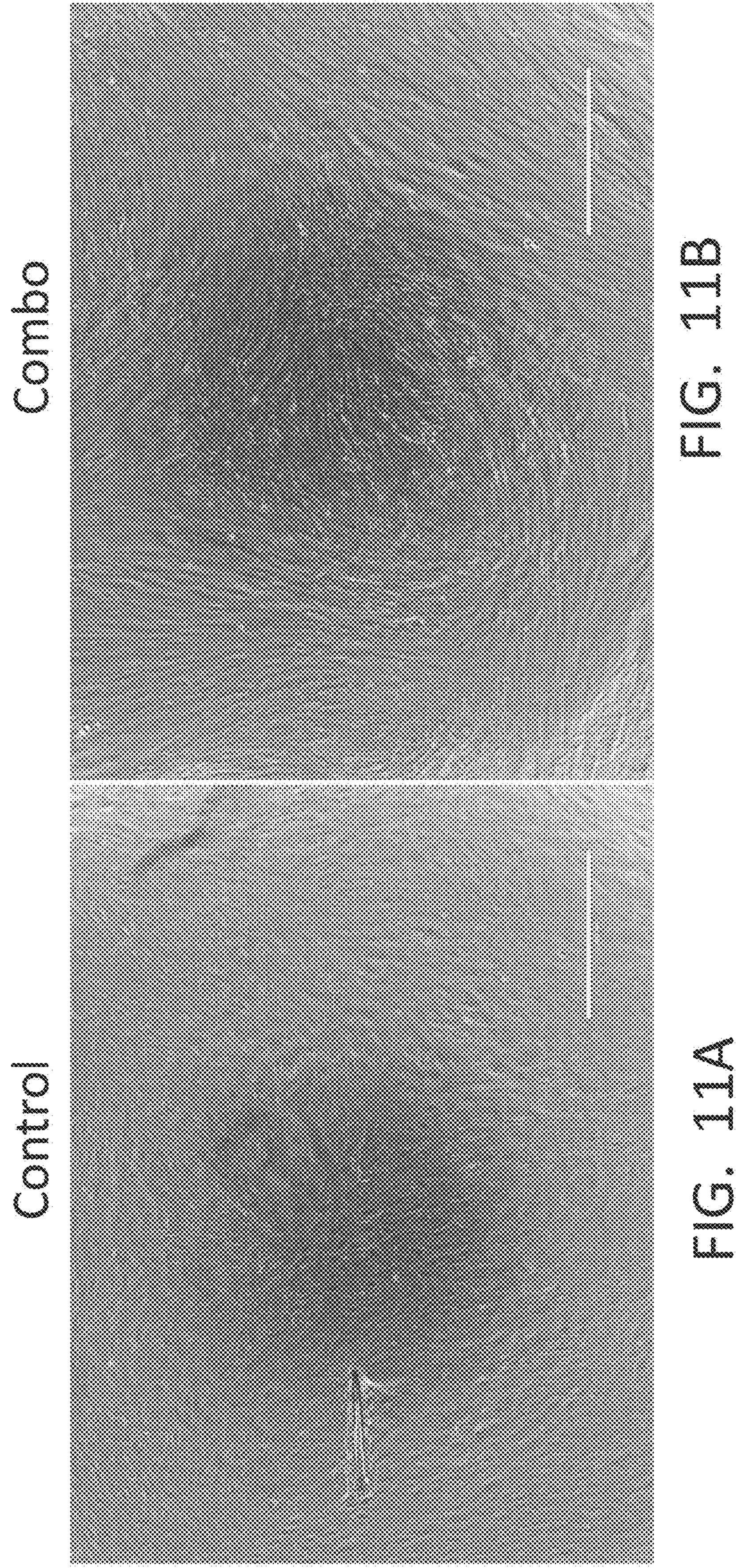
FIG. 11A is a bright-field image depicting ARPE-19) cells 7 days post-treatment of control cells.
FIG. 11B is a bright-field image depicting ARPE-19 cells 7 days post-treatment with TGFβ2, TNFα, and IL-6 (from Preprotec).

ARPE-19 cells at 7 days post treatment with TGFβ2 , TNFα, and IL-6 (all from Preprotec) showed Epithelial-Mesenchymal transition (FIG. 11B) as compared to control (FIG. 11A). ARPE-19 cells underwent EMT with combination treatment (e.g., combination of TGFβ2, TNFα, and IL-16), FIG. 12.

Figure 13:
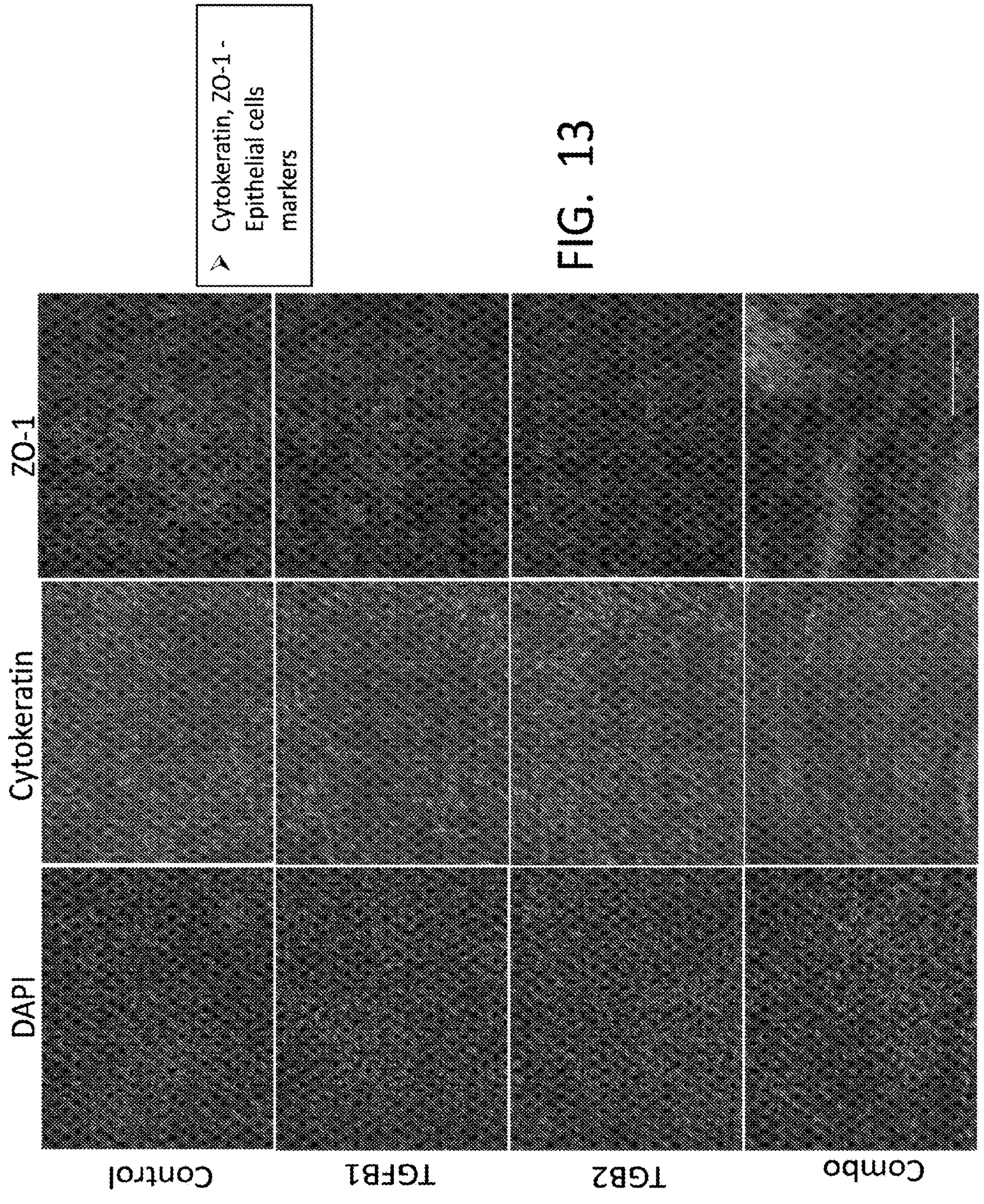
FIG. 13 are immunofluorescence staining images of mature ARPE-19 cells 7 days post treatment with TGFβ1, TGFβ2, and combination of TGFβ2, TNFα and IL-6 (10 ng/ml). A reduction in the epithelial markers, cytokeratin (middle panel) and Zonula occludens-1 (ZO-1) (right panel) in the treatments was observed as compared to controls. Losing ZO-1 organization is a marker of EMT. Therefore data showed that combination treatment also impacted ZO-1 distribution.
Figures 14A, 14B, 14C, 14D:
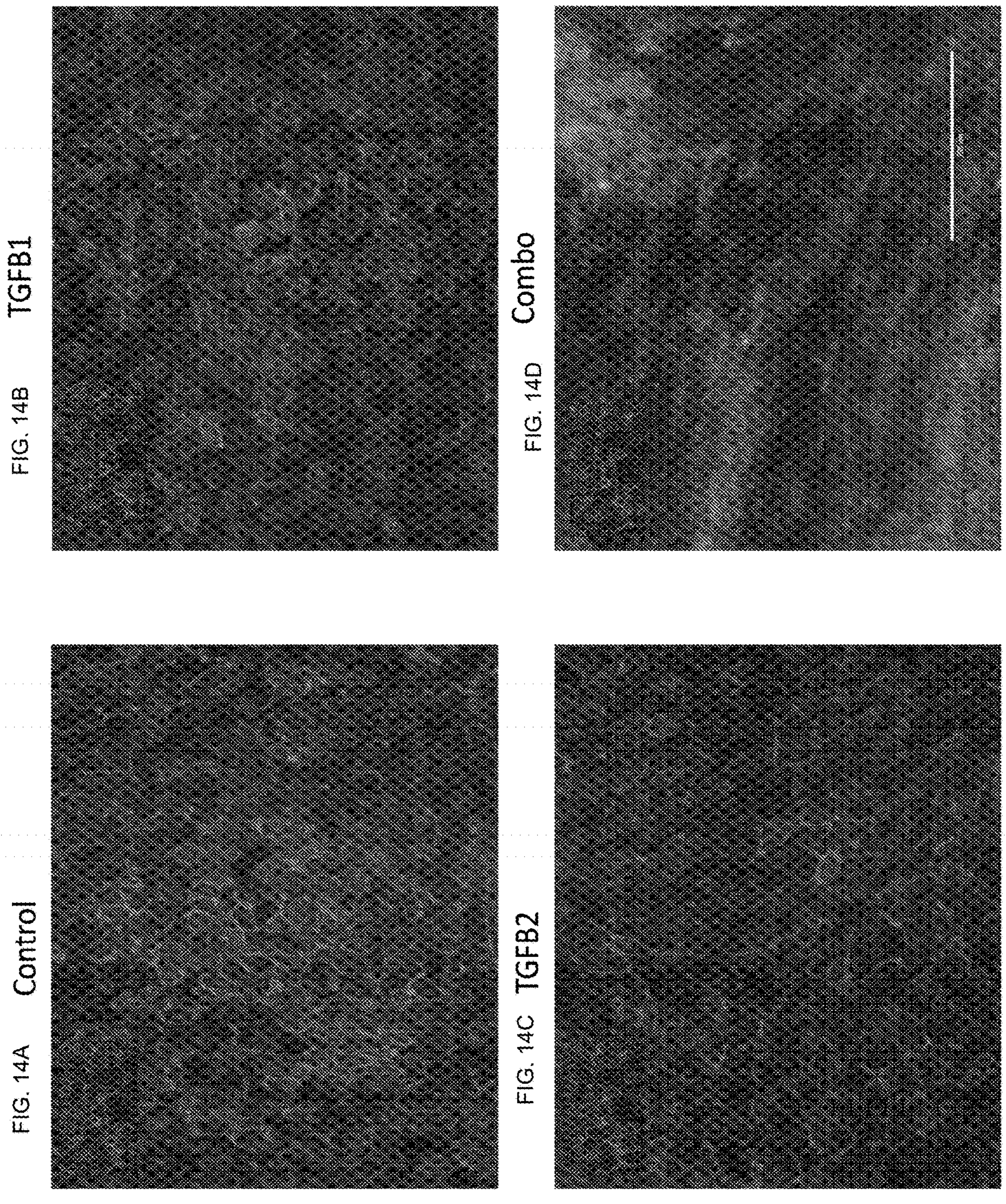
FIG. 14A is an immunofluorescence image depicting mature ARPE-19 cells 7 days post treatment of untreated control.
FIG. 14B is an immunofluorescence image depicting mature ARPE-19 cells 7 days post treatment with TGFBI.
FIG. 14C is an immunofluorescence image depicting mature ARPE-19 cells 7 days post treatment with TGFβ2.
FIG. 14D is an immunofluorescence image depicting mature ARPE-19 cells 7 days post treatment with a combination of TGF822, TNFα, and IL-6 (10 ng/ml each). A reduction in the epithelial markers Zonula oceludens-1 in the treatments was observed as compared to controls.

ARPE-19 cells 7 days post treatment with TGFβ1, TGFβ2, and combination of TGFβ2, TNFα and IL-6 (10 ng/ml each) showed a reduction in the epithelial markers. cytokeratin (FIG. 13, middle panel) and Zonula occludens-1 (ZO-1) (FIG. 13, right panel) in the treatments compared to controls. Losing ZO-1 organization is a marker of EMT, and therefore the data showed that the combination treatment also impacted ZO-1 distribution (FIG. 13). Additionally, ARPE-19 cells 7 days post treatment with TGFβ1, TGFβ2, and combination of TGFβ2, TNFo and IL-6 (10 ng/ml) showed a reduction in the epithelial markers Zonula occludens-1 in the treatments compared to controls (FIG. 14A-14D).

RUNX1 Expression Increases with EMT

Figure 15:
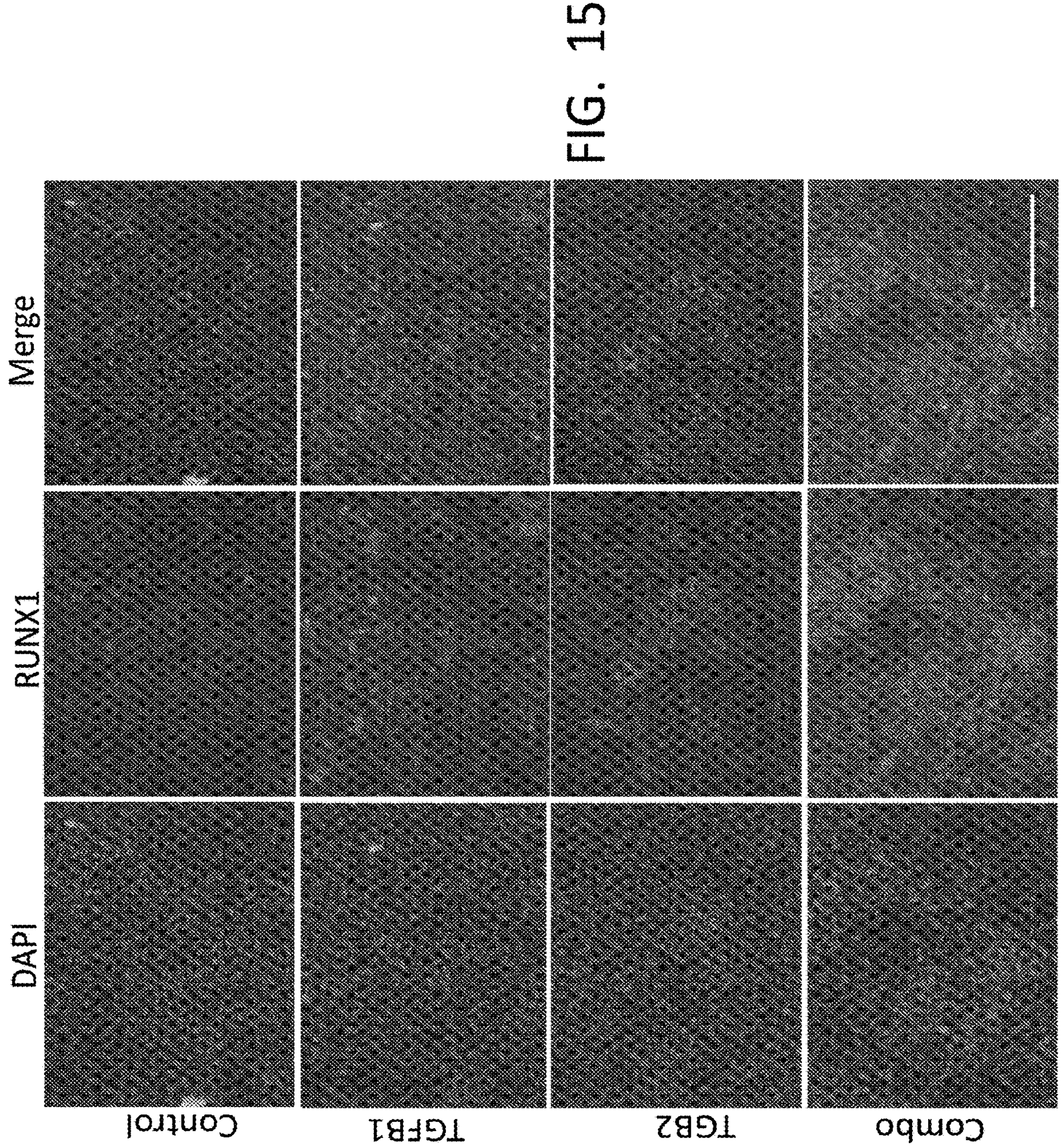
FIG. 15 are immunofluorescence staining images of ARPE-19 cells 7 days post treatment with TGFβ1, TGFβ2, and combination of TGFβ2, TNFα and IL-6 (10 ng/ml each). A significant increase in the RUNX1 expression in the treatments was observed as compared to controls. This indicated that RUNX1 expression increased with EMT.

ARPE-19 cells 7 days post treatment with TGFβ1, TGFβ2, and combination of TGFβ2, TNFα and IL-6 (10 ng/ml each) showed a significant increase in the RUNX1 expression in the treatments compared to controls (FIG. 15). This indicated that RUNX1 expression increased with EMT. ARPE-19 cells 7 days post treatment with a combination of TGFβ2, TNFα and IL-6 (10 ng/ml) showed a significant increase in the RUNX1 expression in the treatments compared to controls (FIG. 16, which depicts magnified data from FIG. 13).

ARPE-19 cells 7 days post treatment with a combination of TGFβ2, TNFα and IL-6 (10 ng/ml each) showed a significant increase in the RUNX1 expression (FIG. 17, middle panel) and a reduction in the epithelial marker cytokeratin (FIG. 17, right panel) in the treatments compared to controls. This showed that RUNX1 increased expression and was also present at the 3-week time point when ZO-1 changes of distribution were present.

Cell Culture

ARPE-19 cells (ATCC) were grown to confluence and maintained in 1% for 7-10 days. Cells were treated with a combination of TGFβ2, TNFα and IL-6 (each at 10 ng/ml) for 7 days and images were taken.

Immunofluorescence

Figure 12:
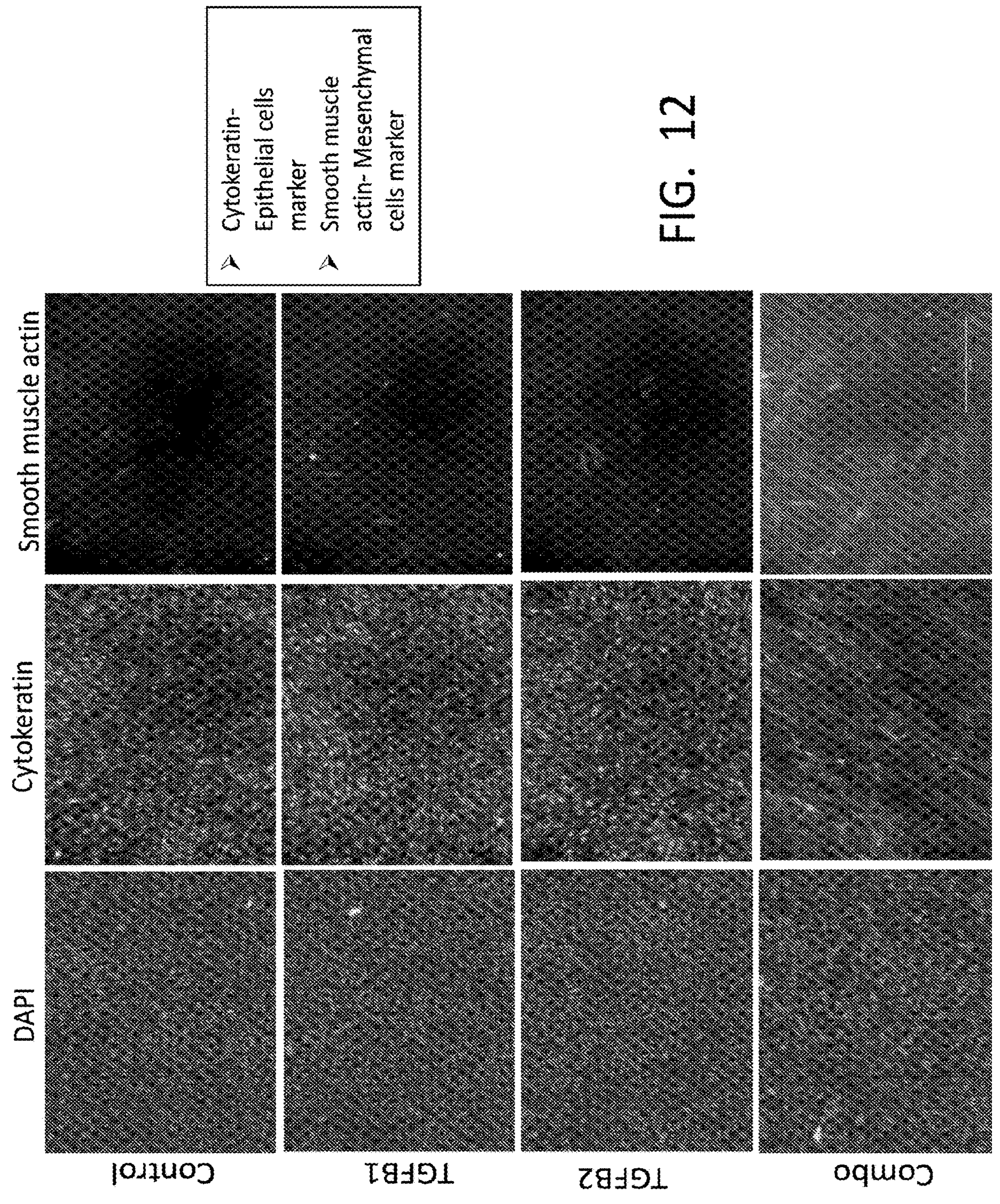
FIG. 12 are immunofluorescence staining images of ARPE-19 cells 7 days post treatment with TGFβ1, TGFβ2, and combination of TGFβ2, TNFα and IL-6 (10 ng/ml each). A reduction in the epithelial marker (cytokeratin-middle panel) was observed, and increase in the mesenchymal marker (smooth muscle actin-right panel) in the treatments was compared as compared to controls. This showed that ARPE-19 cells underwent EMT with combination treatment.

ARPE-19 cells were grown to confluence and maintained in 1% for 7-10 days. Cells were treated with TGβ1, TGFβ2, and a combination of TGFβ2, TNFα and IL-6 (10 ng/ml) for 7 days (combo). Cells were washed and fixed with 4% paraformaldehyde for 10 minutes at room temperature. Cells were incubated with primary antibodies, mouse anti-cytokeratin (1:250; Abcam) or smooth muscle actin (1:50; DAKO) overnight at 4° C. The following day, cells were incubated with secondary antibody goat anti-mouse 488 (1:300; Life Technologies) for 2 hours at room temperature and DAPI. Cells were washed with PBS and imaged (FIG. 12).

ARPE-19 cells were grown to confluence and maintained in 1% for 3 weeks. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibodies, mouse anti-cytokeratin (1:250; Abcam) or rabbit anti ZO1 (1:250; Life Technologies) overnight at 4° C. The following day, cells were incubated with secondary antibody goat anti-mouse 488 and goat anti- rabbit 594 (1:300; Life Technologies) for 2 hours at room temperature and DAPI. Cells were washed with PBS and imaged.

ARPE-19 cells were grown to confluence and maintained in 1% for 3 weeks. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibody rabbit anti ZOI (1:250; Life Technologies) overnight at 4° C. The following day, cells were incubated with secondary antibody goat anti-rabbit 594 (1:300; Life Technologies) for 2 hours at room temperature and DAPI. Cells were washed with PBS and imaged (FIG. 14A-14D).

ARPE-19 cells were grown to confluence and maintained in 1% for 7-10 days, Cells were treated with TGβ1, TGFβ2, and a combination of TGFβ2, TNFα and IL-6 (10) ng/ml) for 7 days. Cells were washed and fixed with 4% paraformaldehyde for 10 minutes at room temperature. Cells were incubated with primary antibody rabbit anti-RUNX1 (1:100; LifeSpan Biosciences) overnight at 4° C. The following day, cells were incubated with secondary antibody goat anti-mouse 594 (1:300; Life Technologies) for 2 hours at room temperature and DAPI. Cells were washed with PBS and imaged (FIG. 15).

Figure 16:
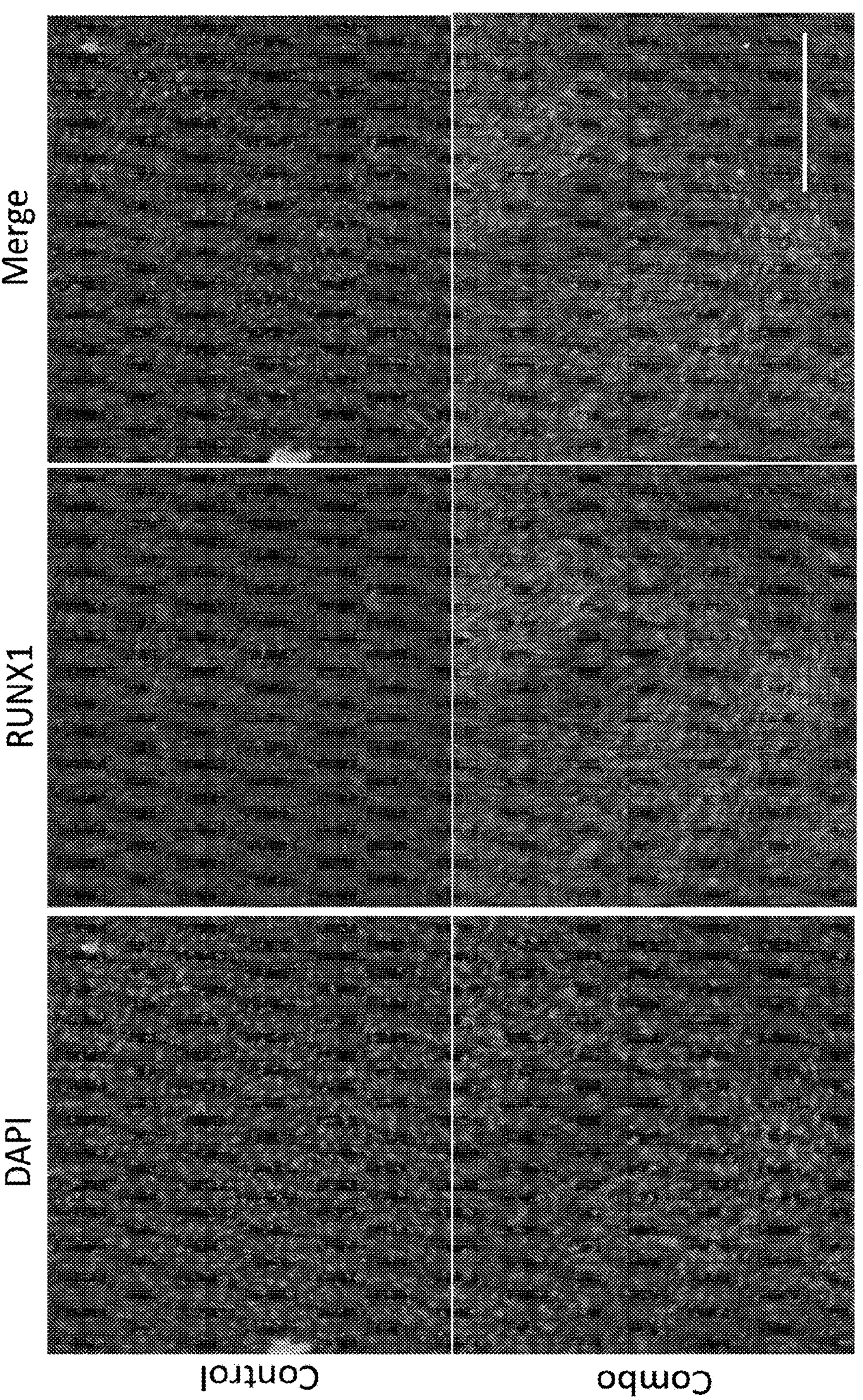
FIG. 16 are immunofluorescence staining of ARPE-19 cells 7 days post treatment with a combination of TGFβ2, TNFα and IL-6 (10 ng/ml each). A significant increase in the RUNX1 expression in the treatments compared to controls was observed.

ARPE-19 cells were grown to confluence and maintained in 1% for 7-10 days. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibody rabbit anti-RUNX1 (1:100; LifeSpan Biosciences) overnight at 4° C. The following day, cells were incubated with secondary antibody goat anti-rabbit 594 (1:300; Life Technologies) for 2 hours at room temperature and DAPI. Cells were washed with PBS and imaged (FIG. 16).

Figure 17:
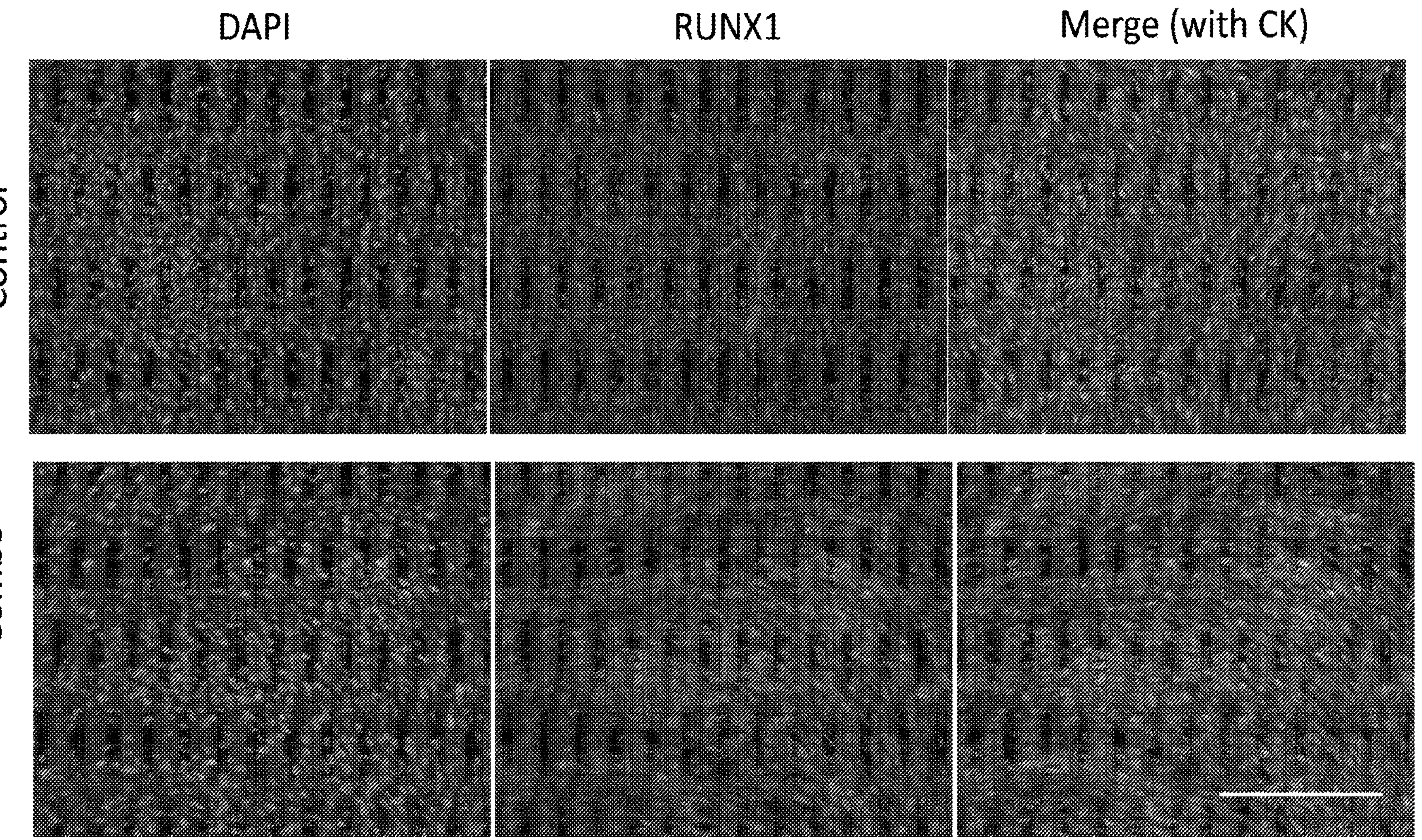
FIG. 17 are immmofluorescence staining images of ARPE-19 cells 7 days post treatment with a combination of TGFβ2, TNFα and IL-6 (10 ng/ml each). A significant increase in the RUNX1 expression (middle panel) and a reduction in the epithelial marker cytokeratin (merge-right panel) in the treatments was observed compared to controls. This showed that RUNX1 increased expression was also present at the 3-week time point when ZO-1 changes of distribution were present.
Figures 18A, 18B, 18C, 18D:
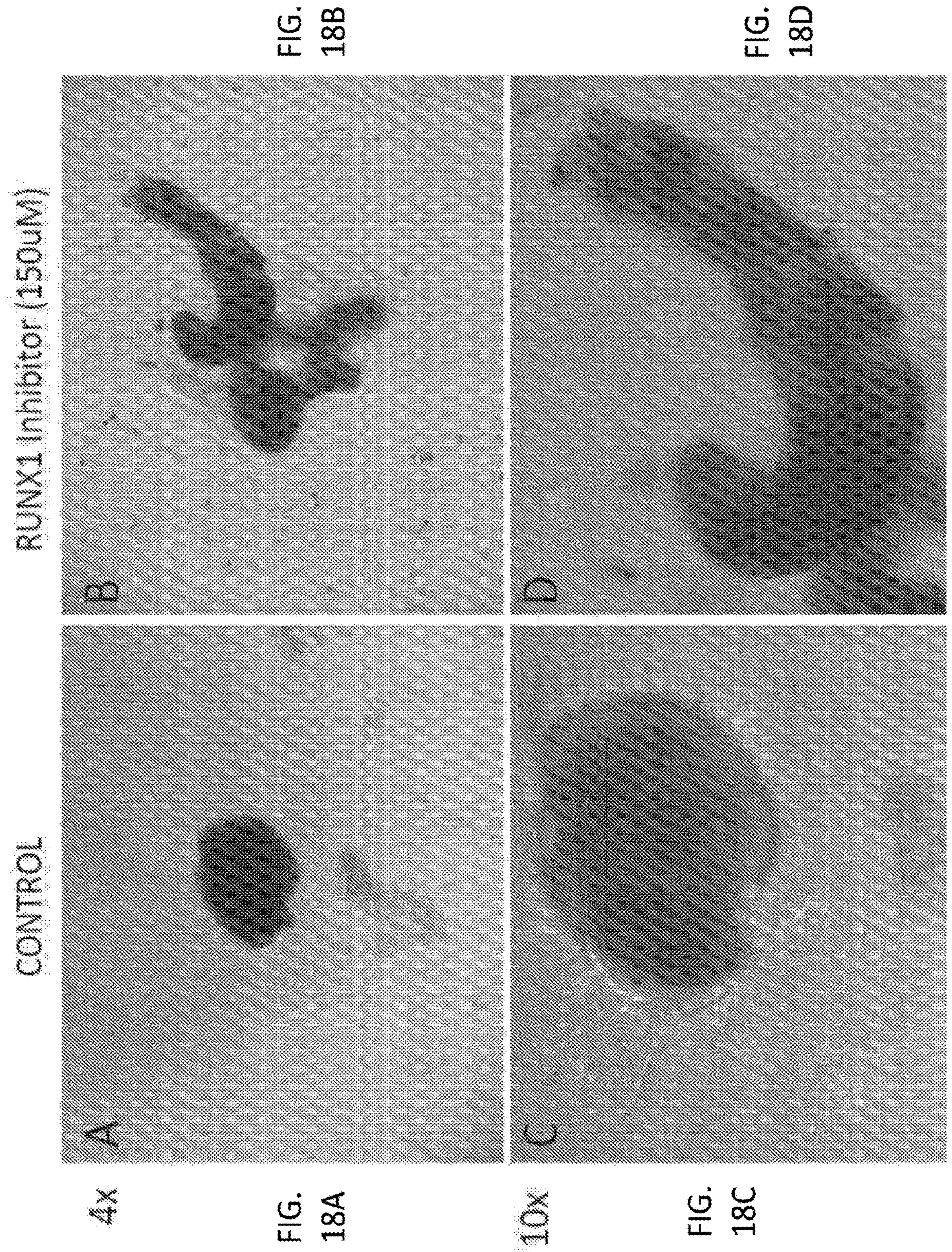
FIG. 18A is an image depicting a primary explant culture treated with a control (4× magnification).
FIG. 18B is an image depicting a primary explant culture treated with RUNX1 inhibitor, Ro5-3335 at 150 μM (4× magnification).
FIG. 18C is an image depicting a primary explant culture treated with a control (10× magnification).
FIG. 18D is an image depicting a primary explant culture treated with RUNX1 inhibitor, Ro5-3335 (10× magnification). Growth was observed from control explants compared to the explants treated with RUNX1 inhibitor, which showed no growth after 4 days.

ARPE-19 cells were grown to confluence and maintained in 1% for 7-10 days. Cells were treated with a combination of TGFβ2, TNFα and IL-6 (10 ng/ml) for 7 days. Cells were washed and fixed with 4% paraformaldehyde for 10 minutes at room temperature. Cells were incubated with primary antibodies rabbit anti-RUNX1 (1:100; LifeSpan Biosciences) and mouse anti-cytokeratin (1:250; Abcam) overnight at 4° C. The following day, cells were incubated with secondary antibodies goat anti-mouse 488 and goat anti-rabbit 594 (1:300; Life Technologies) for 2 hours at room temperature and DAPI. Cells were washed with PBS and imaged (FIG. 17).

Example 4: RUNX1 Expression and Effect of RUNX1 Inhibitor

RUNX1 expression is common in membranes from different donors with PVR

RUNX1 expression was a common feature in membranes from different donors with PVR (FIG. 19A and 19B). Freshly obtained donor human PVR membrane (Case 1 "PVR 01" and 3 "PVR 03") were fixed in 10% formalin overnight and sectioned (6 μm). Serial sections were deparaffinized in 100% xylene, rehydrated in a series of ethanol steps and washed in phosphate buffered saline (PBS). Heat-induced epitope retrieval was performed in boiling citrate buffer (pH 6). The slides were blocked and incubated with primary antibody rabbit anti-RUNX1 (1:100; LifeSpan Biosciences) overnight at 4° C.', followed by incubation with secondary goat anti rabbit Alexa Fluor 594 (1:300 Life Technologies) and DAPI. The slides were then washed and imaged. These data indicate common RUNX1 expression (e.g., level of RUNX1) among different donors with PVR. The proliferation marker, Ki67, has a similar pattern for RUNX1

Figure 20B:
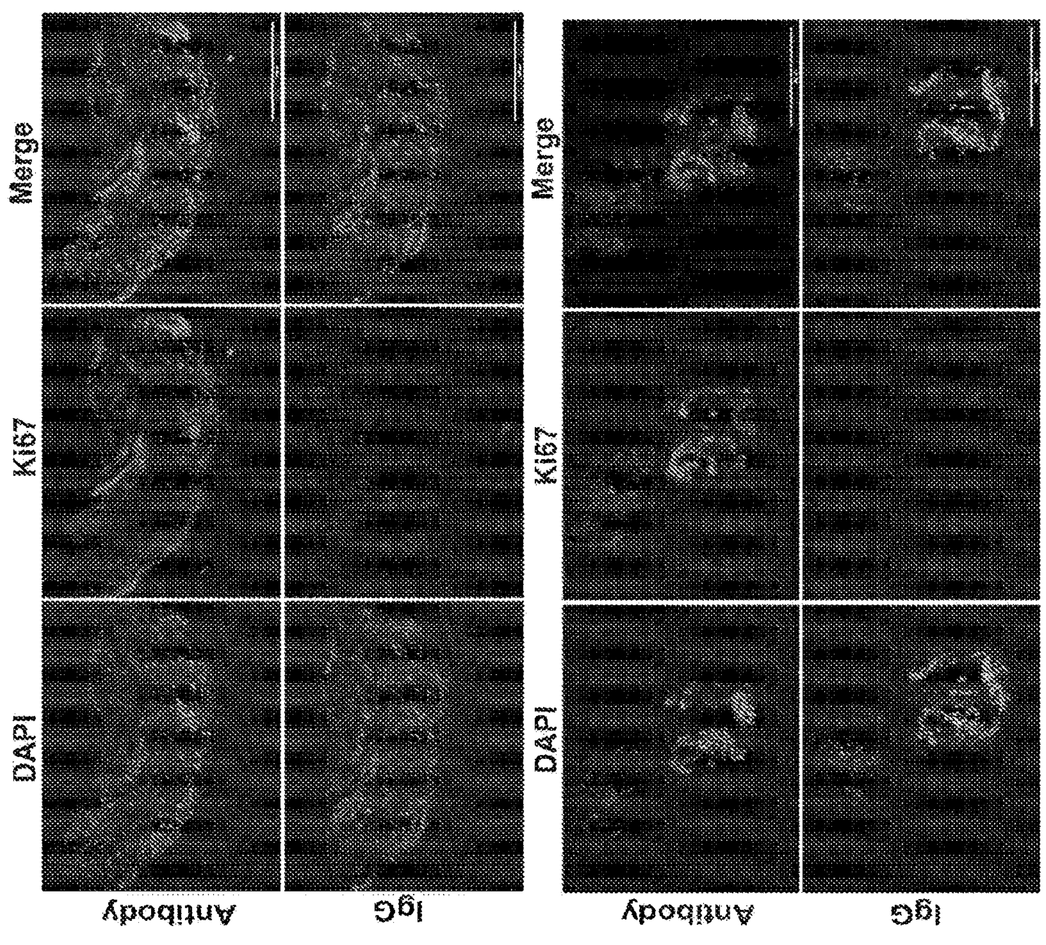
FIG. 20B are immunofluorescence staining images of Ki67 (bottom, middle, FIG. 20B), RUNX1 (top, middle, FIG. 20A) and counterstained with DAPI in contiguous sections of membranes obtained from patients with PVR. These images showed that the population of cells expressing RUNX1 within PVR membranes actively proliferated, as demonstrated by their expression of Ki67. Scale bars-400 microns.

The population of cells expressing RUNX1 within PVR membranes actively proliferated, as demonstrated by their expression of Ki67 (FIG. 20A and 20B). Freshly obtained donor human PVR membrane was fixed in 10% formalin overnight and sectioned (6 μm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody rabbit anti-Ki67 (1:100; Novus Biologicals) overnight at 4° C.followed by incubation with secondary goat anti rabbit Alexa Fluor 594 (1:300 Life Technologies) and DAPI. Slides were washed and imaged. For RUNX1, the slides were blocked and incubated with primary antibody rabbit anti-RUNX1 (1:100; LifeSpan Biosciences) overnight at 4° C.followed by incubation with secondary goat anti rabbit Alexa Fluor 594 (1:300 Life Technologies) and DAPI. Slides were washed and imaged. These data demonstrate that cells expressing RUNX1 within the PVR membrane were actively proliferating. This was demonstrated by the expression of Ki67.

RUNX1 Protein Expression Levels are Increased in Growth Factor-Induced EMT

Figure 21B:
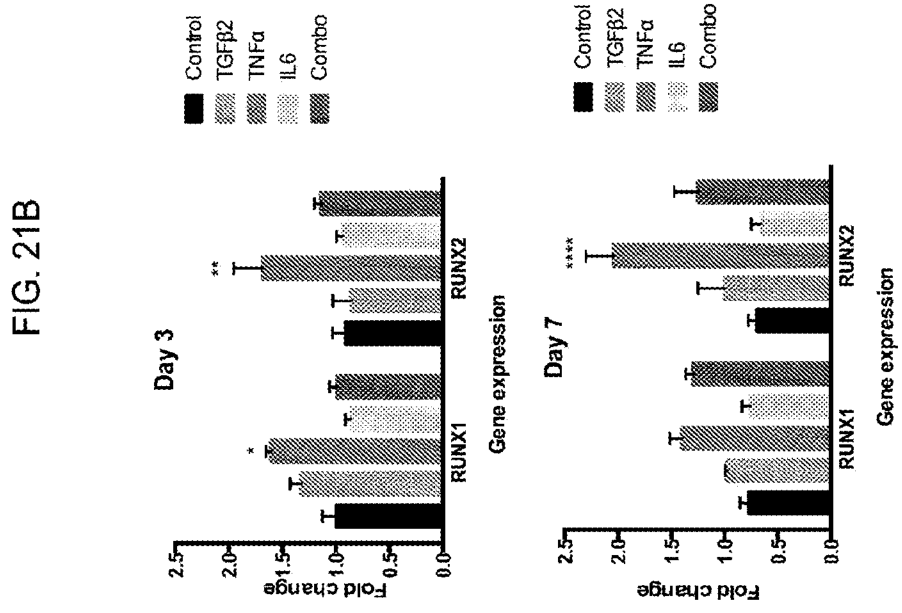
FIG. 21B are bar graphs indicating that an increase in RUNX1 and runt related transcription factor 2 (RUNX2) RNA expression was observed upon treatment with growth factors (TGFβ2, TNFα, and IL-6, each at 10 ng/ml) at 3 and 7 days post treatment. ("Con" depicts control). *$P<0.05$. $P<0.01$, **$P<0.0001$.

RUNX1 protein expression levels were increased in growth factor induced EMT (FIG. 21A and 21B). Increased levels of RUNX1 protein was observed upon treatment with growth factors TGFβ2, TNFα and combination treatment, including TGFβ2, TNFα and IL-6 at 3 and 7 days post treatment. Increase in RUNX1 and RUNX2 RNA expression was also observed upon treatment with growth factors at 3 and 7 days post treatment. ARPE-19 cells were seeded into 6-well pates at a density of 100,000 cells in complete media. At confluence cells were treated with growth factors TGFβ2. TNFα and a combination treatment of TGFβ2, TNFα and IL-6. Cells were washed with ice-cold PBS, lysed and collected at 3 and 7 day time points, and immunoblotted for RUNX1 (1:200, SantaCruz Biotechnology, Dallas, Texas) and B-Actin (1:1000, Cell Signaling Technology, Danvers. MA) as a loading control. ARPE-19 cells were also seeded into 6-well pates at a density of 100,000 cells, in complete media. At confluence, cells were treated with growth factors TGFβ2, TNFα and a combination treatment of TGFβ2, TNFα and IL-6. Cells were washed with PBS, lysed and collected. Quantitative RT-PCR of mRNA expression was performed and values were reported as relative fold change in expression level. These data indicate that an increase in RUNX1 protein level, and RUNX1 RNA was observed with growth factor treatment.

RUNX1 Inhibition Resulted in Inhibition of EMT

Figure 22:
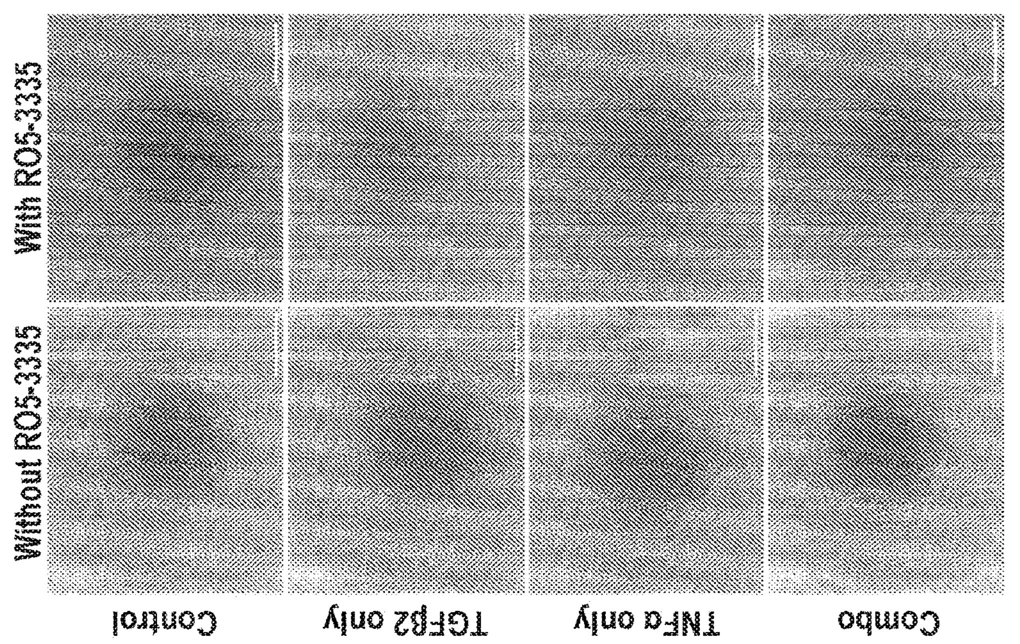
FIG. 22 are bright field images depicting ARPE-19 cells 3 days post treatment with TGFβ2, TNFα, and a combination of TGFβ2, TNFα and IL-6 with RUNX1 inhibitor (Ro5-3335). 150 μM of Ro5-3335 showed either no or reduced EMT (right panels), compared to vehicle treatment (left panels). EMT was determined by morphological changes including cell shape. This data demonstrated that RUNX1 inhibition using Ro5-3335 resulted in inhibition of EMT. Scale bars-400 microns.

RUNX1 inhibition, using Ro5-3335, resulted in inhibition of EMT. ARPE-19 cells were grown to confluence and maintained in 1% serum for 7-10 days (FIG. 22). Cells were treated with growth factors TGFβ2, TNFα and IL-6 (10 ng/ml each) for 3 days, with 150 μM RUNX1 inhibitor (Ro5-3335, Calbiochem) or without (e.g., vehicle). The results demonstrated no (or reduced) EMT compared to vehicle treated cells. EMT was determined by morphological changes including cell shape.

Figures 23A, 23B:
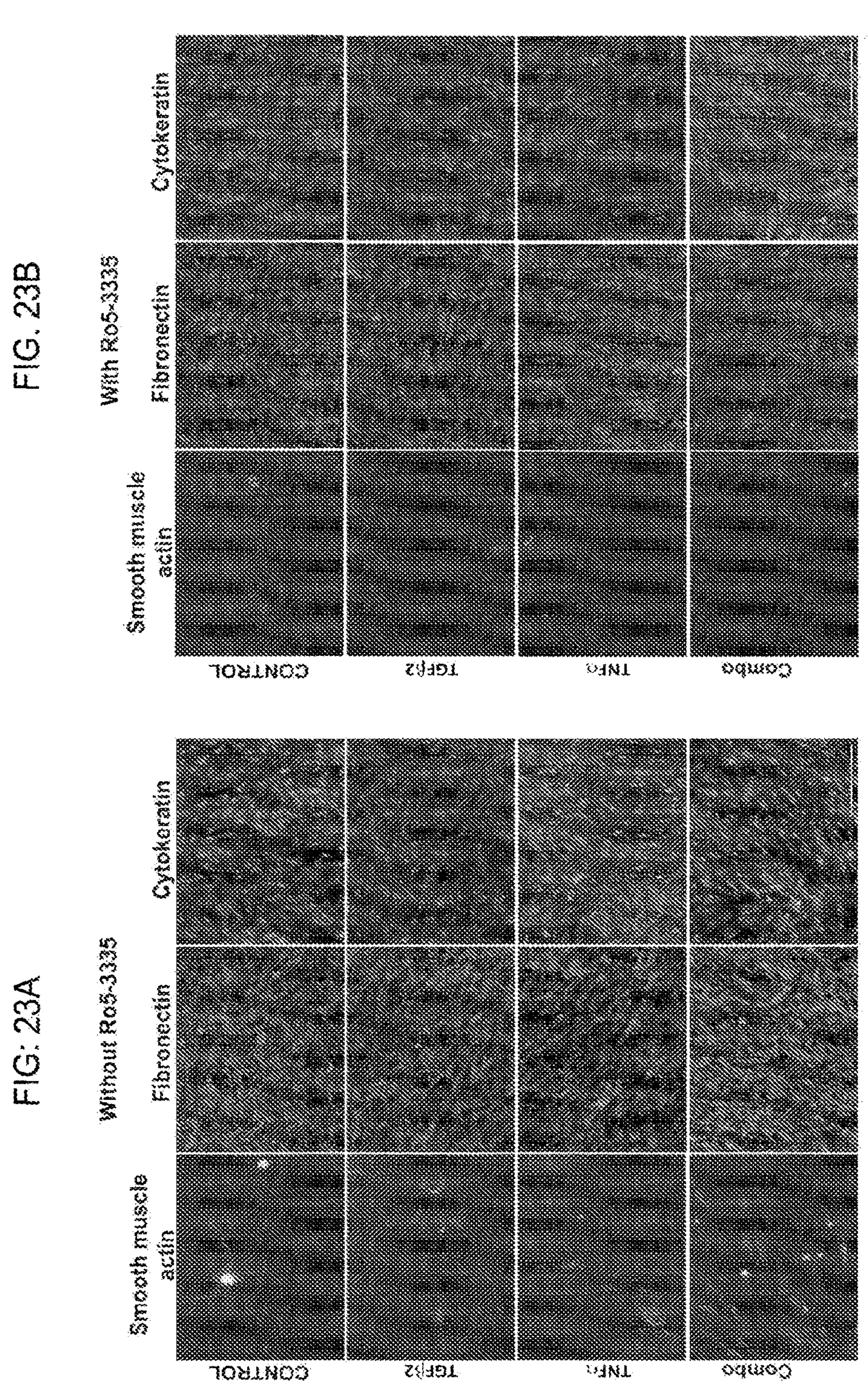
FIG. 23A are immunofluorescence staining images of ARPE-19 cells 3 days post treatment with TGFβ2, TNFα, and combination of TGFβ2, TNFα and IL-6 (10 ng/ml each). Also shown is treatment without a RUNX1 small molecule inhibitor (Ro5-3335), assessed as a reduction in the epithelial marker (cytokeratin-right panel) and an increase in the mesenchymal markers such as fibronectin (middle panel) and smooth muscle actin (left panel). Scale bars—200 microns.
FIG. 23B are immunofluorescence staining images of ARPE-19 cells 3 days post treatment with TGFβ2, TNFα, and combination of TGFβ2, TNFα and IL-6 (10 ng/mL each). The data showed that treatment with a RUNX1 small molecule inhibitor (Ro5-3335) prevented EMT, which was assessed as a reduction in the epithelial marker (cytokeratin—right panel) and an increase in the mesenchymal markers such as fibronectin (middle panel) and smooth muscle actin (left panel). Scale bars—200 microns.

Furthermore, treatment with RUNX1 small molecule inhibitor, Ro5-335, in ARPE-19 cells prevented EMT. This was assessed by the reduction in the epithelial marker, cytokeratin, and an increase in the mesenchymal markers such as fibronectin, and smooth muscle actin (FIG. 23A and 23B). ARPE-19 cells were grown to confluence and maintained in 1% for 7-10 days. Cells were treated with TGFβ2, TNFα, and a combination of TGFβ2, TNFα and IL-6 (10 ng/ml each) for 3 days with or without 150 uM RUNX1 inhibitor (Ro5-3335, Calbiochem) or vehicle. Cells were washed and fixed with 4% paraformaldehyde for 10 minutes at room temperature. Cells were incubated with primary antibodies, mouse anti-cytokeratin (1:250; Abcam), or rabbit anti-fibronectin (1:500, Sigma) or smooth muscle actin (1:50; DAKO) overnight at 4° C. The following day, cells were incubated with secondary antibody goat anti-mouse 488 or goat anti-rabbit 594 (1:300; Life Technologies) respectively for 2 hours at room temperature and DAPI. Cells were washed with PBS and imaged. These data showed that inhibition of RUNX1 (e.g., with a small molecule), prevented EMT.

Growth Factors Induced EMT in C-PVR Cells Derived from Human Proliferative Vitreoretinopathy Membranes Growth factors, e.g., TNFα, TGFβ2 and IL-6 induced EMT in C-PVR cells derived from human proliferative vitreoretinopathy membranes (FIG. 24). EMT was assessed by morphological changes including cell shape, such as elongated, fibroblast-like shaped cells in the combination treatment (e.g., TNFα, TGFβ2 and IL-6). C-PVR cells were grown to confluence. Cells were treated with a combination of TGFβ2, TNFα and a combination of TGFβ2, TNFα and IL-6 (10 ng/ml each) for 7 days. These data demonstrate that growth factors induced EMT in C-PVR cells.

Furthermore, growth factors (e.g., TGFβ2, TNFα, and combination with TGFβ2, TNFα, and IL-6) induced EMT in C-PVR cells from human proliferative vitreoretinopathy (FIG. 25). C-PVR cells were grown to confluence. Cells were treated with TGFβ2, TNFα and a combination of TGFβ2, TNFα and IL-6 (10 ng/ml each) for 7 days. Cells were washed and fixed with 4% paraformaldehyde for 10 minutes at room temperature. Cells were incubated with primary antibodies, mouse anti-cytokeratin (1:250; Abcam) or smooth muscle actin (1:50; DAKO) overnight at 4° C. The following day, cells were incubated with secondary antibody goat anti-mouse 488 (1:300; Life Technologies) for 2 hours at room temperature and DAPI. Cells were washed with PBS and imaged. These data demonstrated that growth factors (e.g., TGFβ2, TNFα, and combination with TGFβ2, TNFα, and IL-6) induced EMT in C-PVR cells from human proliferative vitreoretinopathy (e.g., caused changes in cytokeratin and a-smooth muscle actin).

RUNX1 Expression Levels were Increased in Growth Factor-Induced EMT

An increase in RUNX1 expression (e.g., RNA) and RUNX1 protein was observed in growth-factor induced EMT ((FIG. 26A and 26B). C-PVR cells were seeded into 12-well pates. At confluence, cells were treated with growth factors TGFβ2, TNFα and a combination treatment of TGFβ2, TNFα and IL-6. Cells were washed with PBS, lysed and collected. Quantitative RT-PCR of mRNA expression was performed and values were reported as relative fold change in expression level. C-PVR cells were also seeded into 6-well pates. At confluence, cells were treated with growth factors TGFβ2, TNFα and a combination treatment of TGFβ2, TNFα and IL-6. Cells were washed with ice-cold PBS, lysed and collected at 7 day time point and immunoblotted for RUNX1 (1:200, SantaCruz Biotechnology, Dallas, Texas), N-Cadherin (1:500, Santa Cruz Biotechnology), Snail (1: 500, Abcam), Twist (Abcam) and Beta-Actin (1:1000, Cell Signaling Technology, Danvers, MA) as a loading control. These data demonstrate that growth factors (e.g., TGFβ2 and combination—TGFβ2, TNFα, and IL-6) caused changes in EMT markers in C-PVR cells.

Figure 27B:
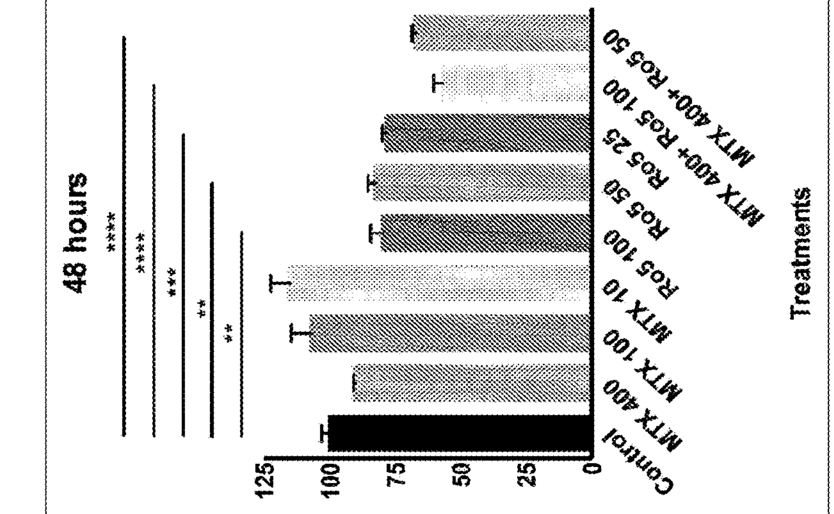
FIG. 27B is a bar graph showing results of a CyQuant cell proliferation assay 48 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 48 hours. This experiment showed that RUNX1 inhibition was more efficacious than treatment with methotrexate at inhibiting growth of ARPE-19 cells. The data also showed that RUNX1 inhibition can be used as an adjuvant in combination to treatments like methotrexate. *P<0.05, P<0.01, *P<0.001, ****P<0.0001.
Figure 27A:
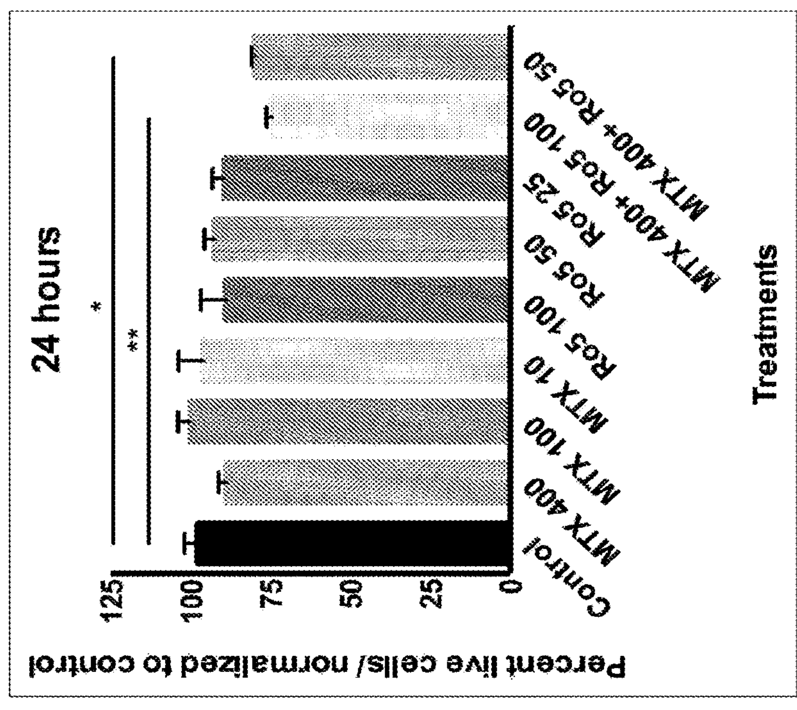
FIG. 27A is a bar graph showing results of a CyQuant cell proliferation assay 24 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 24 hours. This experiment showed that RUNX1 inhibition was more efficacious than treatment with methotrexate at inhibiting growth of ARPE-19 cells. The data also showed that RUNX1 inhibition can be used as an adjuvant in combination to treatments like methotrexate.*P<0.05. P<0.01, *P<0.001, ****P<0.0001.
Figures 28A, 28B:
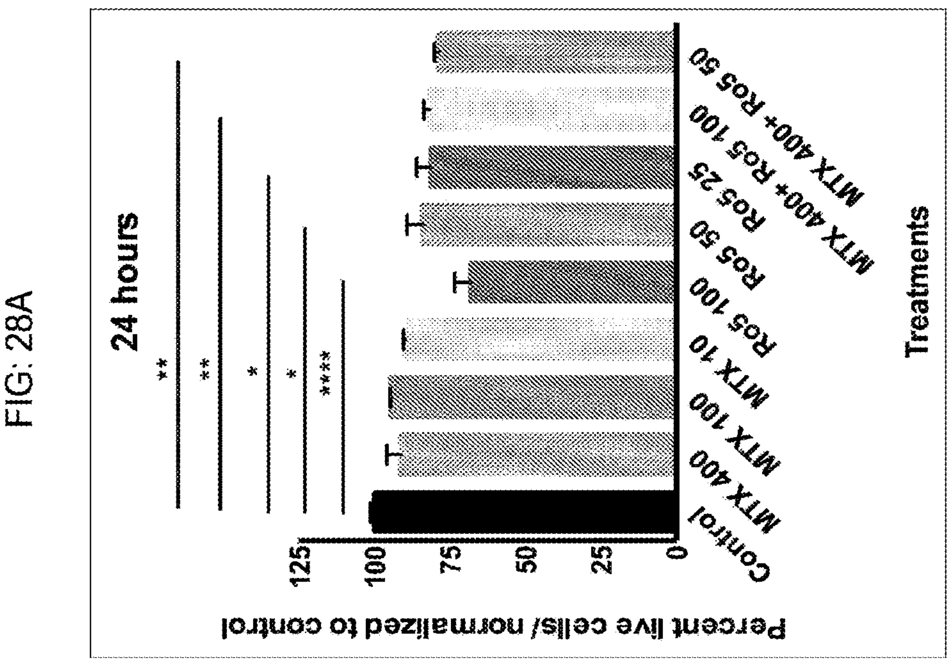
FIG. 28A is a bar graph showing results of a cell proliferation assay at 24 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 24 hours. This experiment showed that RUNX1 inhibition was more efficacious than treatment with methotrexate at inhibiting growth of C-PVR cells. The data also showed that RUNX1 inhibition can be used as an adjuvant in combination to treatments like methotrexate. *P<0.05, P<0.01, *P<0.001, ****P<0.0001.
FIG. 28B is a bar graph showing results of a cell proliferation assay at 48 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 48 hours. This experiment showed that RUNX1 inhibition was more efficacious than treatment with methotrexate at inhibiting growth of C-PVR cells. The data also showed that RUNX1 inhibition can be used as an adjuvant in combination to treatments like methotrexate. *P<0.05, P<0.01, *P<0.001, ****P<0.0001.
Figure 30B:
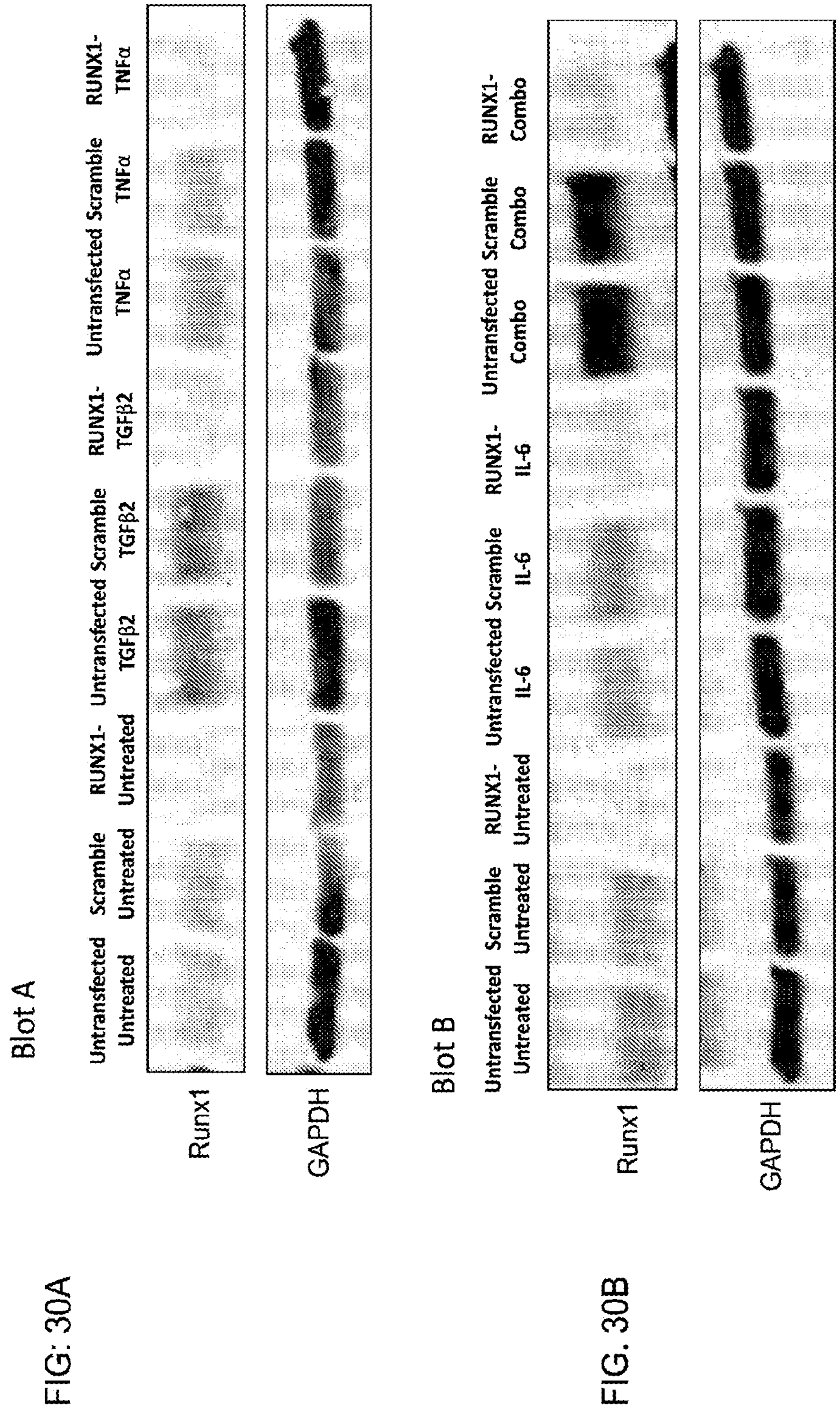
FIG. 30B is an image of an immunoblot showing RUNX1 protein levels in ARPE-19 cells treated with IL-6 or with a combination of these growth factors (combination comprises TGFβ2, TNFα, and IL-6). These data showed that each of these growth factors induced protein expression of RUNX1 and that such induction was stronger when the growth factors were combined. It also showed that siRNA treatment efficient reduced the induction of RUNX1 triggered by each of these growth factors alone or in combination. These data demonstrated that RUNX1 inhibition can be used to limit the effect of these growths factors as it relates to PVR.

RUNX1 Inhibition was More Effective at Inhibiting Growth of ARPE-19 Cells and C-PVR Cells, as Compared to Methotrexate RUNX1 inhibition was more efficacious at inhibiting growth of ARPE-19 cells, as compared to treatment with methotrexate (FIG. 27A and 27B). Furthermore, the data reported that RUNX1 inhibition could be used as an adjuvant in combination to treatments (e.g., such as methotrexate). ARPE 19 cells were cultured in 96 well plates for 8 hours, followed by treatment with RUNX1 inhibitor (Ro5-3335, Calbiochem) or Methotrexate (Sigma) in growth media or vehicle only for a period of 24 or 48 hours. The cells were washed and the CyQuant Direct nucleic acid stain was added and incubated at 37° C. in the incubator. Fluorescence read outs were measured at wavelengths as instructed in the protocol. These data demonstrated the comparison of efficacy of methotrexate and RUNX1 inhibitor, and indicated that RUNX1 inhibition was more effective. Similar results were also observed in C-PVR cells. For example, it was shown that RUNX1 inhibition was more efficacious than treatment with methotrexate at inhibiting growth of C-PVR cells (FIG. 28A and FIG. 28B).

Figure 31:
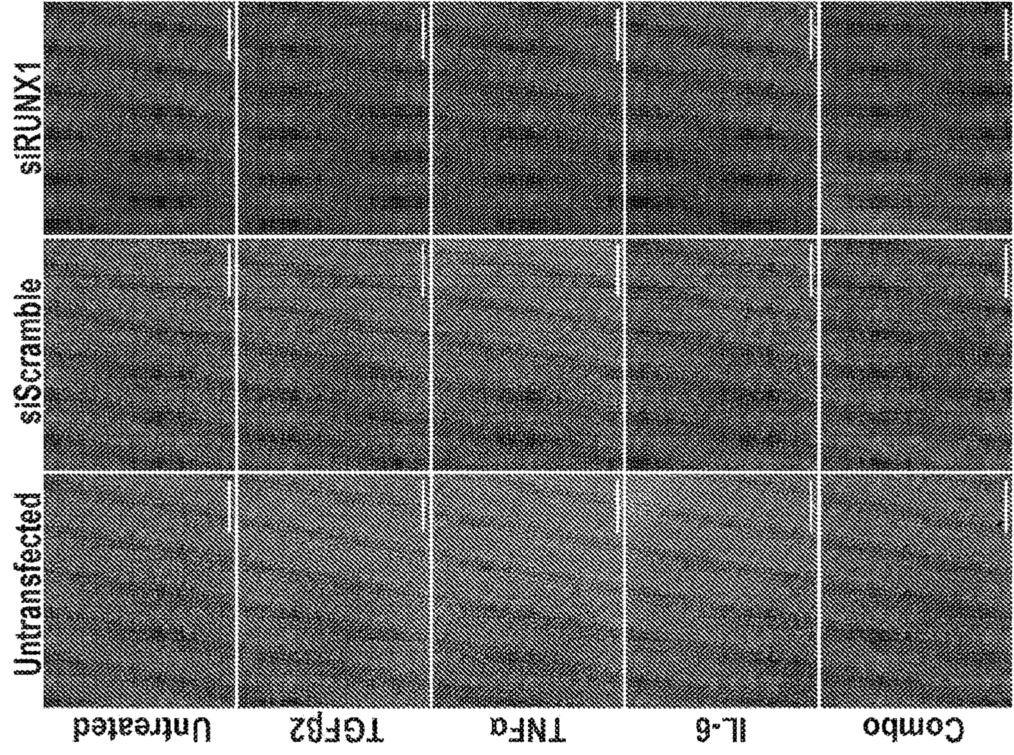
FIG. 31 is a series of bright field images of C-PVR cells, 72 hours after RUNX1 knockdown and 48 hours post treatment with a combination of TGFβ2, TNFα and IL-6, and which showed no or reduced EMT (right bottom picture) compared to un-transfected (right top) and Scramble (right middle). EMT was determined by morphological changes including cell shape. These data demonstrate that RUNX1 inhibition using siRNA resulted in inhibition of EMT. Scale bars—1000 microns.

RUNX1 Knockdown Inhibited EMT in ARPE-19 Cells and Partially Inhibited EMT in C-PVR Cells RUNX1 inhibition using siRNA resulted in the inhibition of EMT (FIG. 29). ARPE-19 cells were grown to 60-70% confluence. Cells were transfected with siScramble or siRUNX1overnight in and treated with growth factors TGFβ2, TNFα and IL-6 (10 ng/ ml) for 2 days. Bright field images were taken using the EVOS microscope. The data demonstrated that RUNX1 knockdown inhibited EMT in ARPE-19 cells. Similarly, RUNX1 inhibition using siRNA resulted in inhibition of EMT in C-PVR cells (FIG. 31). C-PVR cells were grown to 60-70% confluence. Cells were transfected with siScramble or siRUNX1 overnight in and treated with growth factors TGFβ2, TNFα and IL-6 (10 ng/ml each) for 2 days. Bright field images were taken using the EVOS microscope, and showed inhibition of EMT. EMT was determined by morphological changes (e.g., cell shape).

Growth Factor Triggered RUNX1 Induction was Inhibited Using siRNA

Growth factor triggered RUNX1 induction was inhibited using siRNA. ARPE~19 cells were grown to 60-70% confluence. Cells were transfected with siScramble or siRUNX1 overnight in and treated with growth factors TGFβ2. TNFα and IL-6 (10 ng/ ml) for 2 days.

Cells were washed with ice-cold PBS, lysed and collected and immunoblotted for RUNX1 (1:200, SantaCruz Biotechnology, Dallas, Texas), and glyceraldehyde 3-phosphate dehydrogenase (GAPDH) (1:1000, SantaCruz Biotechnology) as a loading control. These data show that each of these growth factors (e.g., TGFβ2, TNFα and IL-6) induced protein expression of RUNX1 and that such induction was stronger when the growth factors were combined. Furthermore, the data also showed that siRNA treatment efficient reduced the induction of RUNX1 triggered by each of these growth factors alone or in combination. This data demonstrated that RUNX1 inhibition can be used to limit the effect of these growths factors as it relates to PVR.

Significant Reduction of Human PVR was Observed in an Explant Model After Treatment with RUNX1 Inhibitor After treatment with a RUNX1 inhibitor, RoS-3335, a significant reduction of human PVR in an explant model was observed (FIG. 32A-32B and FIG. 33A-33B). This result was observed from two different donors. PVR membranes were freshly obtained from patients and placed in growth factor-reduced Matrigel (BD Biosciences) seeded in 24 well plates. 30 μl of matrigel were used to coat the bottom of 24 well plates without touching the edges of the well. After seeding the PVR membrane, explant plates were incubated in a 37° C. cell incubator without medium for 10 minutes in order for the Matrigel to solidify. 500 μl of medium was added to each well and incubated at 37° C. with 5% $CO_2$. The explants were treated with RUNX1 inhibitor (Ro5-3335). Phase contrast photos of individual explants were taken daily.

Synergistic Effect was Observed with the Combination of RUNX1 Inhibition and Methotrexate Explant data reveled the reduction of the growth of PVR membranes in an explant model. Furthermore, a synergistic effect was observed, when RUNX1 inhibition (e.g., with Ro5-3335) was combined with methotrexate (FIG. 34A and 34B). PVR membranes were freshly obtained from patients, placed in growth factor-reduced Matrigel (BD Biosciences), and seeded in 24 well plates. 30 μl of matrigel was used to coat the bottom of 24 well plates without touching the edges of the well. After seeding, the PVR membrane explant plates were incubated in a 37° C. cell incubator without medium for 10 minutes in order for the Matrigel to solidify. 500 μl of medium was added to each well and incubated at 37° C. with 5% $CO_2$. The explants were treated with RUNX1 inhibitor (Ro5-3335) or a combination of Ro5-3335 and methotrexate. Phase contrast photos of individual explants were taken daily.

Lenlidomide Inhibited Proliferation in C-PVR Cells

C-PVR cells were treated with lenalidomide, and it was found that lenalidomide treatment significantly reduced proliferation of C-PVR cells. Lenalidomide treatment alone or in combination with a RUNX1 inhibitor may be used for the treatment of PVR.

Lenlidomide inhibited proliferation in C-PVR cells at 48 and 72 hours, with 40 and 80 nM (FIG. 35A-35D). A CyQuant Cell Proliferation Assay was performed 48 and 72 hours post-treatment, with lenalidomide at 40 nM, and 80 nM. The data were compared to vehicle treated, and showed a significant reduction in percent live cells at 72 hours. C-PVR cells were cultured in 96 well plates for 8 hours, followed by treatment with lenalidomide (Sigma-Aldrich) in growth media or vehicle only for a period of 48 or 72 hours. The cells were washed, and CyQuant Direct and nucleic acid stain was added and incubated at 37° C. Fluorescence read outs were measured at wavelengths as instructed in the protocol.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating or reducing the severity of proliferative vitreoretinopathy (PVR) in a human subject comprising: diagnosing a PVR in a subject, wherein said diagnosing a PVR comprises the steps of:

(a) providing an ocular test sample from said subject, (b) assaying the level of RUNX1 protein or mRNA in the test sample; and (c) diagnosing the subject as having aberrant PVR if the level of RUNX1 protein or mRNA is elevated in the test sample compared to a normal control; and administering to the subject a small molecule RUNX1 inhibitor that comprises the structure of Formula I:

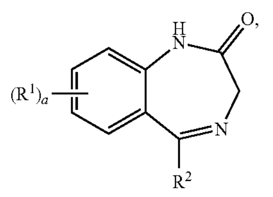

or a pharmaceutically acceptable salt or ester thereof, wherein each $R^1$ is individually selected from halogen, alkyl, aryl, heteroaryl, or alkoxy, and $R^2$ is selected from aryl or heteroaryl, and a is 0 to 4;

Formula III:

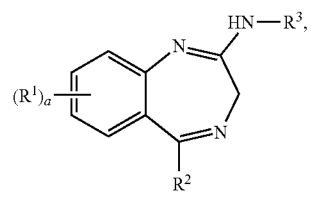

or a pharmaceutically acceptable salt or ester thereof, wherein each $R^1$ is individually selected from halogen, alkyl, aryl, heteroaryl, or alkoxy, $R^2$ is selected from aryl or heteroaryl;

$R^3$ is alkyl or aryl, and a is 0 to 4; or

Formula V:

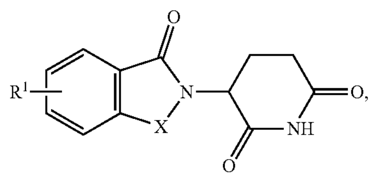

or a pharmaceutically acceptable salt or ester thereof, wherein $R^1$ is $H_3$, $NH_2$, or NHC (O) $CH_3$, and X is $CH_2$ or C(O).

2. The method of claim 1, wherein the test sample from the subject is an ocular sample obtained during ocular surgery.

3. The method of claim 1, wherein the level of RUNX1 protein is measured by ELISA, Western blot analysis, immunohistochemistry, or immunofluorescence.

4. The method of claim 1, wherein the level of RUNX1 mRNA is measured by Q-RT-PCR.

5. The method of claim 1, wherein the small molecule is Ro5-3335, Ro24-7429, or lenalidomide.

6. The method of claim 1, wherein the RUNX1 inhibitor is administered during or after intraocular surgery.

* * * * *

SEQUENCE LISTING

```
Sequence total quantity: 39
SEQ ID NO: 1           moltype = AA  length = 453
FEATURE                Location/Qualifiers
source                 1..453
                       mol_type = protein
                       organism = Homo sapiens
SEQUENCE: 1
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRRHR  180
QKLDDQTKPG SLSFSERLSE LEQLRRTAMR VSPHHPAPTP NPRASLNHST AFNPQPQSQM  240
QDTRQIQPSP PWSYDQSYQY LGSIASPSVH PATPISPGRA SGMTTLSAEL SSRLSTAPDL  300
TAFSDPRQFP ALPSISDPRM HYPGAFTYSP TPVTSGIGIG MSAMGSATRY HTYLPPPYPG  360
SSQAQGGPFQ ASSPSYHLYY GASAGSYQFS MVGGERSPPR ILPPCTNAST GSALLNPSLP  420
NQSDVVEAEG SHSNSPTNMA PSARLEEAVW RPY                               453

SEQ ID NO: 2           moltype = AA  length = 472
FEATURE                Location/Qualifiers
source                 1..472
                       mol_type = protein
                       organism = Homo sapiens
SEQUENCE: 2
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRRHR  180
QKLDDQTKPG SLSFSERLSE LEQLRRTAMR VSPHHPAPTP NPRASLNHST AFNPQPQSQM  240
QDTRQIQPSP PWSYDQSYQY LGSIASPSVH PATPISPGRA SGMTTLSAEL SSRLSTAPDL  300
TAFSDPRQFP ALPSISDPRM HYPGAFTYSP TPVTSGIGIG MSAMGSATRY HTYLPPPYPG  360
SSQAQGGPFQ ASSPSYHLYY GASAGSYQFS MVGGERSPPR ILPPCTNAST GSALLNPSLP  420
NQSDVVEAEG SHSNSPTNMG GASCSRQARR DPGPWARTPS WGRGRPTDRI SL          472

SEQ ID NO: 3           moltype = AA  length = 250
FEATURE                Location/Qualifiers
source                 1..250
                       mol_type = protein
                       organism = Homo sapiens
SEQUENCE: 3
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRRHR  180
QKLDDQTKPG SLSFSERLSE LEQLRRTAMR VSPHHPAPTP NPRASLNHST AFNPQPQSQM  240
QEEDTAPWRC                                                         250

SEQ ID NO: 4           moltype = AA  length = 257
FEATURE                Location/Qualifiers
source                 1..257
                       mol_type = protein
                       organism = Homo sapiens
SEQUENCE: 4
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRRHR  180
QKLDDQTKPG SLSFSERLSE LEQLRRTAMR VSPHHPAPTP NPRASLNHST AFNPQPQSQM  240
QDTRQIQPSP PWSYDQS                                                 257

SEQ ID NO: 5           moltype = AA  length = 224
FEATURE                Location/Qualifiers
source                 1..224
                       mol_type = protein
```

-continued

```
                        organism = Homo sapiens
SEQUENCE: 5
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRSKC  180
IHLGLVHPPG WYTLQAGILR DHVSDSLGST FPPGGWQAPV KPKS                  224

SEQ ID NO: 6            moltype = AA  length = 188
FEATURE                 Location/Qualifiers
source                  1..188
                        mol_type = protein
                        organism = Homo sapiens
SEQUENCE: 6
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRNSL  180
TWPRYPHI                                                          188

SEQ ID NO: 7            moltype = AA  length = 242
FEATURE                 Location/Qualifiers
source                  1..242
                        mol_type = protein
                        organism = Homo sapiens
SEQUENCE: 7
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVDGP REPRRHRQKL DDQTKPGSLS FSERLSELEQ LRRTAMRVSP  180
HHPAPTPNPR ASLNHSTAFN PQPQSQMQDT RQIQPSPPWS YDQSYQYLGS IASPSVHPAT  240
PI                                                                242

SEQ ID NO: 8            moltype = AA  length = 480
FEATURE                 Location/Qualifiers
source                  1..480
                        mol_type = protein
                        organism = Homo sapiens
SEQUENCE: 8
MASDSIFESF PSYPQCFMRE CILGMNPSRD VHDASTSRRF TPPSTALSPG KMSEALPLGA  60
PDAGAALAGK LRSGDRSMVE VLADHPGELV RTDSPNFLCS VLPTHWRCNK TLPIAFKVVA  120
LGDVPDGTLV TVMAGNDENY SAELRNATAA MKNQVARFND LRFVGRSGRG KSFTLTITVF  180
TNPPQVATYH RAIKITVDGP REPRRHRQKL DDQTKPGSLS FSERLSELEQ LRRTAMRVSP  240
HHPAPTPNPR ASLNHSTAFN PQPQSQMQDT RQIQPSPPWS YDQSYQYLGS IASPSVHPAT  300
PISPGRASGM TTLSAELSSR LSTAPDLTAF SDPRQFPALP SISDPRMHYP GAFTYSPTPV  360
TSGIGIGMSA MGSATRYHTY LPPPYPGSSQ AQGGPFQASS PSYHLYYGAS AGSYQFSMVG  420
GERSPPRILP PCTNASTGSA LLNPSLPNQS DVVEAEGSHS NSPTNMAPSA RLEEAVWRPY  480

SEQ ID NO: 9            moltype = AA  length = 456
FEATURE                 Location/Qualifiers
source                  1..456
                        mol_type = protein
                        organism = Homo sapiens
SEQUENCE: 9
MNPSRDVHDA STSRRFTPPS TALSPGKMSE ALPLGAPDAG AALAGKLRSG DRSMVEVLAD  60
HPGELVRTDS PNFLCSVLPT HWRCNKTLPI AFKVVALGDV PDGTLVTVMA GNDENYSAEL  120
RNATAAMKNQ VARFNDLRFV GRSGRGKSFT LTITVFTNPP QVATYHRAIK ITVDGPREPR  180
RHRQKLDDQT KPGSLSFSER LSELEQLRRT AMRVSPHHPA PTPNPRASLN HSTAFNPQPQ  240
SQMQDTRQIQ PSPPWSYDQS YQYLGSIASP SVHPATPISP GRASGMTTLS AELSSRLSTA  300
PDLTAFSDPR QFPALPSISD PRMHYPGAFT YSPTPVTSGI GIGMSAMGSA TRYHTYLPPP  360
YPGSSQAQGG PFQASSPSYH LYYGASAGSY QFSMVGGERS PPRILPPCTN ASTGSALLNP  420
SLPNQSDVVE AEGSHSNSPT NMAPSARLEE AVWRPY                            456

SEQ ID NO: 10           moltype = AA  length = 468
FEATURE                 Location/Qualifiers
source                  1..468
                        mol_type = protein
                        organism = Homo sapiens
SEQUENCE: 10
MPAAPRGPAQ GEAAARTRSR DASTSRRFTP PSTALSPGKM SEALPLGAPD AGAALAGKLR  60
SGDRSMVEVL ADHPGELVRT DSPNFLCSVL PTHWRCNKTL PIAFKVVALG DVPDGTLVTV  120
MAGNDENYSA ELRNATAAMK NQVARFNDLR FVGRSGRGKS FTLTITVFTN PPQVATYHRA  180
IKITVDGPRE PRRHRQKLDD QTKPGSLSFS ERLSELEQLR RTAMRVSPHH PAPTPNPRAS  240
LNHSTAFNPQ PQSQMQDTRQ IQPSPPWSYD QSYQYLGSIA SPSVHPATPI SPGRASGMTT  300
LSAELSSRLS TAPDLTAFSD PRQFPALPSI SDPRMHYPGA FTYSPTPVTS GIGIGMSAMG  360
SATRYHTYLP PPYPGSSQAQ GGPFQASSPS YHLYYGASAG SYQFSMVGGE RSPPRILPPC  420
TNASTGSALL NPSLPNQSDV VEAEGSHSNS PTNMAPSARL EEAVWRPY                468

SEQ ID NO: 11           moltype = AA  length = 348
FEATURE                 Location/Qualifiers
source                  1..348
                        mol_type = protein
```

-continued

```
                         organism = Homo sapiens
SEQUENCE: 11
MAGNDENYSA ELRNATAAMK NQVARFNDLR FVGRSGRGKS FTLTITVFTN PPQVATYHRA  60
IKITVDGPRE PRRHRQKLDD QTKPGSLSFS ERLSELEQLR RTAMRVSPHH PAPTPNPRAS  120
LNHSTAFNPQ PQSQMQDTRQ IQPSPPWSYD QSYQYLGSIA SPSVHPATPI SPGRASGMTT  180
LSAELSSRLS TAPDLTAFSD PRQFPALPSI SDPRMHYPGA FTYSPTPVTS GIGIGMSAMG  240
SATRYHTYLP PPYPGSSQAQ GGPFQASSPS YHLYYGASAG SYQFSMVGGE RSPPRILPPC  300
TNASTGSALL NPSLPNQSDV VEAEGSHSNS PTNMAPSARL EEAVWRPY              348

SEQ ID NO: 12            moltype = DNA  length = 7274
FEATURE                  Location/Qualifiers
source                   1..7274
                         mol_type = genomic DNA
                         organism = Homo sapiens
SEQUENCE: 12
catagagcca gcgggcgcgg gcgggacggg cgccccgcgg ccggacccag ccagggcacc  60
acgctgcccg gccctgcgcc gccaggcact tctttccggg gctcctaggg acgccagaag  120
gaagtcaacc tctgctgctt ctccttggcc tgcgttggac cttccttttt ttgttgtttt  180
tttttgtttt tccccttctt tccttttgaa ttaactggct tcttggctgg atgttttcaa  240
cttctttcct ggctgcgaac ttttccccaa ttgttttcct tttacaacag ggggagaaag  300
tgctctgtgg tccgaggcga gccgtgaagt tgcgtgtgcg tggcagtgtg cgtggcagga  360
tgtgcgtgcg tgtgtaaccc gagccgcccg atctgtttcg atctgcgccg cggagccctc  420
cctcaaggcc cgctccacct gctgcggtta cgcggcgctc gtgggtgttc gtgcctcgga  480
gcagctaacc ggcgggtgct gggcgacggt ggaggagtat cgtctcgctg ctgcccgagt  540
cagggctgag tcacccagct gatgtagaca gtggctgcct tccgaagagt gcgtgtttgc  600
atgtgtgtga ctctgcggct gctcaactcc caacaaacca gaggaccagc cacaaactta  660
accaacatcc ccaaacccga gttcacagat gtgggagagc tgtagaaccc tgagtgtcat  720
cgactgggcc ttcttatgat tgttgtttta agattagctg aagatctctg aaacgctgaa  780
ttttctgcac tgagcgtttt gacagaattc attgagagaa cagagaacat gacaagtact  840
tctagctcag cactgctcca actactgaag ctgattttca aggctactta aaaaaatctg  900
cagcgtacat taatggattt ctgttgtgtt taaattctcc acagattgta ttgtaaatat  960
tttatgaagt agagcatatg tatatattta tatatacgtg cacatacatt agtagcacta  1020
cctttggaag tctcagctct tgcttttcgg gactgaagcc agttttgcat gataaaagtg  1080
gccttgttac gggagataat tgtgttctgt tgggacttta gacaaaactc acctgcaaaa  1140
aactgacagg cattaactac tggaacttcc aaataatgtg tttgctgatc gttttactct  1200
tcgcataaat attttaggaa gtgtatgaga attttgcctt caggaacttt tctaacagcc  1260
aaagacagaa cttaacctct gcaagcaaga ttcgtggaag atagtctcca ctttttaatg  1320
cactaagcaa tcggttgcta ggagcccatc ctgggtcaga ggccgatccg cagaaccaga  1380
acgttttccc ctcctggact gttagtaact tagtctccct cctcccctaa ccaccccgc   1440
ccccccccac cccccgcagt aataaaggcc cctgaacgtg tatgttggtc tcccgggagc  1500
tgcttgctga agatccgcgc ccctgtcgcc gtctggtagg agctgtttgc agggtcctaa  1560
ctcaatcggc ttgttgtgat gcgtatcccc gtagatgcca gcacgagccg ccgcttcacg  1620
ccgccttcca ccgcgctgag cccaggcaag atgagcgagg cgttgccgct gggcgccccg  1680
gacgccggcg ctgccctggc cggcaagctg aggagcggcg accgcagcat ggtggaggtg  1740
ctggccgacc acccgggcga gctggtgcgc accgacagcc ccaacttcct ctgctccgtg  1800
ctgcctacgc actggcgctg caacaagacc ctgcccatcg ctttcaaggt ggtggcccta  1860
ggggatgttc cagatggcac tctggtcact gtgatggctg gcaatgatga aaactactcg  1920
gctgagctga gaaatgctac cgcagccatg aagaaccagg ttgcaagatt taatgacctc  1980
aggtttgtcg gtcgaagtgg aagagggaaa agcttcactc tgaccatcac tgtcttcaca  2040
aacccaccgc aagtcgccac ctaccacaga gccatcaaaa tcacagtgga tgggccccga  2100
gaacctcgaa gacatcggca gaaactagat gatcagacca agcccgggag cttgtccttt  2160
tccgagcggc tcagtgaact ggagcagctg cggcgcacag ccatgagggt cagcccacac  2220
cacccagccc ccacgcccaa ccctcgtgcc tccctgaacc actccactgc ctttaaccct  2280
cagcctcaga gtcagatgca ggatacaagg cagatccaac catccccacc gtggtcctac  2340
gatcagtcct accaatacct gggatccatt gcctctcctt ctgtgcaccc agcaacgccc  2400
atttcacctg gacgtgccag cggcatgaca accctctctg cagaactttc cagtcgactc  2460
tcaacggcac ccgacctgac agcgttcagc gacccgcgcc agttccccgc gctgccctcc  2520
atctccgacc cccgcatgca ctatccaggc gccttcacct actccccgac gccggtcacc  2580
tcgggcatcg gcatcggcat gtcggccatg ggctcggcca cgcgctacca cacctacctg  2640
ccgccgccct accccggctc gtcgcaagcg cagggaggcc cgttccaagc cagctcgccc  2700
tcctaccacc tgtactacgg cgcctcggcc ggctcctacc agttctccat ggtgggcggc  2760
gagcgctcgc cgccgcgcat cctgccgccc tgcaccaacg cctccaccgg ctccgcgctg  2820
ctcaacccca gcctcccgaa ccagagcgac gtggtggagg ccgagggcag ccacagcaac  2880
tcccccacca acatggcgcc ctccgcgcgc ctggaggagg ccgtgtggag gccctactga  2940
ggcgccaggc ctggcccggc tgggccccgc gggccgccgc cttcgcctcc gggcgcgcgg  3000
gcctcctgtt cgcgacaagc ccgccgggat cccgggccct gggcccggcc accgtcctgg  3060
ggccgagggc gcccgacggc caggatctcg ctgtaggtca ggcccgcgca gcctcctgcg  3120
cccagaagcc cacgccgccg ccgtctgctg gcgccccggc cctcgcggag gtgtccgagg  3180
cgacgcacct cgagggtgtc cgccggcccc agcacccagg ggacgcgctg gaaagcaaac  3240
aggaagattc ccggagggaa actgtgaatg cttctgattt agcaatgctg tgaataaaaa  3300
gaaagatttt ataccttga cttaactttt taaccaagtt gtttattcca aagagtgtgg   3360
aattttggtt ggggtggggg gagaggaggg atgcaactcg ccctgtttgg catctaattc  3420
ttatttttaa tttttccgca ccttatcaat tgcaaaatgc gtatttgcat ttgggtggtt  3480
tttattttta tatacgttta tataaatata tataaattga gcttgcttct ttcttgcttt  3540
gaccatggaa agaaatatga ttccctttc tttaagtttt atttaacttt tcttttggac   3600
ttttgggtag ttgttttttt ttgttttgtt ttgttttttt gagaaacagc tacagctttg  3660
ggtcattttt aactactgta ttcccacaag gaatccccag atatttatgt atcttgatgt  3720
tcagacattt atgtgttgat aatttttaa ttatttaaat gtacttatat taagaaaaat   3780
atcaagtact acattttctt ttgttcttga tagtagccaa agttaaatgt atcacattga  3840
```

-continued

```
agaaggctag aaaaaaagaa tgagtaatgt gatcgcttgg ttatccagaa gtattgttta  3900
cattaaactc cctttcatgt taatcaaaca agtgagtagc tcacgcagca acgtttttaa  3960
taggattttt agacactgag ggtcactcca aggatcagaa gtatggaatt ttctgccagg  4020
ctcaacaagg gtctcatatc taacttcctc cttaaaacag agaaggtcaa tctagttcca  4080
gagggttgag gcaggtgcca ataattacat ctttggagag gatttgattt ctgcccaggg  4140
atttgctcac cccaaggtca tctgataatt tcacagatgc tgtgtaacag aacacagcca  4200
aagtaaactg tgtaggggag ccacatttac ataggaacca aatcaatgaa tttaggggtt  4260
acgattatag caatttaagg gcccaccaga agcaggcctc gaggagtcaa tttgcctctg  4320
tgtgcctcag tggagacaag tgggaaaaca tggtcccacc tgtgcgagac cccctgtcct  4380
gtgctgctca ctcaacaaca tctttgtgtt gctttcacca ggctgagacc ctaccctatg  4440
gggtatatgg gcttttacct gtgcaccagt gtgacaggaa agattcatgt cactactgtc  4500
cgtggctaca attcaaaggt atccaatgtc gctgtaaatt ttatggcact atttttattg  4560
gaggatttgg tcagaatgca gttgttgtac aactcataaa tactaactgc tgattttgac  4620
acatgtgtgc tccaaatgat ctggtggtta tttaacgtac ctcttaaaat tcgttgaaac  4680
gatttcaggt caactctgaa gagtatttga aagcaggact tcagaacagt gtttgatttt  4740
tattttataa atttaagcat tcaaattagg caaatctttg gctgcaggca gcaaaaacag  4800
ctggacttat ttaaaacaac ttgtttttga gttttcttat atatatattg attatttgtt  4860
ttacacacat gcagtagcac tttggtaaga gttaaagagt aaagcagctt atgttgtcag  4920
gtcgttctta tctagagaag agctatagca gatctcggac aaactcagaa tatattcact  4980
ttcatttttg acaggattcc ctccacaact cagtttcata tattattccg tattacattt  5040
ttgcagctaa attaccataa aatgtcagca aatgtaaaaa tttaatttct gaaaagcacc  5100
attagcccat ttcccccaaa ttaaacgtaa atgttttttt tcagcacatg ttaccatgtc  5160
tgacctgcaa aaatgctgga gaaaaatgaa ggaaaaaatt atgtttttca gtttaattct  5220
gttaactgaa gatattccaa ctcaaaacca gcctcatgct ctgattagat aatcttttac  5280
attgaacctt tactctcaaa gccatgtgtg gagggggctt gtcactattg taggctcact  5340
ggattggtca tttagagttt cacagactct taccagcata tatagtattt aattgtttca  5400
aaaaaaatca aactgtagtt gttttggcga taggtctcac gcaacacatt tttgtatgtg  5460
tgtgtgtgtg cgtgtgtgtg tgtgtgtgtg aaaaattgca ttcattgact tcaggtagat  5520
taaggtatct ttttattcat tgccctcagg aaagttaagg tatcaatgag acccttaagc  5580
caatcatgta ataactgcat gtgtctggtc caggagaagt attgaataag ccatttctac  5640
tgcttactca tgtccctatt tatgatttca acatggatac atatttcagt tctttctttt  5700
tctcactatc tgaaaataca tttccctccc tctcttcccc ccaatatctc ccttttttttc  5760
tctcttcctc tatcttccaa accccacttt ctccctcctc cttttcctgt gttctcttaa  5820
gcagatagca catacccccca cccagtacca aatttcagaa cacaagaagg tccagttctt  5880
ccccccttcac ataaaggaac atggtttgtc agcctttctc ctgtttatgg gtttcttcca  5940
gcagaacaga gacattgcca accatattgg atctgcttgc tgtccaaacc agcaaacttt  6000
cctgggcaaa tcacaatcag tgagtaaata gacagccttt ctgctgcctt gggtttctgt  6060
gcagataaac agaaatgctc tgattagaaa ggaaatgaat ggttccactc aaatgtcctg  6120
caatttagga ttgcagattt ctgccttgaa atacctgttt ctttgggaca ttccgtcctg  6180
atgattttta tttttgttgg tttttatttt tggggggaat gacatgtttg ggtcttttat  6240
acatgaaaat ttgtttgaca ataatctcac aaaacatatt ttacatctga acaaaaatgcc  6300
tttttgttta ccgtagcgta tacatttgtt ttgggatttt tgtgtgtttg ttgggaattt  6360
tgtttttagc caggtcagta ttgatgaggc tgatcatttg gctctttttt tccttccaga  6420
agagttgcat caacaaagtt aattgtattt atgtatgtaa atagatttta agcttcatta  6480
taaaatattg ttaatgccta taactttttt tcaatttttt tgtgtgtgtt tctaaggact  6540
ttttcttagg tttgctaaat actgtaggga aaaaaatgct tctttctact ttgtttattt  6600
tagactttaa aatgagctac ttcttattca cttttgtaaa cagctaatag catggttcca  6660
atttttttta agttcacttt ttttgttcta ggggaaatga atgtgcaaaa aaagaaaaag  6720
aactgttggt tatttgtgtt attctggatg tataaaaatc aatggaaaaa aataaacttt  6780
caaattgaaa tgacggtata acacatctac tgaaaaagca acgggaaatg tggtcctatt  6840
taagccagcc ccacctaggg gtctatttgt gtggcagtta ttgggtttgg tcacaaaaca  6900
tcctgaaaat tcgtgcgtgg gcttctttct ccctggtaca aacgtatgga atgcttctta  6960
aaggggaact gtcaagctgg tgtcttcagc cagatgacat gagagaatat cccagaaccc  7020
tctctccaag gtgtttctag atagcacagg agagcaggca ctgcactgtc cacagtccac  7080
ggtacacagt cgggtgggcc gcctcccctc tcctgggagc attcgtcgtg cccagcctga  7140
gcagggcagc tggactgctg ctgttcagga gccaccagag ccttcctctc tttgtaccac  7200
agtttcttct gtaaatccag tgttacaatc agtgtgaatg gcaaataaac agtttgacaa  7260
gtacatacac cata                                                    7274
```

```
SEQ ID NO: 13           moltype = DNA  length = 5967
FEATURE                 Location/Qualifiers
source                  1..5967
                        mol_type = genomic DNA
                        organism = Homo sapiens
SEQUENCE: 13
ctttgggcct cataaacaac cacagaacca caagttgggt agcctggcag tgtcagaagt  60
ctgaacccag catagtggtc agcaggcagg acgaatcaca ctgaatgcaa accacagggt  120
ttcgcagcgt ggtaaaagaa atcattgagt cccccgcctt cagaagaggg tgcattttca  180
ggaggaagcg atggcttcag acagcatatt tgagtcattt ccttcgtacc cacagtgctt  240
catgagagaa tgcatacttg gaatgaatcc ttctagagac gtccacgatg ccagcacgag  300
ccgccgcttc acgccgcctt ccaccgcgct gagcccaggc aagatgagcg aggcgttgcc  360
gctgggcgcc ccggacgccg gcgctgccct ggccggcaag ctgaggagcg gcgaccgcag  420
catggtggag gtgctggccg accacccggg cgagctggtg cgcaccgaca gccccaactt  480
cctctgctcc gtgctgccta cgcactggcg ctgcaacaag accctgccca tcgctttcaa  540
ggtggtggcc ctaggggatg ttccagatgg cactctggtc actgtgatgg ctggcaatga  600
tgaaaactac tcggctgagc tgagaaatgc taccgcagcc atgaagaacc aggttgcaag  660
atttaatgac ctcaggtttg tcggtcgaag tggaagaggg aaaagcttca ctctgaccat  720
cactgtcttc acaaacccac cgcaagtcgc cacctaccac agagccatca aaatcacagt  780
ggatgggccc cgagaacctc gaagacatcg gcagaaacta gatgatcaga ccaagcccgg  840
```

-continued

```
gagcttgtcc ttttccgagc ggctcagtga actggagcag ctgcggcgca cagccatgag  900
ggtcagccca caccacccag cccccacgcc caaccctcgt gcctccctga accactccac  960
tgcctttaac cctcagcctc agagtcagat gcaggataca aggcagatcc aaccatcccc  1020
accgtggtcc tacgatcagt cctaccaata cctgggatcc attgcctctc cttctgtgca  1080
cccagcaacg cccatttcac ctggacgtgc cagcggcatg acaaccctct ctgcagaact  1140
ttccagtcga ctctcaacgg cacccgacct gacagcgttc agcgacccgc gccagttccc  1200
cgcgctgccc tccatctccg acccccgcat gcactatcca ggcgccttca cctactcccc  1260
gacgccggtc acctcgggca tcggcatcgg catgtcggcc atgggctcgg ccacgcgcta  1320
ccacacctac ctgccgccgc cctaccccgg ctcgtcgcaa gcgcagggag gcccgttcca  1380
agccagctcg ccctcctacc acctgtacta cggcgcctcg gccggctcct accagttctc  1440
catggtgggc ggcgagcgct cgccgccgcg catcctgccg ccctgcacca acgcctccac  1500
cggctccgcg ctgctcaacc ccagcctccc gaaccagagc gacgtggtgg aggccgaggg  1560
cagccacagc aactccccca ccaacatggc gccctccgcg cgcctggagg aggccgtgtg  1620
gaggccctac tgaggcgcca ggcctggccc ggctgggccc cgcgggccgc cgccttcgcc  1680
tccgggcgcg cgggcctcct gttcgcgaca agcccgccgg gatcccgggc cctgggcccg  1740
gccaccgtcc tggggccgag ggcgcccgac ggccaggatc tcgctgtagg tcaggcccgc  1800
gcagcctcct gcgcccagaa gcccacgccg ccgccgtctg ctggcgcccc ggccctcgcg  1860
gaggtgtccg aggcgacgca cctcgagggt gtccgccggc cccagcaccc aggggacgcg  1920
ctggaaagca aacaggaaga ttcccggagg gaaactgtga atgcttctga tttagcaatg  1980
ctgtgaataa aaagaaagat tttataccct tgacttaact ttttaaccaa gttgtttatt  2040
ccaaagagtg tggaattttg gttggggtgg ggggagagga gggatgcaac tcgccctgtt  2100
tggcatctaa ttcttatttt taatttttcc gcaccttatc aattgcaaaa tgcgtatttg  2160
catttgggtg gtttttattt ttatatacgt ttatataaat atatataaat tgagcttgct  2220
tctttcttgc tttgaccatg gaaagaaata tgattccctt ttctttaagt tttatttaac  2280
ttttcttttg gacttttggg tagttgtttt tttttgtttt gttttgtttt tttgagaaac  2340
agctacagct ttgggtcatt tttaactact gtattcccac aaggaatccc cagatattta  2400
tgtatcttga tgttcagaca tttatgtgtt gataattttt taattattta aatgtactta  2460
tattaagaaa aatatcaagt actacatttt cttttgttct tgatagtagc caaagttaaa  2520
tgtatcacat tgaagaaggc tagaaaaaaa gaatgagtaa tgtgatcgct tggttatcca  2580
gaagtattgt ttacattaaa ctccctttca tgttaatcaa acaagtgagt agctcacgca  2640
gcaacgtttt taataggatt tttagacact gagggtcact ccaaggatca gaagtatgga  2700
attttctgcc aggctcaaca agggtctcat atctaacttc ctccttaaaa cagagaaggt  2760
caatctagtt ccagagggtt gaggcaggtg ccaataatta catctttgga gaggatttga  2820
tttctgccca gggatttgct caccccaagg tcatctgata atttcacaga tgctgtgtaa  2880
cagaacacag ccaaagtaaa ctgtgtaggg gagccacatt tacataggaa ccaaatcaat  2940
gaatttaggg gttacgatta tagcaattta agggcccacc agaagcaggc ctcgaggagt  3000
caatttgcct ctgtgtgcct cagtggagac aagtgggaaa acatggtccc acctgtgcga  3060
gaccccctgt cctgtgctgc tcactcaaca acatctttgt gttgctttca ccaggctgag  3120
accctaccct atggggtata tggctttta cctgtgcacc agtgtgacag gaaagattca  3180
tgtcactact gtccgtggct acaattcaaa ggtatccaat gtcgctgtaa attttatggc  3240
actattttta ttggaggatt tggtcagaat gcagttgttg tacaactcat aaatactaac  3300
tgctgatttt gacacatgtg tgctccaaat gatctggtgg ttatttaacg tacctcttaa  3360
aattcgttga aacgatttca ggtcaactct gaagagtatt tgaaagcagg acttcagaac  3420
agtgtttgat ttttatttta taaatttaag cattcaaatt aggcaaatct ttggctgcag  3480
gcagcaaaaa cagctggact tatttaaaac aacttgtttt tgagttttct tatatatata  3540
ttgattattt gttttacaca catgcagtag cactttggta agagttaaag agtaaagcag  3600
cttatgttgt caggtcgttc ttatctagag aagagctata gcagatctcg gacaaactca  3660
gaatatattc actttcattt ttgacaggat tccctccaca actcagtttc atatattatt  3720
ccgtattaca tttttgcagc taaattacca taaaatgtca gcaaatgtaa aaatttaatt  3780
tctgaaaagc accattagcc catttccccc aaattaaacg taaatgtttt ttttcagcac  3840
atgttaccat gtctgacctg caaaaatgct ggagaaaaat gaaggaaaaa attatgtttt  3900
tcagtttaat tctgttaact gaagatattc caactcaaaa ccagcctcat gctctgatta  3960
gataatcttt tacattgaac ctttactctc aaagccatgt gtggaggggg cttgtcacta  4020
ttgtaggctc actggattgg tcatttagag tttcacagac tcttaccagc atatatagta  4080
tttaattgtt tcaaaaaaaa tcaaactgta gttgttttgg cgataggtct cacgcaacac  4140
atttttgtat gtgtgtgtgt gtgcgtgtgt gtgtgtgtgt gtgaaaaatt gcattcattg  4200
acttcaggta gattaaggta tctttttatt cattgccctc aggaaagtta aggtatcaat  4260
gagaccctta agccaatcat gtaataactg catgtgtctg gtccaggaga agtattgaat  4320
aagccatttc tactgcttac tcatgtccct atttatgatt tcaacatgga tacatatttc  4380
agttctttct ttttctcact atctgaaaat acatttccct ccctctcttc cccccaatat  4440
ctcccttttt ttctctcttc ctctatcttc caaaccccac tttctccctc ctccttttcc  4500
tgtgttctct taagcagata gcacataccc ccacccagta ccaaatttca gaacacaaga  4560
aggtccagtt cttccccctt cacataaagg aacatggttt gtcagccttt ctcctgttta  4620
tgggtttctt ccagcagaac agagacattg ccaaccatat tggatctgct tgctgtccaa  4680
accagcaaac tttcctgggc aaatcacaat cagtgagtaa atagacagcc tttctgctgc  4740
cttgggtttc tgtgcagata aacagaaatg ctctgattag aaaggaaatg aatggttcca  4800
ctcaaatgtc ctgcaattta ggattgcaga tttctgcctt gaaatacctg tttctttggg  4860
acattccgtc ctgatgattt ttatttttgt tggtttttat ttttgggggg aatgacatgt  4920
ttgggtcttt tatacatgaa aatttgtttg acaataatct cacaaaacat attttacatc  4980
tgaacaaaat gcctttttgt ttaccgtagc gtatacattt gttttgggat ttttgtgtgt  5040
ttgttgggaa ttttgttttt agccaggtca gtattgatga ggctgatcat ttggctcttt  5100
ttttccttcc agaagagttg catcaacaaa gttaattgta tttatgtatg taaatagatt  5160
ttaagcttca ttataaaata ttgttaatgc ctataacttt ttttcaattt ttttgtgtgt  5220
gtttctaagg actttttctt aggtttgcta aatactgtag ggaaaaaaat gcttcttttct  5280
actttgttta ttttagactt taaaatgagc tacttcttat tcacttttgt aaacagctaa  5340
tagcatggtt ccaatttttt ttaagttcac ttttttttgtt ctaggggaaa tgaatgtgca  5400
aaaaaagaaa aagaactgtt ggttatttgt gttattctgg atgtataaaa atcaatggaa  5460
aaaaataaac tttcaaattg aaatgacggt ataacacatc tactgaaaaa gcaacgggaa  5520
atgtggtcct atttaagcca gcccccacct agggtctatt tgtgtggcag ttattgggtt  5580
```

-continued

```
tggtcacaaa acatcctgaa aattcgtgcg tgggcttctt tctccctggt acaaacgtat  5640
ggaatgcttc ttaaagggga actgtcaagc tggtgtcttc agccagatga catgagagaa  5700
tatcccagaa ccctctctcc aaggtgtttc tagatagcac aggagagcag gcactgcact  5760
gtccacagtc cacggtacac agtcgggtgg gccgcctccc ctctcctggg agcattcgtc  5820
gtgcccagcc tgagcagggc agctggactg ctgctgttca ggagccacca gagccttcct  5880
ctctttgtac cacagtttct tctgtaaatc cagtgttaca atcagtgtga atggcaaata  5940
aacagtttga caagtacata caccata                                     5967

SEQ ID NO: 14          moltype = DNA  length = 2722
FEATURE                Location/Qualifiers
source                 1..2722
                       mol_type = genomic DNA
                       organism = Homo sapiens
SEQUENCE: 14
catagagcca gcgggcgcgg gcgggacggg cgcccegcgg ccggacccag ccagggcacc  60
acgctgcccg gccctgcgcc gccaggcact tctttccggg gctcctaggg acgccagaag  120
gaagtcaacc tctgctgctt ctccttggcc tgcgttggac cttccttttt ttgttgtttt  180
tttttgtttt tcccctttct tccttttgaa ttaactggct tcttggctgg atgttttcaa  240
cttctttcct ggctgcgaac ttttccccaa ttgttttcct tttacaacag ggggagaaag  300
tgctctgtgg tccgaggcga gccgtgaagt tgcgtgtgcg tggcagtgtg cgtggcagga  360
tgtgcgtgcg tgtgtaaccc gagccgcccg atctgtttcg atctgcgccg cggagccctc  420
cctcaaggcc cgctccacct gctgcggtta cgcggcgctc gtgggtgttc gtgcctcgga  480
gcagctaacc ggcgggtgct gggcgacggt ggaggagtat cgtctcgctg ctgcccgagt  540
cagggctgag tcacccagct gatgtagaca gtggctgcct tccgaagagt gcgtgtttgc  600
atgtgtgtga ctctgcggct gctcaactcc caacaaacca gaggaccagc cacaaactta  660
accaacatcc ccaaacccga gttcacagat gtgggagagc tgtagaaccc tgagtgtcat  720
cgactgggcc ttcttatgat tgttgtttta agattagctg aagatctctg aaacgctgaa  780
ttttctgcac tgagcgtttt gacagaattc attgagagaa cagagaacat gacaagtact  840
tctagctcag cactgctcca actactgaag ctgattttca aggctactta aaaaaatctg  900
cagcgtacat taatggattt ctgttgtgtt taaattctcc acagattgta ttgtaaatat  960
tttatgaagt agagcatatg tatatattta tatatacgtg cacatacatt agtagcacta  1020
cctttggaag tctcagctct tgcttttcgg gactgaagcc agttttgcat gataaaagtg  1080
gccttgttac gggagataat tgtgttctgt tgggacttta gacaaaactc acctgcaaaa  1140
aactgacagg cattaactac tggaacttcc aaataatgtg tttgctgatc gttttactct  1200
tcgcataaat attttaggaa gtgtatgaga attttgcctt caggaacttt tctaacagcc  1260
aaagacagaa cttaacctct gcaagcaaga ttcgtggaag atagtctcca ctttttaatg  1320
cactaagcaa tcggttgcta ggagcccatc ctgggtcaga ggccgatccg cagaaccaga  1380
acgttttccc ctcctggact gttagtaact tagtctccct cctcccctaa ccaccccgc  1440
cccccccac cccccgcagt aataaaggcc cctgaacgtg tatgttggtc tcccgggagc  1500
tgcttgctga agatccgcgc ccctgtcgcc gtctggtagg agctgtttgc agggtcctaa  1560
ctcaatcggc ttgttgtgat gcgtatcccc gtagatgcca gcacgagccg ccgcttcacg  1620
ccgccttcca ccgcgctgag cccaggcaag atgagcgagg cgttgccgct gggcgccccg  1680
gacgccggcg ctgccctggc cggcaagctg aggagcggcg accgcagcat ggtggaggtg  1740
ctggccgacc acccgggcga gctggtgcgc accgacagcc ccaacttcct ctgctccgtg  1800
ctgcctacgc actggcgctg caacaagacc ctgcccatcg ctttcaaggt ggtggcccta  1860
ggggatgttc cagatggcac tctggtcact gtgatggctg gcaatgatga aaactactcg  1920
gctgagctga gaaatgctac cgcagccatg aagaaccagg ttgcaagatt taatgacctc  1980
aggtttgtcg gtcgaagtgg aagagggaaa agcttcactc tgaccatcac tgtcttcaca  2040
aacccaccgc aagtcgccac ctaccacaga gccatcaaaa tcacagtgga tgggccccga  2100
gaacctcgaa gacatcggca gaaactagat gatcagacca agcccgggag cttgtccttt  2160
tccgagcggc tcagtgaact ggagcagctg cggcgcacag ccatgagggt cagcccacac  2220
cacccagccc ccacgcccaa ccctcgtgcc tccctgaacc actccactgc ctttaaccct  2280
cagcctcaga gtcagatgca ggaggaagac acagcaccct ggagatgtta aggcagaagt  2340
cagttcttct gtccatccct ctccccagcc aggatagagc tatcttttcc atctcatcct  2400
cagaagagac tcagaagaaa gatgacagcc ctcagaatgc acgttatgag gaaggcagaa  2460
tgtgggtctg taattcctcc gtgtcccttc tcccctctg caaaccgtcg taacaataat  2520
agttcctaac acatgggaca attgtgagga ttaaatgagt tagcctgcag aaatcacttg  2580
atgcacagca catgggaagc attgtgtgta tttattaatc cttcacaaag tctttgagat  2640
atatttttat caaatattta gcatggatcc cggtacactt tcaatactta ataaatggtc  2700
aatgttattc tttttcacta tt                                          2722

SEQ ID NO: 15          moltype = DNA  length = 6230
FEATURE                Location/Qualifiers
source                 1..6230
                       mol_type = genomic DNA
                       organism = Homo sapiens
SEQUENCE: 15
agggcggctg ctgcccctg gcgtccgcca gagcccgcgg cgcgtcccga cagctccgcg  60
cagtccgggc ccgcccggga aaggcctcca cgccagtcaa ccccggcccc ctcctgcgtc  120
cgggcccgcg gcaacgcccg gggacagtcc ctgcgcggca gcggccacag caccctagcc  180
ctgggggagg gaggagcggg cgtcaggggc cccgtgaggt cggcgaggga cccccgcgcc  240
ggggagctta attgaggggc tccgcgggga ccacaaagca gcccgcggtg gaacggggcc  300
gggatccggg gactgggttg cagccccggg gtggatgaga ggccccggga ggtgcagggc  360
ccggcaggga gggcgtggag ggactcatgg tgacgggagc agcctccgct gggagggagc  420
cccgccgggc ggggtcggag ttggcagcgc acgccggacc gggggcgggg ccctccgagc  480
tccgcgaaaa tgcccgcagc accgcgggga ccggcgcagg gggaagcggc cgcccgcacg  540
cgaagccggg atgccagcac gagccgccgc ttcacgccgc cttccaccgc gctgagccca  600
ggcaagatga gcgaggcgtt gccgctgggc gccccggacg ccggcgctgc cctggccggc  660
aagctgagga gcggcgaccg cagcatggtg gaggtgctgg ccgaccaccc gggcgagctg  720
```

-continued

```
gtgcgcaccg acagccccaa cttcctctgc tccgtgctgc ctacgcactg gcgctgcaac  780
aagaccctgc ccatcgcttt caaggtggtg gccctagggg atgttccaga tggcactctg  840
gtcactgtga tggctggcaa tgatgaaaac tactcggctg agctgagaaa tgctaccgca  900
gccatgaaga accaggttgc aagatttaat gacctcaggt ttgtcggtcg aagtggaaga  960
gggaaaagct tcactctgac catcactgtc ttcacaaacc caccgcaagt cgccacctac  1020
cacagagcca tcaaaatcac agtggatggg ccccgagaac ctcgaagaca tcggcagaaa  1080
ctagatgatc agaccaagcc cgggagcttg tccttttccg agcggctcag tgaactggag  1140
cagctgcggc gcacagccat gagggtcagc ccacaccacc cagcccccac gcccaaccct  1200
cgtgcctccc tgaaccactc cactgccttt aaccctcagc ctcagagtca gatgcaggat  1260
acaaggcaga tccaaccatc ccaccgtgg tcctacgatc agtcctacca atacctggga  1320
tccattgcct ctccttctgt gcacccagca acgcccattt cacctggacg tgccagcggc  1380
atgacaaccc tctctgcaga actttccagt cgactctcaa cggcacccga cctgacagcg  1440
ttcagcgacc cgcgccagtt ccccgcgctg ccctccatct ccgacccccg catgcactat  1500
ccaggcgcct tcacctactc cccgacgccg gtcacctcgg gcatcggcat cggcatgtcg  1560
gccatgggct cggccacgcg ctaccacacc tacctgccgc cgccctaccc cggctcgtcg  1620
caagcgcagg gaggcccgtt ccaagccagc tcgccctcct accacctgta ctacggcgcc  1680
tcggccggct cctaccagtt ctccatggtg ggcggcgagc gctcgccgcc gcgcatcctg  1740
ccgccctgca ccaacgcctc caccggctcc gcgctgctca accccagcct cccgaaccag  1800
agcgacgtgg tggaggccga gggcagccac agcaactccc ccaccaacat ggcgccctcc  1860
gcgcgcctgg aggaggccgt gtggaggccc tactgaggcg ccaggcctgg cccggctggg  1920
ccccgcgggc cgccgccttc gcctccgggc gcgcgggcct cctgttcgcg acaagcccgc  1980
cgggatcccg ggccctgggc ccggccaccg tcctggggcc gagggcgccc gacggccagg  2040
atctcgctgt aggtcaggcc cgcgcagcct cctgcgccca gaagcccacg ccgccgccgt  2100
ctgctggcgc cccggccctc gcggaggtgt ccgaggcgac gcacctcgag ggtgtccgcc  2160
ggccccagca cccaggggac gcgctggaaa gcaaacagga agattcccgg agggaaactg  2220
tgaatgcttc tgatttagca atgctgtgaa taaaaagaaa gattttatac ccttgactta  2280
actttttaac caagttgttt attccaaaga gtgtggaatt ttggttgggg tgggggggaga  2340
ggagggatgc aactcgccct gtttggcatc taattcttat ttttaatttt tccgcacctt  2400
atcaattgca aaatgcgtat ttgcatttgg gtggttttta tttttatata cgtttatata  2460
aatatatata aattgagctt gcttctttct tgctttgacc atggaaagaa atatgattcc  2520
cttttcttta agttttattt aacttttctt ttggactttt gggtagttgt tttttttgt  2580
tttgttttgt ttttttgaga aacagctaca gctttgggtc atttttaact actgtattcc  2640
cacaaggaat ccccagatat ttatgtatct tgatgttcag acatttatgt gttgataatt  2700
ttttaattat ttaaatgtac ttatattaag aaaaatatca agtactacat tttcttttgt  2760
tcttgatagt agccaaagtt aaatgtatca cattgaagaa ggctagaaaa aaagaatgag  2820
taatgtgatc gcttggttat ccagaagtat tgtttacatt aaactccctt tcatgttaat  2880
caaacaagtg agtagctcac gcagcaacgt ttttaatagg atttttagac actgagggtc  2940
actccaagga tcagaagtat ggaattttct gccaggctca acaagggtct catatctaac  3000
ttcctcctta aaacagagaa ggtcaatcta gttccagagg gttgaggcag gtgccaataa  3060
ttacatcttt ggagaggatt tgatttctgc ccagggattt gctcacccca aggtcatctg  3120
ataatttcac agatgctgtg taacagaaca cagccaaagt aaactgtgta ggggagccac  3180
atttacatag gaaccaaatc aatgaattta ggggttacga ttatagcaat ttaagggccc  3240
accagaagca ggcctcgagg agtcaatttg cctctgtgtg cctcagtgga gacaagtggg  3300
aaaacatggt cccacctgtg cgagaccccc tgtcctgtgc tgctcactca acaacatctt  3360
tgtgttgctt tcaccaggct gagaccctac cctatggggt atatgggctt ttacctgtgc  3420
accagtgtga caggaaagat tcatgtcact actgtccgtg gctacaattc aaaggtatcc  3480
aatgtcgctg taaattttat ggcactattt ttattggagg atttggtcag aatgcagttg  3540
ttgtacaact cataaatact aactgctgat tttgacacat gtgtgctcca aatgatctgg  3600
tggttattta acgtacctct taaaattcgt tgaaacgatt tcaggtcaac tctgaagagt  3660
atttgaaagc aggacttcag aacagtgttt gatttttatt ttataaattt aagcattcaa  3720
attaggcaaa tctttggctg caggcagcaa aaacagctgg acttatttaa aacaacttgt  3780
ttttgagttt tcttatatat atattgatta tttgttttac acacatgcag tagcactttg  3840
gtaagagtta aagagtaaag cagcttatgt tgtcaggtcg ttcttatcta gagaagagct  3900
atagcagatc tcggacaaac tcagaatata ttcactttca tttttgacag gattccctcc  3960
acaactcagt ttcatatatt attccgtatt acatttttgc agctaaatta ccataaaatg  4020
tcagcaaatg taaaaattta atttctgaaa agcaccatta gcccatttcc cccaaattaa  4080
acgtaaatgt tttttttcag cacatgttac catgtctgac ctgcaaaaat gctggagaaa  4140
aatgaaggaa aaaattatgt ttttcagttt aattctgtta actgaagata ttccaactca  4200
aaaccagcct catgctctga ttagataatc ttttacattg aacctttact ctcaaagcca  4260
tgtgtggagg gggcttgtca ctattgtagg ctcactggat tggtcattta gagtttcaca  4320
gactcttacc agcatatata gtatttaatt gtttcaaaaa aaatcaaact gtagttgttt  4380
tggcgatagg tctcacgcaa cacatttttg tatgtgtgtg tgtgtgcgtg tgtgtgtgtg  4440
tgtgtgaaaa attgcattca ttgacttcag gtagattaag gtatcttttt attcattgcc  4500
ctcaggaaag ttaaggtatc aatgagaccc ttaagccaat catgtaataa ctgcatgtgt  4560
ctggtccagg agaagtattg aataagccat ttctactgct tactcatgtc cctatttatg  4620
atttcaacat ggatacatat ttcagttctt tctttttctc actatctgaa aatacatttc  4680
cctccctctc ttccccccaa tatctccctt tttttctctc ttcctctatc ttccaaaccc  4740
cactttctcc ctcctccttt tcctgtgttc tcttaagcag atagcacata cccccaccca  4800
gtaccaaatt tcagaacaca agaaggtcca gttcttcccc cttcacataa aggaacatgg  4860
tttgtcagcc tttctcctgt ttatgggttt cttccagcag aacagagaca ttgccaacca  4920
tattggatct gcttgctgtc caaaccagca aactttcctg ggcaaatcac aatcagtgag  4980
taaatagaca gcctttctgc tgccttgggt ttctgtgcag ataaacagaa atgctctgat  5040
tagaaaggaa atgaatggtt ccactcaaat gtcctgcaat ttaggattgc agatttctgc  5100
cttgaaatac ctgtttcttt gggacattcc gtcctgatga tttttatttt tgttggtttt  5160
tatttttggg gggaatgaca tgtttgggtc ttttatacat gaaaatttgt ttgacaataa  5220
tctcacaaaa catattttac atctgaacaa aatgcctttt tgtttaccgt agcgtataca  5280
tttgttttgg gatttttgtg tgtttgttgg gaattttgtt tttagccagg tcagtattga  5340
tgaggctgat catttggctc tttttttcct tccagaagag ttgcatcaac aaagttaatt  5400
gtatttatgt atgtaaatag attttaagct tcattataaa atattgttaa tgcctataac  5460
```

-continued

```
ttttttcaa tttttttgtg tgtgtttcta aggacttttt cttaggtttg ctaaatactg  5520
tagggaaaaa aatgcttctt tctactttgt ttattttaga ctttaaaatg agctacttct  5580
tattcacttt tgtaaacagc taatagcatg gttccaattt tttttaagtt cactttttt  5640
gttctagggg aaatgaatgt gcaaaaaaag aaaaagaact gttggttatt tgtgttattc  5700
tggatgtata aaaatcaatg gaaaaaaata aactttcaaa ttgaaatgac ggtataacac  5760
atctactgaa aaagcaacgg gaaatgtggt cctatttaag ccagccccca cctagggtct  5820
atttgtgtgg cagttattgg gtttggtcac aaaacatcct gaaaattcgt gcgtgggctt  5880
ctttctccct ggtacaaacg tatggaatgc ttcttaaagg ggaactgtca agctggtgtc  5940
ttcagccaga tgacatgaga gaatatccca gaaccctctc tccaaggtgt ttctagatag  6000
cacaggagag caggcactgc actgtccaca gtccacggta cacagtcggg tgggccgcct  6060
cccctctcct gggagcattc gtcgtgccca gcctgagcag ggcagctgga ctgctgctgt  6120
tcaggagcca ccagagcctt cctctctttg taccacagtt tcttctgtaa atccagtgtt  6180
acaatcagtg tgaatggcaa ataaacagtt tgacaagtac atacaccata             6230

SEQ ID NO: 16          moltype = DNA  length = 1452
FEATURE                Location/Qualifiers
source                 1..1452
                       mol_type = genomic DNA
                       organism = Homo sapiens
SEQUENCE: 16
acagttaaat ttgtaatttg ggttgtgtga aaacttcttt gggcctcata aacaaccaca  60
gaaccacaag ttgggtagcc tggcagtgtc agaagtctga acccagcata gtggtcagca  120
ggcaggacga atcacactga atgcaaacca cagggtttcg cagcgtggta aaagaaatca  180
ttgagtcccc cgccttcaga agagggtgca ttttcaggag gaagcgatgg cttcagacag  240
catatttgag tcatttcctt cgtacccaca gtgcttcatg agagaatgca tacttggaat  300
gaatccttct agagacgtcc acgatgccag cacgagccgc cgcttcacgc cgccttccac  360
cgcgctgagc ccaggcaaga tgagcgaggc gttgccgctg ggcgccccgg acgccggcgc  420
tgccctggcc ggcaagctga ggagcggcga ccgcagcatg gtggaggtgc tggccgacca  480
cccgggcgag ctggtgcgca ccgacagccc caacttcctc tgctccgtgc tgcctacgca  540
ctggcgctgc aacaagaccc tgcccatcgc tttcaaggtg gtggccctag ggggatgttcc  600
agatggcact ctggtcactg tgatggctgg caatgatgaa aactactcgg ctgagctgag  660
aaatgctacc gcagccatga agaaccaggt tgcaagattt aatgacctca ggtttgtcgg  720
tcgaagtgga agagggaaaa gcttcactct gaccatcact gtcttcacaa acccaccgca  780
agtcgccacc taccacagag ccatcaaaat cacagtggat gggccccgag aacctcgaag  840
acatcggcag aaactagatg atcagaccaa gcccgggagc ttgtcctttt ccgagcggct  900
cagtgaactg gagcagctgc ggcgcacagc catgagggtc agcccacacc acccagcccc  960
cacgcccaac cctcgtgcct ccctgaacca ctccactgcc tttaaccctc agcctcagag  1020
tcagatgcag gaggaagaca cagcaccctg gagatgttaa ggcagaagtc agttcttctg  1080
tccatccctc tccccagcca ggatagagct atcttttcca tctcatcctc agaagagact  1140
cagaagaaag atgacagccc tcagaatgca cgttatgagg aaggcagaat gtgggtctgt  1200
aattcctccg tgtcccttct ccccctctgc aaaccgtcgt aacaataata gttcctaaca  1260
catgggacaa ttgtgaggat taaatgagtt agcctgcaga aatcacttga tgcacagcac  1320
atgggaagca ttgtgtgtat ttattaatcc ttcacaaagt ctttgagata tatttttatc  1380
aaatatttag catggatccc ggtacacttt caatacttaa taaatggtca atgttattct  1440
ttttcactat ta                                                      1452

SEQ ID NO: 17          moltype = DNA  length = 4693
FEATURE                Location/Qualifiers
source                 1..4693
                       mol_type = genomic DNA
                       organism = Homo sapiens
SEQUENCE: 17
acagttaaat ttgtaatttg ggttgtgtga aaacttcttt gggcctcata aacaaccaca  60
gaaccacaag ttgggtagcc tggcagtgtc agaagtctga acccagcata gtggtcagca  120
ggcaggacga atcacactga atgcaaacca cagggtttcg cagcgtggta aaagaaatca  180
ttgagtcccc cgccttcaga agagggtgca ttttcaggag gaagcgatgg cttcagacag  240
catatttgag tcatttcctt cgtacccaca gtgcttcatg agagaatgca tacttggaat  300
gaatccttct agagacgtcc acgatgccag cacgagccgc cgcttcacgc cgccttccac  360
cgcgctgagc ccaggcaaga tgagcgaggc gttgccgctg ggcgccccgg acgccggcgc  420
tgccctggcc ggcaagctga ggagcggcga ccgcagcatg gtggaggtgc tggccgacca  480
cccgggcgag ctggtgcgca ccgacagccc caacttcctc tgctccgtgc tgcctacgca  540
ctggcgctgc aacaagaccc tgcccatcgc tttcaaggtg gtggccctag ggggatgttcc  600
agatggcact ctggtcactg tgatggctgg caatgatgaa aactactcgg ctgagctgag  660
aaatgctacc gcagccatga agaaccaggt tgcaagattt aatgacctca ggtttgtcgg  720
tcgaagtgga agagggaaaa gcttcactct gaccatcact gtcttcacaa acccaccgca  780
agtcgccacc taccacagag ccatcaaaat cacagtggat gggccccgag aacctcgaag  840
acatcggcag aaactagatg atcagaccaa gcccgggagc ttgtcctttt ccgagcggct  900
cagtgaactg gagcagctgc ggcgcacagc catgagggtc agcccacacc acccagcccc  960
cacgcccaac cctcgtgcct ccctgaacca ctccactgcc tttaaccctc agcctcagag  1020
tcagatgcag gatacaaggc agatccaacc atccccaccg tggtcctacg atcagtccta  1080
ccaatacctg ggatccattg cctctccttc tgtgcaccca gcaacgccca tttcacctgg  1140
acgtgccagc ggcatgacaa ccctctctgc agaactttcc agtcgactct caaacagttg  1200
tgattacttc aggtttcacc agatgcctta gctgctgttc agagcttcac agaatgcctt  1260
ctaagagctt cacaacggca gtactattga catttggggc caaataattc tttgttgggg  1320
ggggtctgtc ctgagcatcg gagaatattt agcagcatcc ttggcctcta gatgccaata  1380
gcatccccct caccccagtt aggacaataa aaaatgtttc cagacattgc caaatttccc  1440
aaggggcaaa actgtcccca ggtgagaacc actgccttcc agtgttcttg ggtggtacag  1500
taaaatagga aaaccaactt aagtgcttgg ttttcacatt acttttggcc attaatgcca  1560
atattttcat ggtacattct gctccaaggc attgagagta gcacaggtat cttggcatct  1620
```

-continued

```
tgtttagctt gtggtttcta gaagcttatc cctcaagaac aaaggcactt gtcagctttt  1680
actgattgtt ctcagggcac ccctctgcac accggctacg gtcttcacct gaaataatgc  1740
ctgttctcct tcaaatgttc ctgctatggg tctatccttt ggaatttatt acataagtct  1800
tttgacttgg tcatcaccca agatcagcac cttatagtcc aagaacccta ggggccaact  1860
cctccagctg actggtgttc agatggtagg gtgacttttt aaataaaagg aatgagtaac  1920
atgtgcactc caaagtccca tatcacagtt acatttgtga atatcctgga cttcaatcac  1980
ccaaggagta agagagaaca ttttatggca tgggagtgtg aagtagataa aaaccatgcc  2040
tcatttcaga acccaagaat gattcttttc tttttggagg gaggacagaa ttccagatga  2100
gctttcacag tggcatagaa cagtatggga gactgctctt caatttggca gaactccctc  2160
tgagaaatca agcctggagc acaggcctga aaagtgttgt cataaacctg gaggcaggag  2220
gggggtggaa tacataaaag gaaagtggct gcctggccga cagctttgag aacctgacac  2280
tgctctgtgg ctgctttgcc ttttaatcca gcccgacagc tttgtgctct gcccctcttc  2340
ccggccccag ccccacctgg gcttccttct gcgctgggga cttggactct gtctgtctct  2400
ctctctctat cctttgcaga cagactccac accttgtctg aaaagagttg tcatctagag  2460
gtttactttt ttttttcttt ttcaaaaaaa attaatgttt agctgccaac ctgggcgaca  2520
gacagcatgc attaatctga gtcatgcaaa agctcctttt aaggcagcca ttacctgctc  2580
aggttgttta atcctctggg ggcagtagga ggggccctgt agcgaggctg ctttcatcca  2640
tgtcaagctg gagagcgaag acttgagctg tcatggcaaa tatttagccc catcaatggg  2700
aaaacacttc caaccaaaat acctggacct cctaagcccc agatttccta ctcttaaaaa  2760
ctctctgtga atatcagggg atcccaactc cccccacact tctgctgaat caggggacac  2820
caggccagcc aaaaggacag aagagctaca gctggatggg tgaactgcgc agactgatgg  2880
gtttgaataa gggatctgag acaagacaca aagatgaaaa ccaacatttg aatatagcat  2940
ttgaatctga gcatatctag aaggcctaag atattgtatt atcaaaatgt gtgtaaaaaa  3000
gatagtttga ccaaatggat ggtcttttgt agtatgacgt tgctcatgtg tacatagaag  3060
aaggatcaca ggcagcattg cagctctttc ttttggatgt tctcctcaca agtgaaagaa  3120
ctattttccc ccaacagctg agaccataac atcattccag tacttatgtc catgacaaat  3180
cacggactca ctctggattc cagtaacttg gtaccatcac cacattacca tgtagtagtt  3240
ggaacctact ggcagagcat gtccagacat tgctgtaaaa cagggtgacc tttcgttcat  3300
tttccagtgg attcaccttt ttgtctcagg gcaaatgaag caagaggaat aatgggcaga  3360
gtcatttatt tgtgtccaga gtattgcatc agatgacaac aaactgactg tatttgccta  3420
atgcttttcc tcctgtccca gcttctccgt agactctata aatctaaatg gaaaaatgga  3480
gtaaagcttc ctgttaactc tcaaacatgt cacagctctc catgtcagca aaaacaagtg  3540
acacagggct tgctcacaga tggccccaaa gagcgggcag ggatgaaccc tgtggaatga  3600
ggtgtggcct ggctcgagaa tgactagagt gtggccaagg aagggcagcc tcagaaccac  3660
tgtccgttta caacgtttct cctgcccaca tgtctgcctg gctttgaaaa gattaacagg  3720
agtgtttgtt tgaaagtcag actcctggtt tcctcattag tgaagggatc tgctacagac  3780
ttgggctgtt tctataaact ttaattacct ctgatgagga gtgtatcccc tcatcacatt  3840
caccccaaag gtacagagga gttcattttt aaaaatgtgt tagagcaata aaaggccatt  3900
agagggaggg aggatggggt gtggaagaga cgagagagcg agcgagagag agagaaaaca  3960
cactagctct ccctgctgga ataataggct tgaaatatga ggaagttgat caactgccgc  4020
tgccttccaa aaacagatta atccaccttg gtagctttcc tttcagagca agcttttggc  4080
tctgtcgact ttctctatca gcctgaactc aaaaggacac aggccacatg ccatctgagc  4140
ttaagagtta ttttgtgtgt tgatctgaga acttcacatt ttaaaacaat gaattcatgt  4200
ttctactgtt tgttgctgtc tgtggatttg ctgatataaa gaggagagtc ctagcctggt  4260
catttaatga ataattctaa ggaacctgaa cttctccagg gtgcccttct acatctgcag  4320
tggtggttct cagctggggt gactttgctt ccgtcacccc acccgcagga tatctggcaa  4380
tgtctggaga cattctgagt tgtcacaaga ggggcgggcg atgctactaa cacctaatgg  4440
gtaaagcaga gatgctgcca cacatcctac gatgaacgag acagccccct ccaccccagc  4500
aaatcatgat ctggcccaaa atgtcaacag tgtcaacagt tgagaaactc tgatctacag  4560
atatagggaa ccctgcctaa tacacaaatc ctccgtagtt cccaagggcg gcctgtagcg  4620
gcacccgacc tgacagcgtt cagcgacccg cgccagttcc ccgcgctgcc ctccatctcc  4680
gacccccgca tgc                                                     4693
```

```
SEQ ID NO: 18           moltype = DNA  length = 5772
FEATURE                 Location/Qualifiers
source                  1..5772
                        mol_type = genomic DNA
                        organism = Homo sapiens
SEQUENCE: 18
acagttaaat ttgtaatttg ggttgtgtga aaacttcttt gggcctcata aacaaccaca  60
gaaccacaag ttgggtagcc tggcagtgtc agaagtctga acccagcata gtggtcagca  120
ggcaggacga atcacactga atgcaaacca cagggtttcg cagcgtggta aaagaaatca  180
ttgagtcccc cgccttcaga agagggtgca ttttcaggag gaagcgatgg cttcagacag  240
catatttgag tcatttcctt cgtacccaca gtgcttcatg agagatgcca gcacgagccg  300
ccgcttcacg ccgccttcca ccgcgctgag cccaggcaag atgagcgagg cgttgccgct  360
gggcgccccg gacgccggcg ctgccctggc cggcaagctg aggagcggcg accgcagcat  420
ggtggaggtg ctggccgacc acccgggcga gctggtgcgc accgacagcc ccaacttcct  480
ctgctccgtg ctgcctacgc actggcgctg caacaagacc ctgcccatcg ctttcaaggt  540
ggtggcccta ggggatgttc cagatggcac tctggtcact gtgatggctg gcaatgatga  600
aaactactcg gctgagctga gaaatgctac cgcagccatg aagaaccagg ttgcaagatt  660
taatgacctc aggtttgtcg gtcgaagtgg aagagggaaa agcttcactc tgaccatcac  720
tgtcttcaca aacccaccgc aagtcgccac ctaccacaga gccatcaaaa tcacagtgga  780
tgggccccga gaacctcgaa atacaaggca gatccaacca tccccaccgt ggtcctacga  840
tcagtcctac caatacctgg gatccattgc ctctccttct gtgcacccag caacgcccat  900
ttcacctgga cgtgccagcg gcatgacaac cctctctgca gaactttcca gtcgactctc  960
aacggcaccc gacctgacag cgttcagcga cccgcgccag ttccccgcgc tgccctccat  1020
ctccgacccc cgcatgcact atccaggcgc cttcacctac tccccgacgc cggtcacctc  1080
gggcatcggc atcggcatgt cggccatggg ctcggccacg cgctaccaca cctacctgcc  1140
gccgccctac cccggctcgt cgcaagcgca gggaggcccg ttccaagcca gctcgccctc  1200
```

-continued

```
ctaccacctg tactacggcg cctcggccgg ctcctaccag ttctccatgg tgggcggcga  1260
gcgctcgccg ccgcgcatcc tgccgccctg caccaacgcc tccaccggct ccgcgctgct  1320
caaccccagc ctcccgaacc agagcgacgt ggtggaggcc gagggcagcc acagcaactc  1380
ccccaccaac atggcgccct ccgcgcgcct ggaggaggcc gtgtggaggc cctactgagg  1440
cgccaggcct ggcccggctg ggccccgcgg gccgccgcct tcgcctccgg gcgcgcgggc  1500
ctcctgttcg cgacaagccc gccgggatcc cgggccctgg gcccggccac cgtcctgggg  1560
ccgagggcgc ccgacggcca ggatctcgct gtaggtcagg cccgcgcagc ctcctgcgcc  1620
cagaagccca cgccgccgcc gtctgctggc gccccggccc tcgcggaggt gtccgaggcg  1680
acgcacctcg agggtgtccg ccggccccag cacccagggg acgcgctgga aagcaaacag  1740
gaagattccc ggagggaaac tgtgaatgct tctgatttag caatgctgtg aataaaaaga  1800
aagattttat accccttgact taactttta accaagttgt ttattccaaa gagtgtggaa  1860
ttttggttgg ggtgggggga gaggagggat gcaactcgcc ctgtttggca tctaattctt  1920
atttttaatt tttccgcacc ttatcaattg caaaatgcgt atttgcattt gggtggtttt  1980
tatttttata tacgtttata taaatatata taaattgagc ttgcttcttt cttgctttga  2040
ccatggaaag aaatatgatt ccccttttctt taagttttat ttaacttttc ttttggactt  2100
ttgggtagtt gtttttttt gttttgtttt gtttttttga gaaacagcta cagctttggg  2160
tcatttttaa ctactgtatt cccacaagga atccccagat atttatgtat cttgatgttc  2220
agacatttat gtgttgataa ttttttaatt atttaaatgt acttatatta agaaaaatat  2280
caagtactac attttctttt gttcttgata gtagccaaag ttaaatgtat cacattgaag  2340
aaggctagaa aaaaagaatg agtaatgtga tcgcttggtt atccagaagt attgtttaca  2400
ttaaactccc tttcatgtta atcaaacaag tgagtagctc acgcagcaac gtttttaata  2460
ggatttttag acactgaggg tcactccaag gatcagaagt atggaatttt ctgccaggct  2520
caacaagggt ctcatatcta acttcctcct taaaacagag aaggtcaatc tagttccaga  2580
gggttgaggc aggtgccaat aattacatct ttggagagga tttgatttct gcccagggat  2640
ttgctcaccc caaggtcatc tgataatttc acagatgctg tgtaacagaa cacagccaaa  2700
gtaaactgtg taggggagcc acatttacat aggaaccaaa tcaatgaatt taggggttac  2760
gattatagca atttaagggc ccaccagaag caggcctcga ggagtcaatt tgcctctgtg  2820
tgcctcagtg gagacaagtg ggaaaacatg gtcccacctg tgcgagaccc cctgtcctgt  2880
gctgctcact caacaacatc tttgtgttgc tttcaccagg ctgagaccct accctatggg  2940
gtatatgggc ttttacctgt gcaccagtgt gacaggaaag attcatgtca ctactgtccg  3000
tggctacaat tcaaaggtat ccaatgtcgc tgtaaatttt atggcactat ttttattgga  3060
ggatttggtc agaatgcagt tgttgtacaa ctcataaata ctaactgctg attttgacac  3120
atgtgtgctc caaatgatct ggtggttatt taacgtacct cttaaaattc gttgaaacga  3180
tttcaggtca actctgaaga gtatttgaaa gcaggacttc agaacagtgt ttgattttta  3240
ttttataaat ttaagcattc aaattaggca aatctttggc tgcaggcagc aaaaacagct  3300
ggacttattt aaaacaactt gtttttgagt tttcttatat atatattgat tatttgtttt  3360
acacacatgc agtagcactt tggtaagagt taaagagtaa agcagcttat gttgtcaggt  3420
cgttcttatc tagagaagag ctatagcaga tctcggacaa actcagaata tattcacttt  3480
catttttgac aggattccct ccacaactca gtttcatata ttattccgta ttacattttt  3540
gcagctaaat taccataaaa tgtcagcaaa tgtaaaaatt taatttctga aaagcaccat  3600
tagcccattt cccccaaatt aaacgtaaat gtttttttc agcacatgtt accatgtctg  3660
acctgcaaaa atgctggaga aaaatgaagg aaaaaattat gtttttcagt ttaattctgt  3720
taactgaaga tattccaact caaaaccagc ctcatgctct gattagataa tcttttacat  3780
tgaaccttta ctctcaaagc catgtgtgga gggggcttgt cactattgta ggctcactgg  3840
attggtcatt tagagtttca cagactctta ccagcatata tagtatttaa ttgtttcaaa  3900
aaaaatcaaa ctgtagttgt tttggcgata ggtctcacgc aacacatttt tgtatgtgtg  3960
tgtgtgtgcg tgtgtgtgtg tgtgtgtgaa aaattgcatt cattgacttc aggtagatta  4020
aggtatcttt ttattcattg ccctcaggaa agttaaggta tcaatgagac ccttaagcca  4080
atcatgtaat aactgcatgt gtctggtcca ggagaagtat tgaataagcc atttctactg  4140
cttactcatg tccctattta tgatttcaac atggatacat atttcagttc tttcttttc  4200
tcactatctg aaaatacatt tccctccctc tcttcccccc aatatctccc ttttttctc  4260
tcttcctcta tcttccaaac cccactttct ccctcctcct tttcctgtgt tctcttaagc  4320
agatagcaca tacccccacc cagtaccaaa tttcagaaca caagaaggtc cagttcttcc  4380
cccttcacat aaaggaacat ggtttgtcag cctttctcct gtttatgggt ttcttccagc  4440
agaacagaga cattgccaac catattggat ctgcttgctg tccaaaccag caaactttcc  4500
tgggcaaatc acaatcagtg agtaaataga cagcctttct gctgccttgg gtttctgtgc  4560
agataaacag aaatgctctg attagaaagg aaatgaatgg ttccactcaa atgtcctgca  4620
atttaggatt gcagatttct gccttgaaat acctgtttct ttgggacatt ccgtcctgat  4680
gatttttatt tttgttggtt tttatttttg gggggaatga catgtttggg tcttttatac  4740
atgaaaattt gtttgacaat aatctcacaa aacatatttt acatctgaac aaaatgcctt  4800
tttgtttacc gtagcgtata catttgtttt gggattttg tgtgtttgtt gggaattttg  4860
tttttagcca ggtcagtatt gatgaggctg atcatttggc tctttttttc cttccagaag  4920
agttgcatca acaaagttaa ttgtatttat gtatgtaaat agattttaag cttcattata  4980
aaatattgtt aatgcctata actttttttc aattttttg tgtgtgtttc taaggacttt  5040
ttcttaggtt tgctaaatac tgtagggaaa aaaatgcttc tttctacttt gtttatttta  5100
gactttaaaa tgagctactt cttattcact tttgtaaaca gctaatagca tggttccaat  5160
ttttttaag ttcacttttt ttgttctagg ggaaatgaat gtgcaaaaaa agaaaaagaa  5220
ctgttggtta tttgtgttat tctggatgta taaaaatcaa tggaaaaaaa taaactttca  5280
aattgaaatg acggtataac acatctactg aaaaagcaac gggaaatgtg gtcctattta  5340
agccagcccc cacctagggt ctatttgtgt ggcagttatt gggtttggtc acaaaacatc  5400
ctgaaaattc gtgcgtgggc ttctttctcc ctggtacaaa cgtatggaat gcttcttaaa  5460
ggggaactgt caagctggtg tcttcagcca gatgacatga gagaatatcc cagaaccctc  5520
tctccaaggt gtttctagat agcacaggag agcaggcact gcactgtcca cagtccacgg  5580
tacacagtcg ggtgggccgc ctcccctctc ctgggagcat tcgtcgtgcc cagcctgagc  5640
agggcagctg gactgctgct gttcaggagc caccagagcc ttcctctctt tgtaccacag  5700
tttcttctgt aaatccagtg ttacaatcag tgtgaatggc aaataaacag tttgacaagt  5760
acatacacca ta                                                  5772
```

SEQ ID NO: 19 moltype = DNA length = 5811

-continued

```
FEATURE                Location/Qualifiers
source                 1..5811
                       mol_type = genomic DNA
                       organism = Homo sapiens
SEQUENCE: 19
acagttaaat ttgtaatttg ggttgtgtga aaacttcttt gggcctcata aacaaccaca  60
gaaccacaag ttgggtagcc tggcagtgtc agaagtctga acccagcata gtggtcagca  120
ggcaggacga atcacactga atgcaaacca cagggtttcg cagcgtggta aaagaaatca  180
ttgagtcccc cgccttcaga agagggtgca ttttcaggag gaagcgatgg cttcagacag  240
catatttgag tcatttcctt cgtacccaca gtgcttcatg agagaatgca tacttggaat  300
gaatccttct agagacgtcc acgatgccag cacgagccgc cgcttcacgc cgccttccac  360
cgcgctgagc ccaggcaaga tgagcgaggc gttgccgctg ggcgccccgg acgccggcgc  420
tgccctggcc ggcaagctga ggagcggcga ccgcagcatg gtggaggtgc tggccgacca  480
cccgggcgag ctggtgcgca ccgacagccc caacttcctc tgctccgtgc tgcctacgca  540
ctggcgctgc aacaagaccc tgcccatcgc tttcaaggtg gtggccctag ggatgttcc  600
agatggcact ctggtcactg tgatggctgg caatgatgaa aactactcgg ctgagctgag  660
aaatgctacc gcagccatga agaaccaggt tgcaagattt aatgacctca ggtttgtcgg  720
tcgaagtgga agagggaaaa gcttcactct gaccatcact gtcttcacaa acccaccgca  780
agtcgccacc taccacagag ccatcaaaat cacagtggat gggccccgag aacctcgaaa  840
tacaaggcag atccaaccat ccccaccgtg gtcctacgat cagtcctacc aatacctggg  900
atccattgcc tctccttctg tgcacccagc aacgcccatt tcacctggac gtgccagcgg  960
catgacaacc ctctctgcag aactttccag tcgactctca acggcacccg acctgacagc  1020
gttcagcgac ccgcgccagt tccccgcgct gccctccatc tccgaccccc gcatgcacta  1080
tccaggcgcc ttcacctact ccccgacgcc ggtcacctcg ggcatcggca tcggcatgtc  1140
ggccatgggc tcggccacgc gctaccacac ctacctgccg ccgccctacc ccggctcgtc  1200
gcaagcgcag ggaggcccgt tccaagccag ctcgccctcc taccacctgt actacggcgc  1260
ctcggccggc tcctaccagt tctccatggt gggcggcgag cgctcgccgc cgcgcatcct  1320
gccgccctgc accaacgcct ccaccggctc cgcgctgctc aaccccagcc tcccgaacca  1380
gagcgacgtg gtggaggccg agggcagcca cagcaactcc cccaccaaca tggcgccctc  1440
cgcgcgcctg gaggaggccg tgtggaggcc ctactgaggc gccaggcctg gcccggctgg  1500
gccccgcggg ccgccgcctt cgcctccggg cgcgcgggcc tcctgttcgc gacaagcccg  1560
ccgggatccc gggccctggg cccggccacc gtcctggggc cgagggcgcc cgacggccag  1620
gatctcgctg taggtcaggc ccgcgcagcc tcctgcgccc agaagcccac gccgccgccg  1680
tctgctggcg ccccggccct cgcggaggtg tccgaggcga cgcacctcga gggtgtccgc  1740
cggccccagc acccagggga cgcgctggaa agcaaacagg aagattcccg gagggaaact  1800
gtgaatgctt ctgatttagc aatgctgtga ataaaaagaa agattttata cccttgactt  1860
aactttttaa ccaagttgtt tattccaaag agtgtggaat tttggttggg gtgggggag  1920
aggagggatg caactcgccc tgtttggcat ctaattctta tttttaattt ttccgcacct  1980
tatcaattgc aaaatgcgta tttgcatttg ggtggttttt atttttatat acgtttatat  2040
aaatatatat aaattgagct tgcttctttc ttgctttgac catggaaaga aatatgattc  2100
ccttttcttt aagttttatt taacttttct tttggacttt tgggtagttg ttttttttg  2160
ttttgttttg tttttttgag aaacagctac agctttgggt catttttaac tactgtattc  2220
ccacaaggaa tccccagata tttatgtatc ttgatgttca gacatttatg tgttgataat  2280
tttttaatta tttaaatgta cttatattaa gaaaaatatc aagtactaca ttttcttttg  2340
ttcttgatag tagccaaagt taaatgtatc acattgaaga aggctagaaa aaaagaatga  2400
gtaatgtgat cgcttggtta tccagaagta ttgtttacat taaactccct ttcatgttaa  2460
tcaaacaagt gagtagctca cgcagcaacg tttttaatag gatttttaga cactgagggt  2520
cactccaagg atcagaagta tggaattttc tgccaggctc aacaagggtc tcatatctaa  2580
cttcctcctt aaaacagaga aggtcaatct agttccagag ggttgaggca ggtgccaata  2640
attacatctt tggagaggat ttgatttctg cccagggatt tgctcacccc aaggtcatct  2700
gataatttca cagatgctgt gtaacagaac acagccaaag taaactgtgt aggggagcca  2760
catttacata ggaaccaaat caatgaattt aggggttacg attatagcaa tttaagggcc  2820
caccagaagc aggcctcgag gagtcaattt gcctctgtgt gcctcagtgg agacaagtgg  2880
gaaaacatgg tcccacctgt gcgagaccc ctgtcctgtg ctgctcactc aacaacatct  2940
ttgtgttgct ttcaccaggc tgagacccta ccctatgggg tatatgggct tttacctgtg  3000
caccagtgtg acaggaaaga ttcatgtcac tactgtccgt ggctacaatt caaaggtatc  3060
caatgtcgct gtaaatttta tggcactatt tttattggag gatttggtca gaatgcagtt  3120
gttgtacaac tcataaatac taactgctga ttttgacaca tgtgtgctcc aaatgatctg  3180
gtggttattt aacgtacctc ttaaaattcg ttgaaacgat ttcaggtcaa ctctgaagag  3240
tatttgaaag caggacttca gaacagtgtt tgatttttat tttataaatt taagcattca  3300
aattaggcaa atctttggct gcaggcagca aaaacagctg gacttattta aaacaacttg  3360
tttttgagtt ttcttatata tatattgatt atttgtttta cacacatgca gtagcacttt  3420
ggtaagagtt aaagagtaaa gcagcttatg ttgtcaggtc gttcttatct agagaagagc  3480
tatagcagat ctcggacaaa ctcagaatat attcactttc atttttgaca ggattccctc  3540
cacaactcag tttcatatat tattccgtat tacattttg cagctaaatt accataaaat  3600
gtcagcaaat gtaaaaattt aatttctgaa aagcaccatt agcccatttc ccccaaatta  3660
aacgtaaatg tttttttca gcacatgtta ccatgtctga cctgcaaaaa tgctggagaa  3720
aaatgaagga aaaaattatg tttttcagtt taattctgtt aactgaagat attccaactc  3780
aaaaccagcc tcatgctctg attagataat cttttacatt gaacctttac tctcaaagcc  3840
atgtgtggag ggggcttgtc actattgtag gctcactgga ttggtcattt agagtttcac  3900
agactcttac cagcatatat agtatttaat tgtttcaaaa aaaatcaaac tgtagttgtt  3960
ttggcgatag gtctcacgca acacattttt gtatgtgtgt gtgtgtgcgt gtgtgtgtgt  4020
gtgtgtgaaa aattgcattc attgacttca ggtagattaa ggtatctttt tattcattgc  4080
cctcaggaaa gttaaggtat caatgagacc cttaagccaa tcatgtaata actgcatgtg  4140
tctggtccag gagaagtatt gaataagcca tttctactgc ttactcatgt ccctatttat  4200
gatttcaaca tggatacata tttcagttct ttctttttct cactatctga aaatacattt  4260
ccctccctct cttcccccca atatctccct tttttctct cttcctctat cttccaaacc  4320
ccactttctc cctcctcctt ttcctgtgtt ctcttaagca gatagcacat acccccaccc  4380
agtaccaaat ttcagaacac aagaaggtcc agttcttccc ccttcacata aaggaacatg  4440
```

-continued

```
gtttgtcagc ctttctcctg tttatgggtt tcttccagca gaacagagac attgccaacc  4500
atattggatc tgcttgctgt ccaaaccagc aaactttcct gggcaaatca caatcagtga  4560
gtaaatagac agcctttctg ctgccttggg tttctgtgca gataaacaga aatgctctga  4620
ttagaaagga aatgaatggt tccactcaaa tgtcctgcaa tttaggattg cagatttctg  4680
ccttgaaata cctgtttctt tgggacattc cgtcctgatg atttttattt ttgttggttt  4740
ttatttttgg ggggaatgac atgtttgggt cttttataca tgaaaatttg tttgacaata  4800
atctcacaaa acatatttta catctgaaca aaatgccttt ttgtttaccg tagcgtatac  4860
atttgttttg ggattttttgt gtgtttgttg ggaattttgt ttttagccag gtcagtattg  4920
atgaggctga tcatttggct ctttttttcc ttccagaaga gttgcatcaa caaagttaat  4980
tgtatttatg tatgtaaata gattttaagc ttcattataa aatattgtta atgcctataa  5040
cttttttttca atttttttgt gtgtgtttct aaggactttt tcttaggttt gctaaatact  5100
gtagggaaaa aaatgcttct ttctactttg tttattttag actttaaaat gagctacttc  5160
ttattcactt ttgtaaacag ctaatagcat ggttccaatt ttttttaagt tcactttttt  5220
tgttctaggg gaaatgaatg tgcaaaaaaa gaaaaagaac tgttggttat ttgtgttatt  5280
ctggatgtat aaaaatcaat ggaaaaaaat aaactttcaa attgaaatga cggtataaca  5340
catctactga aaaagcaacg ggaaatgtgg tcctatttaa gccagccccc acctagggtc  5400
tatttgtgtg gcagttattg ggtttggtca caaaacatcc tgaaaattcg tgcgtgggct  5460
tctttctccc tggtacaaac gtatggaatg cttcttaaag gggaactgtc aagctggtgt  5520
cttcagccag atgacatgag agaatatccc agaaccctct ctccaaggtg tttctagata  5580
gcacaggaga gcaggcactg cactgtccac agtccacggt acacagtcgg gtgggccgcc  5640
tcccctctcc tgggagcatt cgtcgtgccc agcctgagca gggcagctgg actgctgctg  5700
ttcaggagcc accagagcct tcctctcttt gtaccacagt ttcttctgta aatccagtgt  5760
tacaatcagt gtgaatggca aataaacagt ttgacaagta catacaccat a           5811

SEQ ID NO: 20          moltype = DNA  length = 5772
FEATURE                Location/Qualifiers
source                 1..5772
                       mol_type = genomic DNA
                       organism = Homo sapiens
SEQUENCE: 20
cactttttaa tgcactaagc aatcggttgc taggagccca tcctgggtca gaggccgatc  60
cgcagaacca gaacgttttc ccctcctgga ctatgccagc acgagccgcc gcttcacgcc  120
gccttccacc gcgctgagcc caggcaagat gagcgaggcg ttgccgctgg gcgccccgga  180
cgccggcgct gccctggccg gcaagctgag gagcggcgac cgcagcatgg tggaggtgct  240
ggccgaccac ccgggcgagc tggtgcgcac cgacagcccc aacttcctct gctccgtgct  300
gcctacgcac tggcgctgca acaagaccct gcccatcgct ttcaaggtgg tggccctagg  360
ggatgttcca gatggcactc tggtcactgt gatggctggc aatgatgaaa actactcggc  420
tgagctgaga aatgctaccg cagccatgaa gaaccaggtt gcaagattta atgacctcag  480
gtttgtcggt cgaagtggaa gagggaaaag cttcactctg accatcactg tcttcacaaa  540
cccaccgcaa gtcgccacct accacagagc catcaaaatc acagtggatg ggccccgaga  600
acctcgaaga catcggcaga aactagatga tcagaccaag cccgggagct tgtccttttc  660
cgagcggctc agtgaactgg agcagctgcg gcgcacagcc atgagggtca gcccacacca  720
cccagccccc acgcccaacc ctcgtgcctc cctgaaccac tccactgcct ttaaccctca  780
gcctcagagt cagatgcagg atacaaggca gatccaacca tccccaccgt ggtcctacga  840
tcagtcctac caatacctgg gatccattgc ctctccttct gtgcacccag caacgcccat  900
ttcacctgga cgtgccagcg gcatgacaac cctctctgca gaactttcca gtcgactctc  960
aacggcaccc gacctgacag cgttcagcga cccgcgccag ttccccgcgc tgccctccat  1020
ctccgacccc cgcatgcact atccaggcgc cttcacctac tccccgacgc cggtcacctc  1080
gggcatcggc atcggcatgt cggccatggg ctcggccacg cgctaccaca cctacctgcc  1140
gccgccctac cccggctcgt cgcaagcgca gggaggcccg ttccaagcca gctcgccctc  1200
ctaccacctg tactacggcg cctcggccgg ctcctaccag ttctccatgg tgggcggcga  1260
gcgctcgccg ccgcgcatcc tgccgccctg caccaacgcc tccaccggct ccgcgctgct  1320
caaccccagc ctcccgaacc agagcgacgt ggtggaggcc gagggcagcc acagcaactc  1380
ccccaccaac atggcgccct ccgcgcgcct ggaggaggcc gtgtggaggc cctactgagg  1440
cgccaggcct ggcccggctg ggccccgcgg gccgccgcct tcgcctccgg gcgcgcgggc  1500
ctcctgttcg cgacaagccc gccgggatcc cgggccctgg gcccggccac cgtcctgggg  1560
ccgagggcgc ccgacggcca ggatctcgct gtaggtcagg cccgcgcagc ctcctgcgcc  1620
cagaagccca cgccgccgcc gtctgctggc gccccggccc tcgcggaggt gtccgaggcg  1680
acgcacctcg agggtgtccg ccggccccag cacccagggg acgcgctgga aagcaaacag  1740
gaagattccc ggagggaaac tgtgaatgct tctgatttag caatgctgtg aataaaaaga  1800
aagattttat acccttgact taactttttta accaagttgt ttattccaaa gagtgtggaa  1860
ttttggttgg ggtgggggga gaggagggat gcaactcgcc ctgtttggca tctaattctt  1920
atttttaatt tttccgcacc ttatcaattg caaaatgcgt atttgcattt gggtggtttt  1980
tatttttata tacgtttata taaatatata taaattgagc ttgcttcttt cttgctttga  2040
ccatggaaag aaatatgatt ccctttttctt taagttttat ttaacttttc ttttggactt  2100
ttgggtagtt gttttttttt gttttgtttt gttttttttga gaaacagcta cagctttggg  2160
tcatttttaa ctactgtatt cccacaagga atccccagat atttatgtat cttgatgttc  2220
agacatttat gtgttgataa ttttttaatt atttaaatgt acttatatta agaaaaaatat  2280
caagtactac attttctttt gttcttgata gtagccaaag ttaaatgtat cacattgaag  2340
aaggctagaa aaaaagaatg agtaatgtga tcgcttggtt atccagaagt attgtttaca  2400
ttaaactccc tttcatgtta atcaaacaag tgagtagctc acgcagcaac gtttttaata  2460
ggattttttag acactgaggg tcactccaag gatcagaagt atggaatttt ctgccaggct  2520
caacaagggt ctcatatcta acttcctcct taaaacagag aaggtcaatc tagttccaga  2580
gggttgaggc aggtgccaat aattacatct ttggagagga tttgatttct gcccagggat  2640
ttgctcaccc caaggtcatc tgataatttc acagatgctg tgtaacagaa cacagccaaa  2700
gtaaactgtg taggggagcc acatttacat aggaaccaaa tcaatgaatt taggggttac  2760
gattatagca atttaagggc ccaccagaag caggcctcga ggagtcaatt tgcctctgtg  2820
tgcctcagtg gagacaagtg ggaaaacatg gtcccacctg tgcgagaccc cctgtcctgt  2880
gctgctcact caacaacatc tttgtgttgc tttcaccagg ctgagaccct accctatggg  2940
```

-continued

```
gtatatgggc ttttacctgt gcaccagtgt gacaggaaag attcatgtca ctactgtccg  3000
tggctacaat tcaaaggtat ccaatgtcgc tgtaaatttt atggcactat ttttattgga  3060
ggatttggtc agaatgcagt tgttgtacaa ctcataaata ctaactgctg attttgacac  3120
atgtgtgctc caaatgatct ggtggttatt taacgtacct cttaaaattc gttgaaacga  3180
tttcaggtca actctgaaga gtatttgaaa gcaggacttc agaacagtgt ttgattttta  3240
ttttataaat ttaagcattc aaattaggca aatctttggc tgcaggcagc aaaaacagct  3300
ggacttattt aaaacaactt gtttttgagt tttcttatat atatattgat tatttgtttt  3360
acacacatgc agtagcactt tggtaagagt taaagagtaa agcagcttat gttgtcaggt  3420
cgttcttatc tagagaagag ctatagcaga tctcggacaa actcagaata tattcacttt  3480
catttttgac aggattccct ccacaactca gtttcatata ttattccgta ttacattttt  3540
gcagctaaat taccataaaa tgtcagcaaa tgtaaaaatt taatttctga aaagcaccat  3600
tagcccattt cccccaaatt aaacgtaaat gttttttttc agcacatgtt accatgtctg  3660
acctgcaaaa atgctggaga aaaatgaagg aaaaaattat gtttttcagt ttaattctgt  3720
taactgaaga tattccaact caaaaccagc ctcatgctct gattagataa tcttttacat  3780
tgaaccttta ctctcaaagc catgtgtgga gggggcttgt cactattgta ggctcactgg  3840
attggtcatt tagagtttca cagactctta ccagcatata tagtatttaa ttgtttcaaa  3900
aaaaatcaaa ctgtagttgt tttggcgata ggtctcacgc aacacatttt tgtatgtgtg  3960
tgtgtgtgcg tgtgtgtgtg tgtgtgtgaa aaattgcatt cattgacttc aggtagatta  4020
aggtatcttt ttattcattg ccctcaggaa agttaaggta tcaatgagac ccttaagcca  4080
atcatgtaat aactgcatgt gtctggtcca ggagaagtat tgaataagcc atttctactg  4140
cttactcatg tccctattta tgatttcaac atggatacat atttcagttc tttctttttc  4200
tcactatctg aaaatacatt tccctccctc tcttcccccc aatatctccc tttttttctc  4260
tcttcctcta tcttccaaac cccactttct ccctcctcct tttcctgtgt tctcttaagc  4320
agatagcaca taccccccacc cagtaccaaa tttcagaaca caagaaggtc cagttcttcc  4380
cccttcacat aaaggaacat ggtttgtcag cctttctcct gtttatgggt ttcttccagc  4440
agaacagaga cattgccaac catattggat ctgcttgctg tccaaaccag caaactttcc  4500
tgggcaaatc acaatcagtg agtaaataga cagcctttct gctgccttgg gtttctgtgc  4560
agataaacag aaatgctctg attagaaagg aaatgaatgg ttccactcaa atgtcctgca  4620
atttaggatt gcagatttct gccttgaaat acctgtttct ttgggacatt ccgtcctgat  4680
gatttttatt tttgttggtt tttatttttg gggggaatga catgtttggg tcttttatac  4740
atgaaaattt gtttgacaat aatctcacaa aacatatttt acatctgaac aaaatgcctt  4800
tttgtttacc gtagcgtata catttgtttt gggatttttg tgtgtttgtt gggaattttg  4860
tttttagcca ggtcagtatt gatgaggctg atcatttggc tcttttttttc cttccagaag  4920
agttgcatca acaaagttaa ttgtatttat gtatgtaaat agattttaag cttcattata  4980
aaatattgtt aatgcctata acttttttttc aattttttttg tgtgtgtttc taaggacttt  5040
ttcttaggtt tgctaaatac tgtagggaaa aaaatgcttc tttctacttt gtttatttta  5100
gactttaaaa tgagctactt cttattcact tttgtaaaca gctaatagca tggttccaat  5160
ttttttaag ttcacttttt ttgttctagg ggaaatgaat gtgcaaaaaa agaaaaagaa  5220
ctgttggtta tttgtgttat tctggatgta taaaaaatcaa tggaaaaaaa taaactttca  5280
aattgaaatg acggtataac acatctactg aaaaagcaac gggaaatgtg gtcctattta  5340
agccagcccc cacctagggt ctatttgtgt ggcagttatt gggtttggtc acaaaacatc  5400
ctgaaaattc gtgcgtgggc ttctttctcc ctggtacaaa cgtatggaat gcttcttaaa  5460
ggggaactgt caagctggtg tcttcagcca gatgacatga gagaatatcc cagaaccctc  5520
tctccaaggt gtttctagat agcacaggag agcaggcact gcactgtcca cagtccacgg  5580
tacacagtcg ggtgggccgc ctcccctctc ctgggagcat tcgtcgtgcc cagcctgagc  5640
agggcagctg gactgctgct gttcaggagc caccagagcc ttcctctctt tgtaccacag  5700
tttcttctgt aaatccagtg ttacaatcag tgtgaatggc aaataaacag tttgacaagt  5760
acatacacca ta                                                      5772
```

```
SEQ ID NO: 21          moltype = DNA  length = 5964
FEATURE                Location/Qualifiers
source                 1..5964
                       mol_type = genomic DNA
                       organism = Homo sapiens
SEQUENCE: 21
acagttaaat ttgtaatttg ggttgtgtga aaacttcttt gggcctcata aacaaccaca  60
gaaccacaag ttgggtagcc tggcagtgtc agaagtctga acccagcata gtggtcagca  120
ggcaggacga atcacactga atgcaaacca cagggtttcg cagcgtggta aaagaaatca  180
ttgagtcccc cgccttcaga agagggtgca ttttcaggag gaagcgatgg cttcagacag  240
catatttgag tcatttcctt cgtacccaca gtgcttcatg agagatgcca gcacgagccg  300
ccgcttcacg ccgccttcca ccgcgctgag cccaggcaag atgagcgagg cgttgccgct  360
gggcgccccg gacgccggcg ctgccctggc cggcaagctg aggagcggcg accgcagcat  420
ggtggaggtg ctggccgacc acccgggcga gctggtgcgc accgacagcc ccaacttcct  480
ctgctccgtg ctgcctacgc actggcgctg caacaagacc ctgcccatcg ctttcaaggt  540
ggtggcccta ggggatgttc cagatggcac tctggtcact gtgatggctg gcaatgatga  600
aaactactcg gctgagctga gaaatgctac cgcagccatg aagaaccagg ttgcaagatt  660
taatgacctc aggtttgtcg gtcgaagtgg aagagggaaa agcttcactc tgaccatcac  720
tgtcttcaca aacccaccgc aagtcgccac ctaccacaga gccatcaaaa tcacagtgga  780
tgggccccga gaacctcgaa gacatcggca gaaactagat gatcagacca agcccgggag  840
cttgtccttt tccgagcggc tcagtgaact ggagcagctg cggcgcacag ccatgagggt  900
cagcccacac cacccagccc ccacgcccaa ccctcgtgcc tccctgaacc actccactgc  960
ctttaaccct cagcctcaga gtcagatgca ggatacaagg cagatccaac catccccacc  1020
gtggtcctac gatcagtcct accaatacct gggatccatt gcctctcctt ctgtgcaccc  1080
agcaacgccc atttcacctg gacgtgccag cggcatgaca accctctctg cagaactttc  1140
cagtcgactc tcaacggcac ccgacctgac agcgttcagc gacccgcgcc agttccccgc  1200
gctgccctcc atctccgacc cccgcatgca ctatccaggc gccttcacct actccccgac  1260
gccggtcacc tcgggcatcg gcatcggcat gtcggccatg ggctcggcca cgcgctacca  1320
cacctacctg ccgccgccct accccggctc gtcgcaagcg cagggaggcc cgttccaagc  1380
cagctcgccc tcctaccacc tgtactacgg cgcctcggcc ggctcctacc agttctccat  1440
```

-continued

```
ggtgggcggc gagcgctcgc cgccgcgcat cctgccgccc tgcaccaacg cctccaccgg  1500
ctccgcgctg ctcaacccca gcctcccgaa ccagagcgac gtggtggagg ccgagggcag  1560
ccacagcaac tcccccacca acatggcgcc ctccgcgcgc ctggaggagg ccgtgtggag  1620
gccctactga ggcgccaggc ctggcccggc tgggccccgc gggccgccgc cttcgcctcc  1680
gggcgcgcgg gcctcctgtt cgcgacaagc ccgccgggat cccgggccct gggcccggcc  1740
accgtcctgg ggccgagggc gcccgacggc caggatctcg ctgtaggtca ggcccgcgca  1800
gcctcctgcg cccagaagcc cacgccgccg ccgtctgctg gcgcccccggc cctcgcggag  1860
gtgtccgagg cgacgcacct cgagggtgtc cgccggcccc agcacccagg ggacgcgctg  1920
gaaagcaaac aggaagattc ccggagggaa actgtgaatg cttctgattt agcaatgctg  1980
tgaataaaaa gaaagatttt ataccttga cttaactttt taaccaagtt gtttattcca  2040
aagagtgtgg aattttggtt ggggtgggggg gagaggaggg atgcaactcg ccctgtttgg  2100
catctaattc ttatttttaa tttttccgca ccttatcaat tgcaaaatgc gtatttgcat  2160
ttgggtggtt tttattttta tatacgttta tataaatata tataaattga gcttgcttct  2220
ttcttgcttt gaccatggaa agaaatatga ttccttttc tttaagtttt atttaacttt  2280
tcttttggac ttttgggtag ttgttttttt ttgttttgtt ttgttttttt gagaaacagc  2340
tacagctttg ggtcattttt aactactgta ttcccacaag gaatccccag atatttatgt  2400
atcttgatgt tcagacattt atgtgttgat aatttttttaa ttatttaaat gtacttatat  2460
taagaaaaat atcaagtact acattttctt ttgttcttga tagtagccaa agttaaatgt  2520
atcacattga agaaggctag aaaaaaagaa tgagtaatgt gatcgcttgg ttatccagaa  2580
gtattgttta cattaaactc cctttcatgt taatcaaaca agtgagtagc tcacgcagca  2640
acgtttttaa taggattttt agacactgag ggtcactcca aggatcagaa gtatggaatt  2700
ttctgccagg ctcaacaagg gtctcatatc taacttcctc cttaaaacag agaaggtcaa  2760
tctagttcca gagggttgag gcaggtgcca ataattacat ctttggagag gatttgattt  2820
ctgcccaggg atttgctcac cccaaggtca tctgataatt tcacagatgc tgtgtaacag  2880
aacacagcca aagtaaactg tgtaggggag ccacatttac ataggaacca aatcaatgaa  2940
tttaggggtt acgattatag caatttaagg gcccaccaga agcaggcctc gaggagtcaa  3000
tttgcctctg tgtgcctcag tggagacaag tgggaaaaca tggtcccacc tgtgcgagac  3060
cccctgtcct gtgctgctca ctcaacaaca tctttgtgtt gctttcacca ggctgagacc  3120
ctaccctatg ggtatatgg gcttttacct gtgcaccagt gtgacaggaa agattcatgt  3180
cactactgtc cgtggctaca attcaaaggt atccaatgtc gctgtaaatt ttatggcact  3240
atttttattg gaggatttgg tcagaatgca gttgttgtac aactcataaa tactaactgc  3300
tgattttgac acatgtgtgc tccaaatgat ctggtggtta tttaacgtac ctcttaaaat  3360
tcgttgaaac gatttcaggt caactctgaa gagtatttga aagcaggact tcagaacagt  3420
gtttgatttt tattttataa atttaagcat tcaaattagg caaatctttg gctgcaggca  3480
gcaaaaacag ctggacttat ttaaaacaac ttgtttttga gttttcttat atatatattg  3540
attatttgtt ttacacacat gcagtagcac tttggtaaga gttaaagagt aaagcagctt  3600
atgttgtcag gtcgttctta tctagagaag agctatagca gatctcggac aaactcagaa  3660
tatattcact ttcattttg acaggattcc ctccacaact cagtttcata tattattccg  3720
tattacattt ttgcagctaa attaccataa aatgtcagca aatgtaaaaa tttaatttct  3780
gaaaagcacc attagcccat ttcccccaaa ttaaacgtaa atgtttttt tcagcacatg  3840
ttaccatgtc tgacctgcaa aaatgctgga gaaaaatgaa ggaaaaaatt atgtttttca  3900
gtttaattct gttaactgaa gatattccaa ctcaaaacca gcctcatgct ctgattagat  3960
aatcttttac attgaacctt tactctcaaa gccatgtgtg gagggggctt gtcactattg  4020
taggctcact ggattggtca tttagagttt cacagactct taccagcata tatagtattt  4080
aattgtttca aaaaaaatca aactgtagtt gttttggcga taggtctcac gcaacacatt  4140
tttgtatgtg tgtgtgtgtg cgtgtgtgtg tgtgtgtgtg aaaaattgca ttcattgact  4200
tcaggtagat taaggtatct ttttattcat tgccctcagg aaagttaagg tatcaatgag  4260
acccttaagc caatcatgta ataactgcat gtgtctggtc caggagaagt attgaataag  4320
ccatttctac tgcttactca tgtccctatt tatgatttca acatggatac atatttcagt  4380
tctttctttt tctcactatc tgaaaataca tttccctccc tctcttcccc ccaatatctc  4440
cctttttttc tctcttcctc tatcttccaa accccacttt ctccctcctc cttttcctgt  4500
gttctcttaa gcagatagca catacccca cccagtacca aatttcagaa cacaagaagg  4560
tccagttctt ccccttcac ataaaggaac atggtttgtc agcctttctc ctgtttatgg  4620
gtttcttcca gcagaacaga gacattgcca accatattgg atctgcttgc tgtccaaacc  4680
agcaaacttt cctgggcaaa tcacaatcag tgagtaaata gacagccttt ctgctgcctt  4740
gggtttctgt gcagataaac agaaatgctc tgattagaaa ggaaatgaat ggttccactc  4800
aaatgtcctg caatttagga ttgcagattt ctgccttgaa atacctgttt ctttgggaca  4860
ttccgtcctg atgattttta tttttgttgg tttttatttt tgggggggaat gacatgtttg  4920
ggtcttttat acatgaaaat ttgtttgaca ataatctcac aaaacatatt ttacatctga  4980
acaaaatgcc tttttgttta ccgtagcgta tacatttgtt ttgggatttt tgtgtgtttg  5040
ttgggaattt tgtttttagc caggtcagta ttgatgaggc tgatcatttg gctctttttt  5100
tccttccaga agagttgcat caacaaagtt aattgtattt atgtatgtaa atagatttta  5160
agcttcatta taaaatattg ttaatgccta taactttttt tcaatttttt tgtgtgtgtt  5220
tctaaggact ttttcttagg tttgctaaat actgtaggga aaaaaatgct tctttctact  5280
ttgtttattt tagactttaa aatgagctac ttcttattca cttttgtaaa cagctaatag  5340
catggttcca atttttttta agttcacttt ttttgttcta ggggaaatga atgtgcaaaa  5400
aaagaaaaag aactgttggt tatttgtgtt attctggatg tataaaaatc aatggaaaaa  5460
aataaacttt caaattgaaa tgacggtata acacatctac tgaaaaagca acgggaaatg  5520
tggtcctatt taagccagcc cccacctagg gtctatttgt gtggcagtta ttgggtttgg  5580
tcacaaaaca tcctgaaaat tcgtgcgtgg gcttctttct ccctggtaca aacgtatgga  5640
atgcttctta aaggggaact gtcaagctgg tgtcttcagc cagatgacat gagagaatat  5700
cccagaaccc tctctccaag gtgtttctag atagcacagg agagcaggca ctgcactgtc  5760
cacagtccac ggtacacagt cgggtgggcc gcctcccctc tcctgggagc attcgtcgtg  5820
cccagcctga gcagggcagc tggactgctg ctgttcagga gccaccagag ccttcctctc  5880
tttgtaccac agtttcttct gtaaatccag tgttacaatc agtgtgaatg gcaaataaac  5940
agtttgacaa gtacatacac cata                                          5964
```

```
SEQ ID NO: 22          moltype = DNA  length = 6078
FEATURE                Location/Qualifiers
```

```
source                  1..6078
                        mol_type = genomic DNA
                        organism = Homo sapiens
SEQUENCE: 22
gtaatttggg ttgtgtgaaa acttctttgg gcctcataaa caaccacaga accacaagtt  60
gggtagcctg gcagtgtcag aagtctgaac ccagcatagt ggtcagcagg caggacgaat  120
cacactgaat gcaaaccaca gggtttcgca gcgtggtgag catcaccaac ccacagccaa  180
ggcggcgctg gctttttttt tttttttaat ctttaacaat ttgaatattt gtttttacaa  240
aggtaaaaga aatcattgag tcccccgcct tcagaagagg gtgcattttc aggaggaagc  300
gatggcttca gacagcatat ttgagtcatt tccttcgtac ccacagtgct tcatgagaga  360
atgcatactt ggaatgaatc cttctagaga cgtccacgat gccagcacga gccgccgctt  420
cacgccgcct tccaccgcgc tgagcccagg caagatgagc gaggcgttgc cgctgggcgc  480
cccggacgcc ggcgctgccc tggccggcaa gctgaggagc ggcgaccgca gcatggtgga  540
ggtgctggcc gaccacccgg gcgagctggt gcgcaccgac agccccaact tcctctgctc  600
cgtgctgcct acgcactggc gctgcaacaa gaccctgccc atcgctttca aggtggtggc  660
cctaggggat gttccagatg gcactctggt cactgtgatg gctggcaatg atgaaaacta  720
ctcggctgag ctgagaaatg ctaccgcagc catgaagaac caggttgcaa gatttaatga  780
cctcaggttt gtcggtcgaa gtggaagagg gaaaagcttc actctgacca tcactgtctt  840
cacaaaccca ccgcaagtcg ccacctacca cagagccatc aaaatcacag tggatgggcc  900
ccgagaacct cgaagacatc ggcagaaact agatgatcag accaagcccg ggagcttgtc  960
cttttccgag cggctcagtg aactggagca gctgcggcgc acagccatga gggtcagccc  1020
acaccaccca gcccccacgc ccaaccctcg tgcctccctg aaccactcca ctgcctttaa  1080
ccctcagcct cagagtcaga tgcaggatac aaggcagatc caaccatccc caccgtggtc  1140
ctacgatcag tcctaccaat acctgggatc cattgcctct ccttctgtgc acccagcaac  1200
gcccatttca cctggacgtg ccagcggcat gacaaccctc tctgcagaac tttccagtcg  1260
actctcaacg gcacccgacc tgacagcgtt cagcgacccg cgccagttcc ccgcgctgcc  1320
ctccatctcc gacccccgca tgcactatcc aggcgccttc acctactccc cgacgccggt  1380
cacctcgggc atcggcatcg gcatgtcggc catgggctcg gccacgcgct accacaccta  1440
cctgccgccg ccctaccccg gctcgtcgca agcgcaggga ggcccgttcc aagccagctc  1500
gccctcctac cacctgtact acggcgcctc ggccggctcc taccagttct ccatggtggg  1560
cggcgagcgc tcgccgccgc gcatcctgcc gccctgcacc aacgcctcca ccggctccgc  1620
gctgctcaac cccagcctcc cgaaccagag cgacgtggtg gaggccgagg gcagccacag  1680
caactccccc accaacatgg cgccctccgc gcgcctggag gaggccgtgt ggaggcccta  1740
ctgaggcgcc aggcctggcc cggctgggcc ccgcgggccg ccgccttcgc ctccgggcgc  1800
gcgggcctcc tgttcgcgac aagcccgccg ggatcccggg ccctgggccc ggccaccgtc  1860
ctggggccga gggcgcccga cggccaggat ctcgctgtag gtcaggcccg cgcagcctcc  1920
tgcgcccaga agcccacgcc gccgccgtct gctggcgccc cggccctcgc ggaggtgtcc  1980
gaggcgacgc acctcgaggg tgtccgccgg ccccagcacc caggggacgc gctggaaagc  2040
aaacaggaag attcccggag ggaaactgtg aatgcttctg atttagcaat gctgtgaata  2100
aaaagaaaga ttttataccc ttgacttaac tttttaacca agttgtttat tccaaagagt  2160
gtggaatttt ggttggggtg gggggagagg agggatgcaa ctcgccctgt ttggcatcta  2220
attcttattt ttaatttttc cgcaccttat caattgcaaa atgcgtattt gcatttgggt  2280
ggtttttatt tttatatacg tttatataaa tatatataaa ttgagcttgc ttctttcttg  2340
ctttgaccat ggaaagaaat atgattccct tttctttaag ttttatttaa cttttctttt  2400
ggacttttgg gtagttgttt ttttttgttt tgttttgttt ttttgagaaa cagctacagc  2460
tttgggtcat ttttaactac tgtattccca caaggaatcc ccagatattt atgtatcttg  2520
atgttcagac atttatgtgt tgataatttt ttaattattt aaatgtactt atattaagaa  2580
aaatatcaag tactacattt tcttttgttc ttgatagtag ccaaagttaa atgtatcaca  2640
ttgaagaagg ctagaaaaaa agaatgagta atgtgatcgc ttggttatcc agaagtattg  2700
tttacattaa actccctttc atgttaatca aacaagtgag tagctcacgc agcaacgttt  2760
ttaataggat ttttagacac tgagggtcac tccaaggatc agaagtatgg aatttttctgc  2820
caggctcaac aagggtctca tatctaactt cctccttaaa acagagaagg tcaatctagt  2880
tccagagggt tgaggcaggt gccaataatt acatctttgg agaggatttg atttctgccc  2940
agggatttgc tcaccccaag gtcatctgat aatttcacag atgctgtgta acagaacaca  3000
gccaaagtaa actgtgtagg ggagccacat ttacatagga accaaatcaa tgaatttagg  3060
ggttacgatt atagcaattt aagggcccac cagaagcagg cctcgaggag tcaatttgcc  3120
tctgtgtgcc tcagtggaga caagtgggaa aacatggtcc cacctgtgcg agaccccctg  3180
tcctgtgctg ctcactcaac aacatctttg tgttgctttc accaggctga gaccctaccc  3240
tatggggtat atgggctttt acctgtgcac cagtgtgaca ggaaagattc atgtcactac  3300
tgtccgtggc tacaattcaa aggtatccaa tgtcgctgta aattttatgg cactattttt  3360
attggaggat ttggtcagaa tgcagttgtt gtacaactca taaatactaa ctgctgattt  3420
tgacacatgt gtgctccaaa tgatctggtg gttatttaac gtacctctta aaattcgttg  3480
aaacgatttc aggtcaactc tgaagagtat ttgaaagcag gacttcagaa cagtgtttga  3540
tttttatttt ataaatttaa gcattcaaat taggcaaatc tttggctgca ggcagcaaaa  3600
acagctggac ttatttaaaa caacttgttt ttgagttttc ttatatatat attgattatt  3660
tgttttacac acatgcagta gcactttggt aagagttaaa gagtaaagca gcttatgttg  3720
tcaggtcgtt cttatctaga gaagagctat agcagatctc ggacaaactc agaatatatt  3780
cactttcatt tttgacagga ttccctccac aactcagttt catatattat tccgtattac  3840
atttttgcag ctaaattacc ataaaatgtc agcaaatgta aaaatttaat ttctgaaaag  3900
caccattagc ccatttcccc caaattaaac gtaaatgttt tttttcagca catgttacca  3960
tgtctgacct gcaaaaatgc tggagaaaaa tgaaggaaaa aattatgttt ttcagtttaa  4020
ttctgttaac tgaagatatt ccaactcaaa accagcctca tgctctgatt agataatctt  4080
ttacattgaa cctttactct caaagccatg tgtggagggg gcttgtcact attgtaggct  4140
cactggattg gtcatttaga gtttcacaga ctcttaccag catatatagt atttaattgt  4200
ttcaaaaaaa atcaaactgt agttgttttg gcgataggtc tcacgcaaca catttttgta  4260
tgtgtgtgtg tgtgcgtgtg tgtgtgtgtg tgtgaaaaat tgcattcatt gacttcaggt  4320
agattaaggt atctttttat tcattgccct caggaaagtt aaggtatcaa tgagaccctt  4380
aagccaatca tgtaataact gcatgtgtct ggtccaggag aagtattgaa taagccattt  4440
ctactgctta ctcatgtccc tatttatgat ttcaacatgg atacatattt cagttctttc  4500
```

-continued

```
tttttctcac tatctgaaaa tacatttccc tccctctctt ccccccaata tctccctttt  4560
tttctctctt cctctatctt ccaaacccca ctttctccct cctccttttc ctgtgttctc  4620
ttaagcagat agcacatacc cccacccagt accaaatttc agaacacaag aaggtccagt  4680
tcttccccct tcacataaag gaacatggtt tgtcagcctt tctcctgttt atgggtttct  4740
tccagcagaa cagagacatt gccaaccata ttggatctgc ttgctgtcca aaccagcaaa  4800
ctttcctggg caaatcacaa tcagtgagta aatagacagc ctttctgctg ccttgggttt  4860
ctgtgcagat aaacagaaat gctctgatta gaaaggaaat gaatggttcc actcaaatgt  4920
cctgcaattt aggattgcag atttctgcct tgaaatacct gtttctttgg gacattccgt  4980
cctgatgatt tttattttg ttggttttta tttttggggg gaatgacatg tttgggtctt  5040
ttatacatga aaatttgttt gacaataatc tcacaaaaca tattttacat ctgaacaaaa  5100
tgcctttttg tttaccgtag cgtatacatt tgttttggga tttttgtgtg tttgttggga  5160
attttgtttt tagccaggtc agtattgatg aggctgatca tttggctctt tttttccttc  5220
cagaagagtt gcatcaacaa agttaattgt atttatgtat gtaaatagat tttaagcttc  5280
attataaaat attgttaatg cctataactt tttttcaatt tttttgtgtg tgtttctaag  5340
gactttttct taggtttgct aaatactgta gggaaaaaaa tgcttctttc tactttgttt  5400
attttagact ttaaaatgag ctacttctta ttcacttttg taaacagcta atagcatggt  5460
tccaattttt tttaagttca cttttttgt tctaggggaa atgaatgtgc aaaaaaagaa  5520
aaagaactgt tggttatttg tgttattctg gatgtataaa aatcaatgga aaaaaataaa  5580
ctttcaaatt gaaatgacgg tataacacat ctactgaaaa agcaacggga aatgtggtcc  5640
tatttaagcc agcccccacc tagggtctat ttgtgtggca gttattgggt ttggtcacaa  5700
aacatcctga aaattcgtgc gtgggcttct ttctccctgg tacaaacgta tggaatgctt  5760
cttaaagggg aactgtcaag ctggtgtctt cagccagatg acatgagaga atatcccaga  5820
accctctctc caaggtgttt ctagatagca caggagagca ggcactgcac tgtccacagt  5880
ccacggtaca cagtcgggtg ggccgcctcc cctctcctgg gagcattcgt cgtgcccagc  5940
ctgagcaggg cagctggact gctgctgttc aggagccacc agagccttcc tctctttgta  6000
ccacagtttc ttctgtaaat ccagtgttac aatcagtgtg aatggcaaat aaacagtttg  6060
acaagtacat acaccata                                                6078

SEQ ID NO: 23           moltype = AA  length = 521
FEATURE                 Location/Qualifiers
source                  1..521
                        mol_type = protein
                        organism = Homo sapiens
SEQUENCE: 23
MASNSLFSTV TPCQQNFFWD PSTSRRFSPP SSSLQPGKMS DVSPVVAAQQ QQQQQQQQQQ  60
QQQQQQQQQQ QEAAAAAAAA AAAAAAAAAV PRLRPPHDNR TMVEIIADHP AELVRTDSPN  120
FLCSVLPSHW RCNKTLPVAF KVVALGEVPD GTVVTVMAGN DENYSAELRN ASAVMKNQVA  180
RFNDLRFVGR SGRGKSFTLT ITVFTNPPQV ATYHRAIKVT VDGPREPRRH RQKLDDSKPS  240
LFSDRLSDLG RIPHPSMRVG VPPQNPRPSL NSAPSPFNPQ GQSQITDPRQ AQSSPPWSYD  300
QSYPSYLSQM TSPSIHSTTP LSSTRGTGLP AITDVPRRIS DDDTATSDFC LWPSTLSKKS  360
QAGASELGPF SDPRQFPSIS SLTESRFSNP RMHYPATFTY TPPVTSGMSL GMSATTHYHT  420
YLPPPYPGSS QSQSGPFQTS STPYLYYGTS SGSYQFPMVP GGDRSPSRML PPCTTTSNGS  480
TLLNPNLPNQ NDGVDADGSH SSSPTVLNSS GRMDESVWRP Y                      521

SEQ ID NO: 24           moltype = AA  length = 499
FEATURE                 Location/Qualifiers
source                  1..499
                        mol_type = protein
                        organism = Homo sapiens
SEQUENCE: 24
MASNSLFSTV TPCQQNFFWD PSTSRRFSPP SSSLQPGKMS DVSPVVAAQQ QQQQQQQQQQ  60
QQQQQQQQQQ QEAAAAAAAA AAAAAAAAAV PRLRPPHDNR TMVEIIADHP AELVRTDSPN  120
FLCSVLPSHW RCNKTLPVAF KVVALGEVPD GTVVTVMAGN DENYSAELRN ASAVMKNQVA  180
RFNDLRFVGR SGRGKSFTLT ITVFTNPPQV ATYHRAIKVT VDGPREPRRH RQKLDDSKPS  240
LFSDRLSDLG RIPHPSMRVG VPPQNPRPSL NSAPSPFNPQ GQSQITDPRQ AQSSPPWSYD  300
QSYPSYLSQM TSPSIHSTTP LSSTRGTGLP AITDVPRRIS GASELGPFSD PRQFPSISSL  360
TESRFSNPRM HYPATFTYTP PVTSGMSLGM SATTHYHTYL PPPYPGSSQS QSGPFQTSST  420
PYLYYGTSSG SYQFPMVPGG DRSPSRMLPP CTTTSNGSTL LNPNLPNQND GVDADGSHSS  480
SPTVLNSSGR MDESVWRPY                                                499

SEQ ID NO: 25           moltype = AA  length = 521
FEATURE                 Location/Qualifiers
source                  1..521
                        mol_type = protein
                        organism = Homo sapiens
SEQUENCE: 25
MASNSLFSTV TPCQQNFFWD PSTSRRFSPP SSSLQPGKMS DVSPVVAAQQ QQQQQQQQQQ  60
QQQQQQQQQQ QEAAAAAAAA AAAAAAAAAV PRLRPPHDNR TMVEIIADHP AELVRTDSPN  120
FLCSVLPSHW RCNKTLPVAF KVVALGEVPD GTVVTVMAGN DENYSAELRN ASAVMKNQVA  180
RFNDLRFVGR SGRGKSFTLT ITVFTNPPQV ATYHRAIKVT VDGPREPRRH RQKLDDSKPS  240
LFSDRLSDLG RIPHPSMRVG VPPQNPRPSL NSAPSPFNPQ GQSQITDPRQ AQSSPPWSYD  300
QSYPSYLSQM TSPSIHSTTP LSSTRGTGLP AITDVPRRIS DDDTATSDFC LWPSTLSKKS  360
QAGASELGPF SDPRQFPSIS SLTESRFSNP RMHYPATFTY TPPVTSGMSL GMSATTHYHT  420
YLPPPYPGSS QSQSGPFQTS STPYLYYGTS SGSYQFPMVP GGDRSPSRML PPCTTTSNGS  480
TLLNPNLPNQ NDGVDADGSH SSSPTVLNSS GRMDESVWRP Y                      521

SEQ ID NO: 26           moltype = AA  length = 485
FEATURE                 Location/Qualifiers
source                  1..485
```

```
                         mol_type = protein
                         organism = Homo sapiens
SEQUENCE: 26
MRIPVDPSTS RRFSPPSSSL QPGKMSDVSP VVAAQQQQQQ QQQQQQQQQQ QQQQQQQEAA  60
AAAAAAAAAA AAAAAVPRLR PPHDNRTMVE IIADHPAELV RTDSPNFLCS VLPSHWRCNK  120
TLPVAFKVVA LGEVPDGTVV TVMAGNDENY SAELRNASAV MKNQVARFND LRFVGRSGRG  180
KSFTLTITVF TNPPQVATYH RAIKVTVDGP REPRRHRQKL DDSKPSLFSD RLSDLGRIPH  240
PSMRVGVPPQ NPRPSLNSAP SPFNPQGQSQ ITDPRQAQSS PPWSYDQSYP SYLSQMTSPS  300
IHSTTPLSST RGTGLPAITD VPRRISGASE LGPFSDPRQF PSISSLTESR FSNPRMHYPA  360
TFTYTPPVTS GMSLGMSATT HYHTYLPPPY PGSSQSQSGP FQTSSTPYLY YGTSSGSYQF  420
PMVPGGDRSP SRMLPPCTTT SNGSTLLNPN LPNQNDGVDA DGSHSSSPTV LNSSGRMDES  480
VWRPY                                                            485

SEQ ID NO: 27            moltype = AA  length = 514
FEATURE                  Location/Qualifiers
source                   1..514
                         mol_type = protein
                         organism = Mus musculus
SEQUENCE: 27
MRIPVDPSTS RRFSPPSSSL QPGKMSDVSP VVAAQQQQQQ QQQQQQQQQQ QQQQQQQQQQ  60
QQQEAAAAAA AAAAAAAAAA AAVPRLRPPH DNRTMVEIIA DHPAELVRTD SPNFLCSVLP  120
SHWRCNKTLP VAFKVVALGE VPDGTVVTVM AGNDENYSAE LRNASAVMKN QVARFNDLRF  180
VGRSGRGKSF TLTITVFTNP PQVATYHRAI KVTVDGPREP RRHRQKLDDS KPSLFSDRLS  240
DLGRIPHPSM RVGVPPQNPR PSLNSAPSPF NPQGQSQITD PRQAQSSPPW SYDQSYPSYL  300
SQMTSPSIHS TTPLSSTRGT GLPAITDVPR RISDDDTATS DFCLWPSSLS KKSQAGASEL  360
GPFSDPRQFP SISSLTESRF SNPRMHYPAT FTYTPPVTSG MSLGMSATTH YHTYLPPPYP  420
GSSQSQSGPF QTSSTPYLYY GTSSASYQFP MVPGGDRSPS RMVPPCTTTS NGSTLLNPNL  480
PNQNDGVDAD GSHSSSPTVL NSSGRMDESV WRPY                            514

SEQ ID NO: 28            moltype = AA  length = 528
FEATURE                  Location/Qualifiers
source                   1..528
                         mol_type = protein
                         organism = Mus musculus
SEQUENCE: 28
MASNSLFSAV TPCQQSFFWD PSTSRRFSPP SSSLQPGKMS DVSPVVAAQQ QQQQQQQQQQ  60
QQQQQQQQQQ QQQQQQQEAA AAAAAAAAAA AAAAAAVPRL RPPHDNRTMV EIIADHPAEL  120
VRTDSPNFLC SVLPSHWRCN KTLPVAFKVV ALGEVPDGTV VTVMAGNDEN YSAELRNASA  180
VMKNQVARFN DLRFVGRSGR GKSFTLTITV FTNPPQVATY HRAIKVTVDG PREPRRHRQK  240
LDDSKPSLFS DRLSDLGRIP HPSMRVGVPP QNPRPSLNSA PSPFNPQGQS QITDPRQAQS  300
SPPWSYDQSY PSYLSQMTSP SIHSTTPLSS TRGTGLPAIT DVPRRISDDD TATSDFCLWP  360
SSLSKKSQAG ASELGPFSDP RQFPSISSLT ESRFSNPRMH YPATFTYTPP VTSGMSLGMS  420
ATTHYHTYLP PPYPGSSQSQ SGPFQTSSTP YLYYGTSSAS YQFPMVPGGD RSPSRMVPPC  480
TTTSNGSTLL NPNLPNQNDG VDADGSHSSS PTVLNSSGRM DESVWRPY              528

SEQ ID NO: 29            moltype = AA  length = 528
FEATURE                  Location/Qualifiers
source                   1..528
                         mol_type = protein
                         organism = Mus musculus
SEQUENCE: 29
MASNSLFSAV TPCQQSFFWD PSTSRRFSPP SSSLQPGKMS DVSPVVAAQQ QQQQQQQQQQ  60
QQQQQQQQQQ QQQQQQQEAA AAAAAAAAAA AAAAAAVPRL RPPHDNRTMV EIIADHPAEL  120
VRTDSPNFLC SVLPSHWRCN KTLPVAFKVV ALGEVPDGTV VTVMAGNDEN YSAELRNASA  180
VMKNQVARFN DLRFVGRSGR GKSFTLTITV FTNPPQVATY HRAIKVTVDG PREPRRHRQK  240
LDDSKPSLFS DRLSDLGRIP HPSMRVGVPP QNPRPSLNSA PSPFNPQGQS QITDPRQAQS  300
SPPWSYDQSY PSYLSQMTSP SIHSTTPLSS TRGTGLPAIT DVPRRISDDD TATSDFCLWP  360
SSLSKKSQAG ASELGPFSDP RQFPSISSLT ESRFSNPRMH YPATFTYTPP VTSGMSLGMS  420
ATTHYHTYLP PPYPGSSQSQ SGPFQTSSTP YLYYGTSSAS YQFPMVPGGD RSPSRMVPPC  480
TTTSNGSTLL NPNLPNQNDG VDADGSHSSS PTVLNSSGRM DESVWRPY              528

SEQ ID NO: 30            moltype = AA  length = 456
FEATURE                  Location/Qualifiers
source                   1..456
                         mol_type = protein
                         organism = Mus musculus
SEQUENCE: 30
MRIPVDPSTS RRFSPPSSSL QPGKMSDVSP VVAAQQQQQQ QQQQQQQQQQ QQQQQQQQQQ  60
QQQEAAAAAA AAAAAAAAAA AAVPRLRPPH DNRTMVEIIA DHPAELVRTD SPNFLCSVLP  120
SHWRCNKTLP VAFKVVALGE VPDGTVVTVM AGNDENYSAE LRNASAVMKN QVARFNDLRF  180
VGRSGRGKSF TLTITVFTNP PQVATYHRAI KVTVDGPREP RNPRQAQSSP PWSYDQSYPS  240
YLSQMTSPSI HSTTPLSSTR GTGLPAITDV PRRISDDDTA TSDFCLWPSS LSKKSQAGAS  300
ELGPFSDPRQ FPSISSLTES RFSNPRMHYP ATFTYTPPVT SGMSLGMSAT THYHTYLPPP  360
YPGSSQSQSG PFQTSSTPYL YYGTSSASYQ FPMVPGGDRS PSRMVPPCTT TSNGSTLLNP  420
NLPNQNDGVD ADGSHSSSPT VLNSSGRMDE SVWRPY                          456

SEQ ID NO: 31            moltype = AA  length = 421
FEATURE                  Location/Qualifiers
source                   1..421
```

```
                         mol_type = protein
                         organism = Mus musculus
SEQUENCE: 31
MRIPVDPSTS RRFSPPSSSL QPGKMSDVSP VVAAQQQQQQ QQQQQQQQQQ QQQQQQQQQQ  60
QQQEAAAAAA AAAAAAAAAA AAVPRLRPPH DNRTMVEIIA DHPAELVRTD SPNFLCSVLP  120
SHWRCNKTLP VAFKVVALGE VPDGTVVTVM AGNDENYSAE LRNASAVMKN QVARFNDLRF  180
VGRSGRDPRQ AQSSPPWSYD QSYPSYLSQM TSPSIHSTTP LSSTRGTGLP AITDVPRRIS  240
DDDTATSDFC LWPSSLSKKS QAGASELGPF SDPRQFPSIS SLTESRFSNP RMHYPATFTY  300
TPPVTSGMSL GMSATTHYHT YLPPPYPGSS QSQSGPFQTS STPYLYYGTS SASYQFPMVP  360
GGDRSPSRMV PPCTTTSNGS TLLNPNLPNQ NDGVDADGSH SSSPTVLNSS GRMDESVWRP  420
Y                                                                 421

SEQ ID NO: 32            moltype = DNA  length = 5487
FEATURE                  Location/Qualifiers
source                   1..5487
                         mol_type = genomic DNA
                         organism = Homo sapiens
SEQUENCE: 32
gtgtgaatgc ttcattcgcc tcacaaacaa ccacagaacc acaagtgcgg tgcaaacttt  60
ctccaggagg acagcaagaa gtctctggtt tttaaatggt taatctccgc aggtcactac  120
cagccaccga gaccaacaga gtcatttaag gctgcaagca gtatttacaa cagagggtac  180
aagttctatc tgaaaaaaaa aggagggact atggcatcaa acagcctctt cagcacagtg  240
acaccatgtc agcaaaactt cttttgggat ccgagcacca gccggcgctt cagccccccc  300
tccagcagcc tgcagcccgg caaaatgagc gacgtgagcc cggtggtggc tgcgcaacag  360
cagcagcaac agcagcagca gcaacagcag cagcagcagc agcaacagca gcagcagcag  420
caggaggcgg cggcggcggc tgcggcggcg gcggcggcgg cggcggcggc agctgcagtg  480
ccccggttgc ggccgcccca cgacaaccgc accatggtgg agatcatcgc cgaccacccg  540
gccgaactcg tccgcaccga cagccccaac ttcctgtgct cggtgctgcc ctcgcactgg  600
cgctgcaaca agaccctgcc cgtggccttc aaggtggtag ccctcggaga ggtaccagat  660
gggactgtgg ttactgtcat ggcgggtaac gatgaaaatt attctgctga gctccggaat  720
gcctctgctg ttatgaaaaa ccaagtagca aggttcaacg atctgagatt tgtgggccgg  780
agtggacgag gcaagagttt caccttgacc ataaccgtct tcacaaatcc tccccaagta  840
gctacctatc acagagcaat taaagttaca gtagatggac ctcgggaacc cagaaggcac  900
agacagaagc ttgatgactc taaacctagt ttgttctctg accgcctcag tgatttaggg  960
cgcattcctc atcccagtat gagagtaggt gtcccgcctc agaacccacg gccctccctg  1020
aactctgcac caagtccttt taatccacaa ggacagagtc agattacaga ccccaggcag  1080
gcacagtctt ccccgccgtg gtcctatgac cagtcttacc cctcctacct gagccagatg  1140
acgtccccgt ccatccactc taccaccccg ctgtcttcca cacggggcac tgggcttcct  1200
gccatcaccg atgtgcctag gcgcatttca ggtgcttcag aactgggccc tttttcagac  1260
cccaggcagt tcccaagcat ttcatccctc actgagagcc gcttctccaa cccacgaatg  1320
cactatccag ccacctttac ttacaccccg ccagtcacct caggcatgtc cctcggtatg  1380
tccgccacca ctcactacca cacctacctg ccaccacccct accccggctc ttcccaaagc  1440
cagagtggac ccttccagac cagcagcact ccatatctct actatggcac ttcgtcagga  1500
tcctatcagt ttcccatggt gccgggggga gaccggtctc cttccagaat gcttccgcca  1560
tgcaccacca cctcgaatgg cagcacgcta ttaaatccaa atttgcctaa ccagaatgat  1620
ggtgttgacg ctgatggaag ccacagcagt tccccaactg ttttgaattc tagtggcaga  1680
atggatgaat ctgtttggcg accatattga aattcctcag cagtggccca gtggtatctg  1740
ggggccacat cccacacgta tcaatatata catatataga gagagtgcat atatatgtat  1800
atcgattagc tatctacaaa gtgcctattt tttagaagat ttttcattca ctcactcagt  1860
catgatcttg cagccataag agggtagata ttgagaagca gaaggctcaa gagagacaat  1920
tgcaatcgag cttcagattg tttactattt aagatgtact tttacaaagg aacaaagaag  1980
ggaaaaggta tttttgtttt tgttgtttgg tctgttatca tcaataacct gttcatatgc  2040
caattcagag aggtggactc caggttcagg agggagaaga gcaaagccgc ttcctctctg  2100
tgctttgaaa cttcacaccc tcacggtggc agctgtgtat ggaccagtgc cctccgcaga  2160
cagctcacaa aaccagttga ggtgcactaa agggacatga ggtagaatgg atgcttccat  2220
cacagtacca tcattcagaa taactcttcc aatttctgct ttcagacatg ctgcaggtcc  2280
tcatctgaac tgttgggttc gttttttttt ttttttttcc tgctccaaga aagtgacttc  2340
aaaaataact gatcaggata gattatttta ttttactttt taacactcct tctccccttt  2400
tcccactgaa ccaaaaagaa atcccatccc taaaacctgc cttctccttt tatgcaaaac  2460
tgaaaatggc aatacattat tatagccata atggtataga tagtgattgc gtttggctat  2520
gtgttgtttt cttttttttt aaattatgaa tatgtgtaaa atctgaggta acttgctaac  2580
gtgaatggtc atataacttt aaagatatat ttataattat ttaatgacat ttggaccctt  2640
gaaacatttc ttagtgtatt gatatgttga cttcggtctc taaaagtgct ctttattaaa  2700
taacaaattt cttcagtggt ctagagccat atctgaaata ttgctaagca atttcagttc  2760
atccaggcac aatgtgattt taaaaaatac ttccatctcc aaatatttta gatatagatt  2820
gtttttgtga tgtatgaagg aaatgttatg tttagttctt tcagatcttt gaatgcctct  2880
aacacagctt tgccttctaa agcggtaatt agggatttaa aaaacaacct ttagcccttt  2940
atcagcatga aatgctggag tgatgtggtt ttctaatttc tttggggtaa ttatgactct  3000
tgtcatatta aaaagacaag cacaagtaaa tcattgaact acagaaaaat gttctgtggt  3060
ttcatagtta agcaaaactc taaatcgcca ggcttcatag caaagacata gtcagctaaa  3120
agccgcacat gtggatagag ggttcaatta tgagacacct agtacaggag agcaaaattg  3180
caccagagat tcttaaccaa ccagccttac caaacaacac aacaggggaa ccccaatctg  3240
ccttacccaa ggccccactg gcagctttcc acagaatttg catttagagg agcagaatga  3300
catcactgtc ctttgggagt aggtcctctg aaaaggcagc aggttccagc aggtagctga  3360
gctgagagga catatggccc acggggacct acagacagcc tttgacattt gtatttctta  3420
caatggaggg ccaaggaggg caaggggctg tggagtttgg tgtctactag tgtgtatgaa  3480
tttgagctag agtccttctg tggcatgcac tttgaccact cctggcagtc acatggcaga  3540
tttccaagtg caaatcctta atccaaacaa ggatcatcta atgacaccac caggccaatc  3600
cctgctctcc tccccgaaaa gtcagggtcc cttcattgga atcctccacc cacccaagca  3660
```

-continued

```
gaatttagca gagatttgcc ttcaaaccct aacggccccc ttgttctctg gtccttctca  3720
aacccacctt tgtaggccac ccagcattgc aggacagcgt gtggggcagc tggacctgtg  3780
cttcctgcct gggagtctcc cttggaattc atcctgactc cttctaataa aaatggatgg  3840
gaaagcaaaa cactttgcct tctaaaggcc gtataccaag tatgcttaga taaataagcc  3900
acttttctat tacttaagta agaaggaagt agtaattgat actatttatt gtttgtgtgt  3960
ggtagcttga agcacaccac tgtccattta tttgtaagtg taaaatatgt gtgtttgttt  4020
cagcagcact taaaaaagcc agtgtctggt tacacatttc aattttaatt aattgacata  4080
aaaatgctac cgccagtgcc agctgcatcc tatttaatta aaaaggtact atatttgtac  4140
attatttttt aatgttaaaa gggctttttt aagtttacag tacacatacc gagtgacttt  4200
agggatgctt ttgtgttgaa atgttactat agtggctgca ggcagcaacc cagaaacact  4260
ttagaagctt tttttccttg ggaaaaattc aagcacttct tccctccacc ctcactccaa  4320
ccaccccaat gggggtaatt cacatttctt agaacaaatt ctgccctttt ttggtctagg  4380
gattaaaatt ttgtttttct ttctttcttt tttttttttt ttcactgaac ccttaatttg  4440
cactgggtca tgtgtttgat ttgtgatttc aagaccaaag caaagtctta ctactactgt  4500
ggaaccatgt actagttcct gggaattaaa atagcgtggt tctctttgta gcacaaacat  4560
tgctggaatt tgcagtcttt tcaatgcagc cacattttta tccatttcag ttgtctcaca  4620
aattttaacc catatcagag ttccagaaca ggtaccacag ctttggtttt agattagtgg  4680
aataacattc agcccagaac tgagaaactc aacagattaa ctatcgtttg ctctttagac  4740
ggtctcactg cctctcactt gccagagccc tttcaaaatg agcagagaag tccacaccat  4800
tagggaccat ctgtgataaa ttcagaaggg aggagatgtg tgtacagctt taaggattcc  4860
ctcaattccg aggaaaggga ctggcccaga atccaggtta atacatggaa acacgaagca  4920
ttagcaaaag taataattat acctatggta tttgaaagaa caataataaa agacacttct  4980
tccaaacctt gaatttgttg tttttagaaa acgaatgcat ttaaaaatat tttctatgtg  5040
agaatttttt agatgtgtgt ttacttcatg tttacaaata actgtttgct ttttaatgca  5100
gtactttgaa atatatcagc caaaaccata acttacaata atttcttagg tattctgaat  5160
aaaattccat ttcttttgga tatgctttac cattcttagg tttctgtgga acaaaaatat  5220
ttgtagcatt ttgtgtaaat acaagctttc atttttattt tttccaattg ctattgccca  5280
agaattgctt tccatgcaca tattgtaaaa attccgcttt gtgccacagg tcatgattgt  5340
ggatgagttt actcttaact tcaaagggac tatttgtatt gtatgttgca actgtaaatt  5400
gaattatttg gcatttttct catgattgta atattaattt gaagtttgaa tttaattttc  5460
aataaaatgg ctttttttggt tttgtta                                  5487
```

```
SEQ ID NO: 33          moltype = DNA  length = 5553
FEATURE                Location/Qualifiers
source                 1..5553
                       mol_type = genomic DNA
                       organism = Homo sapiens
SEQUENCE: 33
gtgtgaatgc ttcattcgcc tcacaaacaa ccacagaacc acaagtgcgg tgcaaacttt  60
ctccaggagg acagcaagaa gtctctggtt tttaaatggt taatctccgc aggtcactac  120
cagccaccga gaccaacaga gtcatttaag gctgcaagca gtatttacaa cagagggtac  180
aagttctatc tgaaaaaaaa aggagggact atggcatcaa acagcctctt cagcacagtg  240
acaccatgtc agcaaaactt cttttgggat ccgagcacca gccggcgctt cagccccccc  300
tccagcagcc tgcagcccgg caaaatgagc gacgtgagcc cggtggtggc tgcgcaacag  360
cagcagcaac agcagcagca gcaacagcag cagcagcagc agcaacagca gcagcagcag  420
caggaggcgg cggcggcggc tgcggcggcg gcggcggctg cggcggcggc agctgcagtg  480
ccccggttgc ggccgcccca cgacaaccgc accatggtgg agatcatcgc cgaccacccg  540
gccgaactcg tccgcaccga cagccccaac ttcctgtgct cggtgctgcc ctcgcactgg  600
cgctgcaaca agaccctgcc cgtggccttc aaggtggtag ccctcggaga ggtaccagat  660
gggactgtgg ttactgtcat ggcgggtaac gatgaaaatt attctgctga gctccggaat  720
gcctctgctg ttatgaaaaa ccaagtagca aggttcaacg atctgagatt tgtgggccgg  780
agtggacgag gcaagagttt caccttgacc ataaccgtct tcacaaatcc tccccaagta  840
gctacctatc acagagcaat taaagttaca gtagatggac ctcgggaacc cagaaggcac  900
agacagaagc ttgatgactc taaacctagt ttgttctctg accgcctcag tgatttaggg  960
cgcattcctc atcccagtat gagagtaggt gtcccgcctc agaacccacg gccctccctg  1020
aactctgcac caagtccttt taatccacaa ggacagagtc agattacaga ccccaggcag  1080
gcacagtctt ccccgccgtg gtcctatgac cagtcttacc cctcctacct gagccagatg  1140
acgtccccgt ccatccactc taccaccccg ctgtcttcca cacggggcac tgggcttcct  1200
gccatcaccg atgtgcctag gcgcatttca gatgatgaca ctgccacctc tgacttctgc  1260
ctctggcctt ccactctcag taagaagagc caggcaggtg cttcagaact gggccctttt  1320
tcagacccca ggcagttccc aagcatttca tccctcactg agagccgctt ctccaaccca  1380
cgaatgcact atccagccac ctttacttac accccgccag tcacctcagg catgtccctc  1440
ggtatgtccg ccaccactca ctaccacacc tacctgccac caccctaccc cggctcttcc  1500
caaagccaga gtggaccctt ccagaccagc agcactccat atctctacta tggcacttcg  1560
tcaggatcct atcagtttcc catggtgccg gggggagacc ggtctccttc cagaatgctt  1620
ccgccatgca ccaccacctc gaatggcagc acgctattaa atccaaattt gcctaaccag  1680
aatgatggtg ttgacgctga tggaagccac agcagttccc caactgtttt gaattctagt  1740
ggcagaatgg atgaatctgt ttggcgacca tattgaaatt cctcagcagt ggcccagtgg  1800
tatctggggg ccacatccca cacgtatcaa tatatacata tatagagaga gtgcatatat  1860
atgtatatcg attagctatc tacaaagtgc ctatttttta gaagattttt cattcactca  1920
ctcagtcatg atcttgcagc cataagaggg tagatattga gaagcagaag gctcaagaga  1980
gacaattgca atcgagcttc agattgttta ctatttaaga tgtactttta caaaggaaca  2040
aagaagggaa aaggtatttt tgtttttgtt gtttggtctg ttatcatcaa taacctgttc  2100
atatgccaat tcagagaggt ggactccagg ttcaggaggg agaagagcaa agccgcttcc  2160
tctctgtgct ttgaaacttc acaccctcac ggtggcagct gtgtatggac cagtgccctc  2220
cgcagacagc tcacaaaacc agttgaggtg cactaaaggg acatgaggta gaatggatgc  2280
ttccatcaca gtaccatcat tcagaataac tcttccaatt tctgctttca gacatgctgc  2340
aggtcctcat ctgaactgtt gggttcgttt tttttttttt ttttcctgct ccaagaaagt  2400
gacttcaaaa ataactgatc aggatagatt attttatttt actttttaac actccttctc  2460
```

-continued

```
ccccttttccc actgaaccaa aaagaaatcc catccctaaa acctgccttc tccttttatg  2520
caaaactgaa aatggcaata cattattata gccataatgg tatagatagt gattgcgttt  2580
ggctatgtgt tgttttcttt ttttttaaat tatgaatatg tgtaaaatct gaggtaactt  2640
gctaacgtga atggtcatat aactttaaag atatatttat aattatttaa tgacatttgg  2700
acccttgaaa catttcttag tgtattgata tgttgacttc ggtctctaaa agtgctcttt  2760
attaaataac aaatttcttc agtggtctag agccatatct gaaatattgc taagcaattt  2820
cagttcatcc aggcacaatg tgattttaaa aaatacttcc atctccaaat attttagata  2880
tagattgttt ttgtgatgta tgaaggaaat gttatgttta gttctttcag atctttgaat  2940
gcctctaaca cagctttgcc ttctaaagcg gtaattaggg atttaaaaaa caacctttag  3000
ccctttatca gcatgaaatg ctggagtgat gtggttttct aatttctttg gggtaattat  3060
gactcttgtc atattaaaaa gacaagcaca agtaaatcat tgaactacag aaaaatgttc  3120
tgtggtttca tagttaagca aaactctaaa tcgccaggct tcatagcaaa gacatagtca  3180
gctaaaagcc gcacatgtgg atagagggtt caattatgag acacctagta caggagagca  3240
aaattgcacc agagattctt aaccaaccag ccttaccaaa caacacaaca ggggaacccc  3300
aatctgcctt acccaaggcc ccactggcag ctttccacag aatttgcatt tagaggagca  3360
gaatgacatc actgtccttt gggagtaggt cctctgaaaa ggcagcaggt tccagcaggt  3420
agctgagctg agaggacata tggcccacgg ggacctacag acagcctttg acatttgtat  3480
ttcttacaat ggagggccaa ggagggcaag gggctgtgga gtttggtgtc tactagtgtg  3540
tatgaatttg agctagagtc cttctgtggc atgcactttg accactcctg gcagtcacat  3600
ggcagatttc caagtgcaaa tccttaatcc aaacaaggat catctaatga caccaccagg  3660
ccaatccctg ctctcctccc cgaaaagtca gggtcccttc attggaatcc tccacccacc  3720
caagcagaat ttagcagaga tttgccttca aaccctaacg gccccccttgt tctctggtcc  3780
ttctcaaacc cacctttgta ggccacccag cattgcagga cagcgtgtgg ggcagctgga  3840
cctgtgcttc ctgcctggga gtctcccttg gaattcatcc tgactccttc taataaaaat  3900
ggatgggaaa gcaaaacact ttgccttcta aaggccgtat accaagtatg cttagataaa  3960
taagccactt ttctattact taagtaagaa ggaagtagta attgatacta tttattgttt  4020
gtgtgtggta gcttgaagca caccactgtc catttatttg taagtgtaaa atatgtgtgt  4080
ttgtttcagc agcacttaaa aaagccagtg tctggttaca catttcaatt ttaattaatt  4140
gacataaaaa tgctaccgcc agtgccagct gcatcctatt taattaaaaa ggtactatat  4200
ttgtacatta ttttttaatg ttaaaagggc ttttttaagt ttacagtaca cataccgagt  4260
gactttaggg atgcttttgt gttgaaatgt tactatagtg gctgcaggca gcaacccaga  4320
aacactttag aagctttttt tccttgggaa aaattcaagc acttcttccc tccaccctca  4380
ctccaaccac cccaatgggg gtaattcaca tttcttagaa caaattctgc cctttttttgg  4440
tctagggatt aaaattttgt ttttctttct ttcttttttt tttttttttca ctgaaccctt  4500
aatttgcact gggtcatgtg tttgatttgt gatttcaaga ccaaagcaaa gtcttactac  4560
tactgtggaa ccatgtacta gttcctggga attaaaatag cgtggttctc tttgtagcac  4620
aaacattgct ggaatttgca gtcttttcaa tgcagccaca tttttatcca tttcagttgt  4680
ctcacaaatt ttaacccata tcagagttcc agaacaggta ccacagcttt ggttttagat  4740
tagtggaata acattcagcc cagaactgag aaactcaaca gattaactat cgtttgctct  4800
ttagacggtc tcactgcctc tcacttgcca gagccctttc aaaatgagca gagaagtcca  4860
caccattagg gaccatctgt gataaattca gaagggagga gatgtgtgta cagctttaag  4920
gattccctca attccgagga aagggactgg cccagaatcc aggttaatac atggaaacac  4980
gaagcattag caaaagtaat aattatacct atggtatttg aaagaacaat aataaaagac  5040
acttcttcca aaccttgaat ttgttgtttt tagaaaacga atgcatttaa aaatattttc  5100
tatgtgagaa ttttttagat gtgtgtttac ttcatgttta caaataactg tttgcttttt  5160
aatgcagtac tttgaaatat atcagccaaa accataactt acaataattt cttaggtatt  5220
ctgaataaaa ttccatttct tttggatatg ctttaccatt cttaggtttc tgtggaacaa  5280
aaatatttgt agcattttgt gtaaatacaa gctttcattt ttatttttttc caattgctat  5340
tgcccaagaa ttgctttcca tgcacatatt gtaaaaattc cgctttgtgc cacaggtcat  5400
gattgtggat gagtttactc ttaacttcaa agggactatt tgtattgtat gttgcaactg  5460
taaattgaat tatttggcat ttttctcatg attgtaatat taatttgaag tttgaattta  5520
attttcaata aaatggcttt tttggttttg tta                                5553
```

```
SEQ ID NO: 34           moltype = DNA  length = 5235
FEATURE                 Location/Qualifiers
source                  1..5235
                        mol_type = genomic DNA
                        organism = Homo sapiens
SEQUENCE: 34
atgcgtattc ccgtagatcc gagcaccagc cggcgcttca gcccccccctc cagcagcctg  60
cagcccggca aaatgagcga cgtgagcccg gtggtggctg cgcaacagca gcagcaacag  120
cagcagcagc aacagcagca gcagcagcag caacagcagc agcagcagca ggaggcggcg  180
gcggcggctg cggcggcggc ggcggctgcg gcggcggcag ctgcagtgcc ccggttgcgg  240
ccgccccacg acaaccgcac catggtggag atcatcgccg accacccggc cgaactcgtc  300
cgcaccgaca gccccaactt cctgtgctcg gtgctgccct cgcactggcg ctgcaacaag  360
accctgcccg tggccttcaa ggtggtagcc ctcggagagg taccagatgg gactgtggtt  420
actgtcatgg cgggtaacga tgaaaattat tctgctgagc tccggaatgc ctctgctgtt  480
atgaaaaacc aagtagcaag gttcaacgat ctgagatttg tgggccggag tggacgaggc  540
aagagtttca ccttgaccat aaccgtcttc acaaatcctc cccaagtagc tacctatcac  600
agagcaatta aagttacagt agatggacct cgggaaccca gaaggcacag acagaagctt  660
gatgactcta aacctagttt gttctctgac cgcctcagtg atttagggcg cattcctcat  720
cccagtatga gagtaggtgt cccgcctcag aacccacggc cctccctgaa ctctgcacca  780
agtcctttta atccacaagg acagagtcag attacagacc ccaggcaggc acagtcttcc  840
ccgccgtggt cctatgacca gtcttacccc tcctacctga gccagatgac gtccccgtcc  900
atccactcta ccaccccgct gtcttccaca cggggcactg ggcttcctgc catcaccgat  960
gtgcctaggc gcatttcagg tgcttcagaa ctgggccctt tttcagaccc caggcagttc  1020
ccaagcattt catccctcac tgagagccgc ttctccaacc cacgaatgca ctatccagcc  1080
acctttactt acaccccgcc agtcacctca ggcatgtccc tcggtatgtc cgccaccact  1140
cactaccaca cctacctgcc accaccctac cccggctctt cccaaagcca gagtggaccc  1200
```

```
ttccagacca gcagcactcc atatctctac tatggcactt cgtcaggatc ctatcagttt  1260
cccatggtgc cggggggaga ccggtctcct tccagaatgc ttccgccatg caccaccacc  1320
tcgaatggca gcacgctatt aaatccaaat ttgcctaacc agaatgatgg tgttgacgct  1380
gatggaagcc acagcagttc cccaactgtt ttgaattcta gtggcagaat ggatgaatct  1440
gtttggcgac catattgaaa ttcctcagca gtggcccagt ggtatctggg ggccacatcc  1500
cacacgtatc aatatataca tatatagaga gagtgcatat atatgtatat cgattagcta  1560
tctacaaagt gcctattttt tagaagattt ttcattcact cactcagtca tgatcttgca  1620
gccataagag ggtagatatt gagaagcaga aggctcaaga gagacaattg caatcgagct  1680
tcagattgtt tactatttaa gatgtacttt tacaaaggaa caaagaaggg aaaaggtatt  1740
tttgtttttg ttgtttggtc tgttatcatc aataacctgt tcatatgcca attcagagag  1800
gtggactcca ggttcaggag ggagaagagc aaagccgctt cctctctgtg ctttgaaact  1860
tcacaccctc acggtggcag ctgtgtatgg accagtgccc tccgcagaca gctcacaaaa  1920
ccagttgagg tgcactaaag ggacatgagg tagaatggat gcttccatca cagtaccatc  1980
attcagaata actcttccaa tttctgcttt cagacatgct gcaggtcctc atctgaactg  2040
ttgggttcgt tttttttttt ttttttcctg ctccaagaaa gtgacttcaa aaataactga  2100
tcaggataga ttattttatt ttactttttta acactccttc tcccctttttc ccactgaacc  2160
aaaaagaaat cccatcccta aaacctgcct tctccttttta tgcaaaactg aaaatggcaa  2220
tacattatta tagccataat ggtatagata gtgattgcgt ttggctatgt gttgttttct  2280
ttttttttaa attatgaata tgtgtaaaat ctgaggtaac ttgctaacgt gaatggtcat  2340
ataactttaa agatatattt ataattattt aatgacattt ggacccttga aacatttctt  2400
agtgtattga tatgttgact tcggtctcta aaagtgctct ttattaaata acaaatttct  2460
tcagtggtct agagccatat ctgaaatatt gctaagcaat ttcagttcat ccaggcacaa  2520
tgtgatttta aaaaatactt ccatctccaa atattttaga tatagattgt ttttgtgatg  2580
tatgaaggaa atgttatgtt tagttctttc agatctttga atgcctctaa cacagctttg  2640
ccttctaaag cggtaattag ggatttaaaa aacaaccttt agccctttat cagcatgaaa  2700
tgctggagtg atgtggtttt ctaatttctt tggggtaatt atgactcttg tcatattaaa  2760
aagacaagca caagtaaatc attgaactac agaaaaatgt tctgtggttt catagttaag  2820
caaaactcta aatcgccagg cttcatagca aagacatagt cagctaaaag ccgcacatgt  2880
ggatagaggg ttcaattatg agacacctag tacaggagag caaaattgca ccagagattc  2940
ttaaccaacc agccttacca aacaacacaa caggggaacc ccaatctgcc ttacccaagg  3000
ccccactggc agctttccac agaatttgca tttagaggag cagaatgaca tcactgtcct  3060
ttgggagtag gtcctctgaa aaggcagcag gttccagcag gtagctgagc tgagaggaca  3120
tatggcccac ggggacctac agacagcctt tgacatttgt atttcttaca atggagggcc  3180
aaggagggca aggggctgtg gagtttggtg tctactagtg tgtatgaatt tgagctagag  3240
tccttctgtg gcatgcactt tgaccactcc tggcagtcac atggcagatt tccaagtgca  3300
aatccttaat ccaaacaagg atcatctaat gacaccacca ggccaatccc tgctctcctc  3360
cccgaaaagt cagggtccct tcattggaat cctccaccca cccaagcaga atttagcaga  3420
gatttgcctt caaaccctaa cggccccctt gttctctggt ccttctcaaa cccacctttg  3480
taggccaccc agcattgcag gacagcgtgt ggggcagctg gacctgtgct tcctgcctgg  3540
gagtctccct tggaattcat cctgactcct tctaataaaa atggatggga aagcaaaaca  3600
ctttgccttc taaaggccgt ataccaagta tgcttagata aataagccac ttttctatta  3660
cttaagtaag aaggaagtag taattgatac tatttattgt ttgtgtgtgg tagcttgaag  3720
cacaccactg tccatttatt tgtaagtgta aaatatgtgt gtttgtttca gcagcactta  3780
aaaaagccag tgtctggtta cacatttcaa ttttaattaa ttgacataaa aatgctaccg  3840
ccagtgccag ctgcatccta tttaattaaa aaggtactat atttgtacat tattttttaa  3900
tgttaaaagg gctttttttaa gtttacagta cacataccga gtgactttag ggatgctttt  3960
gtgttgaaat gttactatag tggctgcagg cagcaaccca gaaacacttt agaagctttt  4020
tttccttggg aaaaattcaa gcacttcttc cctccaccct cactccaacc accccaatgg  4080
gggtaattca catttcttag aacaaattct gccctttttt ggtctaggga ttaaaatttt  4140
gtttttcttt ctttcttttt tttttttttt cactgaaccc ttaatttgca ctgggtcatg  4200
tgtttgattt gtgatttcaa gaccaaagca aagtcttact actactgtgg aaccatgtac  4260
tagttcctgg gaattaaaat agcgtggttc tctttgtagc acaaacattg ctggaatttg  4320
cagtcttttc aatgcagcca catttttatc catttcagtt gtctcacaaa ttttaaccca  4380
tatcagagtt ccagaacagg taccacagct ttggttttag attagtggaa taacattcag  4440
cccagaactg agaaactcaa cagattaact atcgtttgct ctttagacgg tctcactgcc  4500
tctcacttgc cagagccctt tcaaaatgag cagagaagtc cacaccatta gggaccatct  4560
gtgataaatt cagaagggag gagatgtgtg tacagcttta aggattccct caattccgag  4620
gaaagggact ggcccagaat ccaggttaat acatggaaac acgaagcatt agcaaaagta  4680
ataattatac ctatggtatt tgaaagaaca ataataaaag acacttcttc caaaccttga  4740
atttgttgtt tttagaaaac gaatgcattt aaaaatattt tctatgtgag aattttttag  4800
atgtgtgttt acttcatgtt tacaaataac tgtttgcttt ttaatgcagt actttgaaat  4860
atatcagcca aaaccataac ttacaataat ttcttaggta ttctgaataa aattccattt  4920
cttttggata tgctttacca ttcttaggtt tctgtggaac aaaaatattt gtagcatttt  4980
gtgtaaatac aagctttcat ttttattttt tccaattgct attgcccaag aattgctttc  5040
catgcacata ttgtaaaaat tccgctttgt gccacaggtc atgattgtgg atgagtttac  5100
tcttaacttc aaagggacta tttgtattgt atgttgcaac tgtaaattga attatttggc  5160
atttttctca tgattgtaat attaatttga agtttgaatt taattttcaa taaaatggct  5220
tttttggttt tgtta                                                 5235
```

```
SEQ ID NO: 35           moltype = DNA  length = 6475
FEATURE                 Location/Qualifiers
source                  1..6475
                        mol_type = genomic DNA
                        organism = Mus musculus
SEQUENCE: 35
ctgaagttaa caacgaaaaa ttaacgccag tcggagcagc ctgaggctct cccgcttctc  60
agctttagcg tcgtcagacc gagaagtggt tcccggtcct gagggtgaag tggggagccg  120
aggacgcagg cggcgatgtc ctaggcgggg acctcctccc tacagcttcg ggcgccgagc  180
gagcgcagcg gcgcttctag cggccggcgg gcggcggcag cggctgcgat ccgcaggctc  240
```

-continued

```
cagatctgtc gccccgagat ccgctctccc cccgccccca cttacctccc ggcaccttga  300
aacgcgaggg gggcccgggg cactttgcaa agagcaggag agacgaggct gcgagctaga  360
cggcggcgaa ggagagggcg agaggagaag ccggggaaag gaaggactcg gcggccggag  420
gactcggagc gcgctgccgg cgcggggagc gcgcagcggc ctcggaggag gaggcggagg  480
aggcggcgcg ggcaagcgac ggcgccgcga gctgggcagc cgcgctctgc ttggcggtgg  540
cggacagcga ggagccacac gcaccgccga gatggactgc tgaacctgcg gggctccact  600
accgtactgg aacccggagc ggggcgccag cgcacccagg acacggtgcc ccaaggggcc  660
cctactgcaa gctgttaact tcaagtccct tgcggcggct gggccaaaca cgccccccgcg  720
tcccgctcgt tgcagccacc gccagggact cccaagcctc ccggtggaga tccgcgcctc  780
tcgggtgtcc ccacccgcta ccccgactct gtccggtctc cagtcgccgg cccccagcag  840
actccgcccg gcacacggct tcctcgaact tgatttctca cctcctctgt cccgtcacct  900
ccatcctctt tccgcccccg tctcgcctcc accccctcga tttcctcctc ctcgcccccc  960
atttccaccc tcctccccct cccccggcca cttcgctaac ttgtggctgt tgtgatgcgt  1020
attcctgtag atccgagcac cagccggcgc ttcagccccc cctccagcag cctgcagccc  1080
ggcaagatga gcgacgtgag cccggtggtg gctgcgcagc agcagcaaca gcagcagcag  1140
cagcagcaac agcagcagca acaacagcaa cagcaacaac agcagcagca gcagcagcag  1200
caggaggcgg ccgcagcagc agcggcggca gcggcggcgg cagcagcggc ggcggccgca  1260
gtgccccgat tgaggccgcc gcacgacaac cgcaccatgg tggagatcat cgcggaccac  1320
ccggccgaac tggtccgcac cgacagtccc aacttcctgt gctccgtgct gccctcgcac  1380
tggcggtgca acaagaccct gcccgtggcc ttcaaggttg tagccctcgg agaggtacca  1440
gatgggactg tggttaccgt catggccggg aatgatgaga actactccgc cgagctccga  1500
aatgcctccg ctgttatgaa aaaccaagta gccaggttca acgatctgag atttgtgggc  1560
cggagcggac gaggcaagag tttcaccttg accataacag tcttcacaaa tcctccccaa  1620
gtggccactt accacagagc tattaaagtg acagtggacg gtccccggga accaagaagg  1680
cacagacaga agcttgatga ctctaaacct agtttgttct ctgatcgcct cagtgattta  1740
gggcgcattc ctcatcccag tatgagagta ggtgtcccgc ctcagaaccc acggccctcc  1800
ctgaactctg caccaagtcc ttttaatcca caaggacaga gtcagattac agatcccagg  1860
caggcacagt cttccccacc gtggtcctat gaccagtctt acccctccta tctgagccag  1920
atgacatccc catccatcca ctccaccacg ccgctgtctt ccacacgggg caccgggcta  1980
cctgccatca ctgacgtgcc caggcgtatt tcagatgatg acactgccac ctctgacttc  2040
tgcctctggc cttcctctct cagtaagaag agccaggcag gtgcttcaga actgggccct  2100
ttttcagacc ccaggcagtt cccaagcatt tcatccctca ctgagagccg cttctccaac  2160
ccacgaatgc actacccagc cacctttacc tacacccccgc cagtcacgtc aggcatgtcc  2220
ctcggcatgt ccgccaccac tcactaccac acgtacctgc caccacccta ccccggctct  2280
tcccaaagcc agagtggacc cttccagacc agcagcactc catatctcta ctatggtact  2340
tcgtcagcat cctatcagtt cccaatggta cccgggggag accggtctcc ttccaggatg  2400
gtcccaccat gcaccaccac ctcgaatggc agcacgctat taaatccaaa tttgcctaac  2460
cagaatgatg gtgttgacgc tgacggaagc cacagcagtt ccccaactgt tttgaattct  2520
agcggcagaa tggatgagtc tgtttggcgg ccatattgaa attcgtcaac catggcccag  2580
tggcatgggg gccacatccc gcatgtgtta atatatacat atataaagag agtgcctata  2640
tatgtatatt gattagctaa ctagaagatt tctcattcaa tccctagtca tgatcttgca  2700
accctaagag ggtgggggca gtcataactg ggtttcatat tgtttactat ttaagatgtc  2760
ccctttacca aggaacaaac cgtcaaaggt gttgtctggt ctgttttcat aagtgacctg  2820
ttcccacgcc ggttcagaga ggtggactct gggtctggga ggaaggagag acacttcctc  2880
tctgtgcttt gaaaccacag cctctgctgt gtggcagccg gtacactctg cagacccgct  2940
tacagagtca gatgtggtgc actcagaaag ggacaagagg cagagtggct gcttctgtcc  3000
gctgccgtcc actctgccgt ccacctgttc caaagttttc cttcagactt gctgcaggta  3060
ctcatttgaa cttttgagtt cacttttttt ttttcctatt ctaagaaagt gacttcaaaa  3120
atactgatca ggacagataa ttttatttta ccttttatat tttctcactt cccccattta  3180
accaaaaaga aatcccgttc cccctccccc gttccttctg cttctccctt tatgcaaact  3240
gaaaatggca atgccttatt attatagcca taatggtata gtgtttgagt tggctgtgtg  3300
ttatgtgttt ttttcttttt ttttcttttt taaattatga atatgtgtaa aatctgaagt  3360
aacttgctaa cgtgaatggt catataactt taaagatata tttataatta tttaatgaca  3420
tttggacatt tggaacattt cttagtgtaa tgatatgttg acttcggtct ctaaaagtgt  3480
gcttcttctt caataccaag tttcttcagt gggctagagc catatcggaa atattgctaa  3540
gcaatctcaa ttccttcagg cataatgtga tttttttttt tttttgaaga taactcccat  3600
ctccaaatag tttagatgta gtttgttttc acgatgtatg aaggagatgc tctgtttctt  3660
tctttcaggc atttgattgc ctctgacaca gctttgcctt ttaaagcaat aattagggat  3720
taaaataaca aaaacaaaac aaaagccacc tatagccctt taacacttaa cgtggcccct  3780
ttactagcat gaaatgctgg agacatgtgg tttcctaatt tctccatttt gggggtggtg  3840
ggagggggga gggtggccat tatgactctt atcatattaa aaagccaagc acaagtgatt  3900
ggttgaactg cagaaaagtg ttctgtggtc tctgagttga gcaaaactct aaattgcagg  3960
cttcgtggtt gagggcctag tcagctgaaa gccacgcgtg tggtaaaggc tcaggcatgg  4020
cttggagaac ctaggaacac attaggagcc tgcacctacc agcctcacca tacagccatt  4080
caggggaacc caaaaagtgc cttacccaag gagggccccc agcagctttc caggaagtcg  4140
aatgaagtcg ctgtcctcgg ggaactggtc agctgaagta gcaaccggta gctgatgtca  4200
gtagacaaca gaacctgtgg ggacctccag gaaacctttg acattggagg ctttcattag  4260
gcagggccaa caagagcagg gaaggccatg tacccattgg tatctgccat tgtgtgtgag  4320
tttgagatcc agccctcctt ggaggatgta ctgtgatcat tcctggtacc ttagggccaa  4380
tccctaagtg tggcttccta atccaggcca gggatcattc agtgatacca ccaggccaat  4440
cccagcattc ctcctgcaca aagtgtttgt gtgtgggggg atagattggg gtggggccac  4500
cttcatttga atcctgagtc attctaagag ttctgcaagc ttttgccttc agcaccctat  4560
accccctcgc tctctgttcc ttctcaggtt gacctttgtc ccaatgcggg acagtccaga  4620
ggcagatggg gacctatgtg tgcctccaac ctgcgttttc ctcagaattc atcctgactc  4680
cctctgacac agattgaggg ggggggggaag aaacccaacc cgcaccaaag caaaacactt  4740
tgccttctaa aggctgtgca ccaagtagac gcagatggtc agcccacctt tgtgtttcct  4800
taagatggaa attgtaactg atgctattta ttgtttgtgt gtggtagctt gaagcacacc  4860
acggtccatg tgtttgtctg atacctattt cagcagcatt tacaaaagcc agtgtctggt  4920
tacacttttc agttttcatt aatcaacatg aaaatgttac cattggtgcc agctgcaccc  4980
```

-continued

```
tatttaattt ttttaagggc actatatttg tacatttcgt ttttaatgtt aaagggcttc  5040
ttaaagttta cagtacagtt atcaagggaa tagaggggat gcattagtgc ctaaatgtta  5100
ttctagtggc tgcaggcagc aacccagaag cagttttgaa aacaggttgt ttccctctgt  5160
cctcccttat ttgggaaaat tcaagtgctt tcttcacctt tcaggcacct cacggtgact  5220
cccgttactt agagcagtct gtcgtcgtct tcttcttctt cctcttcctc ttcctcttcc  5280
tcttcctctt cctcttcctc ttcctcttcc tcttcctctt cttcttcttc ttcttcttct  5340
tcttcttctt cttcttcctc ctagggttta aaatcccccct tcctcttccc ttatctctta  5400
aactcttcat ttgcactggg tcacacgtat gatttgtggt tttaagacca aagcaatgtc  5460
ttattactct tctggagccg tttatgtgta ctaaccaacc cttccctcca cttccctggg  5520
tttagatgca cacggttctc aaaggagcac aaacatggcc agattcacag tgggacccac  5580
acagccatgt taaaaaaaaa aacaaaaaaa aacctcttca cttgtctgag aattttaacc  5640
tgggccccaa ttgctaacgg gcaccatggc ttgggtttca ggttagggaa cgttgcccag  5700
tgagtaacag aaagacttaa ctgatttaat tagtttgccc tcatccttca ctccaagacc  5760
ctaagaaacc gatcagagaa acatctccac accattagag gttgagaagg gaggagccat  5820
gtgggggttc cctccgctcg gaggaaaggc actgactgac ctagttagag tggtagcaga  5880
agcacccatg gtatctgaga gagcaataaa caataaaaga tgatcctccc aagcttagaa  5940
tttgttgttc ttaaagaaga cgatgcatct aaaacaaaga attttttttt ctatgtggga  6000
actttcttcg ttgtctgttt acttcatgtt tacaaataat tgtttgcttt ttaatgcagt  6060
actttaaaaa atatatcagc caaaaccata acttacagta atttttttag gtattctgaa  6120
taaaattcca tgtcttttga tatgtctact gttcttaggt ttctgtggaa caacaacaac  6180
aacaacaaca aaattgtagc attttgtgta aatacagctt tcgttcttat tttttatttt  6240
tctgattgct attgcccaag atttgctttc tatgcacgta ttgtacaaat tgtgctttgt  6300
gccacaggtc atgatcgtgg atgagtttac tctgaacttc aaagggacta tttgtattgt  6360
atgttgcaac tgtaaattga attatttggc atttcccccct ctcatgattg taatattaat  6420
ttgaagtttg aatttaattt tcaataaaaa ggcttttttt ttccttttgg ttttg       6475
```

```
SEQ ID NO: 36          moltype = DNA  length = 5740
FEATURE                Location/Qualifiers
source                 1..5740
                       mol_type = genomic DNA
                       organism = Mus musculus
SEQUENCE: 36
atgcttcatt cgcctcacaa acaaccacag aaccacaagt gcggtgcaaa ctttctccag  60
gaagactgca agaaggctct ggcgtttaaa tggttaatct ctgcaggtca ctaccagcca  120
ccgagaccaa ccgagtcagt gagtgctcta accacagtcc atgcaggaat atttaaggct  180
gcaagcagta tttacaacag agggcacaag ttctatctgg aaaaaaaagg agggactatg  240
gcgtcaaaca gcctcttcag cgcagtgaca ccgtgtcagc aaagcttctt ttgggatccg  300
agcaccagcc ggcgcttcag ccccccctcc agcagcctgc agcccggcaa gatgagcgac  360
gtgagcccgg tggtggctgc gcagcagcag caacagcagc agcagcagca gcaacagcag  420
cagcaacaac agcaacagca acaacagcag cagcagcagc agcagcagga ggcggccgca  480
gcagcagcgg cggcagcggc ggcggcagca gcggcggcgg ccgcagtgcc ccgattgagg  540
ccgccgcacg acaaccgcac catggtggag atcatcgcgg accacccggc cgaactggtc  600
cgcaccgaca gtcccaactt cctgtgctcc gtgctgccct cgcactggcg gtgcaacaag  660
accctgcccg tggccttcaa ggttgtagcc ctcggagagg taccagatgg gactgtggtt  720
accgtcatgg ccgggaatga tgagaactac tccgccgagc tccgaaatgc ctccgctgtt  780
atgaaaaacc aagtagccag gttcaacgat ctgagatttg tgggccggag cggacgaggc  840
aagagtttca ccttgaccat aacagtcttc acaaatcctc cccaagtggc cacttaccac  900
agagctatta aagtgacagt ggacggtccc cgggaaccaa gaaggcacag acagaagctt  960
gatgactcta aacctagttt gttctctgat cgcctcagtg atttagggcg cattcctcat  1020
cccagtatga gagtaggtgt cccgcctcag aacccacggc cctccctgaa ctctgcacca  1080
agtcctttta atccacaagg acagagtcag attacagatc ccaggcaggc acagtcttcc  1140
ccaccgtggt cctatgacca gtcttacccc tcctatctga gccagatgac atccccatcc  1200
atccactcca ccacgccgct gtcttccaca cggggcaccg ggctacctgc catcactgac  1260
gtgcccaggc gtatttcaga tgatgacact gccacctctg acttctgcct ctggccttcc  1320
tctctcagta agaagagcca ggcaggtgct tcagaactgg gcccttttttc agaccccagg  1380
cagttcccaa gcatttcatc cctcactgag agccgcttct ccaacccacg aatgcactac  1440
ccagccacct ttacctacac cccgccagtc acgtcaggca tgtccctcgg catgtccgcc  1500
accactcact accacacgta cctgccacca ccctaccccg gctcttccca aagccagagt  1560
ggacccttcc agaccagcag cactccatat ctctactatg gtacttcgtc agcatcctat  1620
cagttcccaa tggtacccgg gggagaccgg tctccttcca ggatggtccc accatgcacc  1680
accacctcga atggcagcac gctattaaat ccaaatttgc ctaaccagaa tgatggtgtt  1740
gacgctgacg gaagccacag cagttcccca actgttttga attctagcgg cagaatggat  1800
gagtctgttt ggcggccata ttgaaattcg tcaaccatgg cccagtggca tgggggccac  1860
atcccgcatg tgttaatata tacatatata aagagagtgc ctatatatgt atattgatta  1920
gctaactaga agatttctca ttcaatccct agtcatgatc ttgcaaccct aagagggtgg  1980
gggcagtcat aactgggttt catattgttt actatttaag atgtcccctt taccaaggaa  2040
caaaccgtca aaggtgttgt ctggtctgtt ttcataagtg acctgttccc acgccggttc  2100
agagaggtgg actctgggtc tgggaggaag gagagacact tcctctctgt gctttgaaac  2160
cacagcctct gctgtgtggc agccggtaca ctctgcagac ccgcttacag agtcagatgt  2220
ggtgcactca gaaagggaca agaggcagag tggctgcttc tgtccgctgc cgtccactct  2280
gccgtccacc tgttccaaag ttttccttca gacttgctgc aggtactcat ttgaactttt  2340
gagttcactt tttttttttc ctattctaag aaagtgactt caaaaatact gatcaggaca  2400
gataatttta ttttaccttt tatattttct cacttccccc atttaaccaa aaagaaatcc  2460
cgttcccccct cccccgttcc ttctgcttct ccctttatgc aaactgaaaa tggcaatgcc  2520
ttattattat agccataatg gtatagtgtt tgagttggct gtgtgttatg tgtttttttc  2580
tttttttttc tttttttaaat tatgaatatg tgtaaaatct gaagtaactt gctaacgtga  2640
atggtcatat aactttaaag atatatttat aattatttaa tgacatttgg acatttggaa  2700
catttcttag tgtaatgata tgttgacttc ggtctctaaa agtgtgcttc ttcttcaata  2760
ccaagtttct tcagtgggct agagccatat cggaaatatt gctaagcaat ctcaattcct  2820
```

-continued

```
tcaggcataa tgtgattttt tttttttttt gaagataact cccatctcca aatagtttag  2880
atgtagtttg ttttcacgat gtatgaagga gatgctctgt ttctttcttt caggcatttg  2940
attgcctctg acacagcttt gccttttaaa gcaataatta gggattaaaa taacaaaaac  3000
aaaacaaaag ccacctatag ccctttaaca cttaacgtgg cccctttact agcatgaaat  3060
gctggagaca tgtggtttcc taatttctcc attttggggg tggtgggagg ggggagggtg  3120
gccattatga ctcttatcat attaaaaagc caagcacaag tgattggttg aactgcagaa  3180
aagtgttctg tggtctctga gttgagcaaa actctaaatt gcaggcttcg tggttgaggg  3240
cctagtcagc tgaaagccac gcgtgtggta aaggctcagg catggcttgg agaacctagg  3300
aacacattag gagcctgcac ctaccagcct caccatacag ccattcaggg gaacccaaaa  3360
agtgccttac ccaaggaggg cccccagcag ctttccagga agtcgaatga agtcgctgtc  3420
ctcggggaac tggtcagctg aagtagcaac cggtagctga tgtcagtaga caacagaacc  3480
tgtggggacc tccaggaaac ctttgacatt ggaggctttc attaggcagg gccaacaaga  3540
gcagggaagg ccatgtaccc attggtatct gccattgtgt gtgagtttga gatccagccc  3600
tccttggagg atgtactgtg atcattcctg gtaccttagg gccaatccct aagtgtggct  3660
tcctaatcca ggccagggat cattcagtga taccaccagg ccaatcccag cattcctcct  3720
gcacaaagtg tttgtgtgtg gggggataga ttggggtggg gccaccttca tttgaatcct  3780
gagtcattct aagagttctg caagcttttg ccttcagcac cctataccccc ctcgctctct  3840
gttccttctc aggttgacct ttgtcccaat gcgggacagt ccagaggcag atggggacct  3900
atgtgtgcct ccaacctgcg ttttcctcag aattcatcct gactccctct gacacagatt  3960
gagggggggg ggaagaaacc caacccgcac caaagcaaaa cactttgcct tctaaaggct  4020
gtgcaccaag tagacgcaga tggtcagccc acctttgtgt ttccttaaga tggaaattgt  4080
aactgatgct atttattgtt tgtgtgtggt agcttgaagc acaccacggt ccatgtgttt  4140
gtctgatacc tatttcagca gcatttacaa aagccagtgt ctggttacac ttttcagttt  4200
tcattaatca acatgaaaat gttaccattg gtgccagctg caccctattt aattttttta  4260
agggcactat atttgtacat ttcgttttta atgttaaagg gcttcttaaa gtttacagta  4320
cagttatcaa gggaatagag gggatgcatt agtgcctaaa tgttattcta gtggctgcag  4380
gcagcaaccc agaagcagtt ttgaaaacag gttgtttccc tctgtcctcc cttatttggg  4440
aaaattcaag tgctttcttc acctttcagg cacctcacgg tgactcccgt tacttagagc  4500
agtctgtcgt cgtcttcttc ttcttcctct tcctcttcct cttcctcttc ctcttcctct  4560
tcctcttcct cttcctcttc ctcttcttct tcttcttctt cttcttcttc ttcttcttct  4620
tcctcctagg gtttaaaatc ccccttcctc ttcccttatc tcttaaactc ttcatttgca  4680
ctgggtcaca cgtatgattt gtggttttaa gaccaaagca atgtcttatt actcttctgg  4740
agccgtttat gtgtactaac caacccttcc ctccacttcc ctgggtttag atgcacacgg  4800
ttctcaaagg agcacaaaca tggccagatt cacagtggga cccacacagc catgttaaaa  4860
aaaaaaacaa aaaaaaacct cttcacttgt ctgagaattt taacctgggc cccaattgct  4920
aacgggcacc atggcttggg tttcaggtta gggaacgttg cccagtgagt aacagaaaga  4980
cttaactgat ttaattagtt tgccctcatc cttcactcca agaccctaag aaaccgatca  5040
gagaaacatc tccacaccat tagaggttga gaagggagga gccatgtggg ggttccctcc  5100
gctcggagga aaggcactga ctgacctagt tagagtggta gcagaagcac ccatggtatc  5160
tgagagagca ataaacaata aaagatgatc ctcccaagct tagaatttgt tgttcttaaa  5220
gaagacgatg catctaaaac aaagaatttt tttttctatg tgggaacttt cttcgttgtc  5280
tgtttacttc atgtttacaa ataattgttt gctttttaat gcagtacttt aaaaaatata  5340
tcagccaaaa ccataactta cagtaatttt tttaggtatt ctgaataaaa ttccatgtct  5400
tttgatatgt ctactgttct taggtttctg tggaacaaca acaacaacaa caacaaaatt  5460
gtagcatttt gtgtaaatac agctttcgtt cttatttttt atttttctga ttgctattgc  5520
ccaagatttg ctttctatgc acgtattgta caaattgtgc tttgtgccac aggtcatgat  5580
cgtggatgag tttactctga acttcaaagg gactatttgt attgtatgtt gcaactgtaa  5640
attgaattat ttggcatttc cccctctcat gattgtaata ttaatttgaa gtttgaattt  5700
aattttcaat aaaaaggctt tttttttcct tttggttttg                        5740
```

```
SEQ ID NO: 37          moltype = DNA  length = 5904
FEATURE                Location/Qualifiers
source                 1..5904
                       mol_type = genomic DNA
                       organism = Mus musculus
SEQUENCE: 37
atgcttcatt cgcctcacaa acaaccacag aaccacaagt gcggtgcaaa ctttctccag  60
gaagactgca agaaggctct ggcgtttaaa tggttaatct ctgcaggtca ctaccagcca  120
ccgagaccaa ccgagtcagt gagtgctcta accacagtcc atgcaggaat agtaggtcct  180
tcaaatattt gctcactccg ttttgttttg tttccttgct tttcacatgt taccagctac  240
ataatttctt gacagaaaaa aataaatata aagtctatgt actccaggca tactgtacaa  300
ctaaaacagg gactgggtat ggtttgtatt ttcagtttaa ggctgcaagc agtatttaca  360
acagagggca caagttctat ctggaaaaaa aaggagggac tatggcgtca aacagcctct  420
tcagcgcagt gacaccgtgt cagcaaagct tcttttggga tccgagcacc agccggcgct  480
tcagcccccc ctccagcagc ctgcagcccg gcaagatgag cgacgtgagc ccggtggtgg  540
ctgcgcagca gcagcaacag cagcagcagc agcagcaaca gcagcagcaa caacagcaac  600
agcaacaaca gcagcagcag cagcagcagc aggaggcggc cgcagcagca gcggcggcag  660
cggcggcggc agcagcggcg gcggccgcag tgccccgatt gaggccgccg cacgacaacc  720
gcaccatggt ggagatcatc gcggaccacc cggccgaact ggtccgcacc gacagtccca  780
acttcctgtg ctccgtgctg ccctcgcact ggcggtgcaa caagaccctg cccgtggcct  840
tcaaggttgt agccctcgga gaggtaccag atgggactgt ggttaccgtc atggccggga  900
atgatgagaa ctactccgcc gagctccgaa atgcctccgc tgttatgaaa aaccaagtag  960
ccaggttcaa cgatctgaga tttgtgggcc ggagcggacg aggcaagagt ttcaccttga  1020
ccataacagt cttcacaaat cctccccaag tggccactta ccacagagct attaaagtga  1080
cagtggacgg tccccgggaa ccaagaaggc acagacagaa gcttgatgac tctaaaccta  1140
gtttgttctc tgatcgcctc agtgatttag ggcgcattcc tcatcccagt atgagagtag  1200
gtgtcccgcc tcagaaccca cggccctccc tgaactctgc accaagtcct tttaatccac  1260
aaggacagag tcagattaca gatcccaggc aggcacagtc ttccccaccg tggtcctatg  1320
accagtctta cccctcctat ctgagccaga tgacatcccc atccatccac tccaccacgc  1380
```

```
cgctgtcttc cacacggggc accgggctac ctgccatcac tgacgtgccc aggcgtattt  1440
cagatgatga cactgccacc tctgacttct gcctctggcc ttcctctctc agtaagaaga  1500
gccaggcagg tgcttcagaa ctgggccctt tttcagaccc caggcagttc ccaagcattt  1560
catccctcac tgagagccgc ttctccaacc cacgaatgca ctacccagcc acctttacct  1620
acaccccgcc agtcacgtca ggcatgtccc tcggcatgtc cgccaccact cactaccaca  1680
cgtacctgcc accaccctac cccggctctt cccaaagcca gagtggaccc ttccagacca  1740
gcagcactcc atatctctac tatggtactt cgtcagcatc ctatcagttc ccaatggtac  1800
ccgggggaga ccggtctcct tccaggatgg tcccaccatg caccaccacc tcgaatggca  1860
gcacgctatt aaatccaaat ttgcctaacc agaatgatgg tgttgacgct gacggaagcc  1920
acagcagttc cccaactgtt ttgaattcta gcggcagaat ggatgagtct gtttggcggc  1980
catattgaaa ttcgtcaacc atggcccagt ggcatggggg ccacatcccg catgtgttaa  2040
tatatacata tataaagaga gtgcctatat atgtatattg attagctaac tagaagattt  2100
ctcattcaat ccctagtcat gatcttgcaa ccctaagagg gtgggggcag tcataactgg  2160
gtttcatatt gtttactatt taagatgtcc cctttaccaa ggaacaaacc gtcaaaggtg  2220
ttgtctggtc tgttttcata agtgacctgt tcccacgccg gttcagagag gtggactctg  2280
ggtctgggag gaaggagaga cacttcctct ctgtgctttg aaaccacagc ctctgctgtg  2340
tggcagccgg tacactctgc agacccgctt acagagtcag atgtggtgca ctcagaaagg  2400
gacaagaggc agagtggctg cttctgtccg ctgccgtcca ctctgccgtc cacctgttcc  2460
aaagtttcc  ttcagacttg ctgcaggtac tcatttgaac ttttgagttc acttttttt   2520
tttcctattc taagaaagtg acttcaaaaa tactgatcag gacagataat tttattttac  2580
cttttatatt ttctcacttc ccccatttaa ccaaaaagaa atcccgttcc ccctccccg   2640
ttccttctgc ttctcccttt atgcaaactg aaaatggcaa tgccttatta ttatagccat  2700
aatggtatag tgtttgagtt ggctgtgtgt tatgtgtttt tttctttttt tttctttttt  2760
aaattatgaa tatgtgtaaa atctgaagta acttgctaac gtgaatggtc atataacttt  2820
aaagatatat ttataattat ttaatgacat ttggacattt ggaacatttc ttagtgtaat  2880
gatatgttga cttcggtctc taaaagtgtg cttcttcttc aataccaagt ttcttcagtg  2940
ggctagagcc atatcggaaa tattgctaag caatctcaat tccttcaggc ataatgtgat  3000
tttttttttt ttttgaagat aactcccatc tccaaatagt ttagatgtag tttgttttca  3060
cgatgtatga aggagatgct ctgtttcttt ctttcaggca tttgattgcc tctgacacag  3120
ctttgccttt taaagcaata attagggatt aaaataacaa aaacaaaaca aaagccacct  3180
atagcccttt aacacttaac gtggcccctt tactagcatg aaatgctgga gacatgtggt  3240
ttcctaattt ctccattttg ggggtggtgg gagggggggag ggtggccatt atgactctta 3300
tcatattaaa aagccaagca caagtgattg gttgaactgc agaaaagtgt tctgtggtct  3360
ctgagttgag caaaactcta aattgcaggc ttcgtggttg agggcctagt cagctgaaag  3420
ccacgcgtgt ggtaaaggct caggcatggc ttggagaacc taggaacaca ttaggagcct  3480
gcacctacca gcctcaccat acagccattc aggggaaccc aaaaagtgcc ttacccaagg  3540
agggccccca gcagctttcc aggaagtcga atgaagtcgc tgtcctcggg gaactggtca  3600
gctgaagtag caaccggtag ctgatgtcag tagacaacag aacctgtggg gacctccagg  3660
aaacctttga cattggaggc tttcattagg cagggccaac aagagcaggg aaggccatgt  3720
acccattggt atctgccatt gtgtgtgagt ttgagatcca gccctccttg gaggatgtac  3780
tgtgatcatt cctggtacct tagggccaat ccctaagtgt ggcttcctaa tccaggccag  3840
ggatcattca gtgataccac caggccaatc ccagcattcc tcctgcacaa agtgtttgtg  3900
tgtgggggga tagattgggg tggggccacc ttcatttgaa tcctgagtca ttctaagagt  3960
tctgcaagct tttgccttca gcaccctata ccccctcgct ctctgttcct tctcaggttg  4020
acctttgtcc caatgcggga cagtccagag gcagatgggg acctatgtgt gcctccaacc  4080
tgcgttttcc tcagaattca tcctgactcc ctctgacaca gattgagggg gggggggaaga 4140
aacccaaccc gcaccaaagc aaaacacttt gccttctaaa ggctgtgcac caagtagacg  4200
cagatggtca gcccaccttt gtgtttcctt aagatggaaa ttgtaactga tgctatttat  4260
tgtttgtgtg tggtagcttg aagcacacca cggtccatgt gtttgtctga tacctatttc  4320
agcagcattt acaaaagcca gtgtctggtt acacttttca gttttcatta atcaacatga  4380
aaatgttacc attggtgcca gctgcaccct atttaatttt tttaagggca ctatatttgt  4440
acatttcgtt tttaatgtta aagggcttct taaagtttac agtacagtta tcaagggaat  4500
agaggggatg cattagtgcc taaatgttat tctagtggct gcaggcagca acccagaagc  4560
agttttgaaa acaggttgtt tccctctgtc ctcccttatt tgggaaaatt caagtgcttt  4620
cttcaccttt caggcacctc acggtgactc ccgttactta gagcagtctg tcgtcgtctt  4680
cttcttcttc ctcttcctct tcctcttcct cttcctcttc ctcttcctct tcctcttcct  4740
cttcctcttc ttcttcttct tcttcttctt cttcttcttc ttcttcctcc tagggtttaa  4800
aatccccctt cctcttccct tatctcttaa actcttcatt tgcactgggt cacacgtatg  4860
atttgtggtt ttaagaccaa agcaatgtct tattactctt ctggagccgt ttatgtgtac  4920
taaccaaccc ttccctccac ttccctgggt ttagatgcac acggttctca aaggagcaca  4980
aacatggcca gattcacagt gggacccaca cagccatgtt aaaaaaaaaa acaaaaaaaa  5040
acctcttcac ttgtctgaga attttaacct gggccccaat tgctaacggg caccatggct  5100
tgggtttcag gttagggaac gttgcccagt gagtaacaga aagacttaac tgatttaatt  5160
agtttgccct catccttcac tccaagaccc taagaaaccg atcagagaaa catctccaca  5220
ccattagagg ttgagaaggg aggagccatg tgggggttcc ctccgctcgg aggaaaggca  5280
ctgactgacc tagttagagt ggtagcagaa gcacccatgg tatctgagag agcaataaac  5340
aataaaagat gatcctccca agcttagaat ttgttgttct taaagaagac gatgcatcta  5400
aaacaaagaa tttttttttc tatgtgggaa ctttcttcgt tgtctgttta cttcatgttt  5460
acaaataatt gtttgctttt taatgcagta ctttaaaaaa tatatcagcc aaaaccataa  5520
cttacagtaa ttttttttagg tattctgaat aaaattccat gtcttttgat atgtctactg 5580
ttcttaggtt tctgtggaac aacaacaaca acaacaacaa aattgtagca ttttgtgtaa  5640
atacagcttt cgttcttatt ttttattttt ctgattgcta ttgcccaaga tttgctttct  5700
atgcacgtat tgtacaaatt gtgctttgtg ccacaggtca tgatcgtgga tgagtttact  5760
ctgaacttca aagggactat ttgtattgta tgttgcaact gtaaattgaa ttatttggca  5820
tttccccctc tcatgattgt aatattaatt tgaagtttga atttaatttt caataaaaag  5880
gctttttttt tcctttggt  tttg                                          5904
```

```
SEQ ID NO: 38           moltype = DNA  length = 5829
FEATURE                 Location/Qualifiers
```

-continued

```
source                  1..5829
                        mol_type = genomic DNA
                        organism = Mus musculus
SEQUENCE: 38
ggcggaggag gcggcgcggg caagcgacgg cgccgcgagc tgggcagccg cgctctgctt  60
ggcggtggcg gacagcgagg agccacacgc accgccgaga tggactgctg aacctgcggg  120
gctccactac cgtactggaa cccggagcgg ggcgccagcg cacccaggac acggtgcccc  180
aaggggcccc tactgcaagc tgttaacttc aagtcccttg cggcggctgg gccaaacacg  240
cccccgcgtc ccgctcgttg cagccaccgc cagggactcc caagcctccc ggtggagatc  300
cgcgcctctc gggtgtcccc acccgctacc ccgactctgt ccggtctcca gtcgccggcc  360
cccagcagac tccgcccggc acacggcttc ctcgaacttg atttctcacc tcctctgtcc  420
cgtcacctcc atcctctttc cgcccccgtc tcgcctccac cccctcgatt tcctcctcct  480
cgccccccat ttccaccctc ctccccctcc cccggccact tcgctaactt gtggctgttg  540
tgatgcgtat tcctgtagat ccgagcacca gccggcgctt cagccccccc tccagcagcc  600
tgcagcccgg caagatgagc gacgtgagcc cggtggtggc tgcgcagcag cagcaacagc  660
agcagcagca gcagcaacag cagcagcaac aacagcaaca gcaacaacag cagcagcagc  720
agcagcagca ggaggcggcc gcagcagcag cggcggcagc ggcggcggca gcagcggcgg  780
cggccgcagt gccccgattg aggccgccgc acgacaaccg caccatggtg gagatcatcg  840
cggaccaccc ggccgaactg gtccgcaccg acagtcccaa cttcctgtgc tccgtgctgc  900
cctcgcactg gcggtgcaac aagaccctgc ccgtggcctt caaggttgta gccctcggag  960
aggtaccaga tgggactgtg gttaccgtca tggccgggaa tgatgagaac tactccgccg  1020
agctccgaaa tgcctccgct gttatgaaaa accaagtagc caggttcaac gatctgagat  1080
ttgtgggccg gagcggacga ggcaagagtt tcaccttgac cataacagtc ttcacaaatc  1140
ctccccaagt ggccacttac cacagagcta ttaaagtgac agtggacggt ccccgggaac  1200
caagaaatcc caggcaggca cagtcttccc caccgtggtc ctatgaccag tcttacccct  1260
cctatctgag ccagatgaca tccccatcca tccactccac cacgccgctg tcttccacac  1320
ggggcaccgg gctacctgcc atcactgacg tgcccaggcg tatttcagat gatgacactg  1380
ccacctctga cttctgcctc tggccttcct ctctcagtaa gaagagccag gcaggtgctt  1440
cagaactggg cccttttttca gaccccaggc agttcccaag catttcatcc ctcactgaga  1500
gccgcttctc caacccacga atgcactacc cagccacctt tacctacacc ccgccagtca  1560
cgtcaggcat gtccctcggc atgtccgcca ccactcacta ccacacgtac ctgccaccac  1620
cctaccccgg ctcttcccaa agccagagtg gacccttcca gaccagcagc actccatatc  1680
tctactatgg tacttcgtca gcatcctatc agttcccaat ggtacccggg ggagaccggt  1740
ctccttccag gatggtccca ccatgcacca ccacctcgaa tggcagcacg ctattaaatc  1800
caaatttgcc taaccagaat gatggtgttg acgctgacgg aagccacagc agttccccaa  1860
ctgttttgaa ttctagcggc agaatggatg agtctgtttg gcggccatat tgaaattcgt  1920
caaccatggc ccagtggcat gggggccaca tcccgcatgt gttaatatat acatatataa  1980
agagagtgcc tatatatgta tattgattag ctaactagaa gatttctcat tcaatcccta  2040
gtcatgatct tgcaacccta agagggtggg ggcagtcata actgggtttc atattgttta  2100
ctatttaaga tgtcccttt accaaggaac aaaccgtcaa aggtgttgtc tggtctgttt  2160
tcataagtga cctgttccca cgccggttca gagaggtgga ctctgggtct gggaggaagg  2220
agagacactt cctctctgtg ctttgaaacc acagcctctg ctgtgtggca gccggtacac  2280
tctgcagacc cgcttacaga gtcagatgtg gtgcactcag aaagggacaa gaggcagagt  2340
ggctgcttct gtccgctgcc gtccactctg ccgtccacct gttccaaagt tttccttcag  2400
acttgctgca ggtactcatt tgaacttttg agttcacttt ttttttttcc tattctaaga  2460
aagtgacttc aaaaatactg atcaggacag ataattttat tttacctttt atattttctc  2520
acttccccca tttaaccaaa aagaaatccc gttcccctc ccccgttcct tctgcttctc  2580
cctttatgca aactgaaaat ggcaatgcct tattattata gccataatgg tatagtgttt  2640
gagttggctg tgtgttatgt gttttttctt tttttttct tttttaaatt atgaatatgt  2700
gtaaaatctg aagtaacttg ctaacgtgaa tggtcatata actttaaaga tatatttata  2760
attatttaat gacatttgga catttggaac atttcttagt gtaatgatat gttgacttcg  2820
gtctctaaaa gtgtgcttct tcttcaatac caagtttctt cagtgggcta gagccatatc  2880
ggaaatattg ctaagcaatc tcaattcctt caggcataat gtgatttttt ttttttttg  2940
aagataactc ccatctccaa atagtttaga tgtagtttgt tttcacgatg tatgaaggag  3000
atgctctgtt tctttctttc aggcatttga ttgcctctga cacagctttg ccttttaaag  3060
caataattag ggattaaaat aacaaaaaca aaacaaaagc cacctatagc cctttaacac  3120
ttaacgtggc ccctttacta gcatgaaatg ctggagacat gtggtttcct aatttctcca  3180
ttttggggggt ggtgggaggg gggagggtgg ccattatgac tcttatcata ttaaaaagcc  3240
aagcacaagt gattggttga actgcagaaa agtgttctgt ggtctctgag ttgagcaaaa  3300
ctctaaattg caggcttcgt ggttgagggc ctagtcagct gaaagccacg cgtgtggtaa  3360
aggctcaggc atggcttgga gaacctagga acacattagg agcctgcacc taccagcctc  3420
accatacagc cattcagggg aacccaaaaa gtgccttacc caaggagggc ccccagcagc  3480
tttccaggaa gtcgaatgaa gtcgctgtcc tcggggaact ggtcagctga agtagcaacc  3540
ggtagctgat gtcagtagac aacagaacct gtggggacct ccaggaaacc tttgacattg  3600
gaggctttca ttaggcaggg ccaacaagag cagggaaggc catgtaccca ttggtatctg  3660
ccattgtgtg tgagtttgag atccagccct ccttggagga tgtactgtga tcattcctgg  3720
taccttaggg ccaatcccta agtgtggctt cctaatccag gccagggatc attcagtgat  3780
accaccaggc caatcccagc attcctcctg cacaaagtgt ttgtgtgtgg ggggatagat  3840
tggggtgggg ccaccttcat ttgaatcctg agtcattcta agagttctgc aagcttttgc  3900
cttcagcacc ctataccccc tcgctctctg ttccttctca ggttgacctt tgtcccaatg  3960
cgggacagtc cagaggcaga tggggaccta tgtgtgcctc caacctgcgt tttcctcaga  4020
attcatcctg actccctctg acacagattg aggggggggg gaagaaaccc aacccgcacc  4080
aaagcaaaac actttgcctt ctaaaggctg tgcaccaagt agacgcagat ggtcagccca  4140
cctttgtgtt tccttaagat ggaaattgta actgatgcta tttattgttt gtgtgtggta  4200
gcttgaagca caccacggtc catgtgtttg tctgatacct atttcagcag catttacaaa  4260
agccagtgtc tggttacact tttcagtttt cattaatcaa catgaaaatg ttaccattgg  4320
tgccagctgc accctattta atttttttaa gggcactata tttgtacatt tcgtttttaa  4380
tgttaaaggg cttcttaaag tttacagtac agttatcaag ggaatagagg ggatgcatta  4440
gtgcctaaat gttattctag tggctgcagg cagcaaccca gaagcagttt tgaaaacagg  4500
```

```
ttgtttccct ctgtcctccc ttatttggga aaattcaagt gctttcttca cctttcaggc  4560
acctcacggt gactcccgtt acttagagca gtctgtcgtc gtcttcttct tcttcctctt  4620
cctcttcctc ttcctcttcc tcttcctctt cctcttcctc ttcctcttcc tcttcttctt  4680
cttcttcttc ttcttcttct tcttcttctt cctcctaggg tttaaaatcc cccttcctct  4740
tcccttatct cttaaactct tcatttgcac tgggtcacac gtatgatttg tggttttaag  4800
accaaagcaa tgtcttatta ctcttctgga gccgtttatg tgtactaacc aacccttccc  4860
tccacttccc tgggtttaga tgcacacggt tctcaaagga gcacaaacat ggccagattc  4920
acagtgggac ccacacagcc atgttaaaaa aaaaaacaaa aaaaaacctc ttcacttgtc  4980
tgagaatttt aacctgggcc ccaattgcta acgggcacca tggcttgggt ttcaggttag  5040
ggaacgttgc ccagtgagta acagaaagac ttaactgatt taattagttt gccctcatcc  5100
ttcactccaa gaccctaaga aaccgatcag agaaacatct ccacaccatt agaggttgag  5160
aagggaggag ccatgtgggg gttccctccg ctcggaggaa aggcactgac tgacctagtt  5220
agagtggtag cagaagcacc catggtatct gagagagcaa taaacaataa aagatgatcc  5280
tcccaagctt agaatttgtt gttcttaaag aagacgatgc atctaaaaca aagaattttt  5340
ttttctatgt gggaactttc ttcgttgtct gtttacttca tgtttacaaa taattgtttg  5400
ctttttaatg cagtacttta aaaaatatat cagccaaaac cataacttac agtaattttt  5460
ttaggtattc tgaataaaat tccatgtctt ttgatatgtc tactgttctt aggtttctgt  5520
ggaacaacaa caacaacaac aacaaaattg tagcattttg tgtaaataca gctttcgttc  5580
ttattttta ttttctgat tgctattgcc caagatttgc tttctatgca cgtattgtac   5640
aaattgtgct ttgtgccaca ggtcatgatc gtggatgagt ttactctgaa cttcaaaggg  5700
actatttgta ttgtatgttg caactgtaaa ttgaattatt tggcatttcc ccctctcatg  5760
attgtaatat taatttgaag tttgaattta attttcaata aaaaggcttt ttttttcctt  5820
ttggttttg                                                          5829

SEQ ID NO: 39          moltype = DNA  length = 5724
FEATURE                Location/Qualifiers
source                 1..5724
                       mol_type = genomic DNA
                       organism = Mus musculus
SEQUENCE: 39
ggcggaggag gcggcgcggg caagcgacgg cgccgcgagc tgggcagccg cgctctgctt  60
ggcggtggcg gacagcgagg agccacacgc accgccgaga tggactgctg aacctgcggg  120
gctccactac cgtactggaa cccggagcgg ggcgccagcg cacccaggac acggtgcccc  180
aaggggcccc tactgcaagc tgttaacttc aagtcccttg cggcggctgg gccaaacacg  240
cccccgcgtc ccgctcgttg cagccaccgc cagggactcc caagcctccc ggtggagatc  300
cgcgcctctc gggtgtcccc acccgctacc ccgactctgt ccggtctcca gtcgccggcc  360
cccagcagac tccgcccggc acacggcttc ctcgaacttg atttctcacc tcctctgtcc  420
cgtcacctcc atcctctttc cgcccccgtc tcgcctccac cccctcgatt tcctcctcct  480
cgccccccat ttccaccctc ctccccctcc cccggccact tcgctaactt gtggctgttg  540
tgatgcgtat tcctgtagat ccgagcacca gccggcgctt cagcccccc tccagcagcc  600
tgcagcccgg caagatgagc gacgtgagcc cggtggtggc tgcgcagcag cagcaacagc  660
agcagcagca gcagcaacag cagcagcaac aacagcaaca gcaacaacag cagcagcagc  720
agcagcagca ggaggcggcc gcagcagcag cggcggcagc ggcggcggca gcagcggcgg  780
cggccgcagt gccccgattg aggccgccgc acgacaaccg caccatggtg gagatcatcg  840
cggaccaccc ggccgaactg gtccgcaccg acagtcccaa cttcctgtgc tccgtgctgc  900
cctcgcactg gcggtgcaac aagaccctgc ccgtggcctt caaggttgta gccctcggag  960
aggtaccaga tgggactgtg gttaccgtca tggccgggaa tgatgagaac tactccgccg  1020
agctccgaaa tgcctccgct gttatgaaaa accaagtagc caggttcaac gatctgagat  1080
ttgtgggccg gagcggacga gatcccaggc aggcacagtc ttccccaccg tggtcctatg  1140
accagtctta cccctcctat ctgagccaga tgacatcccc atccatccac tccaccacgc  1200
cgctgtcttc cacacggggc accgggctac ctgccatcac tgacgtgccc aggcgtattt  1260
cagatgatga cactgccacc tctgacttct gcctctggcc ttcctctctc agtaagaaga  1320
gccaggcagg tgcttcagaa ctgggccctt tttcagaccc caggcagttc ccaagcattt  1380
catccctcac tgagagccgc ttctccaacc cacgaatgca ctacccagcc acctttacct  1440
acaccccgcc agtcacgtca ggcatgtccc tcggcatgtc cgccaccact cactaccaca  1500
cgtacctgcc accaccctac cccggctctt cccaaagcca gagtggaccc ttccagacca  1560
gcagcactcc atatctctac tatggtactt cgtcagcatc ctatcagttc ccaatggtac  1620
ccgggggaga ccggtctcct tccaggatgg tcccaccatg caccaccacc tcgaatggca  1680
gcacgctatt aaatccaaat ttgcctaacc agaatgatgg tgttgacgct gacggaagcc  1740
acagcagttc cccaactgtt ttgaattcta gcggcagaat ggatgagtct gtttggcggc  1800
catattgaaa ttcgtcaacc atggcccagt ggcatggggg ccacatcccg catgtgttaa  1860
tatatacata tataaagaga gtgcctatat atgtatattg attagctaac tagaagattt  1920
ctcattcaat ccctagtcat gatcttgcaa ccctaagagg gtgggggcag tcataactgg  1980
gtttcatatt gtttactatt taagatgtcc cctttaccaa ggaacaaacc gtcaaaggtg  2040
ttgtctggtc tgttttcata agtgacctgt tcccacgccg gttcagagag gtggactctg  2100
ggtctgggag gaaggagaga cacttcctct ctgtgctttg aaaccacagc ctctgctgtg  2160
tggcagccgg tacactctgc agacccgctt acagagtcag atgtggtgca ctcagaaagg  2220
gacaagaggc agagtggctg cttctgtccg ctgccgtcca ctctgccgtc cacctgttcc  2280
aaagtttcc ttcagacttg ctgcaggtac tcatttgaac ttttgagttc actttttttt   2340
tttcctattc taagaaagtg acttcaaaaa tactgatcag gacagataat tttattttac  2400
cttttatatt ttctcacttc ccccatttaa ccaaaaagaa atcccgttcc ccctcccccg  2460
ttccttctgc ttctcccttt atgcaaactg aaaatggcaa tgccttatta ttatagccat  2520
aatggtatag tgtttgagtt ggctgtgtgt tatgtgtttt tttctttttt tttcttttt   2580
aaattatgaa tatgtgtaaa atctgaagta acttgctaac gtgaatggtc atataacttt  2640
aaagatatat ttataattat ttaatgacat ttggacattt ggaacatttc ttagtgtaat  2700
gatatgttga cttcggtctc taaaagtgtg cttcttcttc aataccaagt ttcttcagtg  2760
ggctagagcc atatcggaaa tattgctaag caatctcaat tccttcaggc ataatgtgat  2820
ttttttttt ttttgaagat aactcccatc tccaaatagt ttagatgtag tttgttttca   2880
cgatgtatga aggagatgct ctgtttcttt ctttcaggca tttgattgcc tctgacacag  2940
```

-continued

```
ctttgccttt taaagcaata attagggatt aaaataacaa aaacaaaaca aaagccacct  3000
atagcccttt aacacttaac gtggcccctt tactagcatg aaatgctgga gacatgtggt  3060
ttcctaattt ctccattttg ggggtggtgg gagggggggag ggtggccatt atgactctta  3120
tcatattaaa aagccaagca caagtgattg gttgaactgc agaaaagtgt tctgtggtct  3180
ctgagttgag caaaactcta aattgcaggc ttcgtggttg agggcctagt cagctgaaag  3240
ccacgcgtgt ggtaaaggct caggcatggc ttggagaacc taggaacaca ttaggagcct  3300
gcacctacca gcctcaccat acagccattc aggggaaccc aaaaagtgcc ttacccaagg  3360
agggccccca gcagctttcc aggaagtcga atgaagtcgc tgtcctcggg gaactggtca  3420
gctgaagtag caaccggtag ctgatgtcag tagacaacag aacctgtggg gacctccagg  3480
aaacctttga cattggaggc tttcattagg cagggccaac aagagcaggg aaggccatgt  3540
acccattggt atctgccatt gtgtgtgagt ttgagatcca gccctccttg gaggatgtac  3600
tgtgatcatt cctggtacct tagggccaat ccctaagtgt ggcttcctaa tccaggccag  3660
ggatcattca gtgataccac caggccaatc ccagcattcc tcctgcacaa agtgtttgtg  3720
tgtgggggga tagattgggg tggggccacc ttcatttgaa tcctgagtca ttctaagagt  3780
tctgcaagct tttgccttca gcaccctata ccccctcgct ctctgttcct tctcaggttg  3840
acctttgtcc caatgcggga cagtccagag gcagatgggg acctatgtgt gcctccaacc  3900
tgcgttttcc tcagaattca tcctgactcc ctctgacaca gattgagggg ggggggaaga  3960
aacccaaccc gcaccaaagc aaaacacttt gccttctaaa ggctgtgcac caagtagacg  4020
cagatggtca gcccaccttt gtgtttcctt aagatggaaa ttgtaactga tgctatttat  4080
tgtttgtgtg tggtagcttg aagcacacca cggtccatgt gtttgtctga tacctatttc  4140
agcagcattt acaaaagcca gtgtctggtt acacttttca gttttcatta atcaacatga  4200
aaatgttacc attggtgcca gctgcaccct atttaatttt tttaagggca ctatatttgt  4260
acatttcgtt tttaatgtta aagggcttct taaagtttac agtacagtta tcaagggaat  4320
agaggggatg cattagtgcc taaatgttat tctagtggct gcaggcagca acccagaagc  4380
agttttgaaa acaggttgtt tccctctgtc ctcccttatt tgggaaaatt caagtgcttt  4440
cttcaccttt caggcacctc acggtgactc ccgttactta gagcagtctg tcgtcgtctt  4500
cttcttcttc ctcttcctct tcctcttcct cttcctcttc ctcttcctct tcctcttcct  4560
cttcctcttc ttcttcttct tcttcttctt cttcttcttc ttcttcctcc tagggtttaa  4620
aatccccctt cctcttccct tatctcttaa actcttcatt tgcactgggt cacacgtatg  4680
atttgtggtt ttaagaccaa agcaatgtct tattactctt ctggagccgt ttatgtgtac  4740
taaccaaccc ttccctccac ttccctgggt ttagatgcac acggttctca aaggagcaca  4800
aacatggcca gattcacagt gggacccaca cagccatgtt aaaaaaaaaa acaaaaaaaa  4860
acctcttcac ttgtctgaga attttaacct gggccccaat tgctaacggg caccatggct  4920
tgggtttcag gttagggaac gttgcccagt gagtaacaga aagacttaac tgatttaatt  4980
agtttgccct catccttcac tccaagacct taagaaaccg atcagagaaa catctccaca  5040
ccattagagg ttgagaaggg aggagccatg tgggggttcc ctccgctcgg aggaaaggca  5100
ctgactgacc tagttagagt ggtagcagaa gcacccatgg tatctgagag agcaataaac  5160
aataaaagat gatcctccca agcttagaat ttgttgttct taaagaagac gatgcatcta  5220
aaacaaagaa ttttttttc tatgtgggaa ctttcttcgt tgtctgttta cttcatgttt  5280
acaaataatt gtttgctttt taatgcagta ctttaaaaaa tatatcagcc aaaaccataa  5340
cttacagtaa ttttttagg tattctgaat aaaattccat gtcttttgat atgtctactg  5400
ttcttaggtt tctgtggaac aacaacaaca acaacaacaa aattgtagca ttttgtgtaa  5460
atacagcttt cgttcttatt ttttattttt ctgattgcta ttgcccaaga tttgctttct  5520
atgcacgtat tgtacaaatt gtgctttgtg ccacaggtca tgatcgtgga tgagtttact  5580
ctgaacttca aagggactat ttgtattgta tgttgcaact gtaaattgaa ttatttggca  5640
tttccccctc tcatgattgt aatattaatt tgaagtttga atttaatttt caataaaaag  5700
gctttttttt tcctttttggt tttg                                       5724
```